US009181258B2

(12) United States Patent
Casuscelli et al.

(10) Patent No.: US 9,181,258 B2
(45) Date of Patent: *Nov. 10, 2015

(54) SUBSTITUTED 3,4-DIHYDROPYRROLO[1,2-A]PYRAZIN-1(2H)-ONES AS PROTEIN KINASE INHIBITORS

(71) Applicant: NERVIANO MEDICAL SCIENCES S.R.L., Nerviano (IT)

(72) Inventors: Francesco Casuscelli, Dairago (IT); Alessandra Badari, Vedano al Lambro (IT); Sten Christian Orrenius, Nerviano (IT); Claudia Piutti, Nerviano (IT); Teresa Disingrini, Vanzago (IT)

(73) Assignee: NERVIANO MEDICAL SCIENCES S.R.L., Nerviano (MI) (IT)

( * ) Notice: Subject to any disclaimer, the term of this patent is extended or adjusted under 35 U.S.C. 154(b) by 0 days.

This patent is subject to a terminal disclaimer.

(21) Appl. No.: 14/349,536

(22) PCT Filed: Oct. 4, 2012

(86) PCT No.: PCT/EP2012/069588
§ 371 (c)(1),
(2) Date: Apr. 3, 2014

(87) PCT Pub. No.: WO2013/050448
PCT Pub. Date: Apr. 11, 2013

(65) Prior Publication Data
US 2014/0249146 A1 Sep. 4, 2014

(30) Foreign Application Priority Data

Oct. 7, 2011 (EP) .................................... 11184284

(51) Int. Cl.
*A61K 31/4985* (2006.01)
*C07D 241/38* (2006.01)
*C07D 487/04* (2006.01)
*A61K 31/5377* (2006.01)
*A61K 45/06* (2006.01)

(52) U.S. Cl.
CPC .......... *C07D 487/04* (2013.01); *A61K 31/4985* (2013.01); *A61K 31/5377* (2013.01); *A61K 45/06* (2013.01)

(58) Field of Classification Search
CPC ......................... A61K 31/4985; C07D 241/38
USPC .................. 514/249; 544/116, 333, 349, 373; 546/199, 276.7; 548/335.1; 549/59, 549/434
See application file for complete search history.

(56) References Cited

FOREIGN PATENT DOCUMENTS

WO WO 2007/042784 A2 4/2007
WO WO 2010/031816 A1 3/2010

OTHER PUBLICATIONS

Jordan, V. C. Nature Reviews: Drug Discovery, 2, 2003, 205.*
Hackam, et al. JAMA, 296(14), 2006, 1731-1732.*
Amaravadi R. et al., "The Survival Kinases Akt and Pim as Potential Pharmacological Targets", The Journal of Clinical Investigation 115(10):2618-2624 (Oct. 2005).
Beharry Z. et al., "The Pim Protein Kinases Regulate Energy Metabolism and Cell Growth", PNAS 108(2):528-533 (Jan. 11, 2011).
Blanco-Aparicio C. et al., "Pim 1 Kinase Inhibitor ETP-45299 Suppresses Cellular Proliferation and Synergizes With PI3K Inhibition", Cancer Letters 300(2):145-153 (2010).
Brault L et al., "PIM Serine/Threonine Kinases in the Pathogenesis and Therapy of Hematologic Malignancies and Solid Cancers", Haematologica 95(6):1004-1015 (2010).
Choudhary C. et al., "Mislocalized Activation of Oncogenic RTKs Switches Downstream Signaling Outcomes", Molecular Cell 36:326-339 (Oct. 23, 2009).
Cohen A.M. et al., "Increased Expression of the hPim-2 Gene in Human Chronic Lymphocytic Leukemia and Non-Hodgkin Lymphoma", Leukemia & Lymphoma 45(5):951-955 (May 2004).
Cohen P., "Protein Kinases-The Major Drug Targets of the Twenty-First Century?", Nature Reviews-Drug Discovery 1:309-315 (Apr. 2002).
Cohen P., "The Development and Therapeutic Potential of Protein Kinase Inhibitors", Current Opinion in Chemical Biology 3:459-465 (1999).
Heaney F. et al., "a-Keto Amides as Precursors to Heterocycles-Generation and Cycloaddition Reactions of Piperazin-5-One Nitrones", Org. Biomol. Chem. 1:1122-1132 (Mar. 10, 2003).
Hughes D.L., "The Mitsunobu Reaction", Organic Reactions 42:335-357 (1992).
Huttmann A. et al., "Gene Expression Signatures Separate B-Cell Chronic Lymphocytic Leukaemia Prognostic Subgroups Defined by ZAP-70 and CD38 Expression Status", Leukemia 20:1774-1782 (2006).
Kim K-T et al., "Pim-1 is Up-Regulated by Constitutively Activated FLT3 and Plays a Role in FLT3-Mediated Cell Survival", Blood 105(4):1759-1767 (Feb. 15, 2005).
Kumar A. et al., "Crystal Structures of Proto-Oncogene Kinase Pim1: A Target of Aberrant Somatic Hypermutations in Diffuse Large Cell Lymphoma", J. Mol. Biol. 348:183-193 (2005).
Nihira K. et al., "Pim-1 Controls NF-kB Signalling by Stabilizing RelA/p65", Cell Death and Differentiation 17:689-698 (2010).
Marshall J.A. et al., "Total Synthesis of the Germacranolide (+)-Aristolactone Via [2,3] Wittig Ring Contraction", Tetrahedron Letters 28(7):723-726 (1987).

(Continued)

*Primary Examiner* — Douglas M Willis
(74) *Attorney, Agent, or Firm* — Scully, Scott, Murphy & Presser, P.C.

(57) ABSTRACT

The present invention relates to 4-alkyl substituted 3,4-dihydropyrrolo[1,2-a]pyrazin-1(2H)-one derivatives, of formula (I)

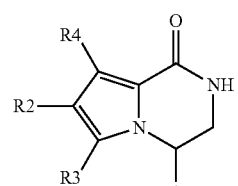

which modulate the activity of protein kinases and are therefore useful in treating diseases caused by dysregulated protein kinase activity. The present invention also provides methods for preparing these compounds, pharmaceutical compositions comprising these compounds, and methods of treating diseases utilizing such these compounds or the pharmaceutical compositions containing them.

15 Claims, No Drawings

(56) References Cited

OTHER PUBLICATIONS

Rosini G., "The Henry (Nitroaldol) Reaction", In Comprehensive Organic Synthesis; Trost B.M. 2:321-340 (1996).

Shah N. et al., "Potential Roles for the PIMI1 Kinase in Human Cancer-A Molecular and Therapeutic Appraisal", European Journal of Cancer 44:2144-2151 (2008).

Tamburini J. et al., "Protein Synthesis is Resistant to Rapamycin and Constitutes a Promising Therapeutic Target in Acute Myeloid Leukemia", Blood 114(8):1618-1627 (Aug. 20, 2009).

Velculescu V.E., "Defining the Blueprint of the Cancer Genome", Carcinogenesis 29(6):1087-1091 (2008).

Wang J. et al., "Pim1 Kinase Synergizes With c-MYC to Induce Advanced Prostate Carcinoma", Oncogene 29:2477-2487 (2010).

Weissman S.A. et al., "Ligand-Free Palladium-Catalyzed Cyanation of Aryl Halides", J. Org. Chem. 70:1508-1510 (2005).

Yeung P Y et al., "A Mild and Efficient Palladium-Catalyzed Cyanation of Aryl Chlorides With K4[Fe(CN)6]", Organic Letters 13(4):648-651 (2011).

International Search Report dated Dec. 13, 2012 received from related Application No. PCT/EP2012/069588.

\* cited by examiner

SUBSTITUTED 3,4-DIHYDROPYRROLO[1,2-A]PYRAZIN-1(2H)-ONES AS PROTEIN KINASE INHIBITORS

BACKGROUND OF THE DISCLOSURE

The present invention relates to 4-alkyl substituted 3,4-dihydropyrrolo[1,2-a]pyrazin-1(2H)-one derivatives, to a process for their preparation, to the pharmaceutical compositions comprising them, and to their use as therapeutic agents, particularly in the treatment of diseases caused by dysregulated protein kinase activity, such as cancer, cell proliferative disorders, viral infections, immune disorders, neurodegenerative disorders and cardiovascular diseases. The malfunctioning of protein kinases (PKs) is the hallmark of numerous diseases. A large share of the oncogenes and proto-oncogenes involved in human cancers encodes for PKs. The enhanced activities of PKs are also implicated in many non-malignant diseases, such as benign prostate hyperplasia, familial adenomatosis, polyposis, neurofibromatosis, psoriasis, vascular smooth cell proliferation associated with atherosclerosis, pulmonary fibrosis, arthritis glomerulonephritis and post-surgical stenosis and restenosis.

PKs are also implicated in inflammatory conditions and in the multiplication of viruses and parasites. PKs may also play a major role in the pathogenesis and development of neurodegenerative disorders.

For a general reference to PKs malfunctioning or deregulation see, for instance, Current Opinion in Chemical Biology 1999, 3, 459-465; Nature Rev. Drug Discov. 2002; and Carcinogenesis 2008, 29, 1087-1091.

Originally identified as activated genes by proviral mutagenesis in a lymphoma mouse model, PIMs (PIM1, PIM2 and/or PIM3 throughout this application) are protein-serine/threonine kinases. PIM kinases are poorly expressed in normal tissues, and overexpressed or even mutated in a discrete number of human cancers, including Lymphoma, Leukaemia, Prostate, Pancreas and Gastric cancers [Shah et al. Eur. J. Cancer, 44, 2144-51, (2008)].

PIM kinases are constitutively active and their activity supports in vitro and in vivo tumor cell growth and survival through modification of an increasing number of common as well as isoform-specific substrates, including several cell cycle regulators and apoptosis mediators. PIM1 but not PIM2 seems also to mediate homing and migration of normal and malignant hematopoietic cells by regulating chemokine receptor surface expression [Brault et al. Haematologica 951004-1015 (2010)].

There is an increasing evidence that PIM1 and PIM2 kinases may be involved in mediating the oncogenic effects of some acute myelogenous leukemias (AML)-associated oncogenes, in particular, the oncogenic role of FLT3-mutations (ITD and KD mut., present in 30% of AMLs) and/or translocations involving the MLL gene (occurring in 20% of AMLs), [Kumar, et al. J. Mol. Biol. 348, 183-193, (2005)]. PIM1 is more expressed in FLT3-ITD-transformed AML cells than in WT bone marrow cells. Data suggest that PIM1 as well as PIM2 inhibition may mediate FLT3-ITD-dependent death of AML cells. Interestingly, cells transformed by FLT3 mutations that confer resistance to small-molecule tyrosine kinase inhibitors were still sensitive to knockdown of PIM2, or PIM1 and PIM2 by RNAi, [Kim et al., Blood 105, 1759-67, (2005)].

Moreover, PIM2 has been reported being over-expressed and associated with progression of several malignancies that originate from the B-cell lineage such as chronic lymphocytic (CLL), diffuse large B-cell lymphoma (DLBCL), mantle cell lymphoma (MCL) or myeloma [Cohen et al., *Leukemia & Lymphoma* 45(5) 951-955 (2004), Huttmann et al. Leukemia 20 1774 (2006)].

In recent studies, it was demonstrated that both NF-κB and Pim kinases are implicated in tumorigenesis, in particular, PIM1 phosphorylation of RelA/p65 at Ser276 is believed to allow defense against ubiquitin-mediated degradation and whereby exerted activation of NF-κB signalling, [Nihira K. et al. Cell Death & Differentiation 2010, 17, 689-698].

In prostate cancers, oncogenic PIM1 kinase is implicated with c-Myc in carcinogenesis, and the c-MYC/Pim1 synergy is critically dependent on PIM1 kinase activity. PIM1 cooperativity with c-MYC in vivo, is explained not only on the c-MYC activity by S62 phosphorylation, but also on the evidence of neuroendocrine (NE) differentiation [Wang J. et al. *Oncogene* (2010) 29, 2477-2487].

Interestingly, PIM and AKT/PKB seem to play partly redundant roles in mediating growth and survival of hematopoietic cells most probably due to overlapping substrates like BAD, p21WAF1/CIP1, p27KIP1, or Cot/Tpl-2 [Choudhary et al., Mol. Cell. 36 326-39 (2009)].

PIM kinases have been shown to control mTOR inhibition (rapamycin) resistance, proliferation and survival. Therefore, a combination of small molecule inhibitors targeting several survival kinases might be essential for a powerful cancer therapeutic platform [Amaravadi R., et al. J. Clin. Invest. 2005, 115 (10) 2618-24]. Oncogenic protein synthesis through eIF4E binding protein 1 (4E-BP1) seems to be mTOR-independent and controlled by PIM2. These observations suggest that the oncogenic eIF4F translation-initiating complex could be blocked with small molecules PIM2 inhibitors [Tamburini J. et al. Blood 2009, 114 (8), 1618-27; Brault L. et al. Haematologica 2010, 95 (6) 1004-1015 and Beharry Z. PNAS 2011 108, 528-533].

Recently two different research groups have reported the successful combination of PIM and PI3K inhibitors. Blanco-Aparicio, C. et al. [Cancer Lett. 2011, 300(2):145-53] combined the PI3K inhibitor GDC-0941 with a PIM1 inhibitor and found a strongly synergistic effect in AML cells. Ebens et al. during the 52$^{nd}$ ASH annual meeting, reported that a pan-PIM inhibition suppressed growth in myeloma cell lines, xenografts, and primary patient samples, both as a single-agent as well as acting synergistically in combination with GDC-0941.

3,4-Dihydro-2h-pyrrolo[1,2-a]pyrazin-1-one derivatives possessing kinase inhibitory activity have been disclosed in WO2010/031816, in the name of the Applicant itself.

BRIEF SUMMARY OF THE DISCLOSURE

Despite these developments, there is still need for effective agents for said diseases.

A new class of 4-alkyl substituted 3,4-dihydropyrrolo[1,2-a]pyrazin-1(2H)-one compounds has now been identified endowed with an activity both on PIM1 and PIM2, higher than previously achieved in the prior art. These compounds were found able to prevent the proliferation of human tumour cells at a remarkably low concentration, thereby maximizing the antitumour efficacy, while simultaneously reducing risk of the side effects linked to the administration of higher amounts of drugs.

Accordingly, a first object of the present invention is to provide a 4-alkyl substituted 3,4-dihydropyrrolo[1,2-a]pyrazin-1(2H)-one compound derivative represented by formula (I):

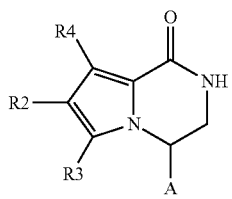

(I)

wherein

A is an optionally substituted group selected from straight or branched $C_1$-$C_6$ alkyl, heterocyclyl and —$(CH_2)_{1-3}$—X—R1;

R1 is hydrogen, halogen, or an optionally substituted group selected from straight or branched $C_1$-$C_6$ alkyl, $C_3$-$C_7$ cycloalkyl, cycloalkyl-alkyl, $C_2$-$C_6$ alkenyl, $C_2$-$C_6$ alkynyl, aryl, arylalkyl, heterocyclyl and heterocyclylalkyl;

R2 is an optionally substituted group selected from straight or branched $C_1$-$C_6$ alkyl, $C_3$-$C_7$ cycloalkyl, cycloalkyl-alkyl, $C_2$-$C_6$ alkenyl, $C_2$-$C_6$ alkynyl, aryl, arylalkyl, heterocyclyl and heterocyclylalkyl;

R3 and R4 are each independently hydrogen, halogen, cyano, or an optionally substituted group selected from straight or branched $C_1$-$C_6$ alkyl, $C_3$-$C_7$ cycloalkyl, cycloalkyl-alkyl, $C_2$-$C_6$ alkenyl, $C_2$-$C_6$ alkynyl, aryl, arylalkyl, heterocyclyl and heterocyclylalkyl;

X is a single bond or a divalent radical selected from —NR'—, and —O—, wherein R' is hydrogen, COR5, C(NH)R5, S(O)$_2$R9, or an optionally substituted straight or branched $C_1$-$C_6$ alkyl, $C_3$-$C_7$ cycloalkyl, cycloalkyl-alkyl, aryl, arylalkyl, heterocyclyl and heterocyclylalkyl or, together with the nitrogen atom to which they are bound, R' and R1 may form a 5 to 7 membered heteroaryl or heterocyclyl group optionally containing one additional heteroatom selected from N, O and S; wherein:

R5 is OR6, NR7R8 or an optionally substituted group selected from straight or branched $C_1$-$C_6$ alkyl, $C_3$-$C_7$ cycloalkyl, cycloalkyl-alkyl, $C_2$-$C_6$ alkenyl, $C_2$-$C_6$ alkynyl, aryl, arylalkyl, heterocyclyl and heterocyclylalkyl wherein:

R6 is a group optionally substituted selected from straight or branched $C_1$-$C_6$ alkyl, $C_3$-$C_7$ cycloalkyl, aryl and heterocyclyl;

R7 and R8 are each independently hydrogen or a group optionally substituted selected from straight or branched $C_1$-$C_6$ alkyl, $C_3$-$C_7$ cycloalkyl, aryl and heterocyclyl;

R9 is an optionally substituted group selected from straight or branched $C_1$-$C_6$ alkyl, $C_3$-$C_7$ cycloalkyl, aryl and heterocyclyl;

and a pharmaceutically acceptable salt thereof.

The present invention also provides methods of synthesizing the substituted derivatives, represented by the formula (I), prepared through a process consisting of standard synthetic transformations and isomers, tautomers, hydrates, solvates, complexes, metabolites, prodrugs, carriers, N-oxides and pharmaceutically acceptable salts.

The present invention also provides a method for treating diseases caused by and/or associated with dysregulated protein kinase activity, particularly ABL, ACK1, AKT1, ALK, AUR1, AUR2, BRK, BUB1, CDC7/DBF4, CDK2/CYCA, CHK1, CK2, EEF2K, EGFR1, EphA2, EphB4, ERK2, FAK, FGFR1, FLT3, GSK3β, Haspin, IGFR1, IKK2, IR, JAK1, JAK2, JAK3, KIT, LCK, LYN, MAPKAPK2, MELK, MET, MNK2, MPS1, MST4, NEK6, NIM1, P38α, PAK-4, PDGFR, PDK1, PERK, PIM1, PIM2, PIM3, PKAα, PKCβ, PLK1, RET, ROS1, SULU1, Syk, TLK2, TRKA, TRKb TYK, VEGFR2, VEGFR3, ZAP70; more particularly PIM1, PIM2, PIM3, which comprises administering to a mammal in need thereof an effective amount of a compound of formula (I) as defined above.

A preferred method of the present invention is to treat a disease caused by and/or associated with dysregulated protein kinase activity selected from the group consisting of cancer, cell proliferative disorders, viral infections, immune cell-associated diseases and disorders, neurodegenerative disorders and cardiovascular diseases.

Another preferred method of the present invention is to treat specific types of cancer including but not limited to: carcinoma such as bladder, breast, colon, kidney, liver, lung, including small cell lung cancer, esophagus, gall-bladder, ovary, pancreas, stomach, cervix, thyroid, prostate, and skin, including squamous cell carcinoma; hematopoietic tumors of lymphoid lineage including leukaemia, acute lymphocitic leukaemia, acute lymphoblastic leukaemia, B-cell lymphoma, T-cell-lymphoma, Hodgkin's lymphoma, non-Hodgkin's lymphoma, hairy cell lymphoma and Burkett's lymphoma; hematopoietic tumors of myeloid lineage, including acute and chronic myelogenous leukemias, myelodysplastic syndrome and promyelocytic leukaemia; tumors of mesenchymal origin, including fibrosarcoma and rhabdomyosarcoma; tumors of the central and peripheral nervous system, including astrocytoma neuroblastoma, glioma and schwannomas; other tumors, including melanoma, seminoma, teratocarcinoma, osteosarcoma, xeroderma pigmentosum, keratoxanthoma, thyroid follicular cancer, Kaposi's sarcoma and mesothelioma, highly aneuploid tumors and tumors which do overexpress mitotic checkpoint.

Another preferred method of the present invention is to treat specific cellular proliferation disorders such as, for example, benign prostate hyperplasia, familial adenomatosis polyposis, neurofibromatosis, psoriasis, vascular smooth cell proliferation associated with atherosclerosis, pulmonary fibrosis, arthritis, glomerulonephritis and post-surgical stenosis and restenosis.

Another preferred method of the present invention is to treat immune cell-associated diseases and disorders, such as inflammatory and autoimmune diseases, for examples multiple sclerosis, systemic lupus erythematosis, inflammatory bowel diseases (IBD), Crohn's disease, irritable bowel syndrome, pancreatitis, ulcerative colitis, diverticulosis, myasthenia gravis, vasculitis, psoriasis, scleroderma, asthma, allergy, systemic sclerosis, vitiligo, arthritis such as osteoarthritis, juvenile rheumatoid arthritis, ankylosing spondylitis.

Another preferred method of the present invention is to treat viral infections, in particular the prevention of AIDS development in HIV-infected individuals.

The methods defined above may further comprise subjecting the mammal in need thereof to a radiation therapy or chemotherapeutic regimen in combination with at least one cytostatic or cytotoxic agent.

In addition, the method of the present invention also provides tumor angiogenesis and metastasis inhibition as well as the treatment of organ transplant rejection and host versus graft disease.

The present invention also provides a pharmaceutical composition comprising a therapeutically effective amount of a compound of the formula (I) or a pharmaceutically acceptable salt thereof and at least one pharmaceutically acceptable excipient, carrier and/or diluent.

In addition to a compound of formula (I), the pharmaceutical composition of the present invention may further comprise one or more chemotherapeutic—e.g. cytostatic or cytotoxic—agents, antibiotic-type agents, alkylating agents, antimetabolite agents, hormonal agents, immunological agents, interferon-type agents, cyclooxygenase inhibitors (e.g. COX-2 inhibitors), matrixmetalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

The present invention further provides an in vitro method for inhibiting protein kinase activity which comprises contacting the kinase with an effective amount of a compound of formula (I) as defined above.

Additionally, the invention provides a product or kit comprising a compound of formula (I) or a pharmaceutically acceptable salt thereof, as defined above, or pharmaceutical compositions thereof and one or more chemotherapeutic agents, as a combined preparation for simultaneous, separate or sequential use in anticancer therapy.

In another aspect the invention provides a compound of formula (I) or a pharmaceutically acceptable salt thereof, as defined above, for use as a medicament.

Moreover, the invention provides the use of a compound of formula (I) or a pharmaceutically acceptable salt thereof, as defined above, in the manufacture of a medicament with anticancer activity.

Finally, the invention provides a compound of formula (I) or a pharmaceutically acceptable salt thereof, as defined above, for use in a method of treating cancer.

BRIEF DESCRIPTION OF THE DISCLOSURE

Unless otherwise specified, when referring to the compounds of the formula (I) per se as well as to any pharmaceutical composition thereof or to any therapeutic treatment comprising them, the present invention includes all of the hydrates, solvates, complexes, metabolites, prodrugs, carriers, N-oxides and pharmaceutically acceptable salts of the compounds of this invention.

In other words, if easily obtainable from the compounds of the formula (I) as defined above, also their isomers, tautomers, hydrates, solvates, complexes, metabolites, prodrugs, carriers and N— oxides are object of the present invention.

A metabolite of a compound of the formula (I) is any compound into which this same compound of the formula (I) is converted in vivo, for instance upon administration to a mammal in need thereof. Typically, without however representing a limiting example, upon administration of a compound of the formula (I), this same derivative may be converted into a variety of compounds, for instance including more soluble derivatives like hydroxylated derivatives, which are easily excreted. Hence, depending upon the metabolic pathway occurring, any of these hydroxylated derivatives may be regarded as a metabolite of the compounds of the formula (I).

Prodrugs are any covalently bonded compounds, which release in vivo the active parent drug according to the formula (I).

N-oxides are compounds of the formula (I) wherein nitrogen and oxygen are tethered through a dative bond.

In formula (I) as defined above, if a stereogenic center or another form of an isomeric center is present in a compound of the present invention, all forms of such isomer or isomers, including enantiomers and diastereomers, are intended to be covered herein. Compounds containing a stereogenic center may be used as a racemic mixture, an enantiomerically enriched mixture, or the racemic mixture may be separated using well-known techniques and an individual enantiomer may be used alone. In cases in which compounds have unsaturated carbon-carbon double bonds, both the cis (Z) and trans (E) isomers are within the scope of this invention.

In cases wherein compounds may exist in tautomeric forms, such as keto-enol tautomers, each tautomeric form is contemplated as being included within this invention whether existing in equilibrium or predominantly in one form.

The term aryl includes carbocyclic or heterocyclic hydrocarbons with from 1 to 2 ring moieties, either fused or linked to each other by single bonds, wherein at least one of the rings is aromatic; if present, any aromatic heterocyclic hydrocarbon also referred to as heteroaryl group, comprises a 5 to 6 membered ring with from 1 to 3 heteroatoms selected from N, O and S.

Examples of aryl groups according to the invention are, for instance, phenyl, biphenyl, α- or β-naphthyl, dihydronaphthyl, thienyl, benzothienyl, furyl, benzofuranyl, pyrrolyl, imidazolyl, pyrazolyl, thiazolyl, isothiazolyl, oxazolyl, isoxazolyl, pyridyl, pyrazinyl, pyrimidinyl, pyridazinyl, indolyl, isoindolyl, purinyl, quinolyl, isoquinolyl, dihydroquinolinyl, quinoxalinyl, benzodioxolyl, indanyl, indenyl, triazolyl, and the like.

With the term "heterocyclyl" (also known as "heterocycloalkyl") we intend a 3- to 7-membered, saturated or partially unsaturated carbocyclic ring where one or more carbon atoms are replaced by heteroatoms such as nitrogen, oxygen and sulfur. Not limiting examples of heterocyclyl groups are, for instance, pyrane, pyrrolidine, pyrroline, imidazoline, imidazolidine, pyrazolidine, pyrazoline, thiazoline, thiazolidine, dihydrofuran, tetrahydrofuran, 1,3-dioxolane, piperidine, piperazine, morpholine and the like.

With the term "$C_3$-$C_7$ cycloalkyl", we intend, unless otherwise provided, 3- to 7-membered all-carbon monocyclic ring, which may contain one or more double bonds but does not have a completely conjugated π-electron system. Examples of cycloalkyl groups, without limitation, are cyclopropane, cyclobutane, cyclopentane, cyclopentene, cyclohexane, cyclohexene, cyclohexadiene, cycloeptane, cycloeptene, cycloeptadiene.

With the term "straight or branched $C_1$-$C_6$ alkyl", hence comprehensive of $C_1$-$C_4$ alkyl, we intend any of the groups such as, for instance, methyl, ethyl, n-propyl, isopropyl, n-butyl, isobutyl, tert-butyl, sec-butyl, n-pentyl, n-hexyl, and the like.

With the term "straight or branched $C_2$-$C_6$ alkenyl" we intend any of the groups such as, for instance, vinyl, allyl, 1-propenyl, isopropenyl, 1-butenyl, 2-butenyl, 3-butenyl, 2-pentenyl, 1-hexenyl, and the like.

With the term "straight or branched $C_2$-$C_6$ alkynyl" we intend any of the groups such as, for instance, ethynyl, 2-propynyl, 4-pentynyl, and the like.

According to the present invention and unless otherwise provided, any of the above R1-R9 and R' group may be optionally substituted, in any of their free positions, by one or more groups, for instance 1 to 6 groups, independently selected from: halogen atom, nitro, oxo groups (=O), cyano, $C_1$-$C_6$ alkyl, polyfluorinated alkyl, polyfluorinated alkoxy, alkenyl, alkynyl, hydroxyalkyl, aryl, arylalkyl, heterocyclyl, $C_3$-$C_7$ cycloalkyl, hydroxy, alkoxy, aryloxy, heterocyclyloxy, methylenedioxy, alkylcarbonyloxy, arylcarbonyloxy, cycloalkenyloxy, heterocyclylcarbonyloxy, alkylideneaminooxy, carboxy, alkoxycarbonyl, aryloxycarbonyl, cycloalkyloxycarbonyl, heterocyclyloxycarbonyl, amino, ureido, alkylamino, dialkylamino, arylamino, diarylamino, heterocyclylamino, formylamino, alkylcarbonylamino, arylcarbonylamino, heterocyclylcarbonylamino, aminocarbonyl, alkylaminocarbonyl, dialkylaminocarbonyl, arylaminocarbonyl, heterocyclylaminocarbonyl, alkoxycarbonylamino, hydroxyaminocarbonyl alkoxyimino, alkylsulfonylamino, arylsulfonylamino, heterocyclylsulfonylamino, formyl, alkylcarbonyl, arylcarbonyl, cycloalkylcarbonyl, heterocyclylcarbonyl, alkylsulfonyl, arylsulfonyl, aminosulfonyl, alkylaminosulfonyl, dialkylaminosulfonyl, arylaminosulfonyl, heterocyclylaminosulfonyl, arylthio, alkylthio, phosphonate and alkylphosphonate.

In their turn, whenever appropriate, each of the above substituent may be further substituted by one or more of the aforementioned groups.

In this respect, with the term halogen atom we intend a fluorine, chlorine, bromine or iodine atom.

With the term cyano we intend a —CN residue.

With the term nitro we intend a —$NO_2$ group.

With the term alkenyl or alkynyl we intend any of the aforementioned straight or branched $C_2$-$C_6$ alkyl groups further bearing a double or triple bond. Non limiting examples of alkenyl or alkynyl groups of the invention are, for instance, vinyl, allyl, 1-propenyl, isopropenyl, 1-butenyl, 2-butenyl, 3-butenyl, 2-pentenyl, 1-hexenyl, ethynyl, 2-propynyl, 4-pentynyl, and the like.

With the term polyfluorinated alkyl or alkoxy we intend any of the above straight or branched $C_1$-$C_6$ alkyl or alkoxy groups which are substituted by more than one fluorine atom such as, for instance, trifluoromethyl, trifluoroethyl, 1,1,1,3,3,3-hexafluoropropyl, trifluoromethoxy and the like.

With the term alkoxy, aryloxy, heterocyclyloxy and derivatives thereof we intend any of the above $C_1$-$C_6$ alkyl, aryl or heterocyclyl groups linked to the rest of the molecule through an oxygen atom (—O—).

From all of the above, it is clear to the skilled person that any group whose name is a composite name such as, for instance, arylamino has to be intended as conventionally construed by the parts from which it derives, e.g. by an amino group which is further substituted by aryl, wherein aryl is as above defined.

Likewise, any of the terms such as, for instance, alkylthio, alkylamino, dialkylamino, alkoxycarbonyl, alkoxycarbonylamino, heterocyclylcarbonyl, heterocyclylcarbonylamino, cycloalkyloxycarbonyl and the like, include groups wherein the alkyl, alkoxy, aryl, $C_3$-$C_7$ cycloalkyl and heterocyclyl moieties are as above defined.

Pharmaceutically acceptable salts of the compounds of the formula (I) include the acid addition salts with inorganic or organic acids, e.g., nitric, hydrochloric, hydrobromic, sulfuric, perchloric, phosphoric, acetic, trifluoroacetic, propionic, glycolic, fumaric, lactic, oxalic, malonic, malic, maleic, tartaric, citric, benzoic, cinnamic, mandelic, methanesulphonic, isethionic and salicylic acid. Preferably, the acid addition salt of the compounds of the invention is selected between the hydrochloride or mesylate salt.

Pharmaceutically acceptable salts of the compounds of the formula (I) also include the salts with inorganic or organic bases, e.g., alkali or alkaline-earth metals, especially sodium, potassium, calcium ammonium or magnesium hydroxides, carbonates or bicarbonates, acyclic or cyclic amines, preferably methylamine, ethylamine, diethylamine, triethylamine, piperidine and the like.

Preferred compounds of the formula (I) are the compounds wherein:
R2 is an optionally substituted group selected from $C_2$-$C_6$ alkenyl, $C_2$-$C_6$ alkynyl, aryl, arylalkyl, heterocyclyl and heterocyclylalkyl; and
A, R3 and R4 are as defined above.

Another preferred class of compounds of formula (I) are the compounds wherein:
A is —$(CH_2)_{1-3}$—X—R1, wherein X is as defined above and R1 is hydrogen, halogen or an optionally substituted group selected from straight or branched $C_1$-$C_6$ alkyl, $C_3$-$C_7$ cycloalkyl, cycloalkyl-alkyl, arylalkyl and heterocyclyl;
R2 is an optionally substituted group selected from $C_2$-$C_6$ alkynyl, aryl and heterocyclyl; and
R3 and R4 are as defined above.

Another preferred class of compounds of formula (I) are the compounds wherein:
A is —$(CH_2)_{1-3}$—X—R1, wherein X is —NR'—; R' is COR5; R5 is NR7R8 or an optionally substituted group selected from straight or branched $C_1$-$C_6$ alkyl, $C_3$-$C_7$ cycloalkyl, cycloalkyl-alkyl, $C_2$-$C_6$ alkenyl, $C_2$-$C_6$ alkynyl, aryl, arylalkyl, heterocyclyl and heterocyclylalkyl, wherein R7 and R8 are as defined above; and
R1, R2, R3 and R4 are as defined herein before.

Another preferred class of compounds of formula (I) are the compounds wherein:
A is —$(CH_2)_{1-3}$—X—R1, wherein X is —NR'—; R' is COR5; R5 is NR7R8 or an optionally substituted group selected from straight or branched $C_1$-$C_6$ alkyl, $C_3$-$C_7$ cycloalkyl, cycloalkyl-alkyl, aryl, arylalkyl, heterocyclyl and heterocyclylalkyl, wherein R7 and R8 are each independently hydrogen or a group optionally substituted selected from straight or branched $C_1$-$C_6$ alkyl, aryl and heterocyclyl;
R4 is hydrogen, halogen, cyano or an optionally substituted group selected from straight or branched $C_1$-$C_6$ alkyl, $C_3$-$C_7$ cycloalkyl, $C_2$-$C_6$ alkenyl, $C_2$-$C_6$ alkynyl, aryl and heterocyclyl;
and
R1, R2, and R3 are as defined above.

Preferred specific compounds of the formula (I) or a salt thereof are the compounds listed below:
7-(3-chlorophenyl)-4-(2-hydroxyethyl)-6-phenyl-3,4-dihydropyrrolo[1,2-a]pyrazin-1(2H)-one (cpd 2),
7-(3-chlorophenyl)-4-{2-[(1-methylpiperidin-4-yl)amino]ethyl}-3,4-dihydropyrrlo[1,2-a]pyrazin-1(2H)-one (cpd 5),
(4S)-7-(3-chlorophenyl)-4-(2-{[(1S)-1-cyclohexyl-2-(4-methylpiperazin-1-yl)ethyl]amino}ethyl)-3,4-dihydropyrrolo[1,2-a]pyrazin-1(2H)-one (cpd 8),
7-(biphenyl-2-yl)-4-{2-[(1-methylpiperidin-4-yl)amino]ethyl}-3,4-dihydropyrrlo[1,2-a]pyrazin-1(2H)-one (cpd 12),
7-(3-chlorophenyl)-4-{2-[(1-methylpiperidin-4-yl)amino]ethyl}-6-phenyl-3,4-dihydropyrrolo[1,2-a]pyrazin-1(2H)-one (cpd 13),
4-(2-aminoethyl)-7-(3-chlorophenyl)-6-phenyl-3,4-dihydropyrrolo[1,2-a]pyrazin-1(2H)-one (cpd 17),
4-(2-aminoethyl)-7-[3-(trifluoromethoxy)phenyl]-3,4-dihydropyrrolo[1,2-a]pyrazin-1(2H)-one (cpd 18),
4-(2-aminoethyl)-6-bromo-7-[3-(trifluoromethoxy)phenyl]-3,4-dihydropyrrolo[1,2-a]pyrazin-1(2H)-one (cpd 27),
4-(2-aminoethyl)-6-phenyl-7-[3-(trifluoromethoxy)phenyl]-3,4-dihydropyrrolo[1,2-a]pyrazin-1(2H)-one (cpd 28),
4-(2-aminoethyl)-6-(thiophen-3-yl)-7-[3-(trifluoromethoxy)phenyl]-3,4-dihydropyrrolo[1,2-a]pyrazin-1(2H)-one (cpd 29), 4-(2-aminoethyl)-6-(3-methylphenyl)-7-[3-(trifluoromethoxy)phenyl]-3,4-dihydropyrrolo[1,2-a]pyrazin-1(2H)-one (cpd 31), 4-(2-aminoethyl)-6-[4-(hydroxymethyl)phenyl]-7-[3-(trifluoromethoxy)phenyl]-3,4-dihydropyrrolo[1,2-a]pyrazin-1(2H)-one (cpd 33), 4-(2-aminoethyl)-6-phenyl-7-[3-(trifluoromethyl)phenyl]-3,4-dihydropyrrolo[1,2-a]pyrazin-1(2H)-one (cpd 37), 4-(2-aminoethyl)-6-[4-(hydroxymethyl)phenyl]-7-[3-(trifluoromethyl)phenyl]-3,4-dihydropyrrolo[1,2-a]pyrazin-1(2H)-one (cpd 38), 4-(2-aminoethyl)-6-(3-methylphenyl)-7-[3-(trifluoromethyl)phenyl]-3,4-dihydropyrrolo[1,2-a]pyrazin-1(2H)-one (cpd 39), 4-(2-aminoethyl)-6-(thiophen-3-yl)-7-[3-(trifluoromethyl)phenyl]-3,4-dihydropyrrolo[1,2-a]pyrazin-1(2H)-one (cpd 40), 4-(2-aminoethyl)-6-(4-hydroxyphenyl)-7-[3-(trifluoromethyl)phenyl]-3,4-dihydropyrrolo[1,2-a]pyrazin-1(2H)-one (cpd 43), 4-(2-aminoethyl)-7-(2-chloropyridin-4-yl)-6-[4-(hydroxymethyl)phenyl]-3,4-dihydropyrrolo[1,2-a]pyrazin-1(2H)-one (cpd 44), 4-(2-aminoethyl)-7-(2-chloropyridin-4-yl)-6-(3-methylphenyl)-3,4-dihydropyrrolo[1,2-a]pyrazin-1(2H)-one (cpd 45), 4-(2-aminoethyl)-7-(2-fluoropyridin-4-yl)-6-(3-methylphenyl)-3,4-dihydropyrrolo[1,2-a]pyrazin-1(2H)-one (cpd 47), 4-(2-aminoethyl)-7-(6-fluoropyridin-3-yl)-6-phenyl-3,4-dihydropyrrolo[1,2-a]pyrazin-1(2H)-one (cpd 48), 4-(2-aminoethyl)-7-(3,4-difluorophenyl)-6-(3-methylphenyl)-3,4-dihydropyrrolo[1,2-a]pyrazin-1(2H)-one (cpd 49), 4-(2-aminoethyl)-7-(3,4-difluorophenyl)-6-(thiophen-3-yl)-3,4-dihydropyrrolo[1,2-a]pyrazin-1(2H)-one (cpd 51), 4-(2-aminoethyl)-7-(3,4-difluorophenyl)-6-phenyl-3,4-dihydropyrrolo[1,2-a]pyrazin-1(2H)-one (cpd 52), 4-(2-aminoethyl)-7-[2-chloro-5-(trifluoromethoxy)phenyl]-6-(3-methylphenyl)-3,4-dihydropyrrolo[1,2-a]pyrazin-1(2H)-one (cpd 53), 4-(2-aminoethyl)-6-cyclopropyl-7-[3-(trifluoromethoxy)phenyl]-3,4-dihydropyrrolo[1,2-a]pyrazin-1(2H)-one (cpd 54), 4-(2-aminoethyl)-7-(5-chloro-2-fluorophenyl)-6-(thiophen-3-yl)-3,4-dihydropyrrlo[1,2-a]pyrazin-1(2H)-one (cpd 55), 4-(2-aminoethyl)-7-(5-chloro-2-fluorophenyl)-6-phenyl-3,4-dihydropyrrolo[1,2-a]pyrazin-1(2H)-one (cpd 57), 4-(2-aminoethyl)-7-(5-chloro-2-fluorophenyl)-6-(3-methylphenyl)-3,4-dihydropyrrolo[1,2-a]pyrazin-1(2H)-one (cpd 59), 4-(2-aminoethyl)-6-ethynyl-7-[3-(trifluoromethoxy)phenyl]-3,4-dihydropyrrolo[1,2-a]pyrazin-1(2H)-one (cpd 61), 4-(2-chloroethyl)-6-(3-methylphenyl)-7-[3-(trifluoromethoxy)phenyl]-3,4-dihydropyrrolo[1,2-a]pyrazin-1(2H)-one (cpd 63), 4-{4-(2-chloroethyl)-1-oxo-7-[3-(trifluoromethoxy)phenyl]-1,2,3,4-tetrahydropyrrolo[1,2-a]pyrazin-6-yl}benzamide (cpd 68), 4-(2-chloroethyl)-6-{4-[(dimethylamino)methyl]phenyl}-7-[3-(trifluoromethoxy)phenyl]-3,4-dihydropyrrolo[1,2-a]pyrazin-1(2H)-one (cpd 70), 4-(2-chloroethyl)-6-{4-[(4-methyl piperazin-1-yl)methyl]phenyl}-7-[3-(trifluoromethoxy)phenyl]-3,4-dihydropyrrolo[1,2-a]pyrazin-1(2H)-one (cpd 71), 4-{4-(2-hydroxyethyl)-1-oxo-7-[3-(trifluoromethoxy)phenyl]-1,2,3,4-tetrahydropyrrolo[1,2-a]pyrazin-6-yl}benzamide (cpd 77), N-[2-(dimethylamino)ethyl]-4-{4-(2-hydroxyethyl)-1-oxo-7-[3-(trifluoromethoxy)phenyl]-1,2,3,4-tetrahydropyrrolo[1,2-a]pyrazin-6-yl}benzamide (cpd 78), 4-{4-(2-hydroxyethyl)-1-oxo-7-[3-(trifluoromethoxy)phenyl]-1,2,3,4-tetrahydropyrrolo[1,2-a]pyrazin-6-yl}-N,N-dimethylbenzamide (cpd 79), 4-{4-(2-hydroxyethyl)-1-oxo-7-[3-(trifluoromethoxy)phenyl]-1,2,3,4-tetrahydropyrrolo[1,2-a]pyrazin-6-yl}-N-methylbenzamide (cpd 80), 4-{4-(2-hydroxyethyl)-1-oxo-7-[3-(trifluoromethoxy)phenyl]-1,2,3,4-tetrahydropyrrolo[1,2-a]pyrazin-6-yl}-N-(1-methylpiperidin-4-yl)benzamide (cpd 81), 6-{4-[(dimethylamino)methyl]phenyl}-4-(2-hydroxyethyl)-7-[3-(trifluoromethoxy)phenyl]-3,4-dihydropyrrolo[1,2-a]pyrazin-1(2H)-one (cpd 83), 4-(2-hydroxyethyl)-6-[4-(hydroxymethyl)phenyl]-7-[3-(trifluoromethoxy)phenyl]-3,4-dihydropyrrolo[1,2-a]pyrazin-1(2H)-one (cpd 84), (4S)-4-(2-aminoethyl)-6-(thiophen-3-yl)-7-[3-(trifluoromethoxy)phenyl]-3,4-dihydropyrrolo[1,2-a]pyrazin-1(2H)-one (cpd 85), (4R)-4-(2-aminoethyl)-6-(thiophen-3-yl)-7-[3-(trifluoromethoxy)phenyl]-3,4-dihydropyrrolo[1,2-a]pyrazin-1(2H)-one (cpd 86), 4S)-4-(2-aminoethyl)-6-phenyl-7-[3-(trifluoromethoxy)phenyl]-3,4-dihydropyrrolo[1,2-a]pyrazin-1(2H)-one (cpd 87), (4R)-4-(2-aminoethyl)-6-phenyl-7-[3-(trifluoromethoxy)phenyl]-3,4-dihydropyrrolo[1,2-a]pyrazin-1(2H)-one (cpd 88), (4S)-4-(2-aminoethyl)-7-[3-(trifluoromethoxy)phenyl]-3,4-dihydropyrrolo[1,2-a]pyrazin-1(2H)-one (cpd 89), (4S)-4-(3-aminopropyl)-7-[3-(trifluoromethoxy)phenyl]-3,4-dihydropyrrolo[1,2-a]pyrazin-1(2H)-one (cpd 90), (4S)-4-(2-aminoethyl)-6-(3-methylphenyl)-7-[3-(trifluoromethoxy)phenyl]-3,4-dihydropyrrolo[1,2-a]pyrazin-1(2H)-one (cpd 92), (4S)-4-(2-aminoethyl)-6-(4-fluorophenyl)-7-[3-(trifluoromethoxy)phenyl]-3,4-dihydropyrrolo[1,2-a]pyrazin-1(2H)-one (cpd 94), (4S)-6-(4-acetyl phenyl)-4-(2-aminoethyl)-7-[3-(trifluoromethoxy)phenyl]-3,4-dihydropyrrolo[1,2-a]pyrazin-1(2H)-one (cpd 95), (4S)-4-(2-aminoethyl)-6-[4-(methylsulfonyl)phenyl]-7-[3-(trifluoromethoxy)phenyl]-3,4-dihydropyrrolo[1,2-a]pyrazin-1(2H)-one, (cpd 96)

(4S)-4-(2-aminoethyl)-6-[4-(morpholin-4-ylmethyl)phenyl]-7-[3-(trifluoromethoxy)phenyl]-3,4-dihydropyrrolo[1,2-a]pyrazin-1(2H)-one (cpd 99), (4S)-4-(2-aminoethyl)-6-{4-[(4-methyl piperazin-1-yl)methyl]phenyl}-7-[3-(trifluoromethoxy)phenyl]-3,4-dihydropyrrolo[1,2-a]pyrazin-1(2H)-one (cpd 100), (4S)-4-(2-aminoethyl)-6-{4-[(dimethylamino)methyl]phenyl}-7-[3-(trifluoromethoxy)phenyl]-3,4-dihydropyrrolo[1,2-a]pyrazin-1(2H)-one, (cpd 101)

(4S)-4-(3-aminopropyl)-6-phenyl-7-[3-(trifluoromethoxy)phenyl]-3,4-dihydropyrrolo[1,2-a]pyrazin-1(2H)-one (cpd 102), (4S)-4-(3-aminopropyl)-6-(thiophen-3-yl)-7-[3-(trifluoromethoxy)phenyl]-3,4-dihydropyrrolo[1,2-a]pyrazin-1(2H)-one (cpd 103), (4S)-4-(3-aminopropyl)-6-(4-hydroxyphenyl)-7-[3-(trifluoromethoxy)phenyl]-3,4-dihydropyrrolo[1,2-a]pyrazin-1(2H)-one (cpd 104), (4S)-4-(3-aminopropyl)-6-[4-(hydroxymethyl)phenyl]-7-[3-(trifluoromethoxy)phenyl]-3,4-dihydropyrrolo[1,2-a]pyrazin-1(2H)-one (cpd 105), (4S)-4-(2-chloroethyl)-6-{4-[(4-methyl piperazin-1-yl)methyl]phenyl}-7-[3-(trifluoromethoxy)phenyl]-3,4-dihydropyrrolo[1,2-a]pyrazin-1(2H)-one (cpd 106), (4S)-4-(1H-imidazol-4-ylmethyl)-7-[3-(trifluoromethoxy)phenyl]-3,4-dihydropyrrolo[1,2-a]pyrazin-1(2H)-one (cpd 107), (4S)-6-(4-acetylphenyl)-4-(3-aminopropyl)-7-[3-(trifluoromethoxy)phenyl]-3,4-dihydropyrrolo[1,2-a]pyrazin-1(2H)-one (cpd 110), (4S)-4-(3-aminopropyl)-6-(4-fluorophenyl)-7-[3-(trifluoromethoxy)phenyl]-3,4-dihydropyrrolo[1,2-a]pyrazin-1(2H)-one (cpd 111), (4S)-4-(2-aminoethyl)-6-(1,3-benzodioxol-5-yl)-7-[3-(trifluoromethoxy)phenyl]-3,4-dihydropyrrolo[1,2-a]pyrazin-1(2H)-one (cpd 112), (4S)-4-(2-aminoethyl)-6-(3-fluoro-4-methoxyphenyl)-7-[3-(trifluoromethoxy)phenyl]-3,4-dihydropyrrolo[1,2-a]pyrazin-1(2H)-one (cpd 113), (4S)-4-(2-aminoethyl)-6-[4-(2-methylpropoxy)phenyl]-7-[3-(trifluoromethoxy)phenyl]-3,4-dihydropyrrolo[1,2-a]pyrazin-1(2H)-one (cpd 114), (4S)-4-(2-aminoethyl)-6-[4-(dimethylamino)phenyl]-7-[3-(trifluoromethoxy)phenyl]-3,4-dihydropyrrolo[1,2-a]pyrazin-1(2H)-one (cpd 115), (4S)-4-(2-aminoethyl)-6-(4-methoxyphenyl)-7-[3-(trifluoromethoxy)phenyl]-3,4-dihydropyrrolo[1,2-a]pyrazin-1(2H)-one (cpd 116), (4S)-4-(2-aminoethyl)-6-(2-aminopyrimidin-5-yl)-7-[3-(trifluoromethoxy)phenyl]-3,4-dihydropyrrolo[1,2-a]pyrazin-1(2H)-one (cpd 117), (4S)-4-(2-aminoethyl)-6-(naphthalen-2-yl)-7-[3-(trifluoromethoxy)phenyl]-3,4-dihydropyrrolo[1,2-a]pyrazin-1(2H)-one (cpd 118), (4S)-4-(2-aminoethyl)-6-(biphenyl-3-yl)-7-[3-(trifluoromethoxy)phenyl]-3,4-dihydropyrrolo[1,2-a]pyrazin-1(2H)-one (cpd 119), 4-{(4S)-4-(2-aminoethyl)-1-oxo-7-[3-(trifluoromethoxy)phenyl]-1,2,3,4-tetrahydropyrrolo[1,2-a]pyrazin-6-yl}benzenesulfonamide (cpd 120), (4S)-4-(2-aminoethyl)-6-(3-fluorophenyl)-7-[3-(trifluoromethoxy)phenyl]-3,4-dihydropyrrolo[1,2-a]pyrazin-1(2H)-one (cpd 121), (4S)-4-(2-aminoethyl)-6-(4-fluoro-3-methylphenyl)-7-[3-(trifluoromethoxy)phenyl]-3,4-dihydropyrrolo[1,2-a]pyrazin-1(2H)-one (cpd 122), (4S)-4-(2-aminoethyl)-6-[4-(methylsulfanyl)phenyl]-7-[3-(trifluoromethoxy)phenyl]-3,4-dihydropyrrolo[1,2-a]pyrazin-1(2H)-one (cpd 123), (4S)-4-(2-aminoethyl)-6-(4-tert-butylphenyl)-7-[3-(trifluoromethoxy)phenyl]-3,4-dihydropyrrolo[1,2-a]pyrazin-1(2H)-one (cpd 124), (4S)-4-(2-aminoethyl)-7-[3-(trifluoromethoxy)phenyl]-6-[3-(trifluoromethyl)phenyl]-3,4-dihydropyrrolo[1,2-a]pyrazin-1(2H)-one (cpd 125), (4S)-4-(2-aminoethyl)-6-(3-chlorophenyl)-7-[3-(trifluoromethoxy)phenyl]-3,4-dihydropyrrolo[1,2-a]pyrazin-1(2H)-one (cpd 126), (4S)-4-(2-aminoethyl)-6-(4-ethoxy-3-fluorophenyl)-7-[3-(trifluoromethoxy)phenyl]-3,4-dihydropyrrolo[1,2-a]pyrazin-1(2H)-one (cpd 127), 4S)-4-(2-aminoethyl)-6-(4-methoxy-3,5-dimethyl phenyl)-7-[3-(trifluoromethoxy)phenyl]-3,4-dihydropyrrolo[1,2-a]pyrazin-1(2H)-one (cpd 128), (4S)-4-(2-aminoethyl)-6-(3-chloro-4-methoxyphenyl)-7-[3-(trifluoromethoxy)phenyl]-3,4-dihydropyrrolo[1,2-a]pyrazin-1(2H)-one (cpd 129), (4S)-6-[4-(1-aminocyclopropyl)phenyl]-4-(2-aminoethyl)-7-[3-(trifluoromethoxy)phenyl]-3,4-dihydropyrrolo[1,2-a]pyrazin-1(2H)-one (cpd 130), (4S)-6-[4-(1-aminocyclopropyl)phenyl]-4-(propan-2-yl)-7-[3-(trifluoromethoxy)phenyl]-3,4-dihydropyrrolo[1,2-a]pyrazin-1(2H)-one (cpd 131), (4S)-6-(4-ethoxy-3-fluorophenyl)-4-(1H-imidazol-4-ylmethyl)-7-[3-(trifluoromethoxy)phenyl]-3,4-dihydropyrrolo[1,2-a]pyrazin-1(2H)-one (cpd 132), (4S)-4-(1H-imidazol-4-ylmethyl)-6-(3-methylphenyl)-7-[3-(trifluoromethoxy)phenyl]-3,4-dihydropyrrolo[1,2-a]pyrazin-1(2H)-one (cpd 133), (4S)-4-(3-aminopropyl)-6-{4-[(dimethylamino)methyl]phenyl}-7-[3-(trifluoromethoxy)phenyl]-3,4-dihydropyrrolo[1,2-a]pyrazin-1(2H)-one (cpd 134), (4S)-4-(3-aminopropyl)-6-{4-[(4-methyl piperazin-1-yl)methyl]phenyl}-7-[3-(trifluoromethoxy)phenyl]-3,4-dihydropyrrolo[1,2-a]pyrazin-1(2H)-one (cpd 135), (4S)-6-{4-[(dimethylamino)methyl]phenyl}-4-(propan-2-yl)-7-[3-(trifluoromethoxy)phenyl]-3,4-dihydropyrrolo[1,2-a]pyrazin-1(2H)-one (cpd 136), (4S)-6-{4-[(4-methyl piperazin-1-yl)methyl]phenyl}-4-(propan-2-yl)-7-[3-(trifluoromethoxy)phenyl]-3,4-dihydropyrrolo[1,2-a]pyrazin-1(2H)-one (cpd 137), (4S)-6-[4-(aminomethyl)phenyl]-4-(propan-2-yl)-7-[3-(trifluoromethoxy)phenyl]-3,4-dihydropyrrolo[1,2-a]pyrazin-1(2H)-one (cpd 138), (4S)-6-[3-(dimethylamino)prop-1-yn-1-yl]-4-(propan-2-yl)-7-[3-(trifluoromethoxy)phenyl]-3,4-dihydropyrrolo[1,2-a]pyrazin-1(2H)-one (cpd 139), (4S)-6-(3-aminoprop-1-yn-1-yl)-4-(propan-2-yl)-7-[3-(trifluoromethoxy)phenyl]-3,4-dihydropyrrolo[1,2-a]pyrazin-1(2H)-one (cpd 140), 2,2-dimethyl-N-(2-{(4S)-6-(3-methylphenyl)-1-oxo-7-[3-(trifluoromethoxy)phenyl]-1,2,3,4-tetrahydropyrrolo[1,2-a]pyrazin-4-yl}ethyl)propanamide (cpd 141), N-(2-{(4S)-1-oxo-6-phenyl-7-[3-(trifluoromethoxy)phenyl]-1,2,3,4-tetrahydropyrrolo[1,2-a]pyrazin-4-yl}ethyl)acetamide (cpd 142), 2,2-dimethyl-N-(2-{(4S)-1-oxo-6-phenyl-7-[3-(trifluoromethoxy)phenyl]-1,2,3,4-tetrahydropyrrolo[1,2-a]pyrazin-4-yl}ethyl)propanamide (cpd 143), 1-tert-butyl-3-(2-{(4S)-6-(3-methylphenyl)-1-oxo-7-[3-(trifluoromethoxy)phenyl]-1,2,3,4-tetrahydropyrrolo[1,2-a]pyrazin-4-yl}ethyl)urea, (cpd 144), 1-tert-butyl-3-(2-{(4S)-1-oxo-6-phenyl-7-[3-(trifluoromethoxy)phenyl]-1,2,3,4-tetrahydropyrrolo[1,2-a]pyrazin-4-yl}ethyl)urea (cpd 145), 1-butan-2-yl-3-(2-{(4S)-1-oxo-6-phenyl-7-[3-(trifluoromethoxy)phenyl]-1,2,3,4-tetrahydropyrrolo[1,2-a]pyrazin-4-yl}ethyl)urea (cpd 146), N-(2-{(4S)-1-oxo-6-phenyl-7-[3-(trifluoromethoxy)phenyl]-1,2,3,4-tetrahydropyrrolo[1,2-a]pyrazin-4-yl}ethyl)methanesulfonamide (cpd 147), 1-(2-{(4S)-6-(3-methylphenyl)-1-oxo-7-[3-(trifluoromethoxy)phenyl]-1,2,3,4-tetrahydropyrrolo[1,2-a]pyrazin-4-yl}ethyl)guanidine (cpd 148), and 1-(2-{(4S)-6-[4-(methylsulfonyl)phenyl]-1-oxo-7-[3-(trifluoromethoxy)phenyl]-1,2,3,4-tetrahydropyrrolo[1,2-a]pyrazin-4-yl}ethyl)guanidine (cpd 149).

For a reference to any specific compound of the formula (I) of the invention, optionally in the form of a pharmaceutically acceptable salt, see the experimental section and claims.

The present invention also provides a process for the preparation of a compound of formula (I) as defined above, by using the reaction routes and synthetic schemes described below, employing the techniques available in the art and starting materials readily available. The preparation of certain embodiments of the present invention is described in the examples that follow, but those of ordinary skill in the art will recognize that the preparations described may be readily adapted to prepare other embodiments of the present invention. For example, the synthesis of non-examplified compounds according to the invention may be performed by modifications apparent to those skilled in the art, for instance by appropriately protecting interfering groups, by changing to other suitable reagents known in the art, or by making routine modifications of reaction conditions. Alternatively other reactions referred to herein or known in the art will be recognized as having adaptability for preparing other compounds of the invention.

The reported Scheme 1 shows the preparation of compounds of formula (I).

Scheme 1

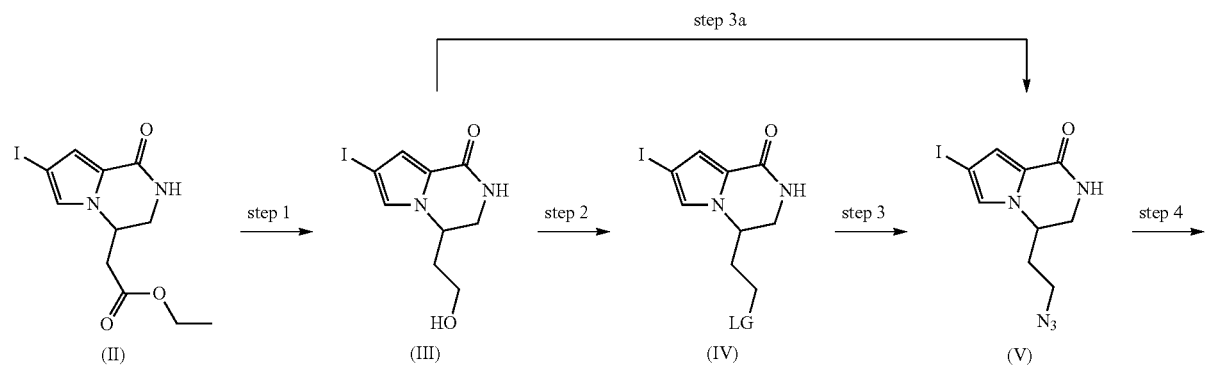

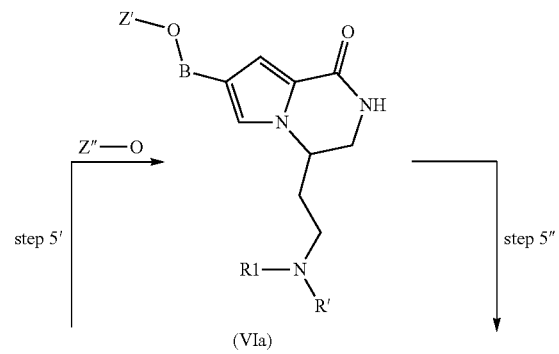

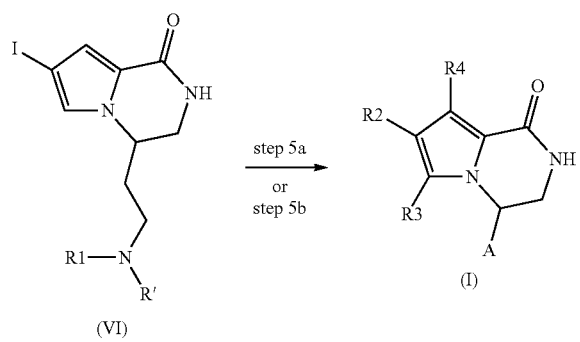

In the above scheme 1, LG is a suitable leaving group such as iodo, bromo, chloro, or a sulphonate group such as —OS(O)$_2$CF$_3$, —OS(O)$_2$CH$_3$ or —OS(O)$_2$Ph-pMe); Z' and Z" are either hydrogen, C$_1$-C$_6$ alkyl or, taken together with the oxygen atoms to which they are bonded, may form an optionally substituted 5 to 6 membered heterocycle; A is a group —(CH$_2$)$_2$—X—R1, wherein X is NR', R' is hydrogen or a protecting group, and R1 is as defined above; R2 is an optionally substituted group selected from straight or branched C$_1$-C$_6$ alkyl, C$_3$-C$_7$ cycloalkyl, cycloalkyl-alkyl, C$_2$-C$_6$ alkenyl, C$_2$-C$_6$ alkynyl, aryl, arylalkyl, heterocyclyl and heterocyclylalkyl; R3 and R4 are hydrogen.

Accordingly, a process of the present invention comprises the following steps:

Step 1) mixing a compound of formula (II)

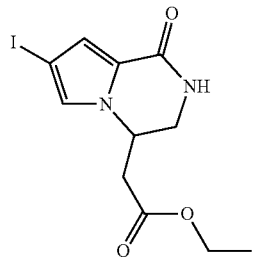

(II)

with a reducing agent;
Step 2) reacting the resultant compound of formula (III)

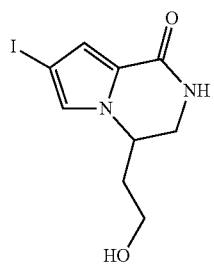

(III)

with an appropriate alcohol activating reagent;
Step 3) reacting the resultant compound of formula (IV)

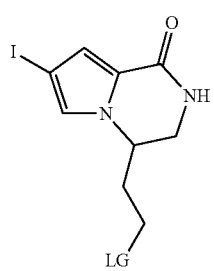

(IV)

wherein LG is a suitable leaving group such as iodo, bromo, chloro, or a sulphonate group such as —OS(O)$_2$CF$_3$, —OS(O)$_2$CH$_3$, or —OS(O)$_2$Ph-pMe, with an azide anion;
or Step 3a) reacting the compound of formula (III) as defined above, with a suitable source of azide in Mitsunobu condition;
Step 4) reacting the resultant compound of formula (V) obtained in step 3) or 3a)

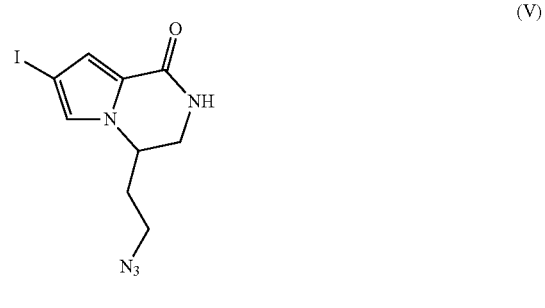 [SMILES: [N-]=[N+]=NCCC1CNC(=O)c2cc(I)cn21]

(V)

with a reducing agent;
Step 5) reacting the resultant compound of formula (VI)

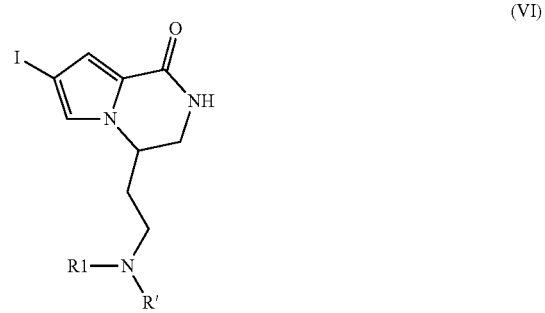

(VI)

wherein R' is hydrogen or a protecting group and R1 is as defined above, according to any one of the alternative steps:

Step 5a) with an organoboron of formula (XII):

R2'B(OZ')OZ"    (XII)

wherein R2' is optionally substituted group selected from straight or branched C$_1$-C$_6$ alkyl, C$_3$-C$_7$ cycloalkyl, cycloalkyl-alkyl, C$_2$-C$_6$ alkenyl, aryl, arylalkyl, heterocyclyl and heterocyclylalkyl;

and Z' and Z" are either hydrogen, C$_1$-C$_6$ alkyl or, taken together with the oxygen atoms to which they are bonded, may form an optionally substituted 5 to 6 membered heterocycle, or Step 5b) with a terminal alkyne of formula (XIII):

R$^a$C≡CH    (XIII)

wherein R$^a$ is hydrogen, or an optionally substituted group selected from straight or branched C$_1$-C$_6$ alkyl, C$_3$-C$_7$ cycloalkyl, cycloalkyl-alkyl, $C_2$-$C_6$ alkenyl, $C_2$-$C_6$ alkynyl, aryl, arylalkyl, heterocyclyl and heterocyclylalkyl;
or
Step 5') first, with a boronyl reagent;
Step 5") then mixing the resultant compound of formula (VIa)

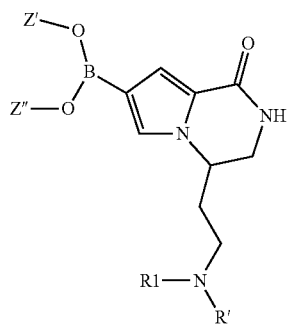

(VIa)

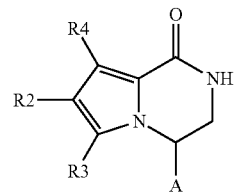

(I)

wherein A is a group —$(CH_2)_2$—X—R1, wherein X is NR', R' is hydrogen or a protecting group, and R1 is as define above; R2 is an optionally substituted group selected from straight or branched $C_1$-$C_6$ alkyl, $C_3$-$C_7$ cycloalkyl, cycloalkyl-alkyl, $C_2$-$C_6$ alkenyl, $C_2$-$C_6$ alkynyl, aryl, arylalkyl, heterocyclyl and heterocyclylalkyl; R3 and R4 are hydrogen;
optionally converting a compound of formula (I) into a different compound of formula (I) by known chemical reactions; and/or, if desired, converting a compound of formula (I) into a pharmaceutically acceptable salt thereof or converting a salt into a free compound of formula (I).

The reported Scheme 2 shows the preparation of a compound of formula (I).

Scheme 2

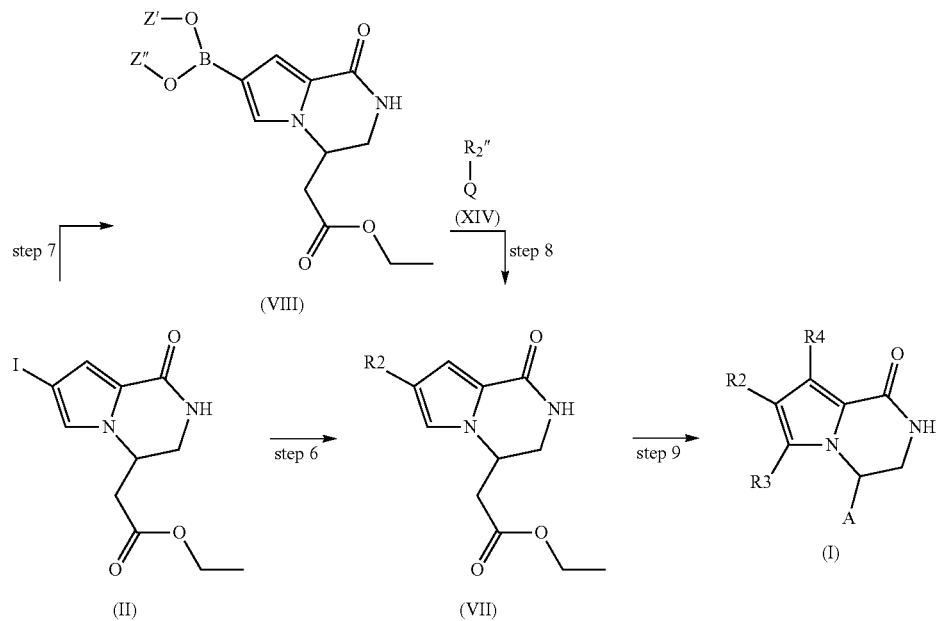

wherein R1, R', Z' and Z" are as defined above, with a compound of formula R2"-Q (XIV) wherein R2" is an optionally substituted group selected from straight or branched $C_1$-$C_6$ alkyl, $C_3$-$C_7$ cycloalkyl, cycloalkyl-alkyl, aryl, arylalkyl, heterocyclyl and heterocyclylalkyl, and Q is an halogen, or a triflate group, or an alkylsulfonyloxy group or an arylsulfonyloxy group, such as a mesylate or a tosylate, to give a compound of formula (I)

In the above scheme 2, Z' and Z" are either hydrogen, $C_1$-$C_6$ alkyl or, taken together with the oxygen atoms to which they are bonded, may form an optionally substituted 5 to 6 membered heterocycle; R2" is an optionally substituted group selected from straight or branched $C_1$-$C_6$ alkyl, $C_3$-$C_7$ cycloalkyl, cycloalkyl-alkyl, aryl, arylalkyl, heterocyclyl and heterocyclylalkyl; Q is a halogen or a triflate group, or an alkylsulfonyloxy group or an arylsulfonyloxy group, such as a mesylate or a tosylate; A is a group —$(CH_2)_2$—X—R1 wherein X is —O—, and R1 is hydrogen; R2 is optionally substituted group selected from straight or branched $C_1$-$C_6$ alkyl, $C_3$-$C_7$ cycloalkyl, cycloalkyl-alkyl, $C_2$-$C_6$ alkenyl, aryl, arylalkyl, heterocyclyl and heterocyclylalkyl; and R3 and R4 are hydrogen.

Accordingly, a process of the present invention comprises the following steps:

Step 6) mixing the compound of formula (II) as defined above, with an organoboron of formula (XII) as defined above;

alternatively

Step 7) first mixing the compound of formula (II) as defined above, with a boronyl reagent;

Step 8) then mixing the resultant compound of formula (VIII)

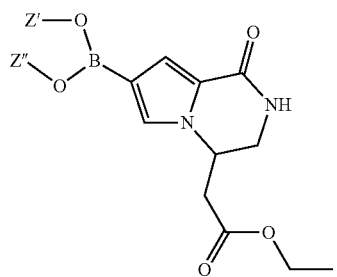

(VIII)

wherein Z' and Z" are as defined above, with a compound of formula R2"-Q (XIV) as defined above;

Step 9) mixing the resultant compound of formula (VII) obtained in step 6) or 8)

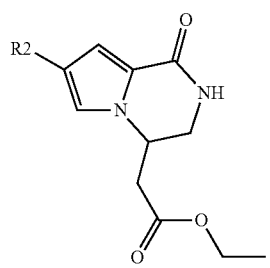

(VII)

wherein R2 is optionally substituted group selected from straight or branched $C_1$-$C_6$ alkyl, $C_3$-$C_7$ cycloalkyl, cycloalkyl-alkyl, $C_2$-$C_6$ alkenyl, aryl, arylalkyl, heterocyclyl and heterocyclylalkyl, with a reducing agent, to give a compound of formula (I)

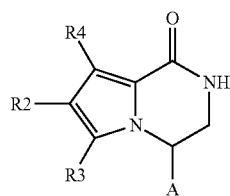

(I)

wherein A is a group —$(CH_2)_2$—X—R1 wherein X is —O—, and R1 is hydrogen; R2 is optionally substituted group selected from straight or branched $C_1$-$C_6$ alkyl, $C_3$-$C_7$ cycloalkyl, cycloalkyl-alkyl, $C_2$-$C_6$ alkenyl, aryl, arylalkyl, heterocyclyl and heterocyclylalkyl; and R3 and R4 are hydrogen;

optionally converting a compound of formula (I) into a different compound of formula (I) by known chemical reactions; and/or, if desired, converting a compound of formula (I) into a pharmaceutically acceptable salt thereof or converting a salt into a free compound of formula (I).

The reported Scheme 3 shows the preparation of a compound of formula (I).

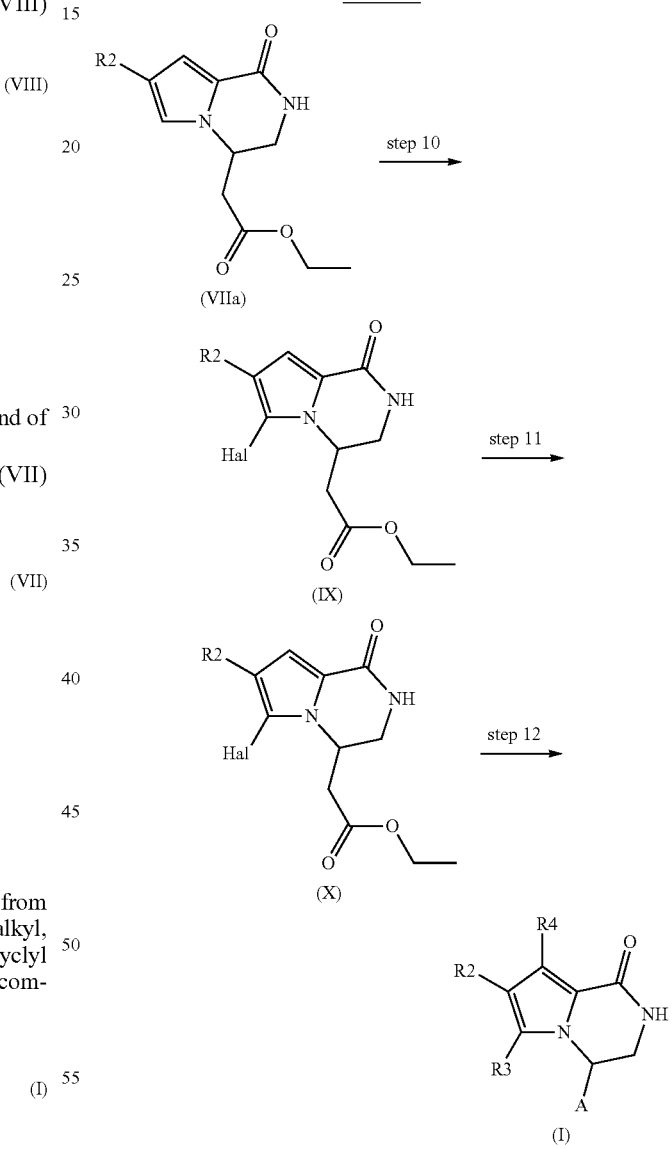

In the above Scheme 3, Hal is halogen; A is a group —$(CH_2)_2$—X—R1 wherein X is —O—, and R1 is hydrogen; R2 is optionally substituted aryl; R3 is an optionally substituted group selected from straight or branched $C_1$-$C_6$ alkyl, $C_3$-$C_7$ cycloalkyl, cycloalkyl-alkyl, $C_2$-$C_6$ alkenyl, $C_2$-$C_6$ alkynyl, aryl, arylalkyl, heterocyclyl and heterocyclylalkyl; and R4 is hydrogen.

Accordingly, a process of the present invention comprises the following steps:

Step 10) reacting the compound of formula (VIIa) wherein R2 is optionally substituted aryl, with an halogenating agent;

Step 11) mixing the resultant compound of formula (IX)

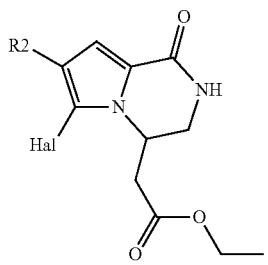

(IX)

wherein R2 is as defined above and Hal is halogen, with an organoboron of formula R3'-B(OZ')OZ" (XIIa) wherein R3' is an optionally substituted group selected from straight or branched $C_1$-$C_6$ alkyl, $C_3$-$C_7$ cycloalkyl, cycloalkyl-alkyl, $C_2$-$C_6$ alkenyl, $C_2$-$C_6$ alkynyl, aryl, arylalkyl, heterocyclyl and heterocyclylalkyl; and Z' and Z" are as defined above;

Step 12) mixing the resultant compound of formula (X)

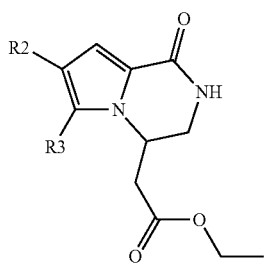

(X)

wherein R2 is aryl and R3 is an optionally substituted group selected from straight or branched $C_1$-$C_6$ alkyl, $C_3$-$C_7$ cycloalkyl, cycloalkyl-alkyl, $C_2$-$C_6$ alkenyl, $C_2$-$C_6$ alkynyl, aryl, arylalkyl, heterocyclyl and heterocyclylalkyl, with a reducing agent to obtain a compound of formula (I)

(I)

wherein A is a group —$(CH_2)_2$—X—R1 wherein X is —O—, and R1 is hydrogen; R2 is optionally substituted aryl; R3 is an optionally substituted group selected from straight or branched $C_1$-$C_6$ alkyl, $C_3$-$C_7$ cycloalkyl, cycloalkyl-alkyl, $C_2$-$C_6$ alkenyl, $C_2$-$C_6$ alkynyl, aryl, arylalkyl, heterocyclyl and heterocyclylalkyl; and R4 is hydrogen;

optionally converting a compound of formula (I) into a different compound of formula (I) by known chemical reactions; and/or, if desired, converting a compound of formula (I) into a pharmaceutically acceptable salt thereof or converting a salt into a free compound of formula (I).

The reported Scheme 4 shows the preparation of a compound of formula (I).

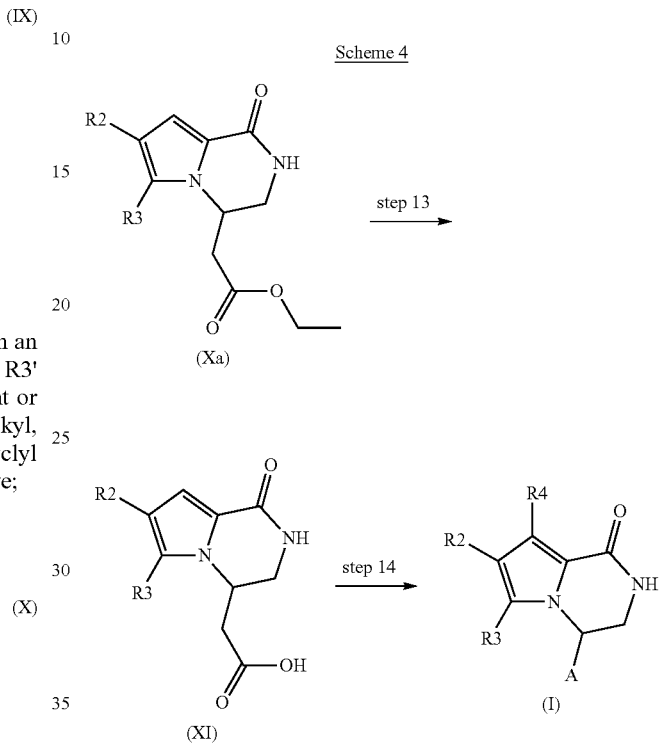

Scheme 4

In the above scheme 4, A is a group —$CH_2$—X—R1 wherein X is NR', and R' and R1 are hydrogen; R2 is an optionally substituted group selected from straight or branched $C_1$-$C_6$ alkyl, $C_3$-$C_7$ cycloalkyl, cycloalkyl-alkyl, $C_2$-$C_6$ alkenyl, $C_2$-$C_6$ alkynyl, aryl, arylalkyl, heterocyclyl and heterocyclylalkyl; and R3 and R4 are hydrogen.

Accordingly, a process of the present invention comprises the following steps:

Step 13) hydrolysing the compound of formula (Xa)

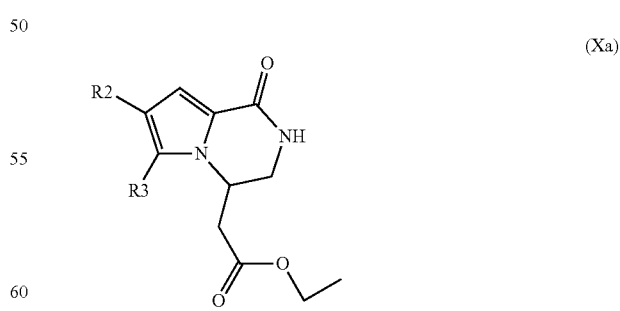

(Xa)

wherein R2 is an optionally substituted group selected from straight or branched $C_1$-$C_6$ alkyl, $C_3$-$C_7$ cycloalkyl, cycloalkyl-alkyl, $C_2$-$C_6$ alkenyl, $C_2$-$C_6$ alkynyl, aryl, arylalkyl, heterocyclyl and heterocyclylalkyl; and R3 is hydrogen, to obtain a compound of formula (XI);

Step 14) reacting the resultant compound of formula (XI)

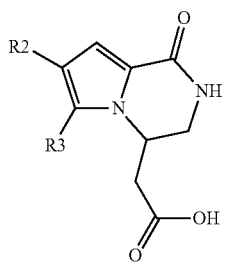
(XI)

wherein R2 and R3 are as defined above, in the condition of Curtius reaction to give a compound of formula (I)

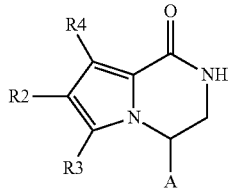
(I)

wherein A is a group —CH$_2$—X—R1 wherein X is NR', and R' and R1 are hydrogen; R2 is an optionally substituted group selected from straight or branched C$_1$-C$_6$ alkyl, C$_3$-C$_7$ cycloalkyl, cycloalkyl-alkyl, C$_2$-C$_6$ alkenyl, C$_2$-C$_6$ alkynyl, aryl, arylalkyl, heterocyclyl and heterocyclylalkyl; and R3 and R4 are hydrogen;
optionally converting a compound of formula (I) into a different compound of formula (I) by known chemical reactions; and/or, if desired, converting a compound of formula (I) into a pharmaceutically acceptable salt thereof or converting a salt into a free compound of formula (I).

The reported Scheme 5 shows the preparation of a compound of formula (I).

Scheme 5

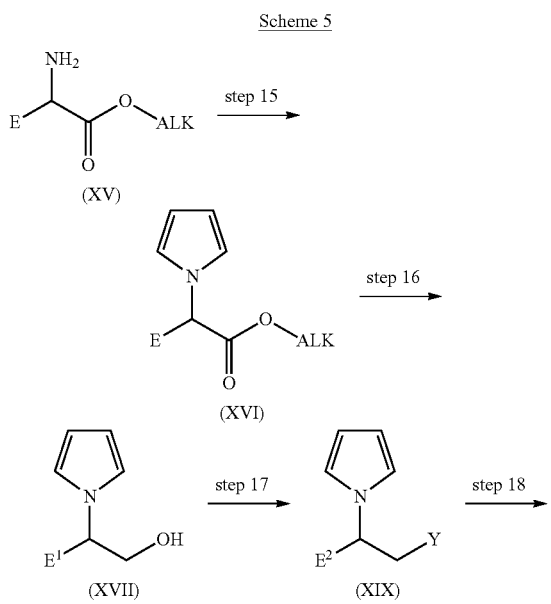

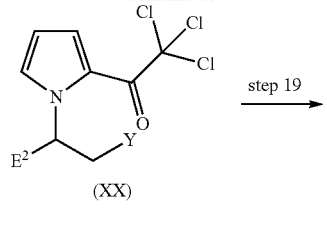
(XX)

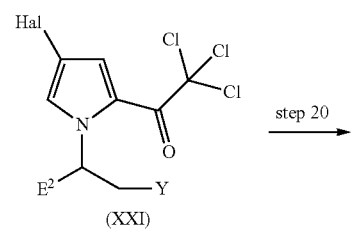
(XXI)

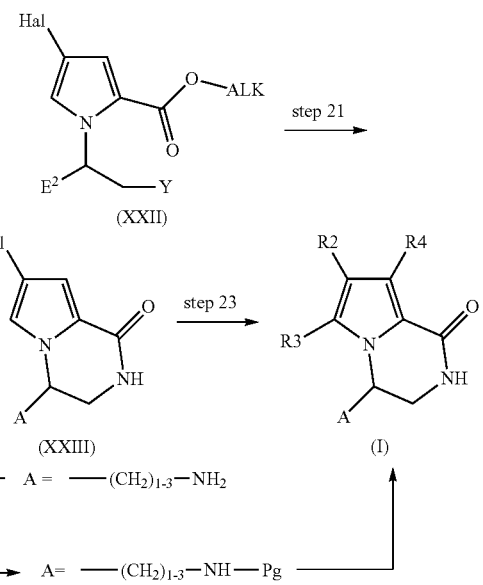

In the above scheme 5, E is an optionally substituted group selected from straight or branched C$_1$-C$_6$ alkyl, heterocyclyl and —(CH$_2$)$_{1-2}$—COOAlk, E$^1$ is an optionally substituted group selected from straight or branched C$_1$-C$_6$ alkyl, heterocyclyl and —(CH$_2$)$_{1-3}$—OH, E$^2$ is an optionally substituted group selected from straight or branched C$_1$-C$_6$ alkyl, heterocyclyl and —(CH$_2$)$_{1-3}$—Y, ALK is C$_1$-C$_6$ alkyl; Y is an azide group (—N$_3$) or an amino group of formula —N(CHO)$_2$, or a phtalimido or an amino group with two protecting groups of formula —N(pg)$_2$; pg is a protecting group such as tert-butylcarbamate or benzyloxy carbonyl; Hal is Halogen; A is an optionally substituted group selected from straight or branched C$_1$-C$_6$ alkyl, heterocyclyl and —(CH$_2$)$_{1-3}$—X—R1, wherein X is NR', R' is hydrogen or a protecting group, and R1 is as defined above; R2 is an optionally substituted group selected from straight or branched C$_1$-C$_6$ alkyl, C$_3$-C$_7$ cycloalkyl, cycloalkyl-alkyl, C$_2$-C$_6$ alkenyl, C$_2$-C$_6$ alkynyl, aryl, arylalkyl, heterocyclyl and heterocyclylalkyl; R3 and R4 are hydrogen.

Accordingly, a process of the present invention comprises the following steps:

Step 15) reacting the compound of formula (XV)

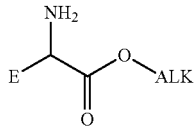
(XV)

wherein E is an optionally substituted group selected from straight or branched $C_1$-$C_6$ alkyl, heterocyclyl and —$(CH_2)_{1-2}$—COOAlk, and ALK is $C_1$-$C_6$ alkyl, under Clauson-Kaas reaction;

Step 16) mixing the resultant pyrrole compound of formula (XVI)

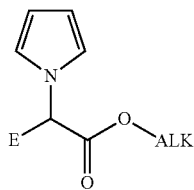
(XVI)

wherein E and ALK are as defined above, with a reducing agent;

Step 17) reacting the resultant compound of formula (XVII)

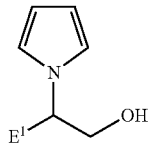
(XVII)

wherein $E^1$ is an optionally substituted group selected from straight or branched $C_1$-$C_6$ alkyl, heterocyclyl and —$(CH_2)_{1-3}$—OH, with an activating agent that converts the OH group into suitable leaving group (LG) and then reacting it with compound of formula Y-z (XVIII), wherein Y is an azide group (—$N_3$) or an amino group of formula —$N(CHO)_2$, or a phtalimido, or an amino group with two protecting group of formula $N(pg)_2$, wherein pg groups are as defined above, and z is hydrogen or alkali metal;

Step 18) acylating the pyrrole ring of the resultant compound of formula (XIX) obtained in step 17

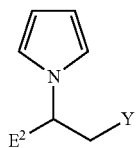
(XIX)

wherein $E^2$ is an optionally substituted group selected from straight or branched $C_1$-$C_6$ alkyl, heterocyclyl and —$(CH_2)_{1-3}$—Y, and Y is as defined above, with trichloroacetyl chloride;

Step 19) reacting the resultant compound of formula (XX)

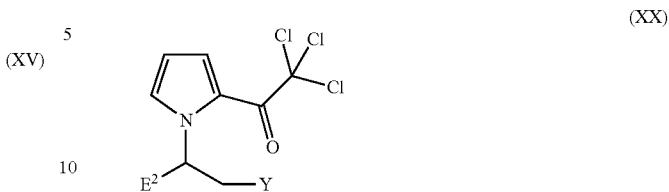
(XX)

wherein $E^2$ and Y are as defined above, with an halogenating agent;

Step 20) reacting the resultant compound of formula (XXI)

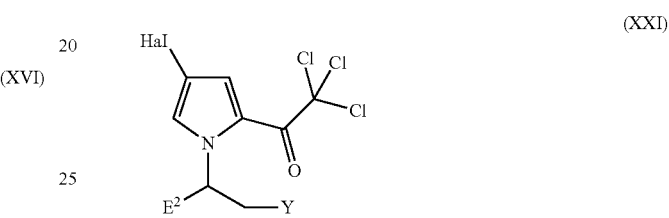
(XXI)

wherein Hal, $E^2$ and Y are as defined above, with an alkoxyde;

Step 21) deprotecting and cyclizing the resultant compound of formula (XXII)

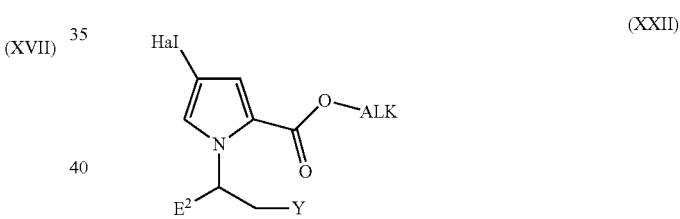
(XXII)

wherein ALK, Hal and $E^2$ are as defined above, and Y is an amino group of formula —$N(CHO)_2$, or a phtalimido, or an amino group with two protecting group of formula $N(pg)_2$;

or

Step 21a) reducing and cyclizing the compound of formula (XXII)

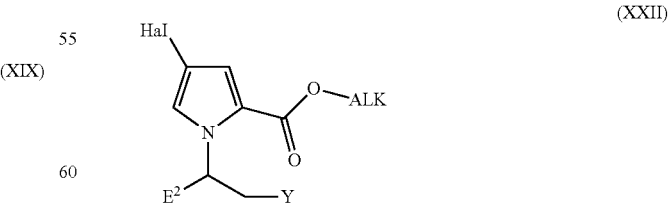
(XXII)

wherein ALK, and $E^2$ are as defined above, and Y is an azido group;

optionally,

Step 22) reacting the resultant compound of formula (XXIII)

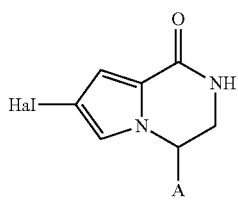
(XXIII)

wherein A is —(CH$_2$)$_{1-3}$—NH$_2$, with a compound of formula pg-T (XXXV) wherein pg is a protecting group such as tert butyl carbamate or benzyloxy carbonyl and T is a good leaving group such as halogen;

Step 23) reacting the resultant compound of formula (XXIII) obtained in step 21), 21a) or 22)

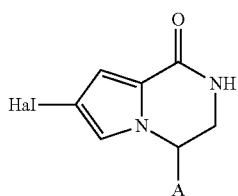
(XXIII)

wherein A is an optionally substituted group selected from straight or branched C$_1$-C$_6$ alkyl, heterocyclyl and —(CH$_2$)$_{1-3}$—X—R1, wherein X and R1 are as defined above according to any one of the alternative steps:

Step 23a) with a organoboron of formula (XII)

R2'B(OZ')OZ"      (XII)

wherein R2' is optionally substituted group selected from straight or branched C$_1$-C$_6$ alkyl, C$_3$-C$_7$ cycloalkyl, cycloalkyl-alkyl, C$_2$-C$_6$ alkenyl, aryl, arylalkyl, heterocyclyl and heterocyclylalkyl; and Z' and Z" are either hydrogen, alkyl or, taken together with the oxygen atoms to which they are bonded, may form an optionally substituted 5 to 6 membered heterocycle, to give a compound of formula (I);
or
Step 23b) with a terminal alkyne of formula (XIII):

R$^a$C≡CH      (XIII)

wherein R$^a$ is hydrogen, or an optionally substituted group selected from straight or branched C$_1$-C$_6$ alkyl, C$_3$-C$_7$ cycloalkyl, cycloalkyl-alkyl, C$_2$-C$_6$ alkenyl, C$_2$-C$_6$ alkynyl, aryl, arylalkyl, heterocyclyl and heterocyclylalkyl; to give a compound of formula (I):

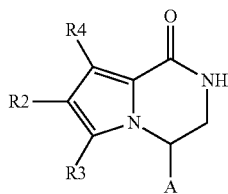
(I)

wherein A is an optionally substituted group selected from straight or branched C$_1$-C$_6$ alkyl, heterocyclyl and —(CH$_2$)$_{1-3}$—X—R1, wherein X is NR', R' is hydrogen or a protecting group, and R1 is as defined above; R2 is as an optionally substituted group selected from straight or branched C$_1$-C$_6$ alkyl, C$_3$-C$_7$ cycloalkyl, cycloalkyl-alkyl, C$_2$-C$_6$ alkenyl, C$_2$-C$_6$ alkynyl, aryl, arylalkyl, heterocyclyl and heterocyclylalkyl; R3 and R4 are hydrogen;

optionally converting a compound of formula (I) into a different compound of formula (I) by known chemical reactions; and/or, if desired, converting a compound of formula (I) into a pharmaceutically acceptable salt thereof or converting a salt into a free compound of formula (I).

The reported Scheme 6 shows the preparation of a compound of formula (I).

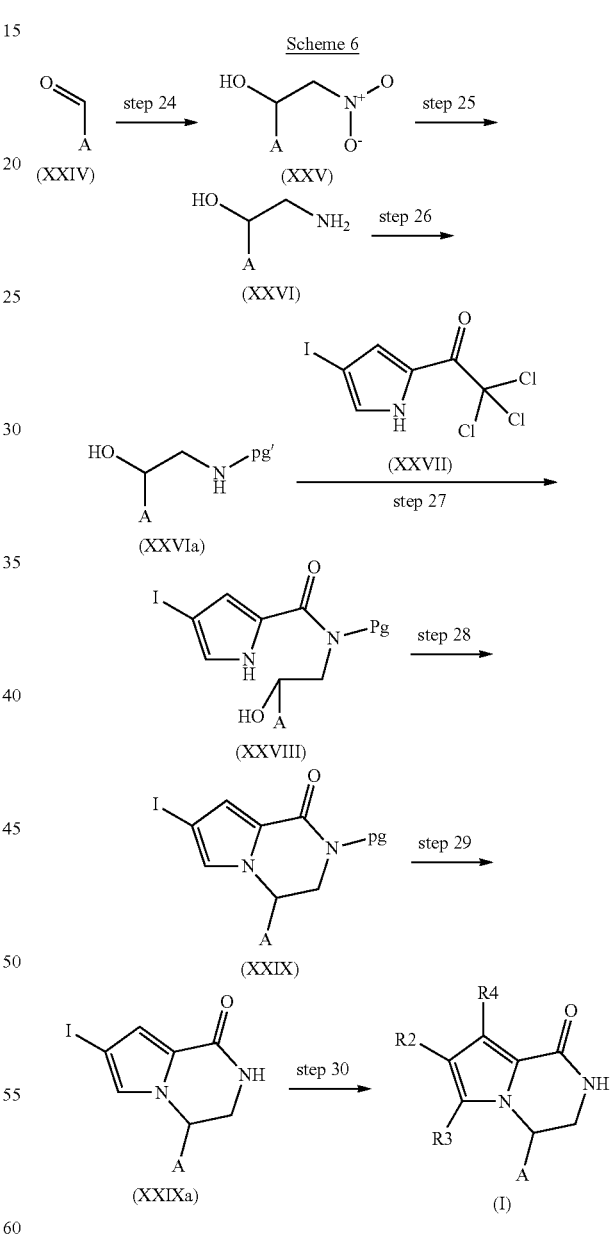

In the above Scheme 6, pg' is a protecting group such as p-methoxybenzyl or 2,4-dimethoxybenzyl; A is an optionally substituted group selected from straight or branched C$_1$-C$_6$ alkyl, heterocyclyl and —(CH$_2$)$_{1-3}$—X—R1, wherein X and R1 are as defined above; R2 is an optionally substituted group selected from straight or branched C$_1$-C$_6$ alkyl, C$_3$-C$_7$ cycloalkyl, cycloalkyl-alkyl, C$_2$-C$_6$ alkenyl, C$_2$-C$_6$ alkynyl, aryl, arylalkyl, heterocyclyl and heterocyclylalkyl; R3 and R4 are hydrogen.

Step 24) reacting the compound of formula (XXIV)

(XXIV)

wherein A is as defined above, with nitromethane CH$_3$NO$_2$;

Step 25) mixing the resultant compound of formula (XXV)

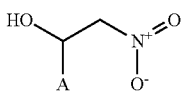
(XXV)

wherein A is as defined above, with a reducing agent;

Step 26) reacting the resultant compound of formula (XXVI)

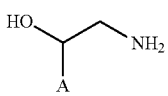
(XXVI)

wherein A is as defined above, with a compound of formula pg'-T (XXXVa) wherein pg' is a protecting group such as p-methoxybenzyl or 2,4-dimethoxybenzyl and T is a leaving group such as halogen;

Step 27) mixing the resultant compound of formula (XXVIa)

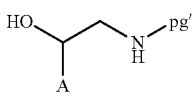
(XXVIa)

wherein A and pg' are as defined above, with a pyrrolo derivative of formula (XXVII)

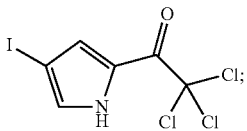
(XXVII)

Step 28) cyclizing the resultant compound of formula (XXVIII)

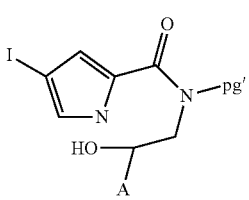
(XXVIII)

wherein A and pg' are as defined above;

Step 29) removing the protecting group from the resultant compound of formula (XXIX)

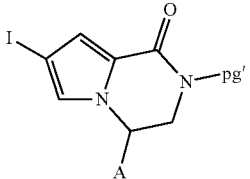
(XXIX)

wherein A is as defined above;

Step 30) reacting the resultant compound of formula (XXIXa)

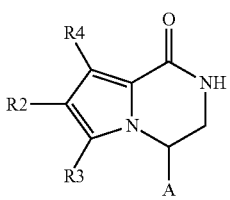
(XXIXa)

wherein A is as defined above, alternatively with:

Step 30a) an organoboron of formula (XII)

R2'B(OZ')OZ''     (XII)

wherein R2' is optionally substituted group selected from straight or branched C$_1$-C$_6$ alkyl, C$_3$-C$_7$ cycloalkyl, cycloalkyl-alkyl, C$_2$-C$_6$ alkenyl, aryl, arylalkyl, heterocyclyl and heterocyclylalkyl, and Z' and Z'' are either hydrogen, alkyl or, taken together with the oxygen atoms to which they are bonded, may form an optionally substituted 5 to 6 membered heterocycle, to give a compound of formula (I); or Step 30b) a terminal alkyne of formula (XIII):

R$^a$C≡CH     (XIII)

wherein R$^a$ is hydrogen, or an optionally substituted group selected from straight or branched C$_1$-C$_6$ alkyl, C$_3$-C$_7$ cycloalkyl, cycloalkyl-alkyl, C$_2$-C$_6$ alkenyl or C$_2$-C$_6$ alkynyl, aryl, arylalkyl, heterocyclyl and heterocyclylalkyl; to give a compound of formula (I)

(I)

wherein A is an optionally substituted group selected from straight or branched C$_1$-C$_6$ alkyl, heterocyclyl and —(CH$_2$)$_{1-3}$—X—R1, wherein X and R1 are as defined above; R2 is an optionally substituted group selected from straight or branched C$_1$-C$_6$ alkyl, C$_3$-C$_7$ cycloalkyl, cycloalkyl-alkyl, C$_2$-C$_6$ alkenyl, C$_2$-C$_6$ alkynyl, aryl, arylalkyl, heterocyclyl and heterocyclylalkyl; R3 and R4 are hydrogen;

optionally converting a compound of formula (I) into a different compound of formula (I) by known chemical reactions; and/or, if desired, converting a compound of formula (I) into a pharmaceutically acceptable salt thereof or converting a salt into a free compound of formula (I).

As said above, the compouonds of the formula (I) which are prepared according to the process object of the invention, can be conveniently converted into other compounds of the formula (I) by operating according to well-known synthetic conditions, the following being examples of possible conversions:

Conv. a) converting a compound of formula (I) where a group —CH₂OH is present, into the corresponding compound of formula (I) with a group —CH₂NR'R1

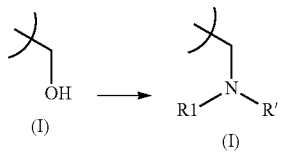

wherein R1 is as defined above and R' is hydrogen or an optionally substituted straight or branched $C_1$-$C_6$ alkyl, $C_3$-$C_7$ cycloalkyl, cycloalkyl-alkyl, aryl, arylalkyl, heterocyclyl and heterocyclylalkyl or, together with the nitrogen atom to which they are bound, R' and R1 may form a 5 to 7 membered heteroaryl or heterocyclyl group optionally containing one additional heteroatom selected from N, O and S, by first converting the group —CH₂OH into —CHO and by then reacting the resulting aldehyde derivative with a compound of formula R1R'NH(XXX), wherein R1 and R' are as defined above, in the presence of a suitable reducing agents;

Conv. b) converting a compound of formula (I) where a group —CH₂OH is present, into the corresponding compound of formula (I) with a group —CH₂NR'R1

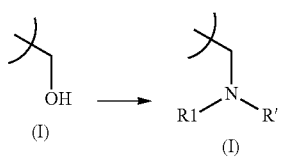

wherein R1 is as defined above and R' is hydrogen or a protecting group of formula —COOR6, wherein R6 is as defined above, by a three-steps sequence encompassing alcohol activation, nucleophilic displacement, and manipulation of the post-nucleophile product to an amine;

Conv. c) converting a compound of formula (I) where a group —CH₂OH is present, into the corresponding compound of formula (I) with a group —CH₂-hal

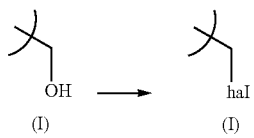

wherein hal is halogen, by activation of an alcohol towards nucleophilic displacement with halide ion with a Mitsunobu-like procedure or in alternative by converting the alcohol to a sulfonate ester;

Conv. d) converting a compound of formula (I) where a group —CH₂OH is present, into the corresponding compound of formula (I) with a group —CH₂NR'R1

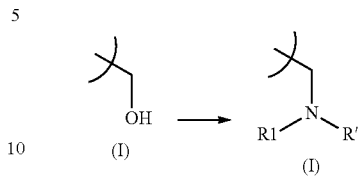

wherein R1 and R' are hydrogen, by using a modified Staudinger procedure to convert a primary alcohol into the corresponding primary amine via the intermediate azide obtained by a Mitsunobu-type reaction;

Conv. e) converting a compound of the formula (I) wherein R3 or R4 is hydrogen into the corresponding compound of the formula (I)

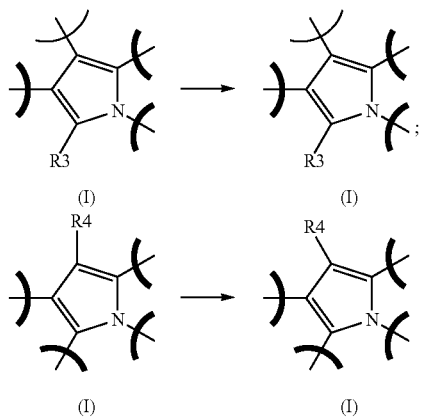

wherein R3 or R4 is an halogen, through reaction with an halogenating agent;

Conv. f) converting a compound of formula (I) wherein R3 or R4 is halogen into the corresponding compound of formula (I)

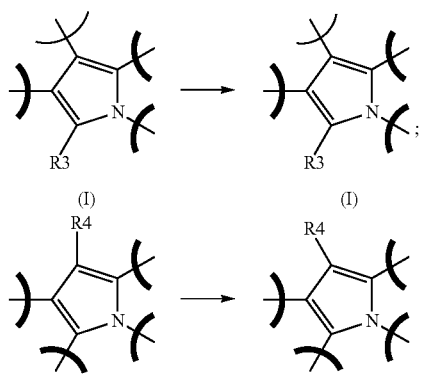

wherein R3 or R4 is cyano, following the condition known in the art for palladium-catalyzed cyanation of aryl halides;

Conv. g) converting a compound of formula (I) wherein R3 or R4 is halogen into the corresponding compound of formula (I)

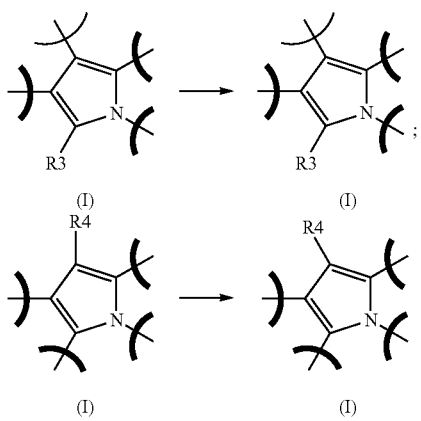

wherein R3 or R4 is an optionally substituted group selected from straight or branched $C_1$-$C_6$ alkyl, $C_3$-$C_7$ cycloalkyl, cycloalkyl-alkyl, aryl, arylalkyl, heterocyclyl and heterocyclylalkyl by reaction with a compound of formula (XXXI) or (XXXII) respectively:

R3''-G (XXXI)

R4''-G (XXXII)

wherein R3'' or R4'' is straight or branched $C_1$-$C_6$ alkyl, $C_3$-$C_7$ cycloalkyl, cycloalkyl-alkyl, aryl, arylalkyl, heterocyclyl and heterocyclylalkyl, and G is a suitable group such as —B(OH)$_2$, —B(OAlk)$_2$, —Sn(Alk)$_4$, ZnHal, or MgHal, under palladium mediated carbon bond formation;

Conv. h) converting a compound of formula (I) wherein R3 or R4 is halogen into the corresponding compound of formula (I)

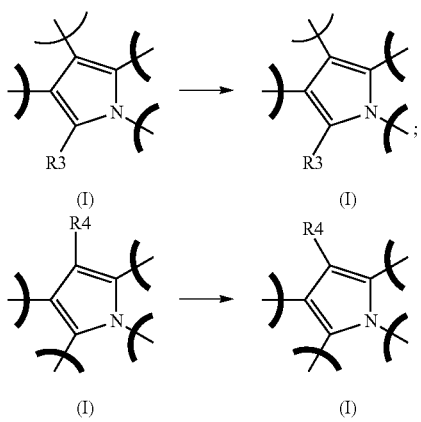

wherein R3 or R4 is $R^a$C≡C—, by reaction with a terminal alkyne of formula (XIII):

$R^a$C≡CH (XIII)

wherein $R^a$ is hydrogen or an optionally substituted group selected from straight or branched C1-C6 alkyl, C3-C7 cycloalkyl, cycloalkyl-alkyl, C2-C6 alkenyl or C2-C6 alkynyl, aryl, arylalkyl, heterocyclyl and heterocyclylalkyl;

Conv. i) converting a compound of the formula (I) where is present a group L-COOPg, wherein L is an optionally substituted group selected from straight or branched $C_1$-$C_6$ alkyl, $C_3$-$C_7$ cycloalkyl, cycloalkylalkyl, $C_2$-$C_6$ alkenyl, $C_2$-$C_6$ alkynyl, aryl, arylalkyl, heterocyclyl and heterocyclylalkyl, and Pg is a suitable protecting group, into the corresponding compound of formula (I)

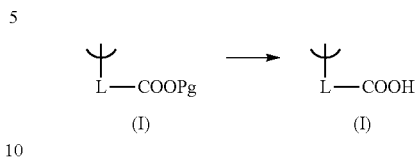

where a group L-COOH is present, wherein L is as defined above, through conditions well known in the literature, see Teodora W. Green, Pere G. M. Wuts;

Conv. j) converting a compound of the formula (I) where a group L-COOH is present wherein L is as defined above, into the corresponding compound of formula (I)

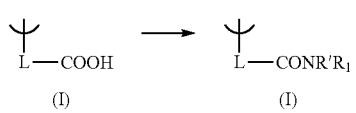

where a group L-CONR'R1 is present, by treatment with an amine of formula R1R'—NH(XXX), wherein R' and R1 are as defined above, in the presence of the suitable condensing agents;

Conv. k) converting a compound of the formula (I) where a group L-CHO is present wherein L is as defined above, into the corresponding compound of formula (I)

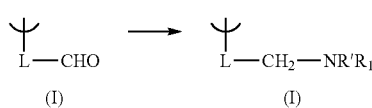

where a group L-CH$_2$NR'R1 is present, wherein R' and R1 are as defined above, by treatment with an amine of formula R1R'—NH(XXX), in the presence of the suitable reducing agents;

Conv. l) converting a compound of formula (I) where a primary or secondary amine is present, into the corresponding compound of formula (I)

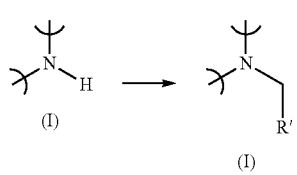

where a secondary or tertiary amine is present, by treatment with a compound of formula R'—CHO (XXXIII) wherein R' is an optionally substituted group selected from straight or branched $C_1$-$C_6$ alkyl, $C_3$-$C_7$ cycloalkyl, cycloalkyl-alkyl, aryl, arylalkyl, heterocyclyl and heterocyclylalkyl;

Conv. m) converting a compound of formula (I) where a primary or secondary amine is present, into the corresponding compound of formula (I)

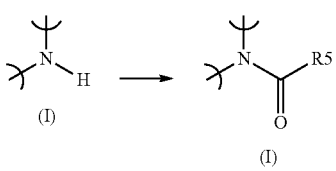

wherein an amide of formula —NCOR5 is present, wherein R5 is an optionally substituted group selected from straight or branched $C_1$-$C_6$ alkyl, $C_3$-$C_7$ cycloalkyl, cycloalkyl-alkyl, $C_2$-$C_6$ alkenyl or $C_2$-$C_6$ alkynyl, aryl, arylalkyl, heterocyclyl and heterocyclylalkyl, by treatment with a compound of formula R5-COW (XXXIV) wherein R5 is as defined above and W is hydroxyl or halogen;

Conv. n) converting a compound of formula (I) where a primary or secondary amine is present, into the corresponding compound of formula (I)

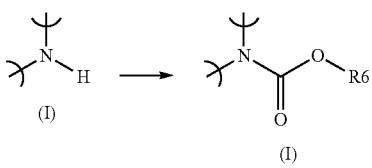

wherein a group of formula —NC(O)OR6 is present, wherein R6 is a group optionally substituted selected from straight or branched $C_1$-$C_6$ alkyl, $C_3$-$C_7$ cycloalkyl, aryl and heterocyclyl, by treatment with a compound of formula R6-OCO-T (XXXVI) wherein R6 is as defined above and T is a good leaving group such as halogen;

Conv. o) converting a compound of formula (I) where a primary or secondary amine is present, into the corresponding compound of formula (I)

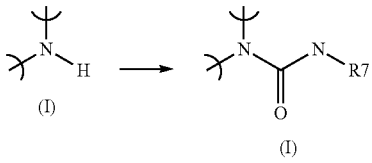

wherein an urea of formula —NC(O)NR7 is present, wherein R7 is a group optionally substituted from straight or branched $C_1$-$C_6$ alkyl, $C_3$-$C_7$ cycloalkyl, aryl, and heterocyclyl, by treatment with a compound of formula R7-N=C=O (XXXVII) wherein R7 is as defined above;

Conv. p) converting a compound of formula (I) where a primary or secondary amine is present, into the corresponding compound of formula (I)

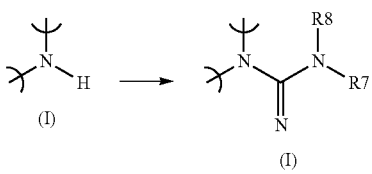

wherein a guanidine group of formula —NC(NH)N(R7)R8 is present, wherein R7 and R8 are each independently hydrogen or a group optionally substituted selected from straight or branched $C_1$-$C_6$ alkyl, $C_3$-$C_7$ cycloalkyl, aryl, and heterocyclyl, by treatment with a compound of formula R7N(R8)C(NH)T (XXXVIII) wherein R7 and R8 are as defined above and T is a suitable leaving group such as —S-Me, N—S(O)$_2$CF$_3$, or 1H-pyrazolyl;

Conv. q) converting a compound of formula (I) where a primary or secondary amine is present, into the corresponding compound of formula (I)

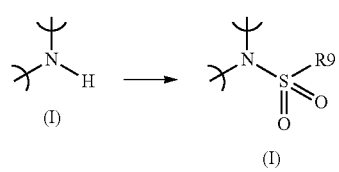

wherein a group of formula —NS(O)$_2$R9 is present, wherein R9 is an optionally substituted group selected from straight or branched $C_1$-$C_6$ alkyl, $C_3$-$C_7$ cycloalkyl, aryl, and heterocyclyl, by treatment with a compound of formula R9-S(O)$_2$Cl (XXXIX) wherein R9 is as defined above;

Conv. r) removing any protecting group or groups and, if desired, forming a salt.

According to step 1 of the process an ester of formula (II) can be reacted in different ways and experimental conditions known in the art with a reducing agent. Preferably it is reacted with a reducing agent such as sodium borohydride, lithium alluminium hydride or the like, in a suitable solvent such as methanol, ethanol or THF at a temperature ranging from 0° C. to room temperature from 2 hours to about 24 hours. The reaction is conveniently performed with sodium borohydride in ethanol at room temperature to obtain a compound of formula (III).

According to step 2 of the process, a compound of formula (III) can be reacted in different ways and experimental conditions known in the art with an alcohol activating reagent, such as a sulphonylating agent. Preferably it is dissolved in a suitable solvent for instance THF, DCM, DMF or the like, in the presence of a suitable base such as triethylamine or diisopropylethylamine and the methanesulfonyl chloride as sulphonylating agent is added therein. The mixture is stirred for a time of about 1 hour to about 6 hours, at a temperature ranging from about 0° C. to room temperature.

According to step 3 of the process, a compound of formula (IV) is reacted with an azide anion in a Sn$_2$ reaction to give the alkyl azide of formula (V). Preferably, the reaction is carried out with sodium azide or an azide exchange resin (Amberlite IR-400), convenient solvents include aprotic solvents such as acetonitrile, DMF, or a mixture thereof. The reaction is performed at a temperature ranging from RT to 80° C. for 2 hours to about 18 hours.

According to step 3a of the process, a compound of formula (III) is transformed into the compound of formula (V) by Mitsunobu-type reaction a widely known reaction to convert alcohol into azide. Said reaction, which is well known to those skilled in the art, can be accomplished using a dialkyl azodicarboxylate, such as diethylazodicarboxylate (DEAD), diisopropyl azodicarboxylate (DIAD) or the like, in the presence of a trialkyl or triaryl phosphine, preferably triphenyl phosphine in the presence of an azide ion source such as nicotinyl azide (NCA) or DPPA (diphenylphosphoryl azide). In alternative, the reaction can be performed with DPPA (diphenylphosphoryl azide) and diazabicycloundecene DBU. The reaction is performed in a convenient solvents such as aprotic solvents such as tetrahydrofuran, 1,4-dioxane, 1,2-dimethoxyethane, acetonitrile and the like at temperatures ranging from 0° C. to RT and for a time ranging from 30 minutes to about 48 hours.

According to step 4 of the process, a compound of formula (VI) is obtained by reduction of the alkyl azide (V) with reducing agents. The reduction of alkyl azides to primary amines constitutes a synthetically useful process that can be accomplished with a wide variety of reagents including catalytic hydrogenation, LAH, sodium or zinc borohydride, triphenylphosphine, Iron-$NH_4Cl$, Indium-$NH_4Cl$ and Zinc-$NH_4Cl$. When the Staudinger reaction is performed, a trialkyl or triaryl phosphine is used in a suitable solvent such as THF at room temperature for 1 hour to about 4 hours. Therefore, the reaction is diluted with water, optionally $(Boc)_2O$ anhydride is added to obtain the compound of formula (VI) with a protecting group, and left on stirring for 18 hours to about 36 hours at room temperature. Alternatively, in the case where the Zinc-$NH_4Cl$ reagents were employed the reaction is performed with the addition of di-tert-butyl dicarbonate for the in situ protection of nitrogen, at reflux in a mixture of solvents including 1,4-dioxane and water for 4 hours to about 8 hours.

According to step 5a of the process, the compound of the formula (VI) is reacted with a derivative of formula (XII), through any of the cross-coupling reactions suitable for the formation of carbon-carbon bonds. Said reactions, which are well known in the art, imply a coupling with a suitable organometal reagent such as for instance organoboron (Suzuki reaction), organotin (Stille reaction), organomagnesium (Kumada reaction), or organozinc (Negishi reaction) and the like. Preferred reaction is the Suzuki reaction where the appropriate boronic derivative is used in the presence of a palladium based catalyst such as $PdCl_2(dppf)_2CH_2Cl_2$ or $Pd_2(dba)_3$ or $Pd(PPh_3)_4$. Convenient solvents include aprotic solvents such as DMF, DCM, MeOH, $CH_3CN$, or in a mixture of solvents, such as dimethoxyethane and water, optionally in the presence of a base such as sodium, cesium carbonate or cesium fluoride, at a temperature ranging from room temperature to 100° C.

According to step 5b of the process, the compound of the formula (VI) is reacted with a derivative of formula (XIII), through the Sonogashira coupling between the alkyne derivative of formula (XIII) and the compound of formula (VI), in the presence of suitable Pd-catalysts include $Pd(PPh_3)_4$, $Pd(PPh_3)_2Cl_2$, suitable ligands include tryphenylphosphine, a base such as triethylamine and an additive such as copper(I) iodide, using N,N-dimethylformamide as the solvent, at a temperature varying from room temperature to reflux and for a time ranging between 4 hours and overnight.

According to step 5' of the process, a compound of formula (VI) can be transformed into an organometal derivative of formula (VIa) such as an organoboron or the like. Preferred organonboron compounds can be obtained for instance reacting a compound of (VI) with a suitable boron compound, such as bis(pinacolato) diboron, pinacolborane, or the like in the presence of a suitable palladium catalyst such as palladium acetate, $PdCl_2$ (dppf)$_2$ and a suitable base, such as KOAc, triethylamine and the like, in solvents such as DMF, 1,4-dioxane, dimethoxyethane, THF or the like, at temperature ranging from 20° C. to reflux and for a time ranging from 30 minutes to about 24 hours.

According to step 5"

of the process, a compound of formula (VIa) is reacted with an appropriate electrophile of formula R2-Q (XIV), wherein Q is an halide or a trifluoromethansulfonate (triflate), a methansulfonate (mesylate) or a p-toluenesulfonate (tosylate) in the presence of a palladium or nickel-based catalyst, such as for instance, tetrakis(triphenylphosphine)palladium, or $PdCl_2(dppf)_2CH_2Cl_2$, and a suitable base, such as $Cs_2CO_3$, $K_2CO_3$, CsF, and the like. Convenient solvents include aprotic solvents such as 1,4-dioxane, dimethoxyethane, THF or the like, at temperature ranging from 20° C. to reflux and for a time ranging from 1 hour to about 24 hours, to give a compound of formula (I).

According to step 6 of the process, the compound of the formula (II) is reacted with a derivative of formula (XII), following the condition described under step 5a.

According to step 7 of the process, a compound of formula (II) can be transformed into an organometal derivative of formula (VIII) such as an organoboron or the like following the condition described under step 5'.

According to step 8 of the process, a compound of formula (VIII) is reacted with an appropriate electrophile of formula R2"-Q (XIV), following the condition described under step 5".

According to step 9 of the process, the direct transformation of a compound of formula (VII) into a compound of formula (I), can be performed according to methods well-known in the art to convert carboxyester groups (—COOEt) into alcohol ($CH_2OH$). Preferably the reaction is carried out with a reducing agent such as borane, sodium or lithium borohydride, in a suitable solvent such as methanol, ethanol or THF at a temperature ranging from 0° C. to room temperature for 2 to about 24 hours.

Alternatively, first a compound of formula (VII) may be converted into the corresponding carboxylic acid derivative through basic or acidic hydrolysis conditions, widely known in the art. Preferably, the reaction is carried out with aqueous alkaline solutions such as aqueous lithium, sodium or potassium hydroxide in the presence of a suitable solvent such as a lower alcohol, THF, DMF or mixtures thereof; preferably the reaction is carried out with lithium hydroxide in THF/Methanol/water mixture, at a temperature ranging from about room temperature to about 80° C. According to the operative conditions being employed, the compound of formula (VII) could be obtained either in its acidic form or, alternatively, as a salt. Then the obtained carboxylic acid is reacted with a condensing agent to form the corresponding mixed anhydride, by using an alkyl chloroformate such as ethyl, isopropyl, benzyl chloroformate, or 1,1'-carbonyldiimidazole in the presence of an amine such as TEA, DIPEA, or pyridine, in a suitable solvent such as, for instance toluene, DCM, THF, DMF and the like, at room temperature. Finally, the so formed anhydride is mixed with a reducing agent such as sodium or lithium borohydride in ethanol THF at a temperature ranging from 0° C. to room temperature for 2 hours to about 24 hours.

According to step 10 of the process, the reaction of a compound of formula (VIIa) wherein R3 is hydrogen can be transformed into the corresponding compound of formula (IX) wherein R3 is halogen, preferably bromine or iodine. The said reaction is performed with halogenating reagent such as NBS or NIS, in a suitable solvent such as DCM or DMF, from −10° C. to room temperature in a period of time varying from 2 hours to about 18 hours. Preferably, the reaction is carried out under neutral conditions in the presence of iodine and silver trifluoroacetate, in DCM at a temperature ranging from 0° C. to room temperature and for a time varying from 2 hours to overnight.

According to step 11
of the process, the reaction of a compound of formula (IX) is reacted with an organoboron of formula R3'-B(OZ')OZ" (XIIa) in a suitable solvent such as DMF, 1,4-dioxane, DME or $CH_3CN$, in the presence of $Pd_2(dba)_3$, $PdCl_2(dppf)$ or $Pd(PPh_3)_4$, optionally in the presence of cesium fluoride or cesium carbonate, at a temperature ranging from room temperature to 100° C. for a time ranging from 2 hours to 6 hours.

According to step 12
of the process, the reaction of a compound of formula (X) with a reducing agent can be carried out in different ways and experimental conditions known in the art. Preferably, it is carried out following the conditions described under step 9).

According to step 13
of the process, the reaction of a compound of formula (Xa) is converted into the corresponding carboxylic acid derivative of formula (XI) through basic or acidic hydrolysis conditions, according to methods widely known in the art. Preferably, the reaction is carried out with aqueous alkaline solutions such as aqueous lithium, sodium or potassium hydroxide in the presence of a suitable solvent such as a lower alcohol, THF, DMF or mixtures thereof; preferably the reaction is carried out with lithium hydroxide in THF/Methanol/water mixture, at a temperature ranging from about room temperature to about 80° C. According to the operative conditions being employed, the compound of formula (XI) could be obtained either in its acidic form or, alternatively, as a salt.

According to step 14
of the process, the compound of formula (I) is obtained by using a one pot Curtius rearrangement process. The one pot transformation of carboxylic acid into amine is most commonly achieved using diphenylphosphoryl azide (DPPA), in a suitable solvent such as THF, Toluene, at a temperature varying from 20° C. to reflux, for about 2 hours to 48 hours.

According to step 15
of the process, a compound of formula (XV) can be converted into a compound of formula (XVI) in different ways according to conventional methods for the pyrrole synthesis. Preferably, the Clauson-Kaas reaction was applied. The said reaction is performed by mixing the amine of formula (XV) and 2,5-dimethoxytetrahydrofurane in the presence of acetic acid, sodium acetate, a suitable solvent such as DCM, THF, in mixture with water, at a temperature ranging from room temperature to 80° C., for 30 minutes to 24 hours.

According to step 16
of the process, a compound of formula (XVII) may be prepared by reduction of a corresponding compound of formula (XVI) as hereinbefore defined. The reaction can be performed according to methods well-known in the art to convert carboxyester groups (—COOEt) into alcohol ($CH_2OH$). When E is —$(CH_2)_{1-2}$—COOAlk, the reduction involves both the carboxyester groups that are present in the compound of formula (XVI). Preferably the reaction is carried out with a reducing agent such as borane, sodium or lithium borohydride, or $LiAlH_4$, in a suitable solvent such as methanol, ethanol or THF at a temperature ranging from 0° C. to room temperature for 2 hours to about 24 hours.

According to step 17
of the process, a compound of formula (XIX) can be obtained by a two-reactions sequence from a compound of formula (XVII) in different ways and experimental conditions known in the art. First the conversion of the OH group into a suitable leaving group is preferably carried out in the presence of a sulphonylating agent such as methanesulfonyl chloride, p-toluensulfonyl chloride, or trifluoromethansulfonate anhydride, in the presence of a suitable base such as triethylamine or diisopropylethylamine in a suitable solvent for instance THF, DCM, DMF or the like. The mixture is stirred for a time of about 1 hour to about 6 hours, at a temperature ranging from about 0° C. to room temperature. The second step is preferably carried out in the presence of sodium azide, sodium di-formamide, sodium di-tert-butyldicarbamide, or potassium phthalimide, in a suitable organic solvent such as acetonitrile, DMF or a mixture thereof. The reaction can be conveniently performed at a temperature ranging from room temperature to reflux, for a time varying from 1 hour to 8 hours.

Alternatively, a compound of formula (XIX) can be also obtained by Mitsunobu reaction. Said reaction, which is well known in the art, can be accomplished using a dialkyl azodicarboxylate, such as diethylazodicarboxylate (DEAD), diisopropyl azodicarboxylate (DIAD) or the like, in the presence of a trialkyl or triaryl phosphine, preferably triphenyl phosphine in the presence of di-tert-butyldicarbamide, phthalimide, or an azide ion source such as nicotinyl azide (NCA) or DPPA (diphenylphosphoryl azide). In alternative, the reaction can be performed with DPPA (diphenylphosphoryl azide) and DBU. Convenient solvents include aprotic solvents such as tetrahydrofuran, 1,4-dioxane, 1,2-dimethoxyethane, acetonitrile and the like at temperatures ranging from 0° C. to RT and for a time ranging from 30 minutes to about 48 hours.

When $E^1$ is —$(CH_2)_{1-3}$—OH, this group is transformed in a group —$(CH_2)_{1-3}$—Y.

According to step 18
of the process, a compound of formula (XX) can be obtained by reacting a compound of formula (XIX) in different ways and experimental conditions, which are widely known in the art of electrophilic acylation of pyrrole. Preferably the reaction is performed by using trichloroacetyl chloride, in anhydrous solvent such as THF, DCM or 1,4-dioxane, in the presence of 2,6-lutidine as organic base, at reflux temperature for 6 to 24 hours.

According to step 19
of the process, a compound of formula (XXI) can be obtained by reacting a compound of formula (XX) in different ways and experimental conditions, which are widely known in the art. Preferably the said reaction is performed with a halogenating reagent such as NCS, NBS, NIS, in a suitable solvent such as DCM, THF, MeOH, DMF, or a mixture thereof, at a temperature from −10° C. to room temperature within 2 to about 18 hours. Preferably, the reaction is carried out under neutral conditions in the presence of iodine and silver trifluoroacetate, in DCM at a temperature ranging from 0° C. to room temperature and for a time from 2 hours to overnight.

According to step 20
of the process, a compound of formula (XXI) is reacted with an alkoxyde such as sodium methoxyde, sodium ethoxyde in a suitable dry solvent such as methanol, ethanol and the like, the reaction is performed at room temperature for 1 to about 4 hours. When $E^2$ is —$(CH_2)_{1-3}$—Y, and Y is an amino group of formula —$N(CHO)_2$, or a phtalimido, or an amino group with two protecting group of formula $N(pg)_2$, the deprotection reaction involve also this group.

According to step 21
of the process, a compound of formula (XXIII) wherein Y is an amino group of formula —$N(CHO)_2$, or a phtalimido, or an amino group with two protecting group of formula $N(pg)_2$ pg is a protecting group such as tert-butylcarbamate, can be transformed into a compound of formula (XXIII) in different ways and experimental conditions known in the art. First the deprotection is performed preferably under acidic conditions, for instance in the presence of an inorganic or organic acid such as hydrochloric, trifluoroacetic or methansulfonic acid, in a suitable solvent such as dichloromethane, 1,4-dioxane, a lower alcohol, such as methanol or ethanol, at a temperature ranging from room temperature to reflux and for a period of time ranging from about 1 hour to about 48 hours. Then the cyclization is carried out under basic conditions such as in the presence of sodium or potassium carbonate, triethylamine, in a suitable solvent, such as THF, DCM, at a temperature ranging from room temperature to reflux and for a period of time ranging from 1 hour to about 48 hours. When $E^2$ is —$(CH_2)_{1-3}$—Y, and Y is an azide group, the reduction reaction involves also this group.

According to step 21a of the process, a compound of formula (XXII) wherein Y is an azide group can undergo reduction and cyclization to give a compound of formula (XXIII) in a variety of ways well known in the art as Staudinger reaction. The said reaction is performed by using a trialkyl or triaryl phosphine in a suitable solvent such as THF at room temperature for 1 to about 4 hours.

According to step 22 of the process, optionally a compound of formula (XXIII) wherein A is —$(CH_2)_{1-3}$—$NH_2$ is transformed into a compound of formula (XXIII) wherein A is —$(CH_2)_{1-3}$—NHpg, in a variety of ways well known to those skilled in the art as introduction of a nitrogen protecting group. When the protecting group is the tert-butoxycarbonyl the reaction may be carried out in the presence of di-tert-butyl-dicarbonate in different solvents such as methanol, ethanol, acetonitrile, THF, dichloromethane, in the presence of a base such as pyridine, triethylamine, DIPEA, sodium or potassium carbonate, at room temperature for a period of time ranging from 1 to about 18 hours.

According to step 23a and b of the process, the transformation of a compound of formula (XXIII) into a compound of formula (I) can be carried out in different ways and experimental conditions. Preferably it is carried out in a way analogous to that reported for step 5a and 5b.

According to step 24 of the process, the compound of formula (XXV) can be prepared under different ways and conditions well known to the person skilled in the art as the nitroaldol reaction or known as Henry reaction. The said reaction is a classical aldol-type reaction between an aldehyde and a nitroalkane (Rosini, G. In Comprehensive organic Synthesis; Trost, B. M., 1996. Vol 2, pp 321-340). Conveniently, the reaction is performed by mixing the aldehyde of formula (XXIV) with nitromethane, in the presence of a suitable base such as sodium or potassium tert-butoxyde, sodium or potassium hydroxide, ammonium acetate, ammonium hydroxide. Convenient solvents include solvents such as THF, diethylether, 1,4-dioxane, methanol, ethanol and the like, at temperature ranging from 0° C. to room temperature, for a period of time varying from 2 hours to 18 hours.

According to step 25 of the process, the reduction of a compound of formula (XXV) to obtain a compound of formula (XXVI) can be accomplished in different ways and conditions widely known in the art to reduce a nitro to an amino group. Preferably the reaction is performed in a suitable solvent such as water, methanol, THF, 1,4-dioxane, DMF or a mixture thereof, in the presence of a suitable reducing agent, such as, for instance, hydrogen, and hydrogenation catalyst, or by treatment with cyclohexene or 1,4-cyclohexadiene and a hydrogenation catalyst, or by treatment with tin(II) chloride, or by treatment with zinc and aqueous hydrochloric acid or acetic acid or ammonium chloride, at temperature ranging from 0° C. to reflux for a time varying from about 1 hour to 48 hours. The hydrogenation catalyst is usually a metal, most often palladium, which can be used as such or supported on carbon.

According to step 26 of the process, the protection of the amino group can be accomplished in a variety of ways and experimental conditions well known in the art. Preferably the reaction can be accomplished by reductive amination, or by alkylation. The compound of formula (XXVI) is reacted with benzaldehyde, 4-methoxy or 2,4-dimethoxy, or 3,4,5-trimethoxy-benzaldehyde, in a suitable solvent such as THF, 1,4-dioxane, DCM, DMF, in the presence of a reducing agent such as sodium cyanoborohydride, sodium triacetoxyborohydride, tetramethylammonium triacetoxyborohydride, optionally in the presence of protic acid, such as hydrochloric, acetic, trifluoroacetic, at a temperature ranging from 0° C. to room temperature. Alternatively, the conversion can be accomplished by using the suitable benzyl or substituted benzyl bromide or chloride or trityl chloride in the presence of a suitable base such as, for instance, sodium, potassium or cesium carbonate, TEA, DIPEA, pyridine and the like, at a temperature ranging from 0° C. to reflux.

According to step 27 of the process, the conversion of the compound of formula (XXVIa) into the corresponding amido derivative of formula (XXVIII), can be carried out in a variety of ways according to conventional methods for obtaining amido derivatives from the corresponding α,α,α-trichloroketones. Preferably the reaction is carried out by reaction of an amine of formula (XXVIa) with a trichloroketone derivative of formula (XXVII) in the presence of N,N-diisopropylethylamine, using dichloromethane as the solvent, for a time varying from about 2 hours to 48 hours.

According to step 28 of the process, the conversion of the compound of formula (XXVIII) into the corresponding compound of formula (XXIX), can be accomplished in different ways and conditions widely known in the art. A typical procedure involves 2 steps encompassing alcohol activation, and intramolecular nucleophilic displacement, that brought to the formation of the pyrazinone ring. First reaction is preferably carried out by dissolving the compound of formula (XXVIII) in a suitable solvent for instance THF, DCM, DMF or the like, in the presence of a suitable base such as triethylamine or diisopropylethylamine, the sulphonylating agent such as methanesulfonyl chloride, is added therein. The mixture is stirred for a period of time of about 1 hour to about 6 hours, at a temperature ranging from about 0° C. to room temperature. Alternatively, the alcohol activation can be performed with a suitable halogenating system such as $I_2/Ph_3P$ or $CBr_3$ with imidazole in a suitable solvent such as, for instance, dichloromethane, THF, acetonitrile and the like, at a temperature ranging from 0° C. to reflux.

In the second reaction of the sequence, the obtained compound is reacted in a suitable solvent for instance THF, DCM, DMF or the like, in the presence of a base such as triethylamine, diisopropylethylamine or DBU, at a temperature ranging from about room temperature to reflux, for a period of time varying from about 2 hours to about 24 hours.

According to step 29 of the process, the transformation of a compound of formula (XXIX) into a compound of formula (XXIXa) is accomplished by deprotection of the nitrogen atom according to conventional methods enabling the selective hydrolysis of, benzyl, 4-methoxybenzyl, 2,4-dimethoxybenzyl, and triphenylmethyl protective groups. Preferably this reaction is run under acidic conditions, for instance in the presence of an inorganic or organic acid such as hydrochloric, trifluoroacetic or methansulfonic acid, in a suitable solvent such as DCM, 1,4-dioxane, a lower alcohol, such as methanol or ethanol, at a temperature ranging from room temperature to reflux and for a period of time ranging from about 1 hour to about 48 hours.

According to step 30a and b of the process, the transformation of a compound of formula (XXIXa) into a compound of formula (I) can be carried out in different ways and experimental conditions. Preferably it is carried out in a way analogous to that reported for step 5a and 5b.

According to conversion (conv. a)

of the process, the conversion of the compound of formula (I) where a group —$CH_2OH$ is present, into the corresponding compound of formula (I) with a group —$CH_2NR'R1$ wherein R1 is as above and R' is as defined above, can be accomplished in a number of ways and operative conditions well established among those skilled in the art. Just as an example a two-steps sequence involving at the first the formation of an aldehyde which is afterwards reacted under reductive amination conditions with amine of formula R1R'NH(XXX), is reported here. Accordingly the compound of formula (I) with a group —$CH_2OH$ is at first converted into the corresponding aldehyde by treatment with an oxidant agent such as for instance 2-Iodoxybenzoic acid (IBX) in a suitable solvent such as ethyl acetate, tetrahydrofuran, and the like, at a temperature ranging from 50° C. to reflux for a suitable time for instance 30 minutes to 4 hours. The obtained aldehyde is afterwards reacted with a suitable amine of formula R1R'NH(XXX), in the presence of a reducing agent, such as for instance, sodium cyanoborohydride, sodium triacetoxyborohydryde, or tetramethylammonium triacetoxyborohydride in a suitable solvent such as tetrahydrofuran, 1,4-dioxane, N,N-dimethylformamide, or mixtures thereof, at a temperature ranging between 0° C. and room temperature, for 30 minutes to 6 hours.

According to conversion (conv. b)

of the process, the conversion of the compound of formula (I) where a group —$CH_2OH$ is present, into the corresponding compound of formula (I) with a group —$CH_2NR'R1$ wherein R1 is as defined above and R' is hydrogen, or a protecting group of formula —COOR6 wherein R6 is as defined above, can be accomplished in a number of ways and operative conditions well established among those skilled in the art. Typical procedures involve 2-3 steps encompassing alcohol activation, nucleophilic displacement, and manipulation of the post-nucleophile product to an amine. First reaction is preferably carried out by dissolving the compound of formula (I) wherein is present a group —$CH_2OH$, in a suitable solvent for instance THF, DCM, DMF or the like, in the presence of a suitable base such as triethylamine or diisopropylethylamine, the sulphonylating agent such as methanesulfonyl chloride, is added therein. The mixture is stirred for a time of about 1 hour to about 6 hours, at a temperature ranging from about 0° C. to room temperature. Second reaction of the sequence, the obtained compound is reacted with azide anion in a Sn2 reaction to give the alkyl azide. Preferably, the reaction is carried out with sodium azide, or azide exchange resin (Amberlite IR-400), in a suitable solvent such as acetonitrile, DMF, or a mixture thereof. The reaction is performed at a temperature ranging from RT to 80° C. for 2 to about 18 hours. Third step of the sequence is the reduction of the alkyl azide with reducing agents. The reduction of alkyl azides to primary amines constitutes a synthetically useful process and can be accomplished with a wide variety of reagents including catalytic hydrogenation, LAH, sodium or zinc borohydride, triphenylphosphine Indium-$NH_4Cl$, Iron-$NH_4Cl$ and Zinc-$NH_4Cl$. When the Staudinger reaction is performed, a trialkyl or triaryl phosphine is used in a suitable solvent such as THF at room temperature for 1 to about 4 hours. Therefore, the reaction will be diluted with water, optionally $(Boc)_2O$ anhydride is added to obtain the compound of formula (I) with a protecting group, and left on stirring for 18 hours to about 36 hours at the same temperature.

Optionally the reduction of the alkyl azide to primary amine can be accomplished with Zinc-$NH_4Cl$, conveniently $(Boc)_2O$ anhydride is added to obtain the compound of formula (I) with a protecting group. The reaction is performed at reflux in a mixture of solvent including 1,4-dioxane and water for 4 hours to about 8 hours.

According to conversion (conv. c)

of the process, the conversion of the compound of formula (I) where a group —$CH_2OH$ is present, into the corresponding compound of formula (I) with a group —$CH_2hal$ wherein hal is halogen, can be accomplished in different ways, according to conventional methods for the transformation of alcohols to alkyl halide derivatives. Activation of an alcohol towards nucleophilic displacement with halide ion can be achieved with a Mitsunobu-like procedure (Org. React. 1992, 42, 335) or in alternative by converting the alcohol to a sulfonate ester, commonly tosylate (p-toluenesulfonate), mesylate(methanesulfonate) or triflate (trifluoromethanesulfonate). As an example, the intermediate sulfonate may react further under the reaction conditions to generate the alkyl chloride directly (Tetrah. Lett. 1987, 28, 723). The reaction is preferably carried out by dissolving the compound of formula (I) in a suitable solvent for instance THF, DCM, DMF or the like, in the presence of a suitable base such as triethylamine or diisopropylethylamine the sulphonylating agent such as methanesulfonyl chloride, is added therein. The mixture is stirred for a time of about 1 hour to about 48 hours, at a temperature ranging from about 0° C. to room temperature.

According to conversion (conv. d)

of the process, the conversion of the compound of formula (I) where a group —$CH_2OH$ is present, into the corresponding compound of formula (I) with a group —$CH_2NR'R1$ wherein R1 and R' are hydrogen, can be accomplished in a number of ways and operative conditions well established among those skilled in the art, preferably it is carried out by using a modified Staudinger procedure, wherein primary alcohols undergo a one pot conversion into the corresponding primary amines via the intermediate azide obtained by a Mitsunobu-type reaction, a widely known reaction to convert alcohol into azide. Said reaction, which is well known in the art, can be accomplished using a dialkyl azodicarboxylate, such as diethylazodicarboxylate (DEAD), diisopropyl azodicarboxylate (DIAD) or the like, in the presence of a trialkyl or triaryl phosphine, preferably triphenyl phosphine in the presence of an azide ion source such as nicotinyl azide (NCA) or DPPA (diphenylphosphoryl azide). In alternative, the reaction can be performed with DPPA (diphenylphosphoryl azide) and DBU. The reaction is performed in a suitable solvent such as tetrahydrofuran, 1,4-dioxane, 1,2-dimethoxyethane, acetonitrile and the like at temperature ranging from 0° C. to RT and for a time ranging from 30 minutes to about 48 hours. Therefore the Staudinger reaction is performed, a trialkyl or triaryl phosphine is used in a suitable solvent such as THF at room temperature for 1 to about 4 hours, followed by hydrolysis with addition of water, optionally (Boc)$_2$O anhydride is added to obtain the compound of formula (I) with a protecting group, and left on stirring for 18 to about 36 hours at the same temperature.

According to conversion (conv. e) of the process, a compound of the formula (I) wherein R3 or R4 is hydrogen is converted into the corresponding compound of formula (I) wherein R3 or R4 is halogen. The said reaction is performed with halogenating reagent such as NCS, NBS, NIS, in a suitable solvent such as DCM, THF, MeOH, DMF or a mixture thereof, from –0° C. to room temperature within 2 to about 18 hours. Preferably, the reaction is carried out under neutral conditions in the presence of iodine and silver trifluoroacetate, in DCM at a temperature ranging from 0° C. to room temperature and for a time from 2 hours to overnight.

According to conversion (conv. f) of the process, a compound of formula (I) wherein R3 or R4 is Br or iodine is converted into the corresponding compound of formula (I) wherein R3 or R4 is CN, following the condition well known for palladium-catalyzed cyanation of aryl halides. The said reaction is performed by using ZnCN or potassium hexacyanoferrate$^{(II)}$ as a source of cyanide in the presence of palladium$^{(II)}$ acetate as catalyst, sodium carbonate, potassium carbonate or cesium carbonate as base, in a suitable solvent such as DMF, N-methylpyrrolidone, or DMA, from 80° C. to reflux, for a time ranging from 4 to about 24 hours (*J. Org. Chem.* 2005, 70, 1508-1510, *Org. Lett.,* 2011, 13 (4), pp 648-651).

According to conversion (conv. q) of the process, a compound of the formula (I) wherein R3 or R4 is halogen is converted into the corresponding compound of formula (I) wherein R3 or R4 is an optionally substituted group selected from straight or branched $C_1$-$C_6$ alkyl, $C_3$-$C_7$ cycloalkyl, cycloalkyl-alkyl, aryl, arylalkyl, heterocyclyl and heterocyclylalkyl, by exploiting any of the cross-coupling reactions suitable for the formation of carbon-carbon bonds. Said reactions, which are well known in the art, imply coupling with a suitable organometal reagent such as for instance organoboron (Suzuki reaction), organotin (Stille reaction), organomagnesium (Kumada reaction), organozinc, or organoalluminium, or organozirconium (Negishi reaction) and the like. Preferred reaction is the Suzuki reaction where the appropriate organoboron derivative is used in the presence of a palladium based catalyst such as PdCl$_2$(dppf)$_2$CH$_2$Cl$_2$ and a base such as sodium or potassium or cesium carbonate, in a mixture of solvents, such as dimethoxyethane or 1,4-dioxane and water, at a temperature varying from room temperature to 80° C. and for a time between 2 hours to overnight.

According to conversion (conv. h) of the process, a compound of formula (I) wherein R3 or R4 is halogen is converted into the corresponding compound of formula (I) wherein R3 or R4 is an alkyne by reaction with compound of formula (XIII). The reaction is carried out through the Sonogashira coupling to give the corresponding compound of formula (I) in the presence of suitable Pd-catalysts include Pd(PPh$_3$)$_4$, Pd(PPh$_3$)$_2$Cl$_2$, suitable ligands include tryphenylphosphine, and an additive such as copper (I) iodide, using N,N-dimethylformamide as the solvent, at a temperature varying from room temperature to reflux and for a time ranging between 4 hours and overnight.

According to conversion (conv. i) of the process, deprotection of the carboxylic residue into the corresponding acid can be achieved through basic or acidic hydrolysis conditions, widely known in the art. Preferably, the reaction is carried out with aqueous alkaline solutions such as aqueous lithium, sodium or potassium hydroxide in the presence of a suitable solvent such as a lower alcohol, THF, DMF or mixtures thereof; preferably the reaction is carried out with lithium hydroxide in THF/Methanol/water mixture, at a temperature ranging from about room temperature to about 80° C. According to the operative conditions being employed, the compound of formula (I) could be obtained either in its acidic form or, alternatively, as a salt.

According to conversion (conv. j) of the process, the amidation of a carboxylic acid into the corresponding amide is carried out in the presence of ammonium chloride or a suitable primary or secondary amine of formula R1R'NH (XXX) under basic conditions, preferably with DIPEA or TEA, in a proper solvent such as dichloromethane, DMF, THF, 1,4-dioxane, or DMA, in the presence of a suitable condensing agent, for instance dicyclohexylcarbodiimide (DCC), 1-ethyl-3-(3'-dimethylaminopropyl)carbodiimide (EDC), 3,4-dihydro-3-hydroxy-4-oxo-1,2,3-benzotriazine (DHBT), O-benzotriazolyltetramethylisouronium tetrafluoroborate (TBTU), benzotriazol-1-yloxytripyrrolidinophosphonium hexafluorophosphate (PyBOP), or 2-(1H-Benzotriazole-1-yl)-1,1,3,3-tetramethyluronium hexafluorophosphate (HBTU). The said reaction is optionally carried out in the presence of a suitable catalyst such as the 4-dimethylaminopyridine, or in the presence of a further coupling reagent such as N-hydroxybenzotriazole. Alternatively, this same reaction is also carried out, for example through a mixed anhydride method, which involves the use of an alkyl chloroformiate such as ethyl, iso-propyl, benzyl chloroformiate, in the presence of a tertiary amine such as TEA, DIPEA, or pyridine, in a suitable solvent such as, for instance toluene, DCM, THF, DMF and the like, at room temperature.

According to conversion (conv. k) of the process, the reductive amination of a compound of formula (I) where a group L-CHO is present, to give the corresponding compound where is present a group L-CH$_2$NR'R1, is carried out by reaction with a suitable amine of formula R1R'NH(XXX), according to conventional methods for carrying out reductive amination. Preferably this reaction is performed with a reducing agent, such as for instance, sodium cyanoborohydride, sodium triacetoxyborohydryde, or tetramethylamonium triacetoxyborohydride in presence of an acid or basic catalyst, such as for instance acetic acid, trifluoroacetic acid, zinc chloride, titanium(IV) chloride or TEA, DIPEA in a suitable solvent such as tetrahydrofuran, 1,4-dioxane, N,N-dimethylformamide, or mixtures thereof, at a temperature ranging between 0° C. and room temperature, for 30 minutes to 6 hours.

According to conversion (conv. l) of the process, a compound of formula (I) wherein a primary or secondary amino group is present, is transformed into the corresponding secondary or tertiary amino derivative. Preferably, the reaction is carried out with an aldehyde of formula R'CHO (XXXIII), under reductive amination conditions, preferably with reducing agent, such as for instance, sodium cyanoborohydride, sodium triacetoxyborohydryde, or tetramethylamonium triacetoxyborohydride in presence of acid or basic catalyst, such as for instance acetic acid, trifluoroacetic acid, zinc chloride, titanium(IV) chloride or TEA, DIPEA, in a suitable solvent such as tetrahydrofuran, 1,4-dioxane, N,N-dimethylformamide, or mixtures thereof, at a temperature ranging between 0° C. and room temperature, for 30 minutes to 6 hours.

According to conversion (conv. m) of the process, a compound of formula (I) wherein a primary or secondary amino group is present, is transformed into the corresponding carboxamide derivative, by reaction with a compound of formula R5-COW (XXXIV). It is clear to the skilled person that this reaction can be accomplished in a variety of ways and operative conditions, which are widely known in the art for the preparation of carboxamides. As an example, when W is an halogen such as chloride, the reaction is performed in a suitable solvent such as for instance, dichloromethane, tetrahydrofuran, 1,4-dioxane, acetonitrile, or N,N-dimethylformamide or the like at a temperature ranging from about −10° C. to reflux and for a suitable time, for instance from about 30 minutes to about 96 hours. The reaction is carried out in the presence of an opportue proton scavenger such as triethylamine, N,N-diisopropylethylamine or pyridine. When W is an hydroxyl group, the reaction is carried out in the presence of a coupling agent such as, for instance, 2-(1H-benzotriazol-1-yl)-1,1,3,3-tetramethyluronium tetrafluoroborate (TBTU), 1,3-dicyclohexylcarbodiimide, 1,3-diisopropylcarbodiimide, 1-(3-dimethylaminopropyl)-3-ethylcarbodiimide, N-cyclohexylcarbodiimide-N'-propylmethyl polystyrene or N-cyclohexylcarbodiimide-N'-methyl polystyrene, in a suitable solvent such as, for instance, dichloromethane, tetrahydrofuran, 1,4-dioxane, acetonitrile, N,N-dimethylformamide at a temperature ranging from about −10° C. to reflux and for a suitable time, for instance from about 30 minutes to about 48 hours. The said reaction is optionally carried out in the presence of a suitable catalyst, for instance 4-dimethylaminopyridine, or in the presence of a further coupling agent such as N-hydroxybenzotriazole.

According to conversion (conv. n)

of the process, a compound of formula (I) wherein a primary or secondary amino group is present, is transformed into the corresponding carbamate derivative, by reaction with a compound of formula R6-OCO-T (XXXVI). It is clear to the skilled person that this reaction can be accomplished in a variety of ways and operative conditions, which are widely known in the art for the preparation of carboxamides. As an example, when T is an halogen such as chloride, the reaction is performed in a suitable solvent such as for instance, dichloromethane, tetrahydrofuran, 1,4-dioxane, acetonitrile, or N,N-dimethylformamide or the like at a temperature ranging from about −10° C. to reflux and for a suitable time, for instance from about 30 minutes to about 96 hours. The reaction is carried out in the presence of an opportue proton scavenger such as triethylamine, N,N-diisopropylethylamine or pyridine. Alternatively, this same reaction is also carried out, with an anhydride of formula R6-OCO-T (XXXVI) wherein T is a leaving group such as —OC(O)OR6, in the presence of a tertiary amine such as TEA, DIPEA, or pyridine, in a suitable solvent such as, for instance toluene, DCM, THF, DMF and the like, at a room temperature.

According to conversion (conv. o)

of the process, a compound of formula (I) wherein a primary or secondary amino group is present, is transformed by reaction with an appropriate isocyanate of formula R7-N=C=O (XXXVII) to yield the corresponding urea. The reaction is preferably carried out in as suitable solvent such as dichloromethane, tetrahydrofuran or the like, at a temperature ranging from about 20° C. to reflux and for a time varying from about 30 minutes to about 48 hours.

According to conversion (conv. p)

of the process, a compound of formula (I) wherein a primary or secondary amino group is present, is transformed into the corresponding guanidine derivative by reaction with a compound of formula R7N(R8)C(NH)T (XXXVIII) wherein R7 and R8 are as defined above and T is a suitable leaving group such as —S-Me, —N—S(O)$_2$CF$_3$, or 1H-pyrazolyl. As an example, this reaction may be carried out under basic conditions, for instance in the presence of triethylamine, or potassium carbonate, in a suitable solvent such as methanol, ethanol, N,N-dimethylformamide, and a mixtures thereof. Preferentially, the reaction is carried out at a temperature ranging from room temperature to about 80° C. and for a time varying from about 30 minutes to about 24 hours.

According to conversion (conv. q)

of the process, a compound of formula (I) wherein a primary or secondary amino group is present, is converted into a compound of formula (I) wherein is present a group of formula —NS(O)$_2$R9, wherein R9 is as defined above. The said conversion is obtained by reaction with sulfonyl compounds such as sulfonyl halides, preferably chloro or bromo, in a suitable solvent, such as DCM, at a temperature between about RT to about the reflux temperature of the solvent, in the presence of a suitable base, such as TEA, DIEA, DMAP.

According to conversion (conv. r)

of the process, the deprotection of the nitrogen atom of a compound of formula (I) wherein R' is a protecting group, can be accomplished according to conventional methods enabling the selective hydrolysis of tert-butoxycarbonyl, benzyl, 4-methoxybenzyl, 2,4-dimethoxybenzyl, and triphenylmethyl protective groups. Preferably this reaction is run under acidic conditions, for instance in the presence of an inorganic or organic acid such as hydrochloric, trifluoroacetic or methansulfonic acid, in a suitable solvent such as DCM, 1,4-dioxane, a lower alcohol, such as methanol or ethanol, at a temperature ranging from room temperature to reflux and for a period of time ranging from about 1 hour to about 48 hours.

From all of the above it is clear to the skilled person that any compound of the formula (I) bearing a functional group which can be further derivatized to another functional group, by working according to methods well known in the art thus leading to other compounds of the formula (I), is intended to be comprised within the scope of the present invention.

It is known to the skilled person that conversion of a chemical function into another may require that one or more reactive centers in the compound containing this function be protected, in order to avoid undesired side reactions. Protection of such reactive centers, and subsequent deprotection at the end of the synthetic transformations, can be accomplished following standard procedures described, for instance, in: Green, Theodora W. and Wuts, Peter G. M.—Protective Groups in Organic Synthesis, Third Edition, John Wiley & Sons Inc., New York (NY), 1999.

According to any variant of the process for preparing the compounds of the formula (I), the starting materials and any other reactants are known or easily prepared according to known methods.

The compounds of the formula (II) and (XXVII) can be prepared as described in WO2010/031816.

The compounds of the formula (XII), (XIIa), (XIII), (XIV), (XV), (XVIII), (XXV), and (XXX) to (XXXIX) are either commercially available or can be prepared with known methods.

From all of the above, it is clear to the skilled person that when preparing the compounds of the formula (I) according to any one of the aforementioned process variants, optional functional groups within the starting materials or the intermediates thereof that could give rise to unwanted side reactions, need to be properly protected according to conventional techniques. Likewise, the conversion of these latter into the free deprotected compounds may be carried out according to known procedures.

As it will be readily appreciated, if the compounds of the formula (I) prepared according to the process described above are obtained as mixture of isomers, their separation using conventional techniques into the single isomers of the formula (I), is within the scope of the present invention.

Conventional techniques for racemate resolution include, for instance, partitioned crystallization of diastereoisomeric salt derivatives or preparative chiral HPLC.

The compounds of the present invention can be administered either as single agents or, alternatively, in combination with known anticancer treatments such as radiation therapy or chemotherapy regimen in combination with cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), matrixmetalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

If formulated as a fixed dose, such combination products employ the compounds of this invention within the dosage range described below and the other pharmaceutically active agent within the approved dosage range.

Compounds of the formula (I) may be used sequentially with known anticancer agents when a combination formulation is inappropriate.

The compounds of the formula (I) of the present invention, suitable for administration to a mammal, e.g., to humans, can be administered by the usual routes and the dosage level depends upon the age, weight, conditions of the patient and administration route.

For example, a suitable dosage adopted for oral administration of a compound of the formula (I) may range from about 10 to about 1000 mg per dose, from 1 to 5 times daily. The compounds of the invention can be administered in a variety of dosage forms, e.g., orally, in the form tablets, capsules, sugar or film coated tablets, liquid solutions or suspensions; rectally in the form suppositories; parenterally, e.g., intramuscularly, or through intravenous and/or intrathecal and/or intraspinal injection or infusion.

The present invention also includes pharmaceutical compositions comprising a compound of the formula (I) or a pharmaceutically acceptable salt thereof in association with a pharmaceutically acceptable excipient, which may be a carrier or a diluent.

The pharmaceutical compositions containing the compounds of the invention are usually prepared following conventional methods and are administered in a suitable pharmaceutical form. For example, the solid oral forms may contain, together with the active compound, diluents, e.g., lactose, dextrose saccharose, sucrose, cellulose, corn starch or potato starch; lubricants, e.g., silica, talc, stearic acid, magnesium or calcium stearate, and/or polyethylene glycols; binding agents, e.g., starches, arabic gum, gelatine methylcellulose, carboxymethylcellulose or polyvinyl pyrrolidone; disintegrating agents, e.g., starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. These pharmaceutical preparations may be manufactured in known manner, for example, by means of mixing, granulating, tabletting, sugar-coating, or film-coating processes.

The liquid dispersions for oral administration may be, e.g., syrups, emulsions and suspensions. As an example, the syrups may contain, as carrier, saccharose or saccharose with glycerine and/or mannitol and sorbitol.

The suspensions and the emulsions may contain, as examples of carriers, natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g., sterile water, olive oil, ethyl oleate, glycols, e.g., propylene glycol and, if desired, a suitable amount of lidocaine hydrochloride.

The solutions for intravenous injections or infusions may contain, as a carrier, sterile water or preferably they may be in the form of sterile, aqueous, isotonic, saline solutions or they may contain propylene glycol as a carrier.

The suppositories may contain, together with the active compound, a pharmaceutically acceptable carrier, e.g., cocoa butter, polyethylene glycol, a polyoxyethylene sorbitan fatty acid ester surfactant or lecithin.

With the aim of better illustrating the present invention, without posing any limitation to it, the following examples are now given.

EXAMPLES

The synthetic preparation of some compounds of the formula (I) of the invention is described in the following examples.

The compounds of the present invention, as prepared according to the following examples, were also characterized by $^1$H NMR or by HPLC/MS analytical data; HPLC/MS data were collected following any one of methods 1, 2, 3 and 4.

HPLC MS Analytic Method 1

The HPLC equipment consisted of a Waters Acquity™ UPLC system equipped with a Waters 2996 PDA detector, a Waters Acquity ELSD™ detector and Waters mod. SQD single quadrupole mass spectrometer, equipped with an electrospray (ESI) ion source. Instrument control, data acquisition and data processing were provided by Empower 2 and MassLynx 4.1 softwares.

HPLC was carried out at 45° C. at a flow rate of 0.7 mL/min using a Waters Acquity™ BEH C18, 1.7 µm, 50×2.1 mm column. Mobile phase A was 0.1% trifluoro acetic acid in water/acetonitrile (95:5), and mobile phase B was $H_2O$/acetonitrile (5:95); the gradient was from 5 to 95% B in 2 minutes then hold 95% B 0.1 minutes. The injection volume was 0.8 µL. The mass spectrometer was operated in positive and in negative ion mode, the capillary voltage was set up at 3 KV (ES$^+$ and ES$^-$); cone was 30 V (ES$^+$ and ES$^-$); the source temperature was 120° C.; full scan, mass range from 100 to 800 amu was set up.

HPLC/MS Analytic Method 2

HPLC-MS analyses were performed on a Finnigan MAT mod. LCQ ion trap mass spectrometer, equipped with an ESI (Electrospray) ion source, the mass spectrometer is directly connected to a HPLC SSP4000 (Thermo Separation) equipped with an autosampler Lc Pal (CTC Analytics) and an UV6000LP PDA detector.

HPLC was carried out at 40° C. at a flow rate of 1.0 mL/min using a Phenomenex Gemini C18, 3 µm, 50×4.6 mm column. Mobile phase A was Acetate Buffer 5 mM pH 4.5: acetonitrile 95:5 (v:v), and mobile phase B was Acetate Buffer 5 mM pH 4.5: acetonitrile 5:95 (v:v) the gradient was from 0 to 100% B in 7 minutes then hold 100% B for 2 minutes before requilibration. Total LC time was 10 minutes. The injection volume was 10 µl.

MS conditions: the LCQ mass spectrometer operates with an electrospray ionization (ESI) interface in positive and negative ion mode. ESI sprayer voltage 4.0 kV, heated capillary temperature 255° C., sheath gas nitrogen with a pressure of 5.0 Bar. A full scan detection mode (from 50 to 1000 amu) was used.

MS/MS experiments were performed on the most intense ion of each scan automatically by Excalibur software. 45% collision energy was used for the fragmentation of the precursor ions.

HPLC/MS Analytic Method 3

The HPLC equipment consisted of a Waters Alliance™ HT 2795 system equipped with a Waters 2996 PDA detector and Waters mod. ZQ 2000 single quadrupole mass spectrometer, equipped with an electrospray (ESI) ion source. Instrument control, data acquisition and data processing were provided by Empower 2 and MassLynx 4.1 softwares. HPLC was carried out at 25° C. at a flow rate of 1.0 mL/min using a Phenomenex Gemini C18, 3 µm, 50×4.6 mm column. Mobile phase A was ammonium acetate 5 mM pH=5.2 buffer with acetonitrile (95:5), and mobile phase B was $H_2O$/acetonitrile (5:95); the gradient was from 10 to 90% B in 8 minutes then ramp to 100% B in 0.1 minutes. The injection volume was 10 µL. The mass spectrometer was operated in positive and in negative ion mode, the capillary voltage was set up at 3.5 kV ($ES^+$) and 2.8 kV ($ES^-$); cone voltage was 14 V ($ES^+$) and 28 V ($ES^-$); the source temperature was 120° C.; full scan, mass range from 100 to 800 amu was set up.

HPLC/MS Analytical Method 4

The HPLC equipment consisted of a Waters Alliance™ HT 2795 system equipped with a Waters 2996 PDA detector and Waters mod. ZQ 2000 single quadrupole mass spectrometer, equipped with an electrospray (ESI) ion source. Instrument control, data acquisition and data processing were provided by Empower 2 and MassLynx 4.1 softwares. HPLC was carried out at 25° C. at a flow rate of 1.2 mL/min using a Waters X-Terra RP18, 3.5 µm, 20×3.0 mm column. Mobile phase A was ammonium hydroxide 0.05% pH=10 buffer with acetonitrile (95:5), and mobile phase B was $H_2O$/acetonitrile (5:95); the gradient was from 10 to 90% B in 4 minutes then ramp to 100% B in 0.1 minutes. The injection volume was 10 µL. The mass spectrometer was operated in positive and in negative ion mode, the capillary voltage was set up at 3.5 kV ($ES^+$) and 2.8 kV ($ES^-$); cone voltage was 14 V ($ES^+$) and 28 V ($ES^-$); the source temperature was 120° C.; full scan, mass range from 100 to 800 amu was set up.

HPLC/MS Analytical Method 5

A Waters Alliance LC mod. 2795 equipped with a variable UV detector mod 2487, a Chemiluminescence Nitrogen detector (CLND, Antek 8060) and a Waters ZQ2000 mass detector (ESI interface) was used in this application. The total flow was splitted and distributed to the three detectors at a fixed ratio (64:15:21 UV:MS:CLND). The liquid chromatograph was equipped with a 30×3.0 mm I.D. column (Waters xBridge C18, 3.5 um particles), thermostated at 50° C. Two mobile phases were used: phase A was 0.05% w/v formic acid (1 mL/L of 50% formic acid Fluka 09676 in highly purified water) and phase B was 70/25/5 (v/v/v) MeOH/iPrOH/$H_2O$ containing 0.035% w/v of formic acid (700 uL/L of 50% formic acid Fluka 09676).

A 5 uL volume of 1 mM nominal sample solution in DMSO was injected (sequential, partial loop mode with no air gaps) and a generic reversed phase gradient analysis (classified as method "#1N63SEQ79") was carried out at 0.8 mL/min from 0% to 100% of phase B (v/v) over 5 min, held 0.7 min at 100% B and steeply reverted to 0% B at 5.71 min, with the run stop time set at 6.3 min. The total analysis time ("between injections") was 7.9 min.

The UV detector was operated at 220 nm, 5 Hz sampling rate. The MS device was operated at 3.2 kV capillary voltage, 30 V cone, 2 V extractor, 0.5 V RF lens, 400 L/hr desolvation flow, 100 L/hr cone flow, 100° C. source temperature, 150° C. desolvation temperature, ESI(+) full scan 120-1200 amu acquisition, at 1.7 Hz sampling rate. The CLND detector was operated at 1050° C. furnace temp, 280 mL/min inlet oxygen flow, 80 mL/min inlet argon, 25 mL/min make-up argon, 30 mL/min ozone, 28 torr vacuum, 750 V PMT voltage, PMT chamber at +10° C., sensitivity high, select 5, 4 Hz sampling rate.

Several compounds of the invention of the formula (I), as prepared according to the following examples, were purified by preparative HPLC. The operative conditions are defined below:

HPLC/MS Preparative Method 1

The HPLC equipment consisted of a Waters FractionLynx™ system equipped with a Waters 2996 PDA detector and Waters mod. ZQ 2000 single quadrupole mass spectrometer, equipped with an electrospray (ESI) ion source. Instrument control, data acquisition and data processing were provided by MassLynx 4.1 software.

HPLC was carried out at 25° C. at a flow rate of 20 mL/min using a Waters X-Terra Prep RP18, 10 µm, 250×19 mm column. Mobile phase A was 0.1% trifluoro acetic acid in water/acetonitrile (95:5), and mobile phase B was acetonitrile; the gradient was from 10 to 90% B in 15 minutes then c. The injection volume was 500 µL.

The mass spectrometer was operated in positive and in negative ion mode, the capillary voltage was set up at 3.25 kV ($ES^+$) and 2.75 kV ($ES^-$); cone voltage was 18 V ($ES^+$) and 25 V ($ES^-$); the source temperature was 120° C.; full scan, mass range from 100 to 800 amu was set up.

HPLC preparative Method 2

The HPLC equipment consisted of a Shimadzu HPLC system equipped with SCL-8A System Controller, two LC-8A Pumps, SPD-6A UV Spectrophotometric Detector and manual Rheodyne injection system. Data acquisition (analogic signal) and data processing were provided by Empower 2 software.

HPLC was carried out at 25° C. at a flow rate of 40 mL/min using a Waters X-Terra MS RP18, 10 µm, 150×30 mm column. Mobile phase A was 0.1% trifluoro acetic acid in water/acetonitrile (95:5), and mobile phase B was $H_2O$/acetonitrile (5:95); the gradient was from 10 to 90% B in 15 minutes then ramp to 100% B in 0.1 minutes. The injection volume was 500 µL.

MS Exact

Exact mass data ESI(+) were obtained on a Waters Q-T of Ultima directly connected with micro HPLC 1100 Agilent as previously described (M. Colombo, F. Riccardi-Sirtori, V. Rizzo, *Rapid Commun. Mass Spectrom.* 2004, 18, 511-517).

$^1$H-NMR spectrometry was performed on a Bruker AVANCE 400 MHz single bay instrument with gradients. It was equipped with a QNP probe (interchangeable 4 nuclei probe—$^1$H, $^{13}$C, $^{19}$F and $^{31}$P) (NMR method 1) or on a Mercury VX 400 operating at 400.45 MHz equipped with a 5 mm double resonance probe 5 mm $^1$H{$^{15}$N—$^{31}$P}z-axis-PFG indirect detection probe.

¹H-NMR spectrometry was performed on a Varian INOVA 599.88 MHz equipped with a ¹H, ¹⁹F z-axis-PFG probe.

Preparation A 4-(2-hydroxyethyl)-7-iodo-3,4-dihydropyrrolo[1,2-a]pyrazin-1(2H)-one [III]

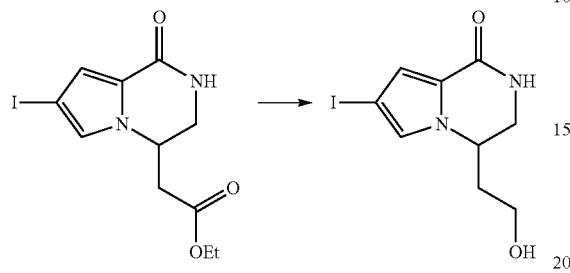

Sodium borohydride (0.870 g, 23.0 mmol) was added to an ice-cooled stirred solution of ethyl(7-iodo-1-oxo-1,2,3,4-tetrahydropyrrolo[1,2-a]pyrazin-4-yl)acetate (1.00 g, 2.87 mmol) in EtOH (30 mL), under $N_2$. The reaction mixture was stirred at room temperature for 18 h, and then it was quenched by water addition (10 ml). The solvent was evaporated to dryness and the residue dissolved in THF (30 ml)/brine (30 ml) and extracted with THF (3×30 mL). The organic phase was dried over $Na_2SO_4$ and concentrated to dryness to give the title compound (0.878 g, 2.87 mmol, 100%) as a solid.

¹H NMR (600 MHz, DMSO-d6) δ 7.69 (br. s., 1H), 7.17 (d, J=1.65 Hz, 1H), 6.70 (d, J=1.65 Hz, 1H), 4.70 (t, J=4.85 Hz, 1H), 4.35 (td, J=7.28, 3.57 Hz, 1H), 3.63 (ddd, J=13.05, 4.35, 1.65 Hz, 1H), 3.42-3.51 (m, 1H), 3.25-3.31 (m, 3H), 1.88 (dt, J=13.51, 6.52 Hz, 1H), 1.79 (dt, J=13.32, 6.80 Hz, 1H).

LCMS (HPLC Method 2): m/z 307 [M+H]⁺@r.t. 2.98 min.
HRMS (ESI) calcd for $C_9H_{12}IN_2O_2$[M+H]⁺ 306.9938 found 306.9945.

Preparation B 2-(7-iodo-1-oxo-1,2,3,4-tetrahydropyrrolo[1,2-a]pyrazin-4-yl)ethyl methanesulfonate [(IV), LG=methansulfonate]

Step 2

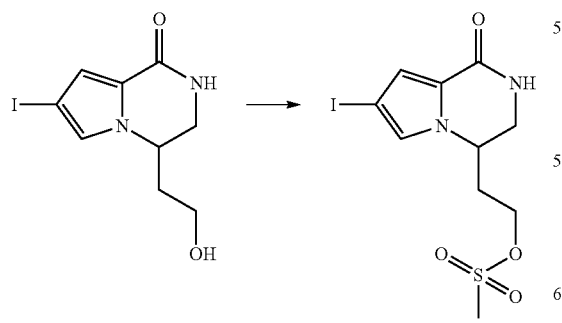

Mesyl chloride (0.172 g, 1.50 mmol) was added to an ice-cooled stirred solution of 4-(2-hydroxyethyl)-7-iodo-3,4-dihydropyrrolo[1,2-a]pyrazin-1(2H)-one (0.230 g, 0.75 mmol) and DIPEA (0.291 g, 2.25 mmol) in DCM (5 ml). The reaction mixture was stirred at room temperature under $N_2$ for 1 h and then it was portioned between DCM and saturated $NaHCO_3$ solution. The title compound was isolated by precipitation from the organic layer as a white solid (0.202 g, 0.52 mmol, 70%).

¹H NMR (600 MHz, DMSO-d6) δ 7.73 (d, J=2.75 Hz, 1H), 7.19-7.22 (m, 1H), 6.73 (d, J=1.65 Hz, 1H), 4.36-4.48 (m, 1H), 4.23-4.31 (m, 1H), 4.17 (ddd, J=5.59, 7.28, 10.58 Hz, 1H), 3.65 (dd, J=3.48, 13.92 Hz, 1H), 3.21 (s, 3H), 2.03-2.21 (m, 2H).

LCMS (HPLC Method 2): m/z 385 [M+H]⁺@r.t. 3.73 min.
HRMS (ESI) calcd for $C_{10}H_{14}IN_2O_4S$ [M+H]⁺ 384.9714 found 384.9715.

Preparation C 4-(2-azidoethyl)-7-iodo-3,4-dihydropyrrolo[1,2-a]pyrazin-1(2H)-one [V]

Step 3

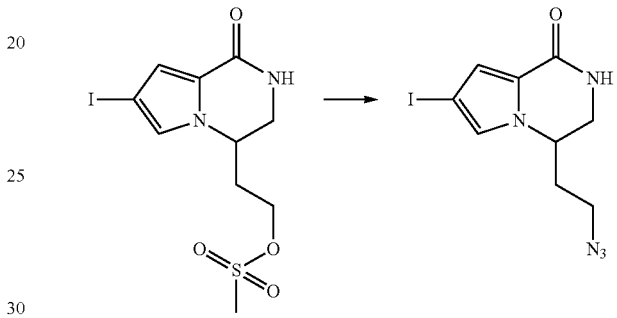

2-(7-iodo-1-oxo-1,2,3,4-tetrahydropyrrolo[1,2-a]pyrazin-4-yl)ethyl methanesulfonate (0.150 g, 0.39 mmol) was reacted with sodium azide (0.076 g, 1.17 mmol) in ACN/DMF (4 ml, 1:1 ratio) for 4 hours at 80° C. under $N_2$. The solvents were removed under vacuum, the residue was partitioned between water and DCM. The organic phase was dried ($Na_2SO_4$), filtered and evaporated, yielding the title compound as a white solid (0.097 g, 0.30 mmol, 75%).

¹H NMR (600 MHz, DMSO-d6) δ 7.72 (br. s., 1H), 7.20 (d, J=1.47 Hz, 1H), 6.72 (d, J=1.65 Hz, 1H), 4.34 (td, J=3.30, 6.96 Hz, 1H), 3.62 (dd, J=4.21, 13.37 Hz, 1H), 3.34 (m, 3H), 1.86-2.05 (m, 2H).

LCMS (HPLC Method 2): m/z 332 [M+H]⁺@r.t. 4.29 min.
HRMS (ESI) calcd for $C_9H_{11}IN_5O$ [M+H]⁺ 332.0003 found 332.0002.

Preparation D tert-butyl[2-(7-iodo-1-oxo-1,2,3,4-tetrahydropyrrolo[1,2-a]pyrazin-4-yl)ethyl]carbamate [VI, R1=H, R'=—CO—OtBu]

Step 4

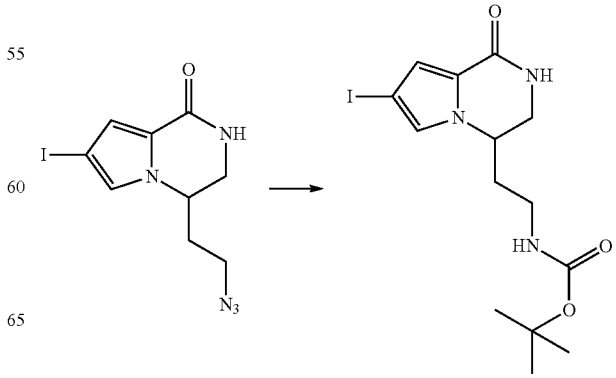

To a solution of 4-(2-azidoethyl)-7-iodo-3,4-dihydropyrrolo[1,2-a]pyrazin-1(2H)-one (0.093 g, 0.28 mmol) in ethanol 5 ml, NH$_4$Cl (0.059 g, 1.12 mmol), Zinc powder (0.073 g 1.12 mmol) and di-t-butyl dicarbonate (0.122 g, 0.560 mmol) were added. The mixture was stirred at 80° C. for 2 hours, the cooled mixture was filtered through a celite pad and the solvent evaporated to dryness. The residue was portioned between ethyl acetate and water, the organic phase was washed with water and brine, dried over Na$_2$SO$_4$, and concentrated. The crude material was purified by flash chromatography eluting with DCM/MeOH 9/0.5, to afford the desired product (0.068 g, 0.17 mmol, 60%).

$^1$H NMR (600 MHz, DMSO-d6) δ 7.69 (d, J=2.93 Hz, 1H), 7.24 (s, 1H), 6.92 (br. S., 1H), 6.70 (d, J=1.65 Hz, 1H), 4.25 (br. S., 1H), 3.62 (dd, J=2.84, 13.28 Hz, 1H), 3.27 (td, J=4.01, 13.05 Hz, 1H), 2.94 (q, J=6.65 Hz, 2H), 1.70-1.89 (m, 2H), 1.38 (s, 9H).

LCMS (HPLC Method 2): m/z 428 [M+Na]$^+$@r.t. 4.59 min.

HRMS (ESI) calcd for C$_{14}$H$_{20}$IN$_3$NaO$_3$ [M+Na]$^+$ 428.0441 found 428.0434.

Example 1 tert-butyl{2-[7-(3,4-difluorophenyl)-1-oxo-1,2,3,4-tetrahydropyrrolo[1,2-a]pyrazin-4-yl]
ethyl}carbamate [(I), R2=3,4-difluorophenyl,
R3=R4=H, A=—CH$_2$CH$_2$—NH—CO—OtBu]

Step 5a

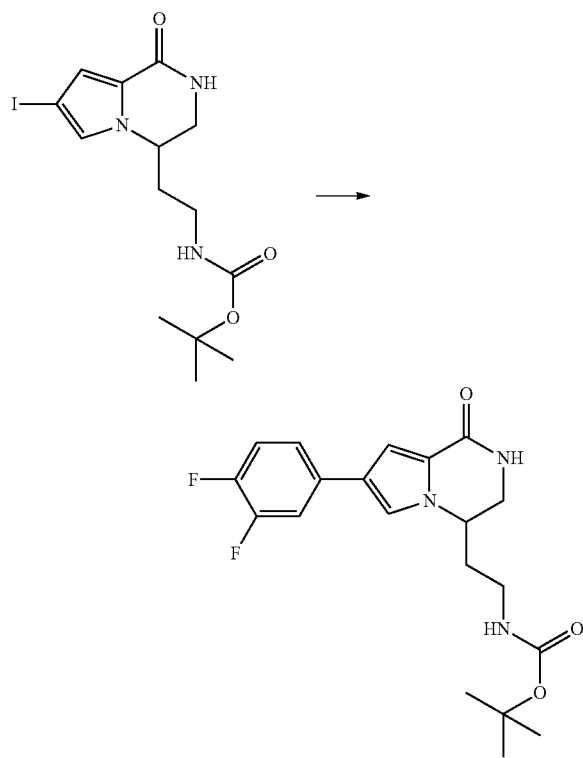

3,4-difluorophenylboronic acid (0.123 g, 0.78 mmol), cesium carbonate (0.546 g, 1.67 mmol) and 1,1'-bis(diphenylphosphino)ferrocenepaladium (0.023 g, 0.028 mmol) complex with dichloromethane, were subsequently added to a solution of tert-butyl[2-(7-iodo-1-oxo-1,2,3,4-tetrahydropyrrolo[1,2-a]pyrazin-4-yl)ethyl]carbamate (0.226 g, 0.558 mmol) in 3 ml of 1,4-dioxane and 1 ml of water, under N$_2$. The mixture was heated at 80° for 2 hours in a sealed vial. The reaction was filtered through a celite pad and the solvent evaporated to dryness. The crude was portioned between ethyl acetate and water, the organic layer dried over sodium sulphate and the solvent removed in vacuo. Purification by flash chromatography on silica gel column (DCM/MeOH 9/0.3) gave the title compound as a white solid (0.170 g, 0.43 mmol, 78%).

$^1$H NMR (600 MHz, DMSO-d6) δ 7.63-7.70 (m, 2H), 7.61 (s, 1H), 7.41-7.45 (m, 1H), 7.31-7.40 (m, 1H), 7.08 (d, J=1.83 Hz, 1H), 6.97 (t, J=5.68 Hz, 1H), 4.11-4.34 (m, J=4.03 Hz, 1H), 3.67 (ddd, J=1.01, 3.98, 12.77 Hz, 1H), 2.93-3.04 (m, 2H), 1.92 (qd, J=6.91, 13.90 Hz, 1H), 1.76-1.86 (m, 1H), 1.38 (s, 9H).

LCMS (HPLC Method 2): m/z 414 [M+Na]$^+$@r.t. 5.24 min.

HRMS (ESI) calcd for C$_{20}$H$_{23}$F$_2$N$_3$NaO$_3$ [M+Na]$^+$ 414.1599 found 414.1586.

According to the same method, but employing the appropriate boronic acid, the following compounds were prepared:

tert-butyl{2-[7-(3-meyhoxyphenyl)-1-oxo-1,2,3,4-tetrahydropyrrolo[1,2-a]pyrazin-4-yl]ethyl}carbamate [(I), R2=3-methoxyphenyl, R3=R4=H, A=—CH$_2$CH$_2$—NH—CO—OtBu]

The title compound was obtained as a white solid (49%).

LCMS (HPLC Method 3): m/z 386 [M+H]$^+$@r.t. 5.2 min.

tert-butyl{2-[7-(3-acetylphenyl)-1-oxo-1,2,3,4-tetrahydropyrrolo[1,2-a]pyrazin-4-yl]ethyl}carbamate [(I), R2=3-acetylphenyl, R3=R4=H, A=—CH$_2$CH$_2$—NH—CO—OtBu]

The title compound was obtained as a white solid (64%).

$^1$H NMR (600 MHz, DMSO-d6) δ 8.13 (s, 1H), 7.85 (d, J=8.06 Hz, 1H), 7.74 (d, J=7.69 Hz, 1H), 7.66-7.72 (m, 3H), 7.46-7.51 (m, 1H), 7.14 (d, J=1.83 Hz, 1H), 6.96-7.00 (m, 1H), 4.29 (br. s., 1H), 3.69 (dd, J=3.66, 12.45 Hz, 1H), 3.01 (q, J=6.59 Hz, 2H), 2.61-2.63 (m, 3H), 1.79-1.99 (m, 2H), 1.38 (s, 9H).

LCMS (HPLC Method 2): m/z 420 [M+Na]$^+$@r.t. 4.68 min.

HRMS (ESI) calcd for C$_{22}$H$_{27}$N$_3$NaO$_4$ [M+Na]$^+$ 420.1984 found 420.1882.

tert-butyl{2-[7-(3-cyanophenyl)-1-oxo-1,2,3,4-tetrahydropyrrolo[1,2-a]pyrazin-4-yl]ethyl}carbamate [(I), R2=3-cyanophenyl, R3=R4=H, A=—CH$_2$CH$_2$—NH—CO—OtBu]

The title compound was obtained as a white solid (67%).

$^1$H NMR (600 MHz, DMSO-d6) δ 8.08 (s, 1H), 7.92-7.96 (m, 1H), 7.69-7.75 (m, 2H), 7.59 (d, J=7.69 Hz, 1H), 7.51-7.54 (m, 1H), 7.17 (d, J=1.65 Hz, 1H), 6.95-7.00 (m, 1H), 4.27 (br. s., 1H), 3.68 (dd, J=2.66, 12.91 Hz, 1H), 2.97-3.04 (m, 2H), 1.76-2.00 (m, 2H), 1.38 (s, 9H).

LCMS (HPLC Method 2): m/z 403 [M+Na]$^+$@r.t. 4.85 min.

HRMS (ESI) calcd for C$_{21}$H$_{24}$N$_4$NaO$_3$ [M+Na]$^+$ 403.174 found 403.1735.

tert-butyl{2-[7-(2-chloropyridin-4-yl)-1-oxo-1,2,3,4-tetrahydropyrrolo[1,2-a]pyrazin-4-yl]ethyl}carbamate [(I), R2=2-chloropyridin-4-yl, R3=R4=H, A=—CH$_2$CH$_2$—NH—CO—OtBu]

The title compound was obtained as a brown solid (61%).

$^1$H NMR (600 MHz, DMSO-d6) δ 8.28 (d, J=5.13 Hz, 1H), 7.91 (s, 1H), 7.77 (br. s., 1H), 7.73 (d, J=0.92 Hz, 1H), 7.62 (dd, J=1.37, 5.22 Hz, 1H), 7.28 (d, J=1.65 Hz, 1H), 6.98 (br. s., 1H), 4.29 (br. s., 1H), 3.65-3.70 (m, 1H), 2.96-3.05 (m, 2H), 1.77-2.00 (m, 2H), 1.38 (s, 9H).

LCMS (HPLC Method 2): m/z 391 [M+H]+@r.t. 4.44 min.
HRMS (ESI) calcd for $C_{19}H_{24}ClN_4O_3[M+H]^+$ 391.1532 found 391.1536.

Preparation E 4-(2-azidoethyl)-7-iodo-3,4-dihydropyrrolo[1,2-a]pyrazin-1(2H)-one [V]

Step 3a

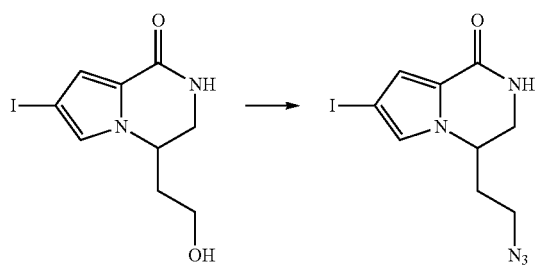 [SMILES: O=C1NCC(CCO)n2cc(I)cc21 ; [N-]=[N+]=NCCC1CNC(=O)c2cc(I)cn21]

To an ice-cooled stirred solution of 4-(2-hydroxyethyl)-7-iodo-3,4-dihydropyrrolo[1,2-a]pyrazin-1(2H)-one (0.800 g, 2.61 mmol), and PPh$_3$ (1.164 g, 4.44 mmol) in ahydrous THF (20 ml), DEAD (0.773 g, 4.44 mmol) was slowly added dropwise under N$_2$. After 15 minutes, NCA (0.580 g, 3.92 mmol) (prepared according to Synthesis, 2004, 17, 2886-2892) was added in one portion, the reaction mixture was allowed to warm to room temperature, and it was stirred overnight. The solvent was removed under reduced pressure, the residue was dissolved in DCM, washed with 2M HCl solution, saturated NaHCO$_3$ solution and brine. The organic layer was dried over Na$_2$SO$_4$ and concentrated to dryness. Purification by flash chromatography on silica gel column (DCM/MeOH 9:0.1) afforded the title compound as a white solid (0.605 g, 1.83 mmol 70%), after diethyl ether trituration.

$^1$H NMR (600 MHz, DMSO-d6) δ 7.72 (br. S., 1H), 7.20 (d, J=1.47 Hz, 1H), 6.72 (d, J=1.65 Hz, 1H), 4.34 (td, J=3.30, 6.96 Hz, 1H), 3.62 (dd, J=4.21, 13.37 Hz, 1H), 3.34 (m, 3H), 1.86-2.05 (m, 2H).

LCMS (HPLC Method 2): m/z 332 [M+H]+@r.t. 4.29 min.
HRMS (ESI) calcd for $C_9H_{11}IN_5O$ [M+H]+ 332.0003 found 332.0002.

Preparation F tert-butyl[2-(7-iodo-1-oxo-1,2,3,4-tetrahydropyrrolo[1,2-a]pyrazin-4-yl)ethyl]carbamate [(VI), R1=H, R'=—CO—OtBu]

Step 4

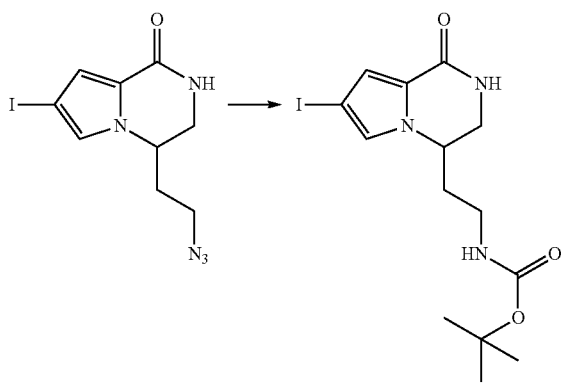 [SMILES: [N-]=[N+]=NCCC1CNC(=O)c2cc(I)cn21 ; CC(C)(C)OC(=O)NCCC1CNC(=O)c2cc(I)cn21]

A solution of 4-(2-azidoethyl)-7-iodo-3,4-dihydropyrrolo[1,2-a]pyrazin-1(2H)-one (0.530 g, 1.60 mmol) and PPh$_3$ (1.258 g, 4.80 mmol) in dry THF (15 ml) was stirred at room temperature for 2 hours, under N$_2$. Water (5 ml) was added and the reaction mixture was stirred at room temperature overnight. Di-t-butyl dicarbonate (0.698 g, 3.2 mmol) was then added and after 1 h at room temperature, the solvent was removed under vacuo, the residue was partitioned between DCM and water. The organic layers were washed with brine, dried over Na$_2$SO$_4$ and concentrated. Purification by flash chromatography on silica gel column (DCM/MeOH 9:0.25) gave the title compound as pale yellow solid (0.473 g, 1.16 mmol, 73%).

$^1$H NMR (600 MHz, DMSO-d6) δ 7.69 (d, J=2.93 Hz, 1H), 7.24 (s, 1H), 6.92 (br. s., 1H), 6.70 (d, J=1.65 Hz, 1H), 4.25 (br. s., 1H), 3.62 (dd, J=2.84, 13.28 Hz, 1H), 3.27 (td, J=4.01, 13.05 Hz, 1H), 2.94 (q, J=6.65 Hz, 2H), 1.70-1.89 (m, 2H), 1.38 (s, 9H).

LCMS (HPLC Method 2): m/z 428 [M+Na]+@r.t. 4.59 min.
HRMS (ESI) calcd for $C_{14}H_{20}IN_3NaO_3$ [M+Na]+ 428.0441 found 428.0434.

Preparation G

Ethyl[7-(3-chlorophenyl)-1-oxo-1,2,3,4-tetrahydro-pyrrolo[1,2-a]pyrazin-4-yl]acetate [(VII), R2=3-chlorophenyl]

Step 6

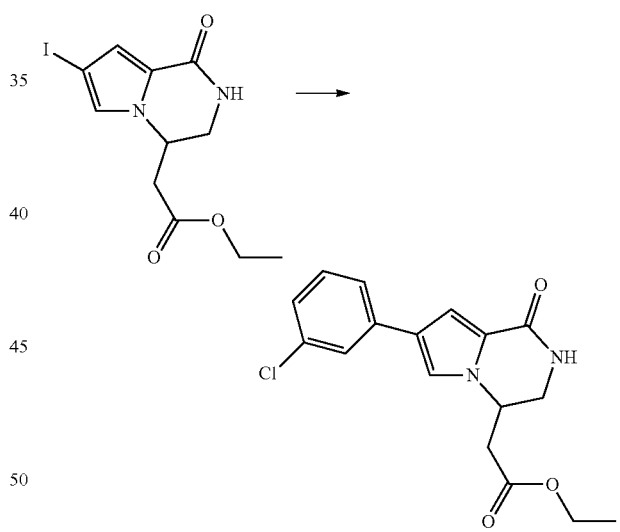

To a solution of ethyl(7-iodo-1-oxo-1,2,3,4-tetrahydropyrrolo[1,2-a]pyrazin-4-yl)acetate (1.00 g, 2.94 mmol) in a degassed (with Ar stream) mixture of 1,4-dioxane/H$_2$O (25/5 mL) was added 3-chloro-phenylboronic acid (898 mg, 5.74 mmol) and cesium carbonate (2.807 g, 8.61 mmol), to which was added 1,1'-bis(diphenylphosphino)ferrocenepalladium (II) dichloride, complex with dichloromethane (1:1). The reaction mixture was capped under argon atmosphere and stirred at 80° for 2 h. The solvent was evaporated under vacuum and the residue partitioned between ethyl acetate and water. The organic phase was dried on Na$_2$SO$_4$ and concentrated to dryness. The crude was purified by chromatography on a silica gel column (eluent: DCM I/EtOAc/EtOH:60/35/5) to afford 0.573 g (60% yield) as a light brown solid.

¹H NMR (400 MHz, DMSO-d6) δ 7.71 (d, J=1.22 Hz, 1H), 7.64 (t, J=1.83 Hz, 1H), 7.58 (d, J=1.83 Hz, 1H), 7.51-7.56 (m, 1H), 7.35 (t, J=7.93 Hz, 1H), 7.20 (ddd, J=0.98, 2.08, 7.93 Hz, 1H), 7.10 (d, J=1.83 Hz, 1H), 4.60-4.69 (m, 1H), 4.11 (dq, J=1.16, 7.10 Hz, 2H), 3.71 (ddd, J=1.89, 4.18, 13.09 Hz, 1H), 3.35-3.42 (m, 1H), 2.89 (dd, J=5.13, 6.84 Hz, 2H), 1.18 (t, J=7.08 Hz, 3H).

HRMS (ESI) calcd for $C_{17}H_{18}ClN_2O_3[M+H]^+$ 333.1001 found 333.1005.

According to this same methodology, but employing suitable substituted derivatives, the following compounds were prepared:

Ethyl {1-oxo-7-[3-(trifluoromethyl)phenyl]-1,2,3,4-tetrahydropyrrolo[1,2-a]pyrazin-4-yl}acetate [(VII), R2=3-(trifluoromethyl)phenyl]

¹H NMR (400 MHz, DMSO-d6) δ 7.86-7.91 (m, 2H), 7.73 (br. s., 1H), 7.67 (d, J=1.83 Hz, 1H), 7.55-7.58 (m, 1H), 7.48-7.51 (m, 1H), 7.18 (d, J=1.83 Hz, 1H), 4.61-4.70 (m, 1H), 4.11 (ttd, J=3.71, 7.22, 10.75 Hz, 2H), 3.69-3.75 (m, 1H), 3.36-3.41 (m, 1H), 2.84-2.98 (m, 2H), 1.18 (t, J=7.14 Hz, 3H).

HRMS (ESI) calcd for $C_{18}H_{18}F_3N_2O_3[M+H]^+$ 367.1264 found 333.1267.

Ethyl[7-(5-chloro-2-fluorophenyl)-1-oxo-1,2,3,4-tetrahydropyrrolo[1,2-a]pyrazin-4-yl]acetate [(VII), R2=2-fluoro-5-Chloro-phenyl]

¹H NMR (600 MHz, DMSO-d6) δ 7.78 (dd, J=6.78, 2.38 Hz, 1H), 7.76 (d, J=2.56 Hz, 1H), 7.52 (s, 1H), 7.22-7.31 (m, 2H), 7.15 (s, 1H), 4.67-4.77 (m, 1H), 4.03-4.14 (m, 2H), 3.70-3.75 (m, 1H), 2.88 (t, J=6.32 Hz, 2H), 1.10-1.19 (m, 3H).

HRMS (ESI) calcd for $C_{17}H_{17}ClFN_2O_3[M+H]^+$ 351.0906 found 351.0912.

Ethyl[7-(2-fluoropyridin-4-yl)-1-oxo-1,2,3,4-tetrahydropyrrolo[1,2-a]pyrazin-4-yl]acetate [(VII), R2=2-fluoropyridin-4-yl]

¹H NMR (400 MHz, DMSO-d6) δ 8.12 (d, J=5.37 Hz, 1H), 7.81 (d, J=1.83 Hz, 1H), 7.80 (br. s., 1H), 7.51-7.58 (m, J=5.25 Hz, 1H), 7.37 (s, 1H), 7.30 (d, J=1.83 Hz, 1H), 4.61-4.74 (m, 1H), 4.03-4.17 (m, 2H), 3.72 (d, J=8.91 Hz, 1H), 3.39 (td, J=4.21, 13.18 Hz, 1H), 2.90 (d, J=7.08 Hz, 2H), 1.17 (t, J=7.08 Hz, 3H).

HRMS (ESI) calcd for $C_{16}H_{17}FN_3O_3[M+H]^+$ 318.1249 found 318.1248.

Example 2

4-(2-hydroxyethyl)-7-[3-(trifluoromethoxy)phenyl]-3,4-dihydropyrrolo[1,2-a]pyrazin-1(2H)-one [(I), R2=3-(trifluoromethoxy)phenyl, R3=R4=H, A=—CH₂CH₂—OH]

Step 9

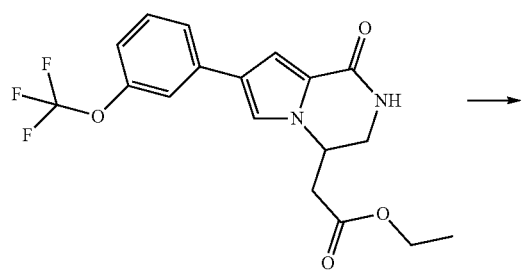

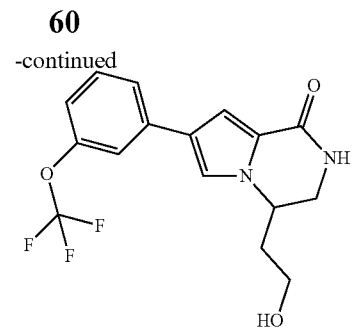

Ethyl {1-oxo-7-[3-(trifluoromethoxy)phenyl]-1,2,3,4-tetrahydropyrrolo[1,2-a]pyrazin-4-yl}acetate (1.67 g, 4.368 mmol) was dissolved in EtOH (25 mL) and treated with a NaBH₄ (0.646 g, 4 eq. 17.471 mmol) at room temperature for 18 h. Solvent was evaporated to dryness and the residue dissolved in H₂O and extracted with AcOEt (3×50 mL). The organic phase was washed with NaOH 1N and brine, dried on Na₂SO₄ and concentrated to dryness to give the title compound (1.480 g, 99% yield) as a off-white solid.

¹H NMR (400 MHz, DMSO-d6) δ 7.68 (br. s., 1H), 7.61-7.66 (m, 2H), 7.57 (s, 1H), 7.45 (t, J=7.99 Hz, 1H), 7.11-7.15 (m, J=8.06 Hz, 1H), 7.10 (d, J=1.83 Hz, 1H), 4.72 (t, J=4.94 Hz, 1H), 4.19-4.41 (m, 1H), 3.69 (ddd, J=1.59, 4.12, 12.85 Hz, 1H), 3.40-3.59 (m, 2H), 1.93-2.04 (m, 1H), 1.70-1.93 (m, 1H).

HRMS (ESI) calcd for $C_{16}H_{16}F_3N_2O_3[M+H]^+$ 341.1008. found: 341.1095.

The following examples were prepared by the procedure of example 2, using the appropriate starting materials:

4-(2-hydroxyethyl)-7-[3-(trifluoromethyl)phenyl]-3,4-dihydropyrrolo[1,2-a]pyrazin-1(2H)-one [(I), R2=3-(trifluoromethyl)phenyl, R3=R4=H, A=—CH₂CH₂—OH](cpd 1)

¹H NMR (400 MHz, DMSO-d6) δ 7.92 (s, 1H), 7.90 (d, J=7.88 Hz, 1H), 7.71 (d, J=1.65 Hz, 1H), 7.70 (br. s., 1H), 7.54-7.58 (m, 1H), 7.47-7.51 (m, 1H), 7.15 (d, J=1.65 Hz, 1H), 4.73 (t, J=4.95 Hz, 1H), 4.34-4.41 (m, 1H), 3.67-3.72 (m, 1H), 3.42-3.56 (m, 2H), 3.37 (t, J=4.21 Hz, 1H), 1.81-2.04 (m, 2H).

HRMS (ESI) calcd for $C_{16}H_{16}F_3N_2O_2[M+H]^+$ 325.1159. found: 325.1150.

7-(5-chloro-2-fluorophenyl)-4-(2-hydroxyethyl)-3,4-dihydropyrrolo[1,2-a]pyrazin-1(2H)-one [(I), R2=2-fluoro-5-Chloro-phenyl, R3=R4=H, A=—CH₂CH₂—OH]

¹H NMR (600 MHz, DMSO-d6) δ 7.79 (dd, J=6.78, 2.38 Hz, 1H), 7.72 (d, J=2.75 Hz, 1H), 7.57 (t, J=1.83 Hz, 1H), 7.19-7.31 (m, 2H), 7.09-7.13 (m, 1H), 4.73 (t, J=4.95 Hz, 1H), 4.33-4.49 (m, 1H), 3.67-3.75 (m, 1H), 3.47-3.54 (m, 1H), 3.39-3.45 (m, 2H), 1.90-1.99 (m, 1H), 1.81-1.88 (m, 1H).

HRMS (ESI) calcd for $C_{15}H_{15}ClFN_2O_2[M+H]^+$ 309.0801 found 309.0806.

7-(2-fluoropyridin-4-yl)-4-(2-hydroxyethyl)-3,4-dihydropyrrolo[1,2-a]pyrazin-1(2H)-one [(I), R2=2-fluoropyridin-4-yl, R3=R4=H, A=—CH₂CH₂—OH]

¹H NMR (400 MHz, DMSO-d6) δ 8.11 (d, J=5.31 Hz, 1H), 7.85 (d, J=1.83 Hz, 1H), 7.77 (d, J=1.83 Hz, 1H), 7.57 (d, J=5.13 Hz, 1H), 7.39 (s, 1H), 7.28 (d, J=1.83 Hz, 1H), 4.74 (t, J=4.95 Hz, 1H), 4.37-4.45 (m, 1H), 3.69 (ddd, J=1.92, 4.17, 12.96 Hz, 1H), 3.52 (qd, J=5.58, 10.92 Hz, 1H), 3.41-3.47 (m, 1H), 3.36 (td, J=4.21, 13.00 Hz, 1H), 1.95-2.04 (m, 1H), 1.83-1.92 (m, 1H).

HRMS (ESI) calcd for $C_{14}H_{15}FN_3O_2[M+H]^+$ 276.1143 found 276.1144.

7-(6-fluoropyridin-3-yl)-4-(2-hydroxyethyl)-3,4-dihydro-pyrrolo[1,2-a]pyrazin-1(2H)-one [(I), R2=6-fluoropyridin-3-yl, R3=R4=H, A=—CH$_2$CH$_2$—OH]

$^1$H NMR (400 MHz, DMSO-d6) δ 8.49 (d, J=2.38 Hz, 1H), 8.18 (dt, J=2.66, 8.20 Hz, 1H), 7.69 (br. s., 1H), 7.61 (d, J=1.83 Hz, 1H), 7.15 (dd, J=2.56, 8.61 Hz, 1H), 7.13 (d, J=1.65 Hz, 1H), 4.72 (br. s., 1H), 4.23-4.46 (m, 1H), 3.63-3.76 (m, 1H), 3.49-3.58 (m, 1H), 3.40-3.49 (m, 1H), 3.33-3.38 (m, 1H), 1.94-2.04 (m, 1H), 1.78-1.93 (m, 1H). HRMS (ESI) calcd for C$_{14}$H$_{15}$FN$_3$O$_2$[M+H]$^+$ 276.1143 found 276.1144.

7-(biphenyl-2-yl)-4-(2-hydroxyethyl)-3,4-dihydropyrrolo[1,2-a]pyrazin-1(2H)-one [(I), R2=biphenyl-2-yl, R3=R4=H, A=—CH$_2$CH$_2$—OH]

LCMS (HPLC Method 2): m/z 333 [M+H]$^+$@r.t. 3.45 min.

7-(biphenyl-3-yl)-4-(2-hydroxyethyl)-3,4-dihydropyrrolo[1,2-a]pyrazin-1(2H)-one [(I), R2=biphenyl-3-yl, R3=R4=H, A=—CH$_2$CH$_2$—OH]

LCMS (HPLC Method 2): m/z 333 [M+H]$^+$@r.t. 3.48 min.

Preparation H

[7-(3-chlorophenyl)-1-oxo-1,2,3,4-tetrahydropyrrolo[1,2-a]pyrazin-4-yl]acetic acid [(XI), R2=3-chlorophenyl, R3=H]

Step 13

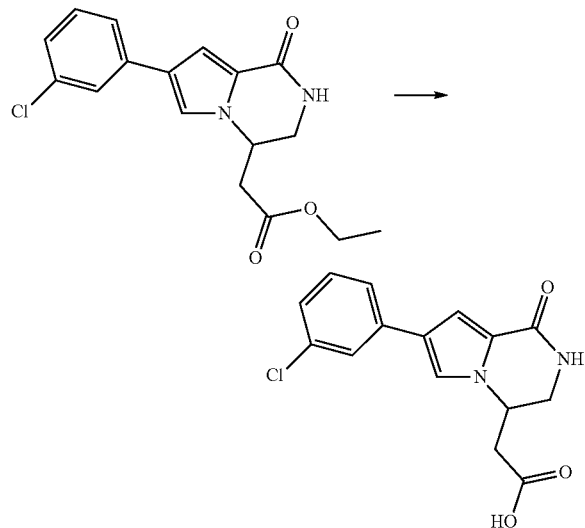

To a solution of ethyl[7-(3-chlorophenyl)-1-oxo-1,2,3,4-tetrahydropyrrolo[1,2-a]pyrazin-4-yl]acetate (0.573 g, 1.72 mmol) in a mixture tetrahydrofuran-water (5:1, 10 mL) was added lithium hydroxide (144 mg, 3.44 mmol) and the reaction mixture was stirred at room temperature for 18 h. The THF was evaporated and the aqueous residue diluted with H$_2$O. The aqueous phase was acidified with hydrochloric acid (1 M) until pH<1 and a precipitation occurred; the solid was filtered, washed with water and dried under vacuum to obtain the title compound as an off-white solid (450 mg, 85% yield).

LCMS (HPLC Method 2): m/z 305 [M+H]$^+$@r.t. 4.11 min.

HRMS (ESI) calcd for C$_{15}$H$_{14}$ClN$_2$O$_3$[M+H]$^+$ 305.0688 found 305.0691.

According to this same methodology, but employing suitable substituted derivatives, the following compounds were prepared:

[7-(biphenyl-2-yl)-1-oxo-1,2,3,4-tetrahydropyrrolo[1,2-a]pyrazin-4-yl]acetic acid [(XI), R2=biphenyl-2-yl, R3=H]

$^1$H NMR (400 MHz, DMSO-d6) δ 12.58 (s, 1H), 7.56 (d, J=2.20 Hz, 1H), 7.47 (dd, J=1.10, 7.69 Hz, 1H), 7.27-7.40 (m, 5H), 7.22-7.26 (m, 1H), 7.17-7.22 (m, 2H), 6.72 (d, J=1.83 Hz, 1H), 6.25 (d, J=1.83 Hz, 1H), 4.40-4.47 (m, 1H), 3.62 (ddd, J=1.77, 4.15, 12.88 Hz, 1H), 2.63-2.73 (m, 1H), 2.53-2.61 (m, 1H).

LCMS (HPLC Method 2): m/z 347 [M+H]$^+$@r.t. 4.53 min.

HRMS (ESI) calcd for C$_{21}$H$_{19}$N$_2$O$_3$ [M+H]$^+$ 347.1390 found 347.1379.

[7-(biphenyl-3-yl)-1-oxo-1,2,3,4-tetrahydropyrrolo[1,2-a]pyrazin-4-yl]acetic acid [(XI), R2=biphenyl-3-yl, R3=H]

$^1$H NMR (400 MHz, DMSO-d6) δ 12.02-13.08 (m, 1H), 7.85 (t, J=1.53 Hz, 1H), 7.71-7.76 (m, 2H), 7.67 (d, J=2.56 Hz, 1H), 7.62 (d, J=1.71 Hz, 1H), 7.56 (td, J=1.60, 7.29 Hz, 1H), 7.40-7.51 (m, 4H), 7.34-7.40 (m, 1H), 7.16 (d, J=1.83 Hz, 1H), 4.57-4.70 (m, 1H), 3.72 (ddd, J=1.89, 4.12, 13.03 Hz, 1H), 3.35-3.43 (m, 1H), 2.76-2.92 (m, 2H).

LCMS (HPLC Method 2): m/z 347 [M+H]$^+$@r.t. 4.64 min.

HRMS (ESI) calcd for C$_{21}$H$_{19}$N$_2$O$_3$ [M+H]$^+$ 347.1390 found 347.1373.

{1-oxo-7-[3-(trifluoromethoxy)phenyl]-1,2,3,4-tetrahydropyrrolo[1,2-a]pyrazin-4-yl}acetic acid [(XI), R2=3-(trifluoromethoxy)phenyl, R3=H]

LCMS (HPLC Method 2): m/z 355 [M+H]$^+$@r.t. 4.74 min.

{1-oxo-7-[3-(trifluoromethyl)phenyl]-1,2,3,4-tetrahydropyrrolo[1,2-a]pyrazin-4-yl}acetic acid [(XI), R2=3-(trifluoromethyl)phenyl, R3=H]

$^1$H NMR (400 MHz, DMSO-d6) δ 12.64 (br. s., 1H), 7.86-7.91 (m, 2H), 7.72 (br. s., 1H), 7.69 (d, J=1.65 Hz, 1H), 7.54-7.60 (m, 1H), 7.50 (d, J=9.16 Hz, 1H), 7.17 (d, J=1.65 Hz, 1H), 4.58-4.65 (m, 1H), 3.71 (td, J=2.04, 11.13 Hz, 1H), 3.38-3.42 (m, 1H), 2.77-2.92 (m, 2H).

LCMS (HPLC Method 2): m/z 339 [M+H]$^+$@r.t. 4.61 min.

HRMS (ESI) calcd for C$_{16}$H$_{14}$F$_3$N$_2$O$_3$[M+H]$^+$ 339.0951 found 339.0952.

{7-[2-chloro-5-(trifluoromethoxy)phenyl]-1-oxo-1,2,3,4-tetrahydropyrrolo[1,2-a]pyrazin-4-yl}acetic acid [(XI), R2=2-chloro-5-(trifluoromethoxy)phenyl, R3=H]

$^1$H NMR (400 MHz, DMSO-d6) δ 11.63-13.10 (br. s., 1H), 7.76 (br. s., 1H), 7.62 (d, J=8.79 Hz, 1H), 7.59 (d, J=1.65 Hz, 1H), 7.56 (d, J=2.75 Hz, 1H), 7.25 (dd, J=1.92, 8.88 Hz, 1H), 7.10 (d, J=1.65 Hz, 1H), 4.65-4.72 (m, 1H), 3.73 (dd, J=2.66, 13.28 Hz, 1H), 2.77-2.86 (m, 2H).

LCMS (HPLC Method 2): m/z 389 [M+H]$^+$@r.t. 4.15 min.

HRMS (ESI) calcd for C$_{16}$H$_{13}$ClF$_3$N$_2$O$_4$ [M+H]$^+$ 389.0511 found 389.0513.

Example 3

7-(3-chlorophenyl)-4-(2-hydroxyethyl)-3,4-dihydro-pyrrolo[1,2-a]pyrazin-1(2H)-one [(I), R2=3-chlorophenyl, R3=R4=H, A=—CH₂CH₂—OH]

Step 9

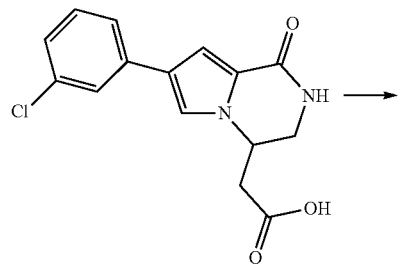

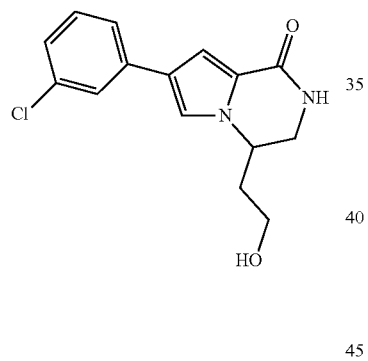

A solution of [7-(3-chlorophenyl)-1-oxo-1,2,3,4-tetrahydropyrrolo[1,2-a]pyrazin-4-yl]acetic acid (403 mg 1.32 mmol), N,N-diisopropylethylamine (DIPEA) (0.687 ml, 3.96 mmol) and ethyl chloroformate (0.187 ml, 1.98 mmol) in dry THF (10 ml), was stirred for 1 h. The volatiles were removed under vacuo and the obtained residue dissolved with EtOAc and portioned with saturated aqueous solution of NaHCO₃, the organic layer was washed with brine dried over Na₂SO₄ and concentrated. The residue was dissolved with dry THF (10 ml) and NaBH₄ (147 mg 3.97 mmol) was added. The mixture was stirred 18 h at room temperature, the solvent was evaporated under vacuum and the residue portioned between EtOAc and water. The organic layer was washed with brine and dried over Na₂SO₄ and concentrated in vacuo. Purification by flash chromatography on silica gel (eluent: DCM/AcOEt/EtOH 6/3/1) provided 300 mg (78% yield) of the title compound as a light yellow foam.

$^1$H NMR (400 MHz, DMSO-d6) δ 7.66 (t, J=1.77 Hz, 2H), 7.61 (d, J=1.83 Hz, 1H), 7.54-7.58 (m, 1H), 7.35 (t, J=7.93 Hz, 1H), 7.20 (ddd, J=0.98, 2.08, 7.93 Hz, 1H), 7.08 (d, J=1.83 Hz, 1H), 4.69-4.75 (m, 1H), 4.30-4.41 (m, 1H), 3.69 (ddd, J=1.77, 4.15, 13.00 Hz, 1H), 3.41-3.57 (m, 3H), 3.32-3.37 (m, 5H), 1.94-2.03 (m, 1H), 1.79-1.88 (m, 1H). LCMS (HPLC Method 2): m/z 291 [M+H]⁺@r.t. 4.82 min.

HRMS (ESI) calcd for $C_{15}H_{16}ClN_2O_3$ [M+H]⁺ 291.0895 found 291.0895.

Preparation I

Ethyl[7-(3-chlorophenyl)-6-iodo-1-oxo-1,2,3,4-tetrahydropyrrolo[1,2-a]pyrazin-4-yl]acetate [(IX), R2=3-chlorophenyl, Hal=iodo]

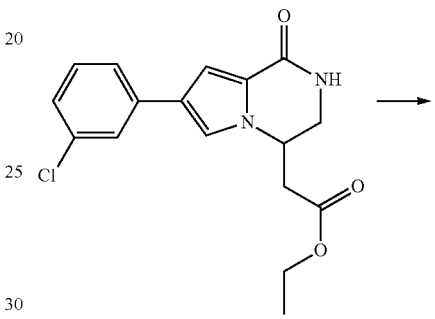

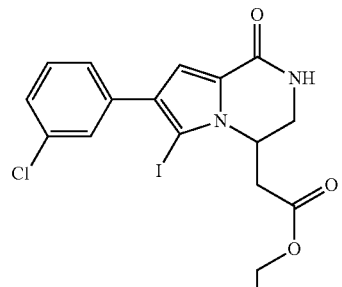

Ethyl[7-(3-chlorophenyl)-1-oxo-1,2,3,4-tetrahydropyrrolo[1,2-a]pyrazin-4-yl]acetate (280 mg, 0.84 mmol) was dissolved in DCM, cooled in an ice bath and CF₃COOAg (186 mg, 0.84 mmol) and Iodine (214 mg, 0.84 mmol) were added. The reaction was then warmed up at room temperature and after 1 hour was complete. It was filtered through paper, evaporated and the crude purified by silica chromatography (eluent: Hexane/AcOEt 3/2) to give 228 mg of desired product (59% yield).

$^1$H NMR (400 MHz, DMSO-d₆) δ 7.80 (d, J=4.88 Hz, 1H), 7.59 (t, J=1.77 Hz, 1H), 7.48-7.54 (m, 1H), 7.45 (t, J=7.81 Hz, 1H), 7.30-7.41 (m, 1H), 7.00 (s, 1H), 4.65-4.81 (m, 1H), 4.12 (q, J=7.08 Hz, 2H), 3.84 (dd, J=4.21, 13.49 Hz, 1H), 3.36-3.47 (m, 1H), 2.81 (dd, J=10.01, 15.50 Hz, 1H), 2.58 (dd, J=3.60, 15.68 Hz, 1H), 1.21 (t, J=7.08 Hz, 3H).

HRMS (ESI) calcd for $C_{17}H_{16}ClIN_2O_3$[M+H]⁺ 458.9967 found 458.9963.

LCMS (HPLC Method 3): m/z 458 [M+H]⁺@r.t. 3.59 min.

Preparation J

Ethyl[7-(3-chlorophenyl)-1-oxo-6-phenyl-1,2,3,4-tetrahydropyrrolo[1,2-a]pyrazin-4-yl]acetate [(X), R2=3-chlorophenyl, R3=phenyl]

Step 11

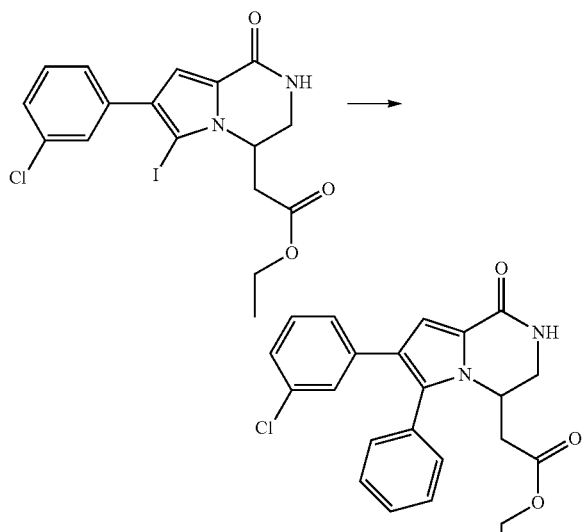

To a solution of ethyl[7-(3-chlorophenyl)-6-iodo-1-oxo-1,2,3,4-tetrahydropyrrolo[1,2-a]pyrazin-4-yl]acetate (123 mg, 0.269 mmol) in 9 ml of 1,4-dioxane and 1 ml of water, under argon atmosphere, phenylboronic acid (130 mg, 1.07 mmol), bis(triphenylphosphine)palladium(II) dichloride (9.4 mg, 0.013 mmol), sodium carbonate (85.0 mg, 0.80 mmol) and lithium chloride (34 mg, 0.81 mmol) were subsequently added. The mixture was heated at 100° for 4 hour in a sealed vial. The reaction was filtered through a celite pad and the solvent evaporated to dryness. The crude was then portioned between ethyl acetate and water, the organic layer dried over sodium sulphate and the solvent removed in vacuo. Purification by flash chromatography on silica gel column (EtOAc/Hex 3/2) led to the wanted compound in 90% yield.

$^1$H NMR (400 MHz, DMSO-d6) δ 7.75 (d, J=4.76 Hz, 1H), 7.46-7.53 (m, 3H), 7.37-7.42 (m, 2H), 7.18-7.24 (m, 1H), 7.13-7.17 (m, 1H), 7.05-7.11 (m, 3H), 4.49-4.56 (m, 1H), 3.82-3.96 (m, 2H), 2.69-2.78 (m, 1H), 2.25-2.36 (m, 1H), 1.05 (t, J=7.14 Hz, 3H).

LCMS (HPLC Method 2): m/z 409 [M+H]$^+$@r.t. 6.80 min.
HRMS (ESI) calcd for $C_{23}H_{21}ClN_2O_3$[M+H]$^+$ 409.1314 found 409.1301.

Example 4

7-(3-chlorophenyl)-4-(2-hydroxyethyl)-6-phenyl-3,4-dihydropyrrolo[1,2-a]pyrazin-1(2H)-one [(I), R2=3-chlorophenyl, R3=Phenyl, R4=H, A=—CH$_2$CH$_2$—OH](cpd 2)

Step 12

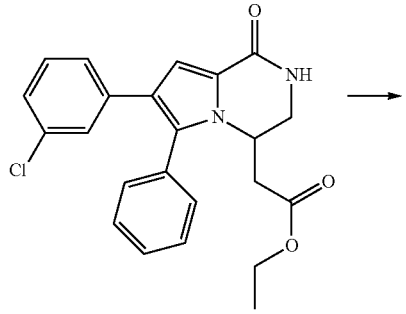

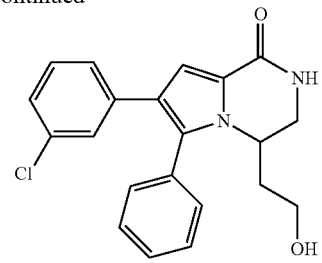

Ethyl[7-(3-chlorophenyl)-1-oxo-6-phenyl-1,2,3,4-tetrahydropyrrolo[1,2-a]pyrazin-4-yl]acetate (155 mg, 0.38 mmol) was dissolved in dry THF under argon atmosphere and LiAlH$_4$ (1.14 ml of a 1M solution) was added. The reaction was complete in 30 min, acidified with 2N HCl and extracted with DCM. The pooled organic layers were dried, filtered and evaporated to give the wanted product as an insoluble solid.

$^1$H NMR (500 MHz, DMSO-d$_6$) δ 7.72 (d, J=4.70 Hz, 1H), 7.46-7.51 (m, 3H), 7.35-7.39 (m, 2H), 7.18-7.24 (m, 1H), 7.12-7.17 (m, 1H), 7.05-7.10 (m, 3H), 4.41 (t, J=4.94 Hz, 1H), 4.24-4.31 (m, 1H), 3.79 (dd, J=3.57, 13.18 Hz, 1H), 3.41 (dd, J=4.67, 13.18 Hz, 1H), 3.02-3.24 (m, 2H), 1.73-1.81 (m, 1H), 1.41-1.49 (m, 1H).

LCMS (HPLC Method 2): m/z 367 [M+H]$^+$@r.t. 4.91 min.
HRMS (ESI) calcd for $C_{21}N_2O_2ClH_{19}$ [M+H]$^+$ 367.1208 found 367.1216.

Example 5

4-(aminomethyl)-7-(3-chlorophenyl)-3,4-dihydropyrrolo[1,2-a]pyrazin-1(2H)-one [(I), R2=3-chlorophenyl, R3=R4=H, A=—CH$_2$—NH$_2$](cpd 3)

Step 14

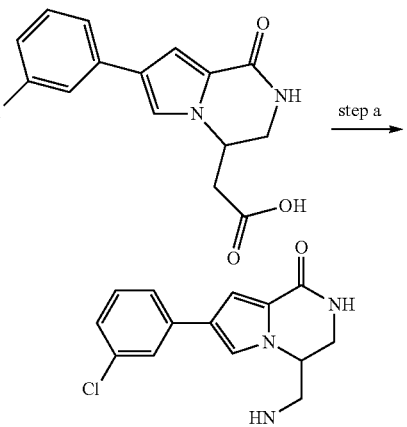

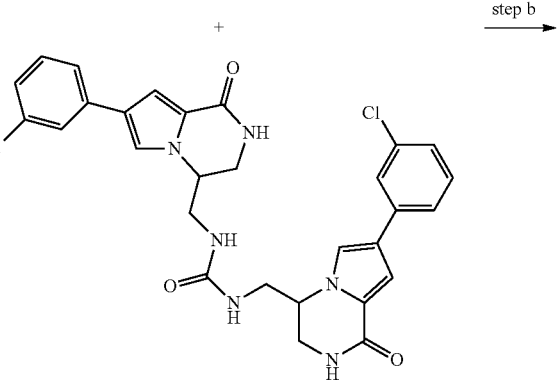

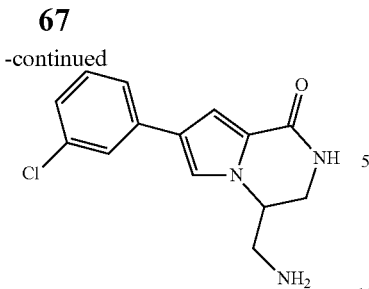

Preparation of {[7-(3-chlorophenyl)-1-oxo-1,2,3,4-tetrahydropyrrolo[1,2-a]pyrazin-4-yl]methyl}carbamic azide.

100 mg (0.328 mmol) of [7-(3-chlorophenyl)-1-oxo-1,2,3,4-tetrahydropyrrolo[1,2-a]pyrazin-4-yl]acetic acid and NaN₃ (664 mg, 0.98 mmol) were suspended in 10 ml of dry THF, 108 mg of DPPA (0.394 mmol) was added. The mixture was stirred at room temperature for 18 h. The volatiles were removed under vacuo and the residue was purified by flash chromatography (DCM/EtOAc/EtOH 6/3/1) to give the desired compound and a secondary compound.

{[7-(3-chlorophenyl)-1-oxo-1,2,3,4-tetrahydropyrrolo[1,2-a]pyrazin-4-yl]methyl}carbamic azide 71 mg (55%)

$^1$H NMR (400 MHz, DMSO-d6) δ 8.29 (t, J=5.92 Hz, 2H), 7.63-7.71 (m, 4H), 7.54-7.59 (m, 4H), 7.36 (t, J=7.87 Hz, 2H), 7.21 (ddd, J=0.92, 2.04, 7.90 Hz, 2H), 7.11 (d, J=1.83 Hz, 2H), 4.26-4.40 (m, 2H), 3.61-3.70 (m, 2H), 3.37-3.48 (m, 6H).

LCMS (HPLC Method 2): m/z 345 [M+H]⁺@r.t. 5.32 min.

1,3-bis{[7-(3-chlorophenyl)-1-oxo-1,2,3,4-tetrahydropyrrolo[1,2-a]pyrazin-4-yl]methyl}urea 37 mg (20%).

$^1$H NMR (400 MHz, DMSO-d6) δ 7.60-7.70 (m, 4H), 7.47-7.58 (m, 4H), 7.28-7.40 (m, 2H), 7.16-7.23 (m, 3H), 7.06-7.14 (m, 3H), 6.25-6.39 (m, 2H), 4.19-4.36 (m, 1H), 3.52-3.65 (m, 1H), 3.39-3.50 (m, 6H).

LCMS (HPLC Method 2): m/z 577 [M+H]⁺@r.t. 5.72 min.

HRMS (ESI) calcd for C₂₉H₂₇Cl₂N₆O₃ [M+H]⁺ 577.1516 found 577.1497.

Step b 71 mg (0.206 mmol) of {[7-(3-chlorophenyl)-1-oxo-1,2,3,4-tetrahydropyrrolo[1,2-a]pyrazin-4-yl]methyl}carbamic azide were dissolved in 10 ml of dry THF, NaOH 1N (2 ml) was added and the mixture was stirred at room temperature for 30 minutes. The reaction was diluted with EtOAc and extracted with water, the organic layer was mixed with HCl 2N (5 ml) for 10 minutes, and then discarded; the aqueous solution was brought to pH 10 with NaOH 23% (10 ml) and portioned between EtOAc (10 ml) and THF (10 ml). The organic layers were washed with brine, dried over Na₂SO₄ and evaporated under reduced pressure to give the title compound 50 mg (89%) as a light yellow solid.

$^1$H NMR (400 MHz, DMSO-d6) δ 7.66 (t, J=1.83 Hz, 1H), 7.64 (d, J=1.83 Hz, 1H), 7.61 (br. S., 1H), 7.54-7.58 (m, 1H), 7.35 (t, J=7.87 Hz, 1H), 7.20 (ddd, J=0.98, 2.08, 7.93 Hz, 1H), 7.07 (d, J=1.83 Hz, 1H), 4.04-4.15 (m, 1H), 3.57-3.66 (m, 1H), 3.50 (td, J=4.20, 12.97 Hz, 1H), 2.82-3.00 (m, 2H).

LCMS (HPLC Method 2): m/z 276 [M+H]⁺@r.t. 4.15 min.

HRMS (ESI) calcd for C₂₉H₂₇Cl₂N₆O₃ [M+H]⁺ 276.0898 found 276.0886.

Preparation K

Dimethyl(2S)-2-(1H-pyrrol-1-yl)butanedioate [(XVI), Alk=methyl, E=—CH₂—CO-OMe]

Step 15

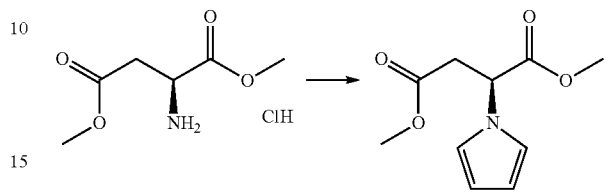

Acetic acid (2.5 ml) and sodium acetate (32.5 mmol, 2.6 g) were added to a solution of dimethyl L-aspartate hydrochloride (29.5 mmol, 5.830 g) in dichloromethane (60 ml) and water (30 ml). Tetrahydro-2,5-dimethoxyfuran (29.5 mmol, 3.8 ml) was added to the resulting mixture heated at 80° C. After 90 min. the solution was cooled and the acqueous layer was washed with DCM. The combined organic layers were washed with brine and then dried, filtered and evaporated. The crude residue was purified by chromatograpgy on silica gel (eluent:Hex/AcOEt:7/3) to give the wanted compound as a colorless viscous oil (4.3 g, 68% yield).

1H NMR (600 MHz, DMSO-d6) δ 6.81 (t, J=2.11 Hz, 2H), 6.00 (t, J=2.11 Hz, 2H), 5.25 (t, J=7.33 Hz, 1H), 3.64 (s, 3H), 3.59 (s, 3H), 3.24 (dd, J=7.51, 16.67 Hz, 1H), 3.04 (dd, J=7.14, 16.85 Hz, 1H).

LCMS (HPLC Method 2): m/z 212 [M+H]⁺@r.t. 4.51 min.

HRMS (ESI) calcd for C₁₀H₁₃NO₄ [M+H]⁺ 212.092 found 212.0918.

According to the same methodology, but employing suitable starting material, the following compound was prepared:

Dimethyl(2S)-2-(1H-pyrrol-1-yl)pentanedioate [(XVI), Alk=methyl, E=—CH₂CH₂—CO-OMe](7.5 g, 65% yield)

HRMS (ESI) calcd for C₁₁H₁₅NO₄ [M+H]⁺ 226.1074 found 226.107.

LCMS (HPLC Method 2): m/z 225 [M+H]⁺@r.t. 5.5 min.

$^1$H NMR (600 MHz, DMSO-d6) δ 6.78 (t, J=2.11 Hz, 2H), 6.03 (t, J=2.11 Hz, 2H), 3.66 (s, 3H), 3.57 (s, 3H), 2.26-2.39 (m, 1H), 2.12-2.22 (m, 2H), 1.94-2.12 (m, 1H).

(2S)-3-methyl-2-(1H-pyrrol-1-yl)butanoic acid [(XVI), Alk=H, E=—CH(CH₃)₂]

compound obtained as a colorless viscous oil (5.4 g, 75% yield)

LCMS (HPLC Method 2): m/z 168 [M+H]+ @r.t. 0.92 min.

HRMS (ESI) calcd for C₉H₁₄NO₂ [M+H]⁺ 168.01019 found 168.1015.

Methyl(2S)-3-(1H-imidazol-4-yl)-2-(1H-pyrrol-1-yl)propanoate [(XVI), Alk=H, E=—CH₂-Imidazol-4-yl]

LCMS (HPLC Method 2): m/z 220 [M+H]+@r.t. 3.1 min.

HRMS (ESI) calcd for C₁₁H₁₃N₃O₂ [M+H]⁺ 220.1081 found 220.1076.

Methyl(2S)-3-[1-(dimethylsulfamoyl)-1H-imidazol-4-yl]-2-(1H-pyrrol-1-yl)propanoate [(XVI), Alk=H, E=CH₂-1-(dimethylsulfamoyl)-1H-imidazol-4-yl]

LCMS (HPLC Method 2): m/z 327 [M+H]+@r.t. 5.34 min.

Preparation L (2S)-2-(1H-pyrrol-1-yl)butane-1,4-diol [(XVII), $E^1$=—$CH_2CH_2$—OH]

Step 16

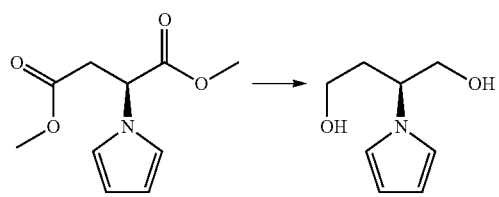

In a two necked flask cooled in an ice bath and under argon atmosphere, dimethyl(2S)-2-(1H-pyrrol-1-yl)butanedioate (20.3 mmol, 4.3 g) was dissolved in 50 ml of dry THF. LiAlH$_4$ (42 ml, 1 M in THF) was cautiously added and the reaction was let warm up at room temperature. When the reaction was completed, it was cooled again to 0° C. and acidified with 2M HCl. Water and AcOEt were added to the quenched reaction and the organic layer was extracted with brine. The crude residue was purified by chromatography on silica gel (eluent: DCM/MeOH:95/5) to give the product as a colourless oil (2.0 g, 63% yield).

$^1$H NMR (600 MHz, DMSO-d6) δ 6.73 (t, J=2.01 Hz, 2H), 5.95 (t, J=2.01 Hz, 2H), 4.82 (t, J=5.40 Hz, 1H), 4.44 (t, J=5.04 Hz, 1H), 4.01-4.12 (m, J=4.76, 10.07 Hz, 1H), 3.58 (t, J=5.68 Hz, 2H), 3.23-3.29 (m, J=6.23, 10.81 Hz, 1H), 3.08-3.17 (m, 1H), 1.85-1.95 (m, 1H), 1.67-1.81 (m, 1H).

LCMS (HPLC Method 2): m/z 156 [M+H]$^+$@r.t. 2.26 min.

HRMS (ESI) calcd for $C_8H_{13}NO_2$ [M+H]$^+$ 156.102 found 156.1017.

According to the same methodology, but employing suitable starting material, the following compound was prepared:

(2S)-2-(1H-pyrrol-1-yl)pentane-1,5-diol [(XVII), $E^1$=—$CH_2CH_2CH_2$—OH]

(4.2 g, 73% yield).

$^1$H NMR (600 MHz, DMSO-d6) δ 6.74 (t, J=2.11 Hz, 2H), 5.95 (t, J=2.11 Hz, 2H), 4.80 (t, J=5.40 Hz, 1H), 4.34 (t, J=5.22 Hz, 1H), 3.80-4.05 (m, 1H), 3.56 (t, J=5.68 Hz, 2H), 1.72-1.88 (m, 1H), 1.53-1.72 (m, 1H), 1.20-1.36 (m, 1H), 0.99-1.20 (m, 1H).

LCMS (HPLC Method 2): m/z 169 [M+H]$^+$@r.t. 3.18 min.

HRMS (ESI) calcd for $C_9H_{15}NO_2$ [M+H]$^+$ 170.1176 found 171.1177.

(2S)-3-methyl-2-(1H-pyrrol-1-yl)butan-1-ol [(XVII), $E^1$=—$CH(CH_3)_2$]

LCMS (HPLC Method 2): m/z 154 [M+H]$^+$@r.t. 4.01 min.

HRMS (ESI) calcd for $C_9H_{15}NO$ [M+H]$^+$ 154.1227 found 154.1225.

4-[(2S)-3-hydroxy-2-(1H-pyrrol-1-yl)propyl]-N,N-dimethyl-1H-imidazole-1-sulfonamide

[(XVII) $E^1$=$CH_2$-1-(dimethylsulfamoyl)-1H-imidazol-4-yl]

LCMS (HPLC Method 2): m/z 299 [M+H]$^+$@r.t. 4.54 min.

HRMS (ESI) calcd for $C_{13}H_{19}N_4O_4S$ [M+H]$^+$ 327.1122 found 327.1120.

HRMS (ESI) calcd for $C_{12}H_{18}N_4O_3S$ [M+H]+ 299.1173 found 299.1173.

Preparation L$^1$ (2S)-2-(1H-pyrrol-1-yl)butane-1,4-diol [(XVII), $E^1$=—$CH_2CH_2$—OH]

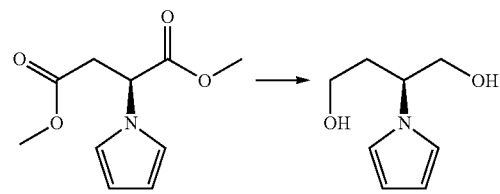

In a two necked flask cooled in an ice bath and under argon atmosphere, dimethyl(2S)-2-(1H-pyrrol-1-yl)butanedioate (19 mmol, 4.0 g) was dissolved in 10 ml of dry THF. LiBH$_4$ (57 mmol 1.14 g) was added portionwise and the reaction was stirred for 6 hours at 0° C. When the reaction was completed, it was quenched by addition of 2M HCl and Ethyl Acetate (30 ml). The aqueous layer was extracted with ethyl acetate 2 times and the combined organic layers were dried, filtered and evaporated. The crude residue was purified by chromatography on silica gel (eluent: DCM/MeOH:95/5) to give the product as a colourless oil (2.8 g, 95% yield, e.e. %=97.5).

1H NMR (600 MHz, DMSO-d6) δ 6.73 (t, J=2.01 Hz, 2H), 5.95 (t, J=2.01 Hz, 2H), 4.82 (t, J=5.40 Hz, 1H), 4.44 (t, J=5.04 Hz, 1H), 4.01-4.12 (m, J=4.76, 10.07 Hz, 1H), 3.58 (t, J=5.68 Hz, 2H), 3.23-3.29 (m, J=6.23, 10.81 Hz, 1H), 3.08-3.17 (m, 1H), 1.85-1.95 (m, 1H), 1.67-1.81 (m, 1H).

LCMS (HPLC Method 2): m/z 156 [M+H]$^+$@r.t. 2.26 min.

HRMS (ESI) calcd for $C_8H_{13}NO_2$ [M+H]$^+$ 156.102 found 156.1017.

Preparation M

1-[(2S)-1,4-diazidobutan-2-yl]-1H-pyrrole [(XIX), Y=$N_3$, $E^2$=—$CH_2CH_2$—$N_3$]

Step 17

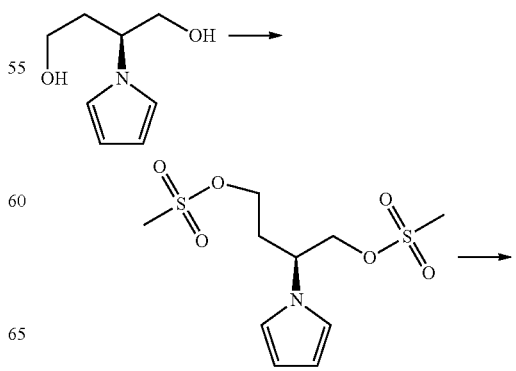

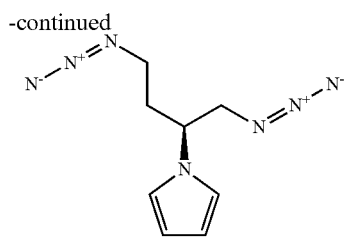

(2S)-2-(1H-pyrrol-1-yl)butane-1,4-diol (2.0 g, 13 mmol) was dissolved in 70 ml of dry THF in the presence of TEA (3.9 ml, 28.40 mmol) and cooled in an ice bath. Methanesulfonylchloride (2.2 ml, 28.4 mmol) was diluted in 5 ml of dry THF and slowly added into the mixture through a dropping funnel. A white precipitate formed. After 10 min. at 0° C., the reaction was warmed up and kept at room temperature until complete. Then, water and EtOAc were added and the resulting organic layer was washed with water and brine. It was then dried, filtered and concentrated under reduced pressure; the resulting crude was directly submitted to the next step without purification or characterization. The crude containing (2S)-4-[(methylsulfonyl)oxy]-2-(1H-pyrrol-1-yl)butyl methanesulfonate was diluted with a mixture of dry DMF (35 ml) and $CH_3CN$ (40 ml) and reacted with sodium azide (5.00 g, 77.17 mmol) for several hours. After reaction completion, it was cooled and worked up with water and AcOEt. The organic layers were washed with brine, dried, filtered and evaporated. The crude residue was purified by chromatography on silica gel (eluent: Hex/AcOEt:8/2) to give a colourless oil (2.18 g, 80% yield over two steps).

$^1$H NMR (600 MHz, DMSO-d6) δ 6.66-6.91 (m, 2H), 5.94-6.13 (m, 2H), 4.14-4.27 (m, 1H), 3.71 (dd, J=8.70, 12.91 Hz, 1H), 3.58 (dd, J=4.40, 12.82 Hz, 1H), 3.21 (td, J=6.09, 12.36 Hz, 1H), 2.99 (td, J=7.46, 12.55 Hz, 1H), 1.86-2.04 (m, 2H).

HRMS (ESI) calcd for $C_8H_{11}N_7$ [M+H]$^+$ 206.1149 found 206.1143.

According to the same methodology, but employing suitable starting material, the following compound was prepared:

1-[(2S)-1,5-diazidopentan-2-yl]-1H-pyrrole [(XIX), Y=$N_3$, $E^2$=—$CH_2CH_2CH_2$—$N_3$]

purified by chromatography on silica gel (eluent: Hex/AcOEt:8/2) to give a colourless oil (4.1 g, 88% yield over two steps).

$^1$H NMR (600 MHz, DMSO-d6) δ 6.84 (t, J=2.01 Hz, 2H), 6.03 (t, J=2.11 Hz, 2H), 4.07-4.19 (m, 1H), 3.68 (dd, J=8.79, 12.82 Hz, 1H), 3.54 (dd, J=4.58, 12.82 Hz, 1H), 3.25 (t, J=6.87 Hz, 2H), 1.76 (q, J=7.69 Hz, 2H), 1.38 (dt, J=7.23, 14.42 Hz, 1H), 1.22 (td, J=7.07, 14.24 Hz, 1H).

LCMS (HPLC Method 2): m/z 220 [M+H]$^+$@r.t. 6.53 min.

HRMS (ESI) calcd for $C_9H_{13}N_7$ [M+H]$^+$ 220.1305 found 220.1302.

1-[(2S)-1-azido-3-methylbutan-2-yl]-1H-pyrrole [(XIX), Y=$N_3$, $E^2$=—$CH_2(CH_3)_2$]

purified by chromatography on silica gel (eluent: Hex/AcOEt:8/2) to give a colourless oil (4.44 g, 82% yield over two steps).

LCMS (HPLC Method 5): m/z 179 [M+H]+ @r.t. 3.86 min.

4-[(2S)-3-azido-2-(1H-pyrrol-1-yl)propyl]-N,N-dimethyl-1H-imidazole-1-sulfonamide [(XIX), Y=$N_3$, $E^2$=$CH_2$-1-(dimethylsulfamoyl)-1H-imidazol-4-yl]

LCMS (HPLC Method 2): m/z 324 [M+H]+@r.t. 5.72 min.

HRMS (ESI) calcd for $C_{12}H_{17}N_7O_2S$ [M+H]$^+$ 324.1237 found 324.1232.

Preparation N 2,2,2-trichloro-1-{1-[(2S)-1,4-diazidobutan-2-yl]-1H-pyrrol-2-yl}ethanone [(XX), Y=$N_3$, $E^2$=—$CH_2CH_2$—$N_3$]

Step 18

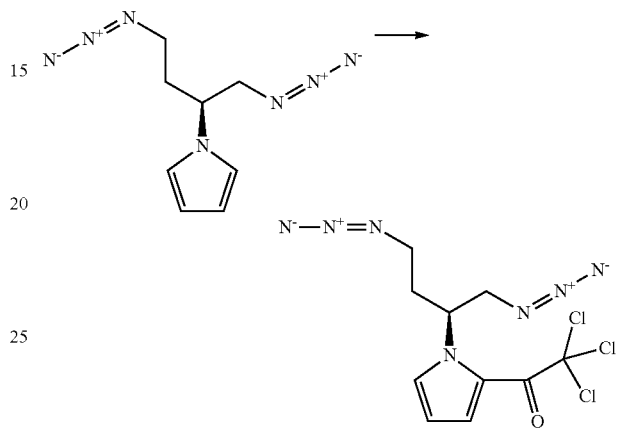

A solution of trichloroacetyl chloride (1.3 ml, 11.8 mmol) in dry DCM (25 ml) was cautiously dropped into a 250 ml flask containing 1-[(2S)-1,4-diazidobutan-2-yl]-1H-pyrrole (2.18 g, 10.7 mmol) diluted in dry DCM (25 ml). The mixture was refluxed until reaction went to completion. The reaction was quenched with water and extracted with DCM. The organic layers were subsequently washed with satured $NaHCO_3$, water and brine. After drying, filtration and evaporation, the crude residue was purified on silica gel (eluent: Hexane/AcOEt:9/1) to give the expected product as a clear oil (2.78 g, 74% yield).

$^1$H NMR (600 MHz, DMSO-d6) δ 7.77 (s, 1H), 7.51-7.59 (m, 1H), 6.45 (dd, J=2.66, 4.30 Hz, 1H), 5.50 (br. s., 1H), 3.68-3.83 (m, 2H), 3.35-3.40 (m, 1H), 3.10 (ddd, J=6.32, 8.06, 12.73 Hz, 1H), 2.03-2.19 (m, 2H).

HRMS (ESI) calcd for $C_{10}H_{10}Cl_3N_7O$ [M+H]$^+$ 371.9904 found 371.9903.

LCMS (HPLC Method 2): m/z 371 [M+H]$^+$@r.t. 7.55 min.

According to the same method, but employing 1-[(2S)-1,5-diazidopentan-2-yl]-1H-pyrrole the following compound was prepared:

2,2,2-trichloro-1-{1-[(2S)-1,5-diazidopentan-2-yl]-1H-pyrrol-2-yl}ethanone [(XX), Y=$N_3$, $E^2$=—$CH_2CH_2CH_2$—$N_3$]

$^1$H NMR (600 MHz, DMSO-d6) δ 7.76 (dd, J=1.47, 2.38 Hz, 1H), 7.54 (dd, J=1.19, 4.30 Hz, 1H), 6.45 (dd, J=2.56, 4.40 Hz, 1H), 5.40 (br. s., 1H), 3.74-3.81 (m, 1H), 3.67-3.73 (m, 1H), 1.84-1.96 (m, 2H), 1.44 (ddd, J=6.87, 9.11, 13.69 Hz, 1H), 1.22-1.35 (m, 1H).

LCMS (HPLC Method 2): m/z 363 [M+H]$^+$@r.t. 7.57 min.

HRMS (ESI) calcd for $C_{11}H_{12}Cl_3N_7O$ [M+H]$^+$ 386.0061 found 386.0064.

1-{1-[(2S)-1-azido-3-methylbutan-2-yl]-1H-pyrrol-2-yl}-2,2,2-trichloroethanone [(XX), Y=$N_3$, $E^2$=—$CH_2(CH_3)_2$]

LCMS (HPLC Method 2): m/z 345 [M+Na]$^+$@r.t. 7.77 min.

HRMS (ESI) calcd for $C_{11}H_{13}Cl_3N_4NaO$ [M+Na]$^+$ 345.0047 found 345.0061.

4-{(2S)-3-azido-2-[2-(trichloroacetyl)-1H-pyrrol-1-yl]propyl}-N,N-dimethyl-1H-imidazole-1-sulfonamide

[(XX), Y=N$_3$, E$^2$=CH$_2$-1-(dimethylsulfamoyl)-1H-imidazol-4-yl]

LCMS (HPLC Method 2): m/z 468 [M+H]$^+$@r.t. 6.81 min.

HRMS (ESI) calcd for $C_{14}H_{16}Cl_3N_7O_3S$ [M+H]$^+$ 468.0174 found 468.0171.

Preparation O 2,2,2-trichloro-1-{1-[(2S)-1,4-diazidobutan-2-yl]-4-iodo-1H-pyrrol-2-yl}ethanone [(XXI) Y=N$_3$, E$^2$=—CH$_2$CH$_2$—N$_3$]

Step 19

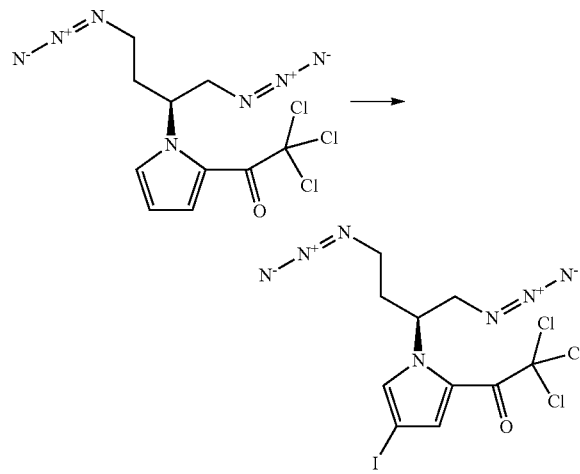

2,2,2-trichloro-1-{1-[(2S)-1,4-diazidobutan-2-yl]-1H-pyrrol-2-yl}ethanone (2.78 g, 7.9 mmol) was dissolved in dry DCM (200 ml) in the presence of silver trifluoroacetate (1.93 g, 8.74 mmol) and the mixture was cooled in an ice bath. Iodine (2.0 g 7.95 mmol) was added portionwise. A milky suspension formed and the mixture was let stir overnight at room temperature. As the reaction was not complete, some more silver trifluoroacetate (0.44 g, 2.0 mmol) and iodine (0.37 g, 1.45 mmol) were added. The suspension was filtered through paper, the residue dried under reduced pressure to give a crude which, after purification by silica chromatography (eluent: Hex/DCM:9/1 and then Hex/DCM: 7/3) led to the wanted product as a colorless oil (1.78 g, 47% yield).

$^1$H NMR (600 MHz, DMSO-d6) δ 7.96 (d, J=1.28 Hz, 1H), 7.56 (d, J=1.47 Hz, 1H), 5.47 (br. s., 1H), 3.75 (d, J=6.41 Hz, 2H), 3.38 (td, J=6.04, 12.45 Hz, 1H), 2.97-3.19 (m, 1H), 2.10-2.20 (m, 1H), 1.98-2.10 (m, 1H).

LCMS (HPLC Method 2): m/z 475 [M+H]$^+$@r.t. 7.26.

According to the same method, but employing 2,2,2-trichloro-1-{1-[(2S)-1,5-diazidopentan-2-yl]-1H-pyrrol-2-yl}ethanone, the following compound was prepared:

2,2,2-trichloro-1-{1-[(2S)-1,5-diazidopentan-2-yl]-4-iodo-1H-pyrrol-2-yl}ethanone [(XXI), Y=N$_3$, E$^2$=—CH$_2$CH$_2$CH$_2$—N$_3$]

$^1$H NMR (600 MHz, DMSO-d$_6$) δ 7.94 (d, J=1.47 Hz, 1H), 7.57 (d, J=1.47 Hz, 1H), 5.36 (br. s., 1H), 3.69-3.80 (m, 2H), 1.82-1.96 (m, 2H), 1.25-1.50 (m, 2H).

LCMS (HPLC Method 2): m/z 488 [M+H]$^+$@r.t. 8.02 min.

1-{1-[(2S)-1-azido-3-methylbutan-2-yl]-4-iodo-1H-pyrrol-2-yl}-2,2-dichloroethanone [(XX), Y=N$_3$, E$^2$=—CH(CH$_3$)$_2$]

LCMS (HPLC Method 2): m/z 448 [M+H]$^+$@r.t. 8.3 min.

4-{(2S)-3-azido-2-[4-iodo-2-(trichloroacetyl)-1H-pyrrol-1-yl]propyl}-N,N-dimethyl-1H-imidazole-1-sulfonamide [(XXI), Y=N$_3$, E$^2$=CH$_2$-1-(dimethylsulfamoyl)-1H-imidazol-4-yl]

LCMS (HPLC Method 2): m/z 593 [M+H]$^+$@r.t. 7.34 min.

HRMS (ESI) calcd for $C_{14}H_{15}Cl_3IN_7O_3S$ [M+H]$^+$ 593.914 found: 593.9137.

Preparation P

Methyl 1-[(2S)-1,4-diazidobutan-2-yl]-4-iodo-1H-pyrrole-2-carboxylate [(XXII), Y=N$_3$, E$^2$=—CH$_2$CH$_2$—N$_3$]

Step 20

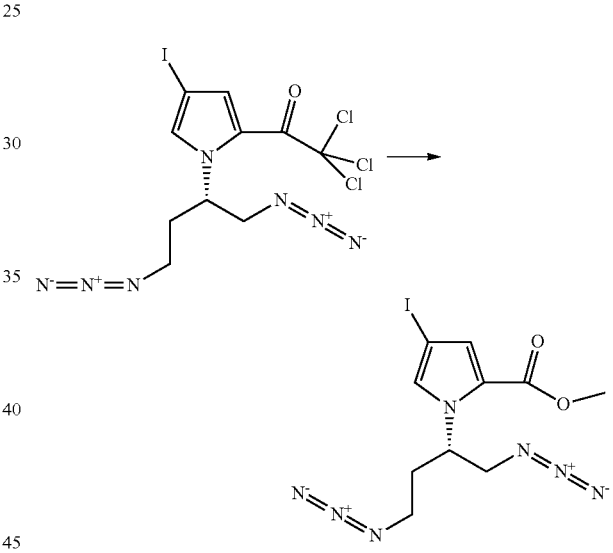

2,2,2-trichloro-1-{1-[(2S)-1,4-diazidobutan-2-yl]-4-iodo-1H-pyrrol-2-yl}ethanone (1.78 g, 3.7 mmol) was dissolved in dry MeOH and reacted with 0.5 M MeONa in THF (7.5 ml, 3.7 mmol). The reaction was performed at room temperature for 3 hours and stopped by adding a satured acqueous solution of NH$_4$Cl. Ethyl acetate was then added, and the organic layer washed with brine, dried and evaporated under reduced pressure. The resulting oil was purified by column chromatography to give the product as a colorless oil (1.4 g, quant. yield).

$^1$H NMR (600 MHz, DMSO-d6) δ 7.30 (s, 1H) 7.16 (d, J=1.3 Hz, 1H) 5.16 (m, 1H) 3.75 (d, J=6.41 Hz, 2H) 3.35-3.42 (m, 1H) 2.98-3.17 (m, 1H) 1.99-2.14 (m, 2H)

LCMS (HPLC Method W2): m/z 390 [M+H]$^+$@r.t. 3.22 min.

According to the same method, but employing 2,2,2-trichloro-1-{1-[(2S)-1,5-diazidopentan-2-yl]-4-iodo-1H-pyrrol-2-yl}ethanone the following compound was prepared:

Methyl 1-[(2S)-1,5-diazidopentan-2-yl]-4-iodo-1H-pyrrole-2-carboxylate [(XXII), Y=N$_3$, A=—CH$_2$CH$_2$CH$_2$—N$_3$]

¹H NMR (600 MHz, DMSO-d6) δ 7.59 (d, J=1.83 Hz, 1H), 6.98 (d, J=1.83 Hz, 1H), 5.43 (br. s., 1H), 3.74 (s, 3H), 3.70-3.75 (m, 1H), 3.65-3.70 (m, 1H), 1.67-1.97 (m, 2H), 1.34-1.45 (m, 1H), 1.17-1.30 (m, 1H).

LCMS (HPLC Method 2): m/z 426 [M+Na]+r.t. 7.32.

HRMS (ESI) calcd for $C_{11}H_{14}IN_7NaO_2$ [M+Na]+ 426.0146 found 426.0166.

Methyl 1-[(2S)-1-azido-3-methylbutan-2-yl]-4-iodo-1H-pyrrole-2-carboxylate [(XXI) Y=$N_3$, $E^2$=—$CH_2(CH_3)_2$]

¹H NMR (600 MHz, DMSO-d6) δ 7.57 (s, 1H), 6.97 (d, J=1.46 Hz, 1H), 5.02-5.29 (m, 1H), 3.81-3.88 (m, 1H), 3.76-3.81 (m, 1H), 3.73 (s, 3H), 1.99-2.12 (m, 1H), 0.94 (d, J=6.78 Hz, 3H), 0.62 (d, J=6.59 Hz, 3H).

LCMS (HPLC Method 2): m/z 362 [M+H]+@r.t. 7.48 min.

HRMS (ESI) calcd for $C_{11}H_{16}IN_4O_2$[M+H]+ 363.0313 found 363.0322.

Methyl 1-{(2S)-1-azido-3-[1-(dimethylsulfamoyl)-1H-imidazol-4-yl]propan-2-yl}-4-iodo-1H-pyrrole-2-carboxylate

[(XXII), Y=$N_3$, $E^2$=$CH_2$-1-(dimethylsulfamoyl)-1H-imidazol-4-yl]

¹H NMR (600 MHz, DMSO-d6) δ 8.01 (d, J=1.28 Hz, 1H), 7.58 (s, 1H), 7.06 (s, 1H), 6.86 (d, J=1.65 Hz, 1H), 5.73 (br. s., 1H), 3.75-3.91 (m, 2H), 3.70 (s, 3H), 2.97-3.12 (m, 2H), 2.67 (s, 6H).

LCMS (HPLC Method 2): m/z 508 [M+H]+@r.t. 6.51 min.

HRMS (ESI) calcd for $C_{14}H_{19}IN_7SO_4$ [M+H]+ 508.0259 found 508.0266.

Preparation Q

Tert-butyl {2-[(4S)-7-iodo-1-oxo-1,2,3,4-tetrahydropyrrolo[1,2-a]pyrazin-4-yl]ethyl}carbamate [(XXIII) A=—$CH_2CH_2$—NH—CO—OtBu]

Step 21 and Step 22

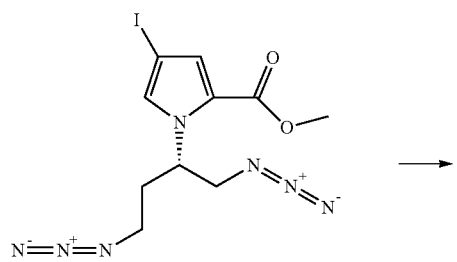

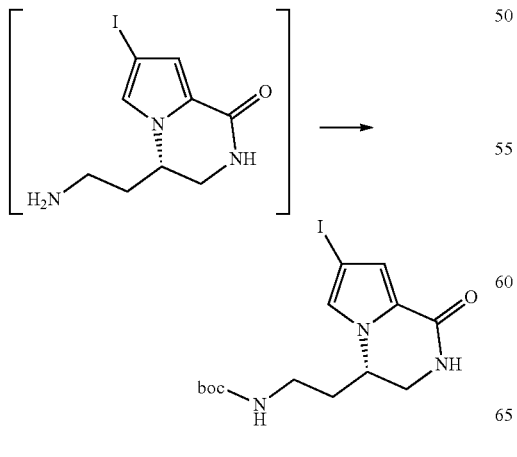

Methyl 1-[(2S)-1,4-diazidobutan-2-yl]-4-iodo-1H-pyrrole-2-carboxylate (1.5 g, 3.86 mmol) was reacted overnight and at room temperature with triphenylphosphine (2.02 g, 7.71 mmol) in dry DCM (40 ml). After reaction completion, the solvent was removed under reduced pressure, and a mixture of 2:1/THF:water (150 ml) was added. After all day under stirring, always at room temperature, the product was completely cyclized and di-tert-butyl dicarbonate (3.2 g, 15.0 mmol) was added. At the end of the reaction, the product was extracted with AcOEt. The organic layers were dried and evaporated and the residue was purified by chromatography on silica gel (eluent: DCM/MeOH: 9/0.1 and DCM/MeOH: 9/0.2) to give the desired product as a spongy white solid (1.2 g, 76% yield over three steps).

¹H NMR (600 MHz, DMSO-d6) δ 7.69 (d, J=3.11 Hz, 1H), 7.24 (s, 1H), 6.92 (t, J=5.22 Hz, 1H), 6.70 (d, J=1.28 Hz, 1H), 4.25 (t, J=6.50 Hz, 1H), 3.62 (dd, J=3.39, 12.91 Hz, 1H), 3.23-3.29 (m, 1H), 2.94 (q, J=6.47 Hz, 2H), 1.65-1.89 (m, 2H), 1.38 (s, 9H).

LCMS (HPLC Method 2): m/z 405 [M+H]+@r.t. 4.6 min.

HRMS (ESI) calcd for $C_{14}H_{20}IN_3NaO_3$ [M+Na]+ 428.0441. found 428.0438.

According to the same method, but employing methyl1-[(2S)-1,5-diazidopentan-2-yl]-4-iodo-1H-pyrrole-2-carboxylate the following compounds were prepared:

tert-butyl{3-[(4S)-7-iodo-1-oxo-1,2,3,4-tetrahydropyrrolo[1,2-a]pyrazin-4-yl]propyl}carbamate [(XXIII), A=—$CH_2$—$CH_2CH_2$—NH—CO—OtBu]

¹H NMR (600 MHz, DMSO-d6) δ 7.67 (br. s., 1H), 7.19 (d, J=1.47 Hz, 1H), 6.83 (br. s., 1H), 6.69 (d, J=1.47 Hz, 1H), 4.24 (br. s., 1H), 3.55-3.61 (m, 1H), 3.25 (td, J=4.03, 13.19 Hz, 1H), 2.83-3.01 (m, 2H), 1.56-1.78 (m, 2H), 1.20-1.46 (m, 11H). LCMS (HPLC Method 2): m/z 420 [M+H]+@r.t. 5.48 min.

HRMS (ESI) calcd for $C_{15}H_{22}IN_3O_3$[M+H]+ 420.0779. found 420.0763.

(4S)-7-iodo-4-(propan-2-yl)-3,4-dihydropyrrolo[1,2-a]pyrazin-1(2H)-one [(XXIII), A=—$CH_2(CH_3)_2$]

LCMS (HPLC Method 2): m/z 304 [M+H]+@r.t. 5.06 min.

HRMS (ESI) calcd for $C_{10}H_{14}IN_2O$ [M+H]+ 305.0146. found 305.0144.

4-{[(4S)-7-iodo-1-oxo-1,2,3,4-tetrahydropyrrolo[1,2-a]pyrazin-4-yl]methyl}-N,N-dimethyl-1H-imidazole-1-sulfonamide [(XXIII), A=$CH_2$-1-(dimethylsulfamoyl)-1H-imidazol-4-yl]

LCMS (HPLC Method 2): m/z 450 [M+H]+@r.t. 4.78 min.

HRMS (ESI) calcd for $C_{13}H_{17}IN_5O_3S$ [M+H]+ 450.0092. found 450.0087.

Example 6 tert-butyl(2-{(4S)-1-oxo-7-[3-(trifluoromethoxy)phenyl]-1,2,3,4-tetrahydropyrrolo[1,2-a]pyrazin-4-yl}ethyl)carbamate [(I), R2=3-(trifluoromethoxy)phenyl, R3=R4=H, A=—$CH_2CH_2$—NH—CO—OtBu]

Step 23a

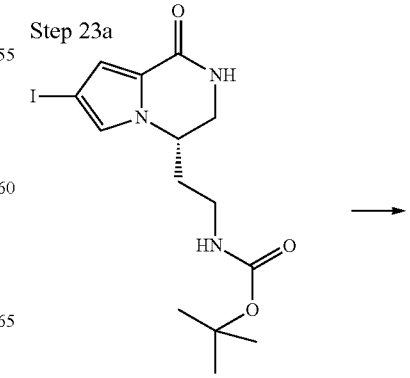

-continued

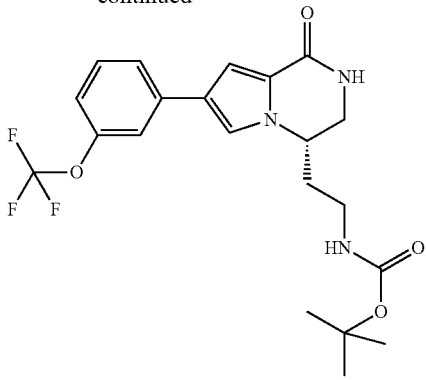

Cesium carbonate (2.76 g, 8.46 mmol), [3-(trifluoromethoxy)phenyl]boronic acid (0.755 g, 3.67 mmol), and 1,1'-bis(diphenylphosphino)ferrocenepaladium complex with dichloromethane (0.115 g, 0.141 mmol) were added to a degassed solution of tert-butyl{2-[(4S)-7-iodo-1-oxo-1,2,3,4-tetrahydropyrrolo[1,2-a]pyrazin-4-yl]ethyl}carbamate (1.144 g, 2.82 mmol) in 30 ml of 1,4-dioxane and 10 ml of water, under argon atmosphere. The mixture was heated at 70° for 2 hours in a sealed vial. The reaction was filtered through a celite pad and the solvent evaporated to dryness. The crude was portioned between ethyl acetate and water, the organic layer dried over sodium sulphate and the solvent removed in vacuo. Purification by flash chromatography on silica gel column (DCM/MeOH, 9/0.3) afforded the title compound as solid (0.904 g, 73%).

$^1$H NMR (600 MHz, DMSO-d6) δ 7.69 (br. s., 2H), 7.63 (d, J=7.88 Hz, 1H), 7.56 (s, 1H), 7.45 (t, J=7.97 Hz, 1H), 7.13 (d, J=8.24 Hz, 1H), 7.11 (d, J=1.83 Hz, 1H), 6.97 (t, J=5.59 Hz, 1H), 4.20-4.33 (m, J=3.11 Hz, 1H), 3.68 (dd, J=2.56, 13.19 Hz, 1H), 3.30-3.38 (m, 1H), 3.00 (q, J=6.59 Hz, 2H), 1.94 (qd, J=6.87, 13.83 Hz, 1H), 1.76-1.87 (m, J=6.73, 6.73, 13.64 Hz, 1H), 1.38 (s, 9H).

LCMS (HPLC Method 2): m/z 462 [M+Na]$^+$@r.t. 6.6 min.
HRMS (ESI) calcd for $C_{21}H_{24}F_3N_3NaO_4$ [M+Na]$^+$ 462.1611 found 462.1594.

According to the same method, the following compounds were prepared:

tert-butyl(3-{(4S)-1-oxo-7-[3-(trifluoromethoxy)phenyl]-1,2,3,4-tetrahydropyrrolo[1,2-a]pyrazin-4-yl}propyl)carbamate [(I), R2=3-(trifluoromethoxy)phenyl, R3=R4=H, A=—CH$_2$—CH$_2$CH$_2$—NH—CO—OtBu]

Purification by flash chromatography on silica gel column (EtOAc/Hex 3/2) led to the wanted compound in 85% yield.

$^1$H NMR (400 MHz, DMSO-d6) δ 7.60-7.71 (m, 3H), 7.55 (s, 1H), 7.45 (t, J=7.99 Hz, 1H), 7.13 (d, J=8.30 Hz, 1H), 7.10 (d, J=1.59 Hz, 1H), 6.72-6.92 (m, 1H), 4.20-4.32 (m, 1H), 3.64 (dd, J=4.27, 13.18 Hz, 1H), 2.80-3.07 (m, 2H), 1.74-1.90 (m, 1H), 1.60-1.74 (m, 1H), 1.16-1.53 (m, 12H).

LCMS (HPLC Method 2): m/z 454 [M+H]$^+$@r.t. 6.52 min.
HRMS (ESI) calcd for $C_{22}H_{26}F_3N_3O_4$[M+H]$^+$ 454.1948 found 454.1954.

(4S)-4-(propan-2-yl)-7-[3-(trifluoromethoxy)phenyl]-3,4-dihydropyrrolo[1,2-a]pyrazin-1(2H)-one
[(I), R2=3-(trifluoromethoxy)phenyl, R3=R4=H, A=—CH$_2$(CH$_3$)$_2$]

LCMS (HPLC Method 2): m/z 338 [M+H]$^+$@r.t. 6.32 min.
HRMS (ESI) calcd for $C_{17}H_{18}F_3N_2O_2$[M+H]$^+$ 339.1315. found 339.1317.

N,N-dimethyl-4-({(4S)-1-oxo-7-[3-(trifluoromethoxy)phenyl]-1,2,3,4-tetrahydropyrrolo[1,2-a]pyrazin-4-yl}methyl)-1H-imidazole-1-sulfonamide

[(I), R2=3-(trifluoromethoxy)phenyl, R3=R4=H, A=CH$_2$-1-(dimethylsulfamoyl)-1H-imidazol-4-yl]

LCMS (HPLC Method 2): m/z 483 [M+H]$^+$@r.t. 5.87 min.
HRMS (ESI) calcd for $C_{20}H_{21}F_3N_5O_4S$ [M+H]$^+$ 484.1261. found 484.1259.

According to the same method, but employing [3-chlorophenyl]boronic acid the following compound was prepared: tert-butyl{3-[(4S)-7-(3-chlorophenyl)-1-oxo-1,2,3,4-tetrahydropyrrolo[1,2-a]pyrazin-4-yl]propyl}carbamate

[(I), R2=3-chlorophenyl, R3=R4=H, A=—CH$_2$—CH$_2$CH$_2$—NH—CO—OtBu]$^1$H NMR (600 MHz, DMSO-d$_6$) δ 7.61-7.68 (m, 3H), 7.56 (d, J=7.88 Hz, 1H), 7.34 (t, J=7.97 Hz, 1H), 7.18-7.22 (m, 1H), 7.07 (d, J=1.83 Hz, 1H), 6.85 (t, J=5.31 Hz, 1H), 4.17-4.29 (m, J=6.50, 6.50 Hz, 1H), 3.64 (dd, J=2.66, 13.10 Hz, 1H), 2.99 (td, J=6.69, 13.00 Hz, 1H), 2.85-2.96 (m, 1H), 1.77-1.86 (m, 1H), 1.62-1.72 (m, 1H), 1.43-1.51 (m, 1H), 1.20-1.41 (m, 10H).

LCMS (HPLC Method 2): m/z 404 [M+H]$^+$@r.t. 6.23 min.
HRMS (ESI) calcd for $C_{21}H_{26}ClN_3O_3$[M+H]$^+$ 404.1736 found 404.1724.

Preparation R tert-butyl 4-(1-hydroxy-2-nitroethyl)piperidine-1-carboxylate [(XXV) A=tert-butyl-4-piperidine-1-carboxylate]

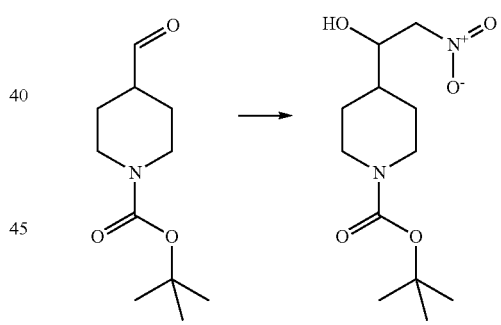

tert-butyl 4-formylpiperidine-1-carboxylate (1.2 g, 5.6 mmol) and nitromethane (0.61 mL, 11.2 mmol) were added to a solution of THF (15 ml) and t-BuOH (15 ml) and addition of K-OtBu (0.63 g, 5.6 mmol) followed. The mixture was stirred at room temperature for 2 h. The reaction mixture was brought to pH 6 using HOAc, diluted with EtOAc (30 mL), and extracted with brine. The aqueous layer was extracted with EtOAc (30 mL×2) The combined organic layers were washed with brine, dried, and concentrated to dryness. The crude material was purified via crystallization with diethyl ether and EtOAc, obtained 0.8 g $^1$H NMR (400 MHz, DMSO-d$_6$) δ 5.38 (d, J=6.35 Hz, 1H), 4.69-4.76 (m, 1H), 4.36 (dd, J=9.70, 12.39 Hz, 1H), 3.87-4.02

(m, 3H), 2.57-2.68 (m, 2H), 1.60-1.72 (m, 1H), 1.44-1.60 (m, 2H), 1.36-1.42 (m, 9H), 1.04-1.21 (m, 2H).

Preparation S tert-butyl 4-(2-amino-1-hydroxyethyl)piperidine-1-carboxylate [(XXVI) A=tert-butyl-4-piperidine-1-carboxylate]

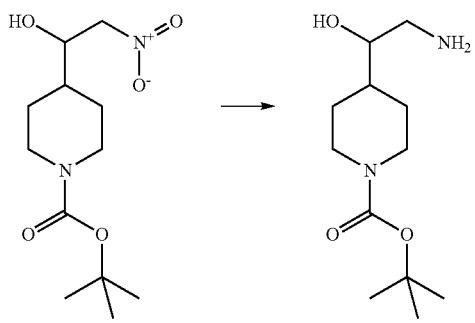 [SMILES: CC(C)(C)OC(=O)N1CCC(C(O)C[N+](=O)[O-])CC1 ; CC(C)(C)OC(=O)N1CCC(C(O)CN)CC1]

To a solution of tert-butyl 4-(1-hydroxy-2-nitroethyl)piperidine-1-carboxylate (780 mg 2.84 mmol), in MeOH (20 ml) were added ammonium formate (693 mg 11.18 mmol) and 10% Pd/C (100 mg) The reaction was stirred at room temperature for 18 hours, then filtered through Celite, washing with MeOH and THF and evaporated, to afford the title compound (554 mg 80% yield).

$^1$H NMR (400 MHz, DMSO-d$_6$) δ 3.89-4.02 (m, 2H), 3.35 (br. s., 1H), 2.79 (dd, J=3.11, 12.76 Hz, 0H), 2.56-2.65 (m, 3H), 1.69 (d, J=13.06 Hz, 1H), 1.44-1.57 (m, 1H), 1.39 (s, 9H), 1.11 (dd, J=4.21, 12.39 Hz, 2H). C12H24N2O3.

Preparation T tert-butyl 4-{2-[(2,4-dimethoxybenzyl)amino]-1-hydroxyethyl}piperidine-1-carboxylate [(XXVIa) A=tert-butyl-4-piperidine-1-carboxylate, pg=2,4-dimethoxybenzyl]

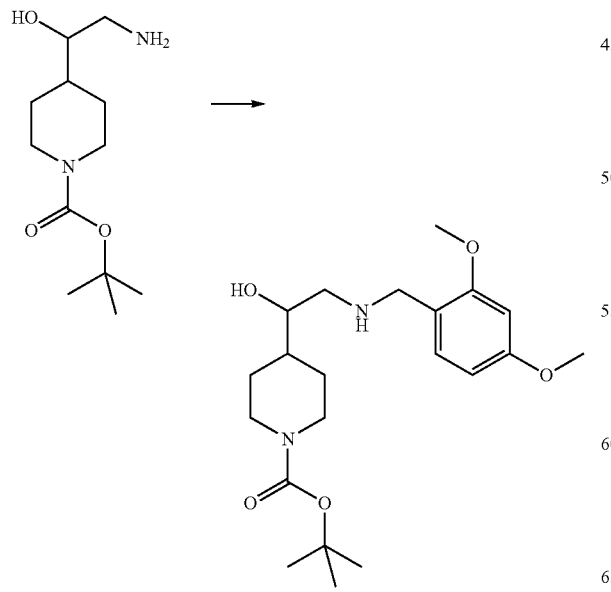

A solution of tert-butyl 4-(2-amino-1-hydroxyethyl)piperidine-1-carboxylate (0.5 g, 2.04 mmol), 2,4-dimethoxybenzaldehyde (0.34 g, 2.04 mmol) and acetic acid (5 μl, 0.092 mmol) in dry THF (10 ml) was stirred at room temperature for 1 h. Sodium cyanoborohydride (0.378 g, 6.0 mmol) was then added and the reaction mixture was stirred at room temperature for 1 hour. The solvent was evaporated, the residue was partioned between EtOAC and water, the organic layer was dried over Na$_2$SO$_4$, filtered and concentrated to dryness. The residue was purified by flash chromatography (SiO$_2$, DCM/EtOH/NH4OH 7/2.5/0.5) and provided the title compound (0.40 g, 50%).

$^1$H NMR (400 MHz, DMSO-d$_6$) δ 7.16 (d, J=8.18 Hz, 1H), 6.52 (d, J=2.44 Hz, 1H), 6.46 (dd, J=2.38, 8.24 Hz, 1H), 4.48-4.60 (m, 1H), 3.83-4.06 (m, J=8.42 Hz, 2H), 3.76 (s, 3H), 3.74 (s, 3H), 3.56-3.68 (m, 2H), 2.61 (br. s., 2H), 2.37-2.47 (m, 1H), 1.59-1.72 (m, J=12.69 Hz, 2H), 1.42-1.49 (m, J=10.74 Hz, 1H), 1.38 (s, 9H), 0.98-1.16 (m, 3H).

LCMS (HPLC Method 2): m/z 395 [M+H]$^+$@r.t. 5.26 min.
HRMS (ESI) calcd for C$_{21}$H$_{34}$N$_2$O$_5$ [M+H]$^+$ 395.2541. found 395.2546.

Preparation U tert-butyl 4-(2-{(2,4-dimethoxybenzyl)[(4-iodo-1H-pyrrol-2-yl)carbonyl]amino}-1-hydroxyethyl)piperidine-1-carboxylate [(XXVIII) A=tert-butyl-4-piperidine-1-carboxylate, pg=2,4-dimethoxybenzyl]

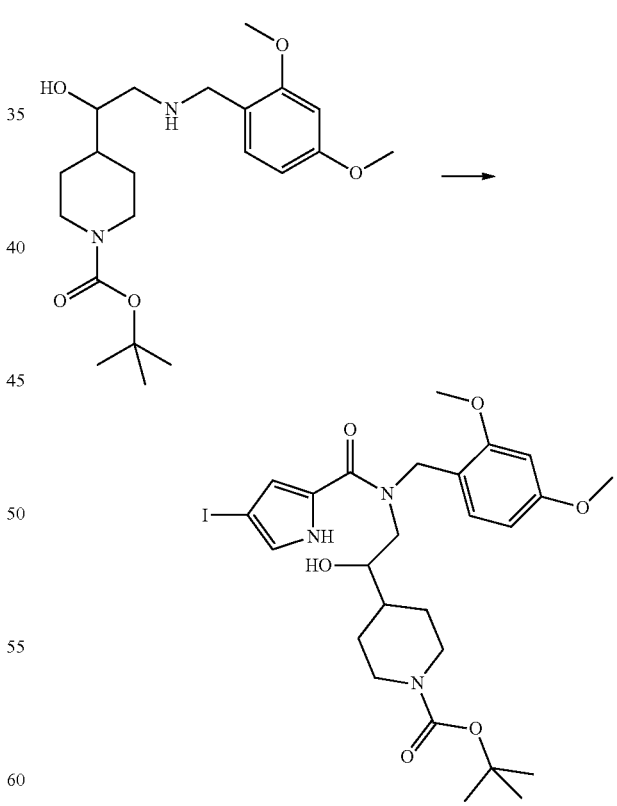

tert-butyl 4-{2-[(2,4-dimethoxybenzyl)amino]-1-hydroxyethyl}piperidine-1-carboxylate (0.4 g, 1.01 mmol) was added to a solution of 1-(4-acetyl-1H-pyrrol-2-yl)-2,2,2-trichloroethanone (0.336 mg, 1.01 mmol) and N,N-diisopropylethylamine (DIPEA) (0.9 mL, 5 mmol) in dioxane (10 mL) and the reaction mixture was stirred at 100° C. for 6 hours. The solvent was evaporated under vacuum and the residue purified by flash chromatography (SiO$_2$, DCM/EtOAc 6/4) to obtain the title compound as a yellow solid (115 mg, 20% yield).

$^1$H NMR (600 MHz, DMSO-d$_6$) δ 11.76 (br. s., 1H), 7.00 (dd, J=1.28, 2.93 Hz, 1H), 6.93 (br. s., 1H), 6.60 (br. s., 1H), 6.50 (br. s., 1H), 6.17 (br. s., 1H), 4.84 (br. s., 1H), 4.73 (d, J=16.48 Hz, 1H), 3.87-4.01 (m, 1H), 3.77-3.80 (m, 3H), 3.75 (s, 3H), 3.55-3.67 (m, 1H), 2.69 (s, 3H), 2.54-2.64 (m, 1H), 1.62 (br. s., 1H), 1.41-1.52 (m, 2H), 1.38 (s, 9H), 0.97-1.21 (m, 2H).

LCMS (HPLC Method 4): m/z 614 [M+H]$^+$@r.t. 3.33 min.

Preparation U$^1$ tert-butyl 4-[2-(2,4-dimethoxybenzyl)-7-iodo-1-oxo-1,2,3,4-tetrahydropyrrolo[1,2-a]pyrazin-4-yl]piperidine-1carboxylate [(XXIX) A=tert-butyl-4-piperidine-1-carboxylate, pg=2,4-dimethoxybenzyl]

Step 28

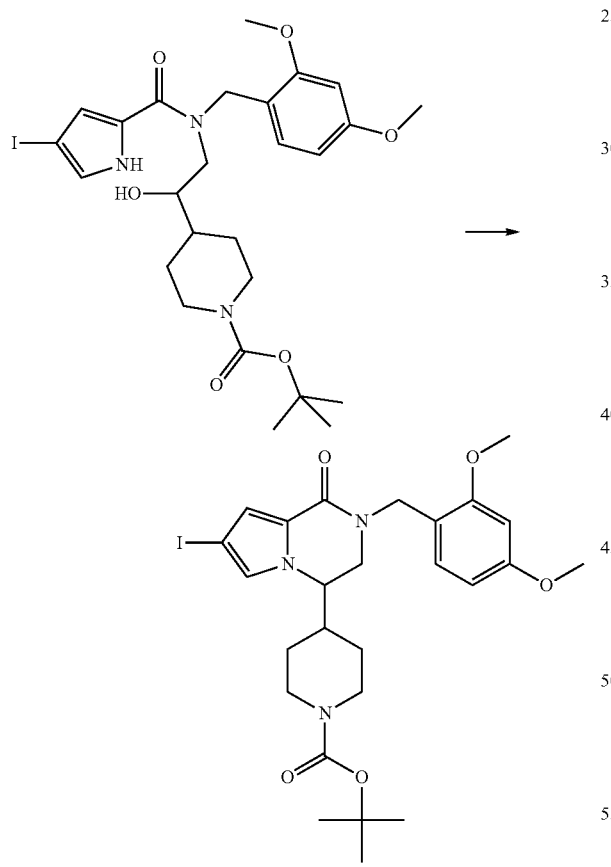

(tert-butyl 4-(2-{(2,4-dimethoxybenzyl)[(4-iodo-1H-pyrrol-2-yl)carbonyl]amino}-1-hydroxyethyl)piperidine-1-carboxylate (530 mg, 0.86 mmol) was dissolved in 70 ml of dry DCM in the presence of TEA (0.7 ml, 5.18 mmol) and cooled in an ice bath. Methanesulfonylchloride (0.2 ml, 2.59 mmol) was slowly added into the mixture. After 10 min. at 0° C., the reaction was warmed up and kept at room temperature until complete. Then, water and EtOAc were added and the resulting organic layer was washed with water and brine. It was then dried, filtered and concentrated under reduced pressure; the resulting crude was directly submitted to the next step without purification or characterization.

The crude containing tert-butyl 4-(2-{(2,4-dimethoxybenzyl)[(4-iodo-1H-pyrrol-2-yl)carbonyl]amino}-1-[(methylsulfonyl)oxy]ethyl)piperidine-1-carboxylate was diluted with dry DCM (20 ml) and reacted with Diaza(1,3)bicyclo[5.4.0]undecane (DBU) (0.2 ml, 1.45 mmol) overnight. After reaction completion, it was worked up with water and AcOEt. The organic layers were washed with brine, dried, filtered and evaporated. The crude residue was purified by chromatography on silica gel (eluent: Hex/AcOEt:7/3) to give a colourless oil (250 mg, 49% yield).

$^1$H NMR (400 MHz, DMSO-d$_6$) δ 7.14 (d, J=8.43 Hz, 1H), 7.13 (d, J=1.47 Hz, 1H), 6.72 (d, J=1.47 Hz, 1H), 6.59 (d, J=2.38 Hz, 1H), 6.52 (dd, J=2.38, 8.43 Hz, 1H), 4.93 (d, J=14.29 Hz, 1H), 4.06 (d, J=14.29 Hz, 1H), 3.93 (d, J=4.12 Hz, 1H), 3.86 (d, J=15.75 Hz, 1H), 3.77 (s, 3H), 3.75 (s, 1H), 3.72-3.74 (m, 1H), 3.69 (dd, J=4.12, 13.65 Hz, 1H), 3.37 (d, J=13.65 Hz, 1H), 2.08-2.46 (m, 3H), 1.47 (br. s., 1H), 1.36 (s, 9H), 1.02 (dq, J=4.30, 12.49 Hz, 1H), 0.78-0.95 (m, 3H).

LCMS (HPLC Method 2): m/z 596 [M+H]$^+$@r.t. 7.10 min.

HRMS (ESI) calcd for C$_{26}$H$_{35}$IN$_3$O$_5$[M+H]$^+$ 596.1616. found 596.11617.

Preparation V

Ethyl[1-oxo-7-(4,4,5,5-tetramethyl-1,3,2-dioxaborolan-2-yl)-1,2,3,4-tetrahydropyrrolo[1,2-a]pyrazin-4-yl]acetate [(VIII), Z', Z"=—C(Me)$_2$—C(Me)$_2$—]

Step 7

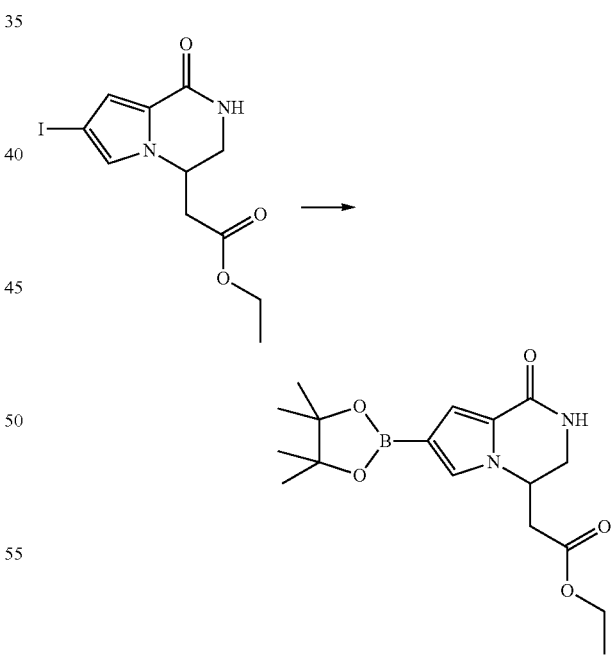

Ethyl(7-iodo-1-oxo-1,2,3,4-tetrahydropyrrolo[1,2-a]pyrazin-4-yl)acetate (200 mg, 0.57 mmol) was reacted with Bis(pinacolato)diboron (729 mg, 2.8 mmol) in the presence of potassium acetate (170 mg, 1.7 mmol) and [1,1'-Bis(diphenylphosphino)ferrocene]dichloropalladium(II), complex with dichloromethane (28 mg, 0.034 mmol) in dry DMF (18 ml) for 3 hours at 70° C. The crude was worked up with water and AcOEt, filtered, evaporated and finally purified on silica gel (eluent: AcOEt/Hex 9/1) to give the wanted compound as a clear oil in 40% yield.

$^1$H NMR (400 MHz, DMSO-d$_6$) δ 7.67 (d, J=2.32 Hz, 1H), 7.24 (d, J=1.46 Hz, 1H), 6.76 (d, J=1.59 Hz, 1H), 4.59-4.70 (m, 1H), 4.04-4.14 (m, 2H), 3.63 (ddd, J=1.65, 4.18, 12.97 Hz, 1H), 3.34-3.39 (m, 1H), 2.83 (d, J=7.20 Hz, 2H), 1.24 (s, 12H), 1.13-1.19 (m, 3H).

LCMS (HPLC Method 2): m/z 348 [M+H]$^+$@r.t. 5.31 min.
HRMS (ESI) calcd for C$_{17}$H$_{25}$BN$_2$O$_5$[M+H]$^+$ 348.1966. found 348.1953.

Example 7

7-(3-chlorophenyl)-4-[2-(dimethylamino)ethyl]-3,4-dihydropyrrolo[1,2-a]pyrazin-1(2H)-one [(I), R2=3-chlorophenyl, R3=R4=H, A=—CH$_2$CH$_2$—NR'R1, R'=R1=Me](cpd 4)

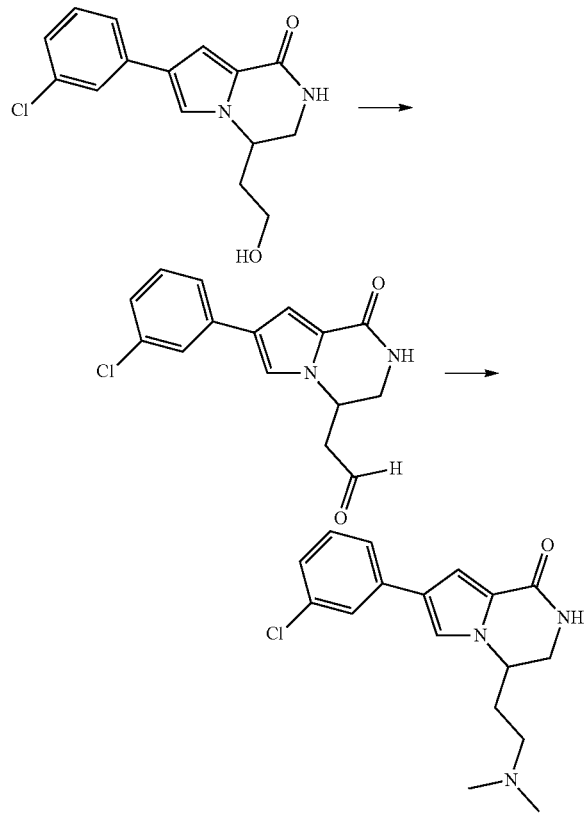

The 7-(3-chlorophenyl)-4-(2-hydroxyethyl)-3,4-dihydropyrrolo[1,2-a]pyrazin-1(2H)-one (290 mg 1 mmol) was dissolved in ethyl acetate (25 ml) and o-iodoxybenzoic acid (IBX) (837 mg 3 mmol) was added. The resulting suspension was heated at 80° C. for 3 h. The solution was then cooled to room temperature, filtered through Celite, and concentrated in vacuo. After cooling to room temperature, the reaction mixture was filtered and the volatiles removed in vacuo, the aldehyde as crude was used for the next reaction.

$^1$H NMR (400 MHz, DMSO-d6) δ 9.73 (t, J=1.10 Hz, 1H), 7.71-7.73 (m, J=1.22 Hz, 1H), 7.64 (t, J=1.83 Hz, 1H), 7.59 (d, J=1.83 Hz, 1H), 7.52-7.56 (m, 1H), 7.31-7.38 (m, 1H), 7.18-7.23 (m, 1H), 7.10 (d, J=1.83 Hz, 1H), 4.77 (quin, J=5.55 Hz, 1H), 3.68 (ddd, J=2.38, 4.09, 13.18 Hz, 1H), 3.04-3.09 (m, 1H).

LCMS (HPLC Method 2): m/z 289 [M+H]$^+$@r.t. 5.20 min.

To the aldehyde (50 mg 0.173 mmol) dissolved with THF (3 ml), sodium triacetoxyborohydride (146 mg, 0.693 mmol), and dimethylamine (10 ul, 0.208 mmol) were added. The reaction mixture was stirred at room temperature for 18 hours. The solvent was evaporated and the obtained crude was purified by chromatography (DCM/MeOH/NH$_4$OH 8/2/0.2) to provide the title compound 40 mg (72%).

$^1$H NMR (400 MHz, DMSO-d6) δ 7.67 (t, J=1.83 Hz, 2H), 7.63 (d, J=1.83 Hz, 1H), 7.55-7.59 (m, 1H), 7.35 (t, J=7.87 Hz, 1H), 7.20 (ddd, J=0.92, 2.14, 7.93 Hz, 1H), 7.08 (d, J=1.83 Hz, 1H), 4.22-4.38 (m, J=6.84, 6.84 Hz, 1H), 3.66 (ddd, J=1.89, 4.24, 13.03 Hz, 1H), 3.34-3.39 (m, 2H), 2.28 (t, J=7.02 Hz, 2H), 2.18 (s, 6H), 2.00 (qd, J=6.63, 13.56 Hz, 1H), 1.79-1.90 (m, 1H).

LCMS (HPLC Method 2): m/z 318 [M+H]$^+$@r.t. 4.37 min.
HRMS (ESI) calcd for C$_{17}$H$_{21}$ClN$_3$O [M+H]$^+$ 318.1368 found 318.1375.

According to the same method, but employing 4-amino-N-methylpiperidine, the following compound was prepared: 7-(3-chlorophenyl)-4-{2-[(1-methylpiperidin-4-yl)amino]ethyl}-3,4-dihydropyrrolo[1,2-a]pyrazin-1(2H)-one [(I), R2=3-chlorophenyl, R3=R4=H, A=—CH$_2$CH$_2$—NR'R1, R'=H, R1=1-methylpiperidin-4-yl](cpd 5) (30 mg 45%).

$^1$H NMR (400 MHz, DMSO-d6) δ 7.67 (br. s., 1H), 7.66 (t, J=1.83 Hz, 1H), 7.64 (d, J=1.83 Hz, 1H), 7.53-7.57 (m, 1H), 7.35 (t, J=7.87 Hz, 1H), 7.19 (ddd, J=0.98, 2.08, 7.93 Hz, 1H), 7.08 (d, J=1.83 Hz, 1H), 4.17-4.36 (m, J=4.33, 4.33 Hz, 1H), 3.65 (ddd, J=2.08, 4.30, 13.03 Hz, 1H), 3.33-3.39 (m, 1H), 2.29-2.35 (m, 10H), 2.17 (s, 3H), 2.01 (qd, J=6.70, 13.47 Hz, 1H), 1.86 (qd, J=7.11, 14.07 Hz, 1H).

LCMS (HPLC Method 2): m/z 387 [M+H]$^+$@r.t. 4.51 min.
HRMS (ESI) calcd for C$_{21}$H$_{28}$ClN$_4$O [M+H]$^+$ 387.1946 found 387.1949.

According to the same method, but employing N-methylpiperazine, the following compound was prepared: 7-(3-chlorophenyl)-4-[2-(4-methylpiperazin-1-yl)ethyl]-3,4-dihydropyrrolo[1,2-a]pyrazin-1(2H)-one [(I), R2=3-chlorophenyl, R3=R4=H, A=—CH$_2$CH$_2$—NR'R1, R', R1=4-methylpiperazin-1-yl](cpd 6) (35 mg 54%).

$^1$H NMR (400 MHz, DMSO-d6) δ 7.67 (br. s., 1H), 7.65 (t, J=1.83 Hz, 1H), 7.62 (d, J=1.83 Hz, 1H), 7.53-7.57 (m, 1H), 7.35 (t, J=7.93 Hz, 1H), 7.20 (ddd, J=0.98, 2.08, 7.93 Hz, 1H), 7.08 (d, J=1.83 Hz, 1H), 4.28-4.42 (m, 1H), 3.63-3.72 (m, 1H), 2.63-2.76 (m, 2H), 2.54-2.63 (m, 2H), 2.26-2.40 (m, 1H), 2.13 (s, 3H), 1.97 (qd, J=6.76, 13.66 Hz, 1H), 1.68-1.91 (m, 5H), 1.17-1.33 (m, 2H).

LCMS (HPLC Method 2): m/z 373 [M+H]$^+$@r.t. 4.44 min.
HRMS (ESI) calcd for C$_{21}$H$_{27}$ClN$_4$O [M+H]$^+$ 373.1790 found 373.1788.

According to the same method, but employing (1S)-1-cyclohexyl-2-(4-methylpiperazin-1-yl)ethylamino, the following compounds were prepared:

(4R)-7-(3-chlorophenyl)-4-(2-{[(1S)-1-cyclohexyl-2-(4-methyl piperazin-1-yl)ethyl]amino}ethyl)-3,4-dihydropyrrolo[1,2-a]pyrazin-1(2H)-one [(I), R2=3-chlorophenyl, R3=R4=H, A=—CH$_2$CH$_2$—NR'R1, R'=H, R1=(1S)-1-cyclohexyl-2-(4-methylpiperazin-1-yl)ethyl](cpd 7)

$^1$H NMR (400 MHz, DMSO-d6) δ 9.55 (br. s., 1H), 8.13 (br. s., 1H), 7.82 (d, J=3.91 Hz, 1H), 7.63-7.69 (m, 2H), 7.55-7.59 (m, 1H), 7.38 (t, J=7.87 Hz, 1H), 7.24 (ddd, J=0.98, 2.07, 7.93 Hz, 1H), 7.16 (d, J=1.71 Hz, 1H), 4.42-4.53 (m, 1H), 3.71-3.85 (m, 1H), 3.17-2.83 (m, 11H), 2.76 (s, 3H), 2.32-2.44 (m, 2H), 2.14 (m, 2H), 1.58-1.75 (m, 8H), 0.95-1.22 (m, 4H).

LCMS (HPLC Method 2): m/z 498 [M+H]+@r.t. 4.99 min.

HRMS (ESI) calcd for $C_{28}H_{41}ClN_5O$ [M+H]+ 498.2994 found 498.2991.

(4S)-7-(3-chlorophenyl)-4-(2-{[(1S)-1-cyclohexyl-2-(4-methyl piperazin-1-yl)ethyl]amino}ethyl)-3,4-dihydropyrrolo[1,2-a]pyrazin-1(2H)-one [(I), R2=3-chlorophenyl, R3=R4=H, A=—CH$_2$CH$_2$—NR'R1, R'=H, R1=(1S)-1-cyclohexyl-2-(4-methylpiperazin-1-yl)ethyl](cpd 8)

$^1$H NMR (400 MHz, DMSO-d6) δ 9.56 (br. s., 1H), 8.14 (br. s., 1H), 7.82 (d, J=4.15 Hz, 1H), 7.64-7.68 (m, 2H), 7.57 (qd, J=0.91, 7.77 Hz, 1H), 7.38 (t, J=7.87 Hz, 1H), 7.24 (ddd, J=0.98, 2.11, 8.03 Hz, 1H), 7.16 (d, J=1.83 Hz, 1H), 4.42-4.49 (m, 1H), 3.76 (br. s., 1H), 2.78-3.11 (m, 11H), 2.72 (br. s., 3H), 2.32-2.44 (m, 3H), 2.14 (m, 2H), 1.58-1.75 (m, 8H), 0.95-1.22 (m, 4H).

LCMS (HPLC Method 2): m/z 498 [M+H]+@r.t. 5.1 min.

HRMS (ESI) calcd for $C_{28}H_{41}ClN_5O$ [M+H]+ 498.2994 found 498.2977.

7-(biphenyl-3-yl)-4-{2-[(3S)-3-hydroxypyrrolidin-1-yl]ethyl}-3,4-dihydropyrrolo[1,2-a]pyrazin-1(2H)-one [(I), R2=biphenyl-3-yl, R3=R4=H, A=—CH$_2$CH$_2$—NR'R1, R', R1=—(3S)-3-hydroxypyrrolidin-1-yl](cpd 9)

$^1$H NMR (400 MHz, DMSO-d6) δ 7.87 (s, 1H), 7.71-7.76 (m, 2H), 7.61-7.67 (m, 2H), 7.59 (td, J=1.57, 7.11 Hz, 1H), 7.41-7.53 (m, 4H), 7.35-7.40 (m, 1H), 7.14 (d, J=1.71 Hz, 1H), 4.66-4.75 (m, 1H), 4.29-4.39 (m, 1H diast A), 4.14-4.25 (m, 1H, diast B), 3.67 (br. s., 1H), 2.67 (td, J=1.83, 3.66 Hz, 2H), 2.35 (m, 3H), 2.00 (m, 2H, 1.88 (m, 2H).

LCMS (HPLC Method 2): m/z 402 [M+H]+@r.t. 4.93 min.

HRMS (ESI) calcd for $C_{25}H_{28}N_3O_2$ [M+H]+ 402.2176 found 402.2165.

7-(biphenyl-2-yl)-4-{2-[(3S)-3-hydroxypyrrolidin-1-yl]ethyl}-3,4-dihydropyrrolo[1,2-a]pyrazin-1(2H)-one [(I), R2=biphenyl-2-yl, R3=R4=H, A=—CH$_2$CH$_2$—NR'R1, R', R1=—(3S)-3-hydroxypyrrolidin-1-yl](cpd 10)

$^1$H NMR (400 MHz, DMSO-d6) δ 7.54 (br. s., 1H), 7.47-7.51 (m, 1H), 7.27-7.41 (m, 5H), 7.17-7.26 (m, 3H), 6.56 (d, J=1.71 Hz, 1H, diast A), 6.54 (d, J=1.71 Hz, 1H, diast B), 6.38 (d, J=1.83 Hz, 1H, diast A), 6.37 (d, J=1.71 Hz, 1H, diast B), 4.67 (d, J=0.49 Hz, 1H), 4.10-4.22 (m, 2H), 3.51-3.62 (m, 1H), 3.25 (m, 1H), 2.67 (m, 1H), 2.24-2.40 (m, 2H), 1.90-2.02 (m, 1H), 1.72 (q, J=6.63 Hz, 2H), 1.48-1.58 (m, 1H).

LCMS (HPLC Method 2): m/z 402 [M+H]+@r.t. 4.71 min.

HRMS (ESI) calcd for $C_{25}H_{28}N_3O_2$ [M+H]+ 402.2176 found 402.2172.

7-(biphenyl-3-yl)-4-{2-[(1-methylpiperidin-4-yl)amino]ethyl}-3,4-dihydropyrrlo[1,2-a]pyrazin-1(2H)-one [(I), R2=biphenyl-3-yl, R3=R4=H, A=—CH$_2$CH$_2$—NR'R1, R'=H, R1=1-methylpiperidin-4-yl)amino](cpd 11)

$^1$H NMR (400 MHz, DMSO-d$_6$) δ 7.85 (t, J=1.46 Hz, 1H), 7.70-7.76 (m, 2H), 7.64 (d, J=1.83 Hz, 2H), 7.57 (td, J=1.71, 7.08 Hz, 1H), 7.41-7.51 (m, 4H), 7.35-7.40 (m, 1H), 7.13 (d, J=1.83 Hz, 1H), 4.33-4.43 (m, 1H), 3.64-3.74 (m, 1H), 2.62-2.73 (m, 3H), 2.54-2.60 (m, 2H), 2.26-2.35 (m, 1H), 2.11 (s, 3H), 1.92-2.04 (m, 1H), 1.80-1.89 (m, 3H), 1.68-1.80 (m, 3H), 1.57-1.68 (m, J=18.80 Hz, 1H), 1.17-1.31 (m, J=8.91, 8.91 Hz, 2H). LCMS (HPLC Method 2): m/z 429 [M+H]+ @r.t. 4.78 min.

HRMS (ESI) calcd for $C_{25}H_{28}N_3O_2$ [M+H]+ 429.2649 found 429.2645.

7-(biphenyl-2-yl)-4-{2-[(1-methylpiperidin-4-yl)amino]ethyl}-3,4-dihydropyrrolo[1,2-a]pyrazin-1(2H)-one [(I), R2=biphenyl-2-yl, R3=R4=H, A=—CH$_2$CH$_2$—NR'R1, R'=H, R1=1-methylpiperidin-4-yl)amino](cpd 12)

$^1$H NMR (400 MHz, DMSO-d6) δ 7.52 (d, J=2.81 Hz, 1H), 7.45-7.51 (m, 1H), 7.26-7.38 (m, 4H), 7.18-7.25 (m, 3H), 6.60 (d, J=1.83 Hz, 1H), 6.35 (d, J=1.83 Hz, 1H), 4.13-4.25 (m, 1H), 3.57 (ddd, J=1.65, 4.24, 12.91 Hz, 1H), 3.21 (td, J=3.81, 13.00 Hz, 1H), 2.62-2.75 (m, 2H), 2.42 (td, J=6.23, 12.21 Hz, 1H), 2.27-2.36 (m, J=1.95, 3.91 Hz, 1H), 2.17-2.27 (m, 1H), 2.12 (s, 3H), 1.86 (dt, J=2.62, 11.44 Hz, 2H), 1.58-1.79 (m, 5H), 1.12-1.26 (m, 3H). LCMS (HPLC Method 2): m/z 429 [M+H]+@r.t. 4.55 min.

HRMS (ESI) calcd for $C_{25}H_{28}N_3O_2$ [M+H]+ 429.2649 found 429.2649.

Example 8

7-(3-chlorophenyl)-4-{2-[(1-methylpiperidin-4-yl)amino]ethyl}-6-phenyl-3,4-dihydropyrrlo[1,2-a]pyrazin-1(2H)-one trifluoroacetate [(I), R2=3-chlorophenyl, R3=phenyl, R4=H, A=—CH$_2$CH$_2$—NR'R1, R'=H, R1=1-methylpiperidin-4-yl)amino] (cpd 13)

Conv. a

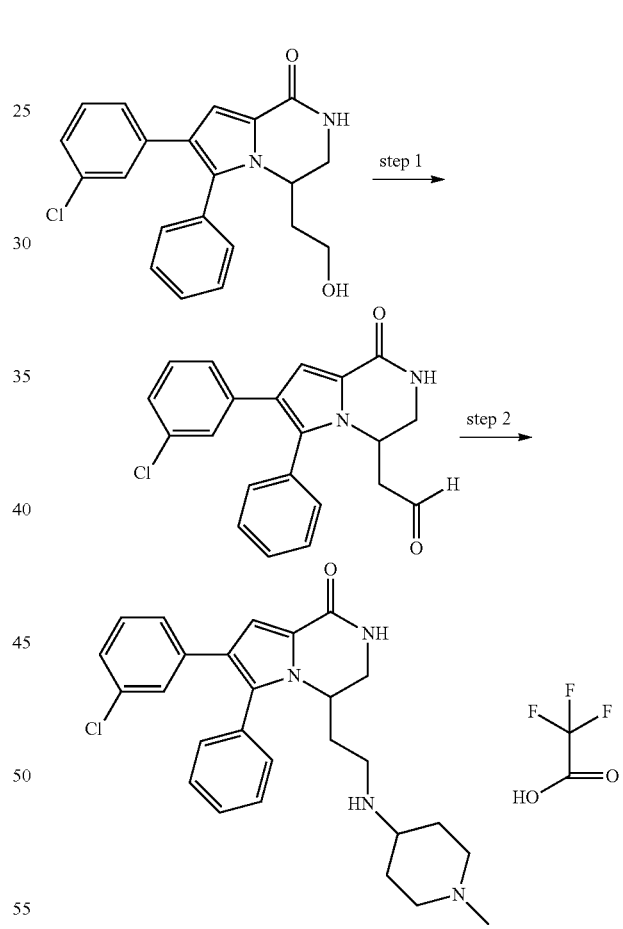

Step 1 preparation of [7-(3-chlorophenyl)-1-oxo-6-phenyl-1,2,3,4-tetrahydropyrrolo[1,2-a]pyrazin-4-yl]acetaldehyde 7-(3-chlorophenyl)-4-(2-hydroxyethyl)-6-phenyl-3,4-dihydropyrrolo[1,2-a]pyrazin-1(2H)-one (215 mg, 0.68 mmol) was refluxed in AcOEt (5 ml) in the presence of IBX (493 mg, 2.0 mmol) until reaction was complete. Water was added, the precipitate was filtered and the organic layer dried, filtered and evaporated to give the product as a mixture of acetals and emiacetals which were submitted to the next step without characterization.

Step 2 [7-(3-chlorophenyl)-1-oxo-6-phenyl-1,2,3,4-tetrahydropyrrolo[1,2-a]pyrazin-4-yl]acetaldehyde (50 mg, 0.14 mmol) was reacted with 1-methylpiperidin-4-amine (11.65 mg, 0.17 mmol) in the presence of sodium triacetoxyborohydride (72.8 mg, 0.34 mmol) in MeOH and some drops of glacial acetic acid at 60° C. for a few hours. When the reaction was complete, it was worked up with water and AcOEt. The organic phase was evaporated and the crude purified by HPLC/MS preparative Method 2 to give the wanted compound as a mixture of enantiomers.

$^1$H NMR (400 MHz, DMSO-$d_6$) δ 9.62 (br. s., 1H), 8.56 (br. s., 2H), 7.80 (d, J=5.00 Hz, 1H), 7.50-7.56 (m, 3H), 7.38-7.45 (m, 2H), 7.15-7.24 (m, 2H), 7.05-7.11 (m, 3H), 4.25-4.36 (m, 1H), 3.86-3.96 (m, 1H), 3.43-3.51 (m, J=12.45 Hz, 1H), 3.09 (br. s., 1H), 2.83-2.97 (m, J=11.23 Hz, 2H), 2.74 (s, 3H), 2.55-2.45 (m, 4H), 2.02-1.72 (m, 4H), 1.50-1.65 (m, 2H).

LCMS (HPLC Method 2): m/z 463 [M+H]$^+$@r.t. 4.87 min.

HRMS (ESI) calcd for $C_{27}H_{31}ClN_4O$ [M+H]$^+$ 463.2259 found 463.2260.

According to the same method, but employing N,N-dimethylethane-1,2-diamine, the following compound was prepared.

7-(3-chlorophenyl)-4-(2-{[2-(dimethylamino)ethyl]amino}ethyl)-6-phenyl-3,4-dihydropyrrolo[1,2-a]pyrazin-1(2H)-one trifluoroacetate [(I), R2=3-chlorophenyl, R3=phenyl, R4=H, A=—CH$_2$CH$_2$—NR'R1, R'=H, R1=2-(dimethylamino)ethylamino](cpd 14)

$^1$H NMR (500 MHz, DMSO-d6) δ 9.71 (br. s., 1H), 8.58 (d, J=7.14 Hz, 2H), 7.85 (d, J=4.67 Hz, 1H), 7.47-7.58 (m, 3H), 7.38-7.44 (m, 2H), 7.13-7.26 (m, 2H), 6.91-7.13 (m, 3H), 4.33 (d, J=3.57 Hz, 1H), 3.90 (dd, J=3.84, 13.45 Hz, 1H), 3.19-3.10 (m, 4H), 2.72-2.86 (m, 6H), 1.84-1.97 (m, 2H), 1.68-1.84 (m, 2H).

LCMS (HPLC Method 2): m/z 437 [M+H]$^+$@r.t. 4.53 min.

HRMS (ESI) calcd for $C_{25}H_{29}ClN_4O_2$M+H]$^+$ 437.2103 found 437.2096.

According to the same method, but employing tert-butyl 3-aminopiperidine-1-carboxylate, the following compound was prepared.

(4S)-7-(3-chlorophenyl)-6-phenyl-4-{2-[(3S)-piperidin-3-ylamino]ethyl}-3,4-dihydropyrrolo[1,2-a]pyrazin-1(2H)-one dihydrochloride [(I), R2=3-chlorophenyl, R3=phenyl, R4=H, A=—CH$_2$CH$_2$—NR'R1, R'=H, R1=—(3S)-piperidin-3-ylamino](cpd 15)

Isolated by HPLC/MS Preparative Method 2

$^1$H NMR (500 MHz, DMSO-$d_6$) δ 8.82-9.04 (m, J=11.53 Hz, 1H), 8.48-8.73 (m, 2H), 7.83 (dd, J=4.67, 9.06 Hz, 1H), 7.50-7.56 (m, 2H), 7.35-7.44 (m, J=4.12 Hz, 2H), 7.13-7.25 (m, 2H), 7.04-7.11 (m, 2H), 4.21-4.40 (m, J=3.84 Hz, 1H), 3.82-3.95 (m, J=11.53 Hz, 1H), 3.20-3.28 (m, 1H), 3.19-3.10 (m, 2H), 2.65-2.84 (m, 3H), 2.45-2.60 (m, 4H), 1.67-1.97 (m, 2H), 1.53 (q, J=12.26 Hz, 1H), 1.29-1.41 (m, 1H).

LCMS (HPLC Method 2): m/z 449 [M+H]$^+$@r.t. 4.4 min.

HRMS (ESI) calcd for $C_{26}H_{29}ClN_4O$ [M+H]$^+$ 449.2103 found 449.2103.

Example 9

Tert-butyl(2-{1-oxo-7-[3-(trifluoromethoxy)phenyl]-1,2,3,4-tetrahydropyrrolo[1,2-a]pyrazin-4-yl}ethyl) carbamate [(I), R2=3-(trifluoromethoxy)phenyl, R3=R4=H, A=—CH$_2$CH$_2$—NH—CO—OtBu]

Conv. b

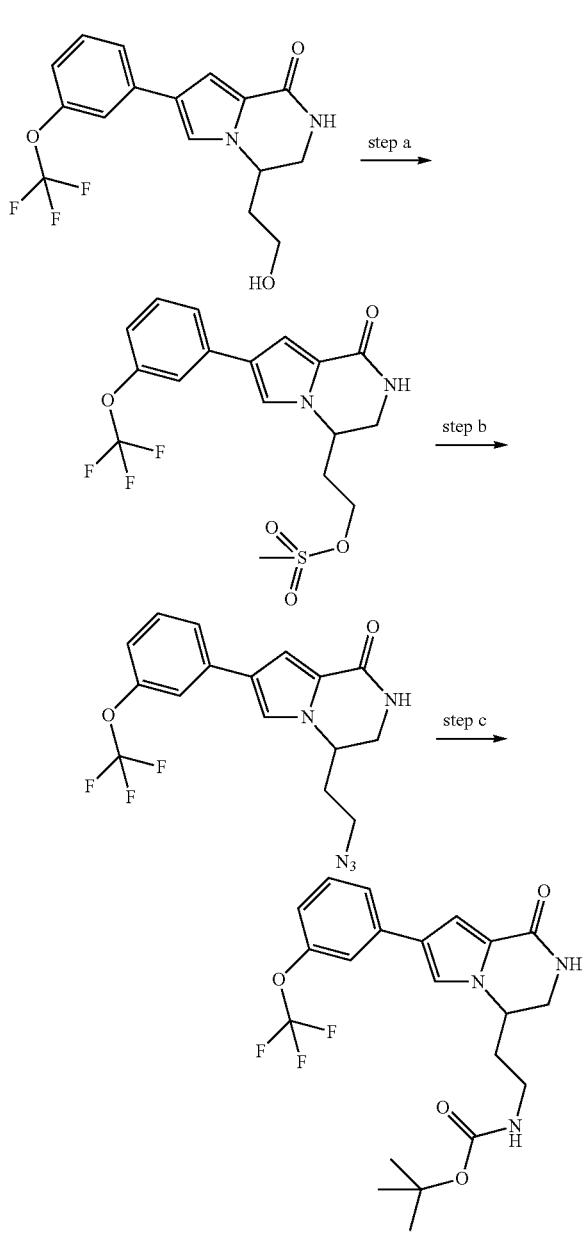

Step a. To a solution of 4-(2-hydroxyethyl)-7-[3-(trifluoromethoxy)phenyl]-3,4-dihydropyrrolo[1,2-a]pyrazin-1(2H)-one (128 mg, 0.37 mmol) in DCM (10 ml), mesyl chloride (58 ul, 0.748 mmol) and TEA (200 ul, 1.48 mmol), were added.

The resulting solution was stirred at room temperature, after 1 h the reaction mixture was portioned between DCM and water. The organic layers were washed with brine, dried over Na$_2$SO$_4$ and concentrated. The crude was triturated with diethyl ether and filtered to give 2-{1-oxo-7-[3-(trifluoromethoxy)phenyl]-1,2,3,4-tetrahydropyrrolo[1,2-a]pyrazin-4-yl}ethyl methanesulfonate as a solid 150 mg (97%).

LCMS (HPLC Method 3): m/z 419 [M+H]+@r.t. 5.75 min.

Working according to the same method, the following compounds were prepared:

2-{1-oxo-7-[3-(trifluoromethyl)phenyl]-1,2,3,4-tetrahydropyrrolo[1,2-a]pyrazin-4-yl}ethyl methanesulfonate $^1$H NMR (400 MHz, DMSO-d6) δ 7.92 (s, 1H), 7.91 (d, J=8.06 Hz, 1H), 7.74 (d, J=2.38 Hz, 1H), 7.72 (d, J=1.65 Hz, 1H), 7.54-7.60 (m, 1H), 7.47-7.53 (m, 1H), 7.19 (d, J=1.83 Hz, 1H), 4.39-4.47 (m, 1H), 4.28-4.36 (m, 1H), 4.23 (ddd, J=5.49, 7.51, 10.62 Hz, 1H), 3.67-3.76 (m, 1H), 3.40 (td, J=4.05, 13.32 Hz, 1H), 3.23 (s, 3H), 2.23-2.29 (m, 1H), 2.13-2.22 (m, 1H).

LCMS (HPLC Method 2): m/z 403 [M+H]+@r.t. 5.77 min.
HRMS (ESI) calcd for $C_{17}H_{18}F_3N_2O_4S$ [M+H]+ 403.0934 found 429.0942.

2-[7-(5-chloro-2-fluorophenyl)-1-oxo-1,2,3,4-tetrahydropyrrolo[1,2-a]pyrazin-4-yl]ethyl methanesulfonate $^1$H NMR (600 MHz, DMSO-d6) δ 7.78-7.81 (m, 1H), 7.77 (d, J=3.48 Hz, 1H), 7.57-7.64 (m, 1H), 7.21-7.31 (m, 2H), 7.13-7.17 (m, 1H), 4.48 (dq, J=7.05, 3.51 Hz, 1H), 4.26-4.36 (m, 1H), 4.21 (dq, J=7.46, 5.27 Hz, 1H), 3.69-3.77 (m, 1H), 3.19-3.23 (m, 3H), 2.11-2.25 (m, 2H).

LCMS (HPLC Method 2): m/z 387 [M+H]+@r.t. 4.77 min.
HRMS (ESI) calcd for $C_{17}H_{18}F_3N_2O_4S$ [M+H]+ 387.0576 found 387.0581.

Step b. 2-{1-oxo-7-[3-(trifluoromethoxy)phenyl]-1,2,3,4-tetrahydropyrrolo[1,2-a]pyrazin-4-yl}ethyl methanesulfonate (150 mg, 0.36 mmol) were reacted with sodium azide (60 mg 0.924 mmol) in acetonitrile/DMF 10 ml/2 ml at 80° C. for 18 hours. The reaction was worked up with water, saturated NaHCO$_3$ and extracted with ethyl acetate. The organic phase, dried on Na$_2$SO$_4$, was filtered and evaporated. The crude was dissolved with diethyl ether and after a while, a solid precipitated, which was filtered to give 104 mg (80%) of 4-(2-azidoethyl)-7-[3-(trifluoromethoxy)phenyl]-3,4-dihydropyrrolo[1,2-a]pyrazin-1(2H)-one.

$^1$H NMR (400 MHz, DMSO-d6) δ 7.72 (d, J=1.95 Hz, 1H), 7.67 (d, J=1.83 Hz, 1H), 7.64 (td, J=1.10, 8.06 Hz, 1H), 7.58 (s, 1H), 7.45 (t, J=7.99 Hz, 1H), 7.03-7.18 (m, 2H), 4.35 (tt, J=4.44, 6.67 Hz, 1H), 3.62-3.72 (m, 1H), 3.45-3.54 (m, 1H), 3.35-3.45 (m, 2H), 2.04-2.16 (m, 1H), 1.92-2.03 (m, J=7.05, 7.05, 7.05, 7.05 Hz, 1H).

LCMS (HPLC Method 2): m/z 366 [M+H]+@r.t. 6.44 min.

Working according to the same method the following compounds were prepared:

4-(2-azidoethyl)-7-(5-chloro-2-fluorophenyl)-3,4-dihydropyrrolo[1,2-a]pyrazin-1(2H)-one $^1$H NMR (600 MHz, DMSO-d6) δ 7.81 (dd, J=6.78, 2.38 Hz, 1H), 7.75 (d, J=3.30 Hz, 1H), 7.59 (t, J=1.74 Hz, 1H), 7.22-7.31 (m, 2H), 7.09-7.18 (m, 1H), 4.41 (tt, J=7.03, 3.69 Hz, 1H), 3.66-3.74 (m, 1H), 3.44-3.52 (m, 1H), 1.92-2.12 (m, 2H).

LCMS (HPLC Method 2): m/z 334 [M+H]+@r.t. 5.36 min.
HRMS (ESI) calcd for $C_{15}H_{14}ClFN_5O$ [M+H]+ 334.0866 found 334.0865.

4-(2-azidoethyl)-7-(6-fluoropyridin-3-yl)-3,4-dihydropyrrolo[1,2-a]pyrazin-1(2H)-one $^1$H NMR (400 MHz, DMSO-d6) δ 8.50 (d, J=2.20 Hz, 1H), 8.19 (dt, J=2.56, 8.15 Hz, 1H), 7.72 (d, J=1.83 Hz, 1H), 7.64 (d, J=1.65 Hz, 1H), 7.36-7.43 (m, 1H), 7.11-7.17 (m, 1H), 4.25-4.43 (m, 1H), 3.68 (ddd, J=1.47, 3.94, 13.10 Hz, 1H), 3.51 (td, J=6.66, 12.87 Hz, 1H), 3.35-3.45 (m, 2H), 2.88 (dd, J=6.87, 11.81 Hz, 1H), 2.04-2.14 (m, 1H), 1.89-2.03 (m, 1H).

LCMS (HPLC Method 2): m/z 301 [M+H]+@r.t. 3.99 min.
HRMS (ESI) calcd for $C_{14}H_{14}ClFN_5O$ [M+H]+ 301.1208 found 334.1213.

Step c. To a solution of 4-(2-azidoethyl)-7-[3-(trifluoromethoxy)phenyl]-3,4-dihydropyrrolo[1,2-a]pyrazin-1(2H)-one (97 mg 0.307 mmol) in ethanol 10 ml, NH$_4$Cl (65 mg 1.299 mmol), Zinc powder (80 mg 1.299 mmol) and di-t-butyl dicarbonate (100 mg 0.461 mmol) were added. The mixture was stirred at 80° C. for 4 hours, the cooled mixture was filtered through a celite pad and the solvent evaporated to dryness. The residue was portioned between ethyl acetate and water, the organic phase was washed with water and brine, dried over Na$_2$SO$_4$, and concentrated. The crude material was purified by flash chromatography eluting with DCM/EtOAc/EtOH 8/2/0.1 to afford the desired product tert-butyl(2-{1-oxo-7-[3-(trifluoromethoxy)phenyl]-1,2,3,4-tetrahydropyrrolo[1,2-a]pyrazin-4-yl}ethyl)carbamate 84 mg (62%) as a white solid.

$^1$H NMR (400 MHz, DMSO-d6) δ 7.66-7.73 (m, 2H), 7.69 (s, 2H), 7.59-7.65 (m, 1H), 7.56 (s, 1H), 7.36-7.48 (m, 1H), 7.13 (td, J=1.04, 8.18 Hz, 1H), 7.11 (d, J=1.83 Hz, 1H), 6.97 (t, J=5.00 Hz, 1H), 4.17-4.34 (m, J=3.48, 3.48 Hz, 1H), 3.62-3.73 (m, 1H), 2.92-3.07 (m, 2H), 1.84 (td, J=6.84, 13.67 Hz, 1H), 1.38 (s, 9H).

LCMS (HPLC Method 2): m/z 440 [M+H]+@r.t. 6.62 min.

Working according to the same method the following compounds were prepared:

tert-butyl{2-[7-(3-chlorophenyl)-1-oxo-1,2,3,4-tetrahydropyrrolo[1,2-a]pyrazin-4-yl]ethyl}carbamate [(I), R2=3-chlorophenyl, R3=R4=H, A=—CH$_2$CH$_2$—NH—CO—OtBu]

$^1$H NMR (400 MHz, DMSO-d6) δ 7.62-7.71 (m, 3H), 7.53-7.58 (m, J=6.84 Hz, 1H), 7.35 (t, J=7.93 Hz, 1H), 7.20 (dd, J=1.65, 7.51 Hz, 1H), 7.08 (d, J=1.71 Hz, 1H), 6.98 (t, J=5.80 Hz, 1H), 4.21-4.30 (m, 1H), 3.60-3.73 (m, 1H), 2.91-3.05 (m, 2H), 1.72-2.00 (m, 2H), 1.39 (s, 9H).

LCMS (HPLC Method 2): m/z 390 [M+H]+@r.t. 6.11 min.

tert-butyl{2-[7-(5-chloro-2-fluorophenyl)-1-oxo-1,2,3,4-tetrahydropyrrolo[1,2-a]pyrazin-4-yl]ethyl}carbamate [(I), R2=5-chloro-2-fluorophenyl, R3=R4=H, A=—CH$_2$CH$_2$—NH—CO—OtBu]

$^1$H NMR (400 MHz, DMSO-d6) δ 7.76 (dd, J=2.38, 6.78 Hz, 1H), 7.70 (d, J=3.30 Hz, 1H), 7.61 (s, 1H), 7.20-7.29 (m, 2H), 7.09 (s, 1H), 6.94 (br. s., 1H), 4.30 (br. s., 1H), 3.66 (dd, J=3.02, 13.10 Hz, 1H), 2.93-2.99 (m, 2H), 1.85-1.93 (m, 1H), 1.75-1.84 (m, 1H), 1.33-1.38 (m, 9H).

LCMS (HPLC Method 2): m/z 430 [M+Na]+@r.t. 5.50 min.

HRMS (ESI) calcd for $C_{20}H_{23}ClFN_3NaO_3$ [M+Na]+ 430.1304 found 430.1305.

tert-butyl(2-{1-oxo-7-[3-(trifluoromethyl)phenyl]-1,2,3,4-tetrahydropyrrolo[1,2-a]pyrazin-4-yl}ethyl)carbamate [(I) R2=3-(trifluoromethyl)phenyl, R3=R4=H, A=—CH$_2$CH$_2$—NH—CO—OtBu]

$^1$H NMR (400 MHz, DMSO-d6) δ 7.84-7.95 (m, 2H), 7.75 (s, 1H), 7.70 (d, J=2.56 Hz, 1H), 7.53-7.60 (m, 1H), 7.46-7.52 (m, 1H), 7.16 (d, J=1.83 Hz, 1H), 6.98 (t, J=5.77 Hz, 1H), 4.22-4.32 (m, 1H), 3.68 (dd, J=3.02, 13.10 Hz, 1H), 3.01 (q, J=6.59 Hz, 2H), 1.90-1.97 (m, 1H), 1.84 (td, J=6.75, 13.42 Hz, 1H), 1.38 (s, 9H).

LCMS (HPLC Method 2): m/z 446 [M+H]+@r.t. 6.47 min.
HRMS (ESI) calcd for $C_{21}H_{25}F_3N_3O_3$[M+H]+ 446.1662 found 446.1652.

tert-butyl{2-[7-(2-fluoropyridin-4-yl)-1-oxo-1,2,3,4-tetrahydropyrrolo[1,2-a]pyrazin-4-yl]ethyl}carbamate [(I) R2=2-fluoropyridin-4-yl, R3=R4=H, A=—CH$_2$CH$_2$—NH—CO—OtBu]

$^1$H NMR (400 MHz, DMSO-d6) δ 8.12 (d, J=5.31 Hz, 1H), 7.89 (s, 1H), 7.77 (d, J=2.20 Hz, 1H), 7.56 (d, J=5.31 Hz, 1H), 7.38 (s, 1H), 7.28 (d, J=1.65 Hz, 1H), 6.98 (br. s., 1H), 4.30 (br. s., 1H), 3.68 (dd, J=2.56, 12.82 Hz, 1H), 2.96-3.04 (m, 2H), 1.80-2.00 (m, 2H), 1.38 (d, J=2.20 Hz, 9H).

LCMS (HPLC Method 2): m/z 375 [M+H]$^+$@r.t. 4.27 min.
HRMS (ESI) calcd for C$_{21}$H$_{25}$F$_3$N$_3$O$_3$[M+H]$^+$ 375.1827 found 375.1835.

Example 10

4-(2-aminoethyl)-7-(3-chlorophenyl)-3,4-dihydropyrrolo[1,2-a]pyrazin-1(2H)-one [(I), R2=3-chlorophenyl, R3=R4=H, A=—CH$_2$CH$_2$—NH$_2$](cpd 16)

Conv. b

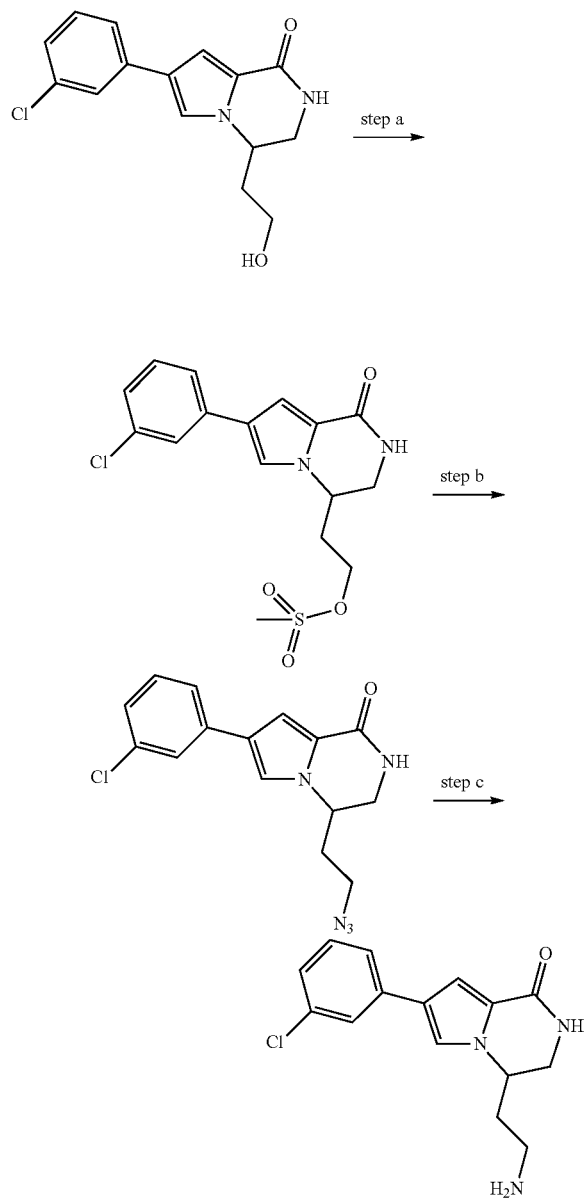

Step a. To a solution of 4-(2-hydroxyethyl)-7-(3-chlorophenyl)-3,4-dihydropyrrolo[1,2-a]pyrazin-1(2H)-one (128 mg, 0.44 mmol) in DCM (10 ml), mesyl chloride (58 ul, 0.748 mmol) and TEA (200 ul, 1.48 mmol), were added. The resulting solution was stirred at room temperature, after 1 h the reaction mixture was portioned between DCM and water. The organic layers were washed with brine, dried over Na$_2$SO$_4$ and concentrated. The crude was triturated with diethyl ether and filtered to give 2-[1-oxo-7-(3-chlorophenyl)-1,2,3,4-tetrahydropyrrolo[1,2-a]pyrazin-4-yl]ethyl methanesulfonate as a solid 157 mg (97%).

LCMS (HPLC Method 3): m/z 369 [M+H]$^+$@r.t. 5.74 min.

Step b. 2-[1-oxo-7-(3-chlorophenyl)-1,2,3,4-tetrahydropyrrolo[1,2-a]pyrazin-4-yl]ethyl methanesulfonate 157 mg (0.42 mmol) were reacted with sodium azide (60 mg 0.924 mmol) in acetonitrile/DMF 10 ml/2 ml at 80° C. for 18 hours. The reaction was worked up with water, saturated NaHCO$_3$ and extracted with ethyl acetate. The organic phase, dried on Na$_2$SO$_4$, was filtered and evaporated. The crude was dissolved with diethyl ether and after a while, a solid precipitated, which was filtered to give 92 mg (70%) of 4-(2-azidoethyl)-7-(3-chlorophenyl)-3,4-dihydropyrrolo[1,2-a]pyrazin-1(2H)-one.

$^1$H NMR (400 MHz, DMSO-d6) δ 7.70 (br. s., 1H), 7.68 (t, J=1.77 Hz, 1H), 7.65 (d, J=1.83 Hz, 1H), 7.57 (td, J=1.24, 7.78 Hz, 1H), 7.35 (t, J=7.87 Hz, 1H), 7.20 (ddd, J=0.98, 2.14, 8.00 Hz, 1H), 7.10 (d, J=1.71 Hz, 1H), 4.28-4.41 (m, 1H), 3.68 (ddd, J=1.89, 4.18, 13.09 Hz, 1H), 3.37-3.54 (m, 2H), 1.91-2.18 (m, 2H).

LCMS (HPLC Method 2): m/z 316 [M+H]$^+$@r.t. 5.90 min.
HRMS (ESI) calcd for C$_{15}$H$_{15}$ClN$_5$O [M+H]$^+$ 316.0960 found 316.0956.

Step c. To a solution of 4-(2-azidoethyl)-7-(3-chlorophenyl)-3,4-dihydropyrrolo[1,2-a]pyrazin-1(2H)-one (240 mg 0.76 mmol) in ethanol 10 ml, NH$_4$Cl (161 mg 3.04 mmol), and zinc powder (198.8 mg 3.04 mmol) were added. The mixture was stirred at 80° C. for 2 hours, cooled and filtered through a celite pad and the solvent evaporated to dryness. The residue was portioned between ethyl acetate and water/HCl 2N at pH 2, and then the organic phase was discharged. The aqueous part was brought to pH 10 by addition of ammonium hydroxide and extracted with EtOAc/THF, washed with brine, dried over Na$_2$SO$_4$, and concentrated. The crude material was taken up with EtOH 20 ml and concentrated to obtain a solid which was filtered and washed with EtOAc, to afford the desired product 160 mg (72%) as a light yellow solid.

$^1$H NMR (400 MHz, DMSO-d6) δ 7.66 (t, J=1.77 Hz, 2H), 7.64 (d, J=1.83 Hz, 1H), 7.54-7.58 (m, 1H), 7.35 (t, J=7.87 Hz, 1H), 7.20 (ddd, J=0.98, 2.17, 7.96 Hz, 1H), 7.08 (d, J=1.83 Hz, 1H), 4.31-4.43 (m, 1H), 3.67 (ddd, J=1.89, 4.24, 13.03 Hz, 1H), 2.61 (t, J=6.96 Hz, 2H), 1.66-2.01 (m, 2H).

LCMS (HPLC Method 2): m/z 290 [M+H]$^+$@r.t. 4.17 min.

Example 11

4-(2-aminoethyl)-7-(3-chlorophenyl)-6-phenyl-3,4-dihydropyrrolo[1,2-a]pyrazin-1(2H)-one trifluoroacetate [(I), R2=3-chlorophenyl, R3=Phenyl, R4=H, A=—CH$_2$CH$_2$—NH$_2$](cpd 17)

Conv. b

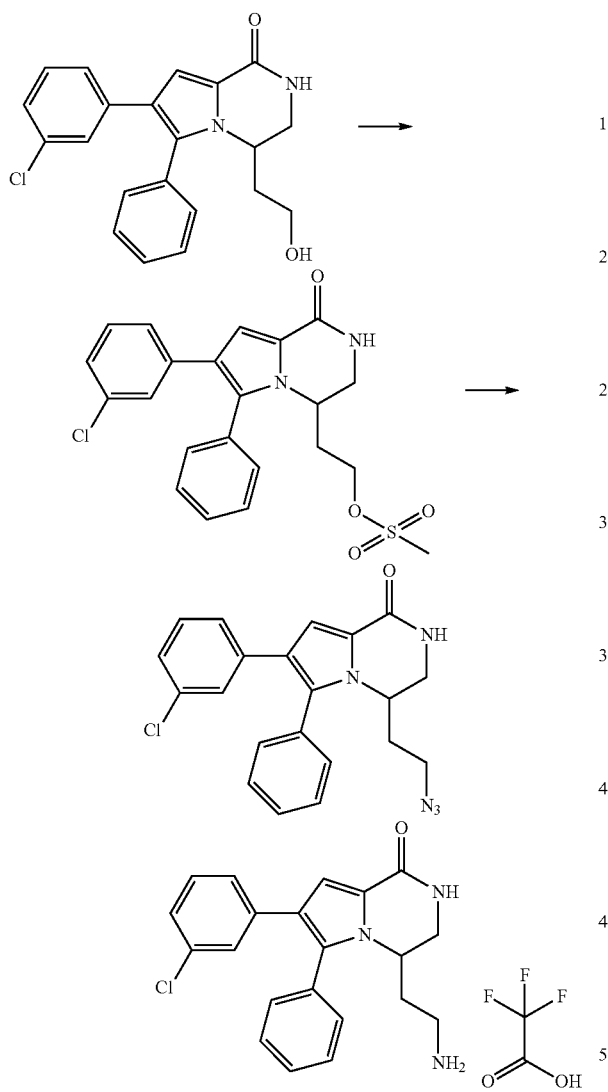

7-(3-chlorophenyl)-4-(2-hydroxyethyl)-6-phenyl-3,4-dihydropyrrolo[1,2-a]pyrazin-1(2H)-one (100 mg, 0.28 mmol) was suspended in dry THF and reacted with methansulphonyl chloride (0.36 mmol, 27 ul) in the presence of TEA (0.36 mmol, 50 ul) for 1 day at room temperature. When reaction was completed, it was dried, diluted with water and AcOEt. The organic phase contained the product which was submitted to the next step without purification and characterization. The crude was diluted in a 1:1 mixture (8 ml) of acetonitrile and dimethylformamide and reacted with sodium azide (55 mg, 0.84 mmol) at 70° C. for about eight hours. The reaction was diluted with water and extracted with AcOEt; the organic phase, after evaporation, was not purified but was diluted with 5 ml of Ethanol 95° to be reacted in the next step, performed with ammonium chloride (38 mg, 0.7 mmol) and zinc powder (24 mg, 0.35 mmol) heating at 80° C. for about 3 hours.

The reaction was washed with water and extracted with AcOEt, which was filtered through paper and evaporated. The crude was purified by HPLC/MS preparative Method 2 to give the wanted compound as a mixture of enantiomers as trifluoroacetic salt.

$^1$H NMR (400 MHz, DMSO-d$_6$) δ 7.79 (d, J=5.13 Hz, 1H), 7.42-7.56 (m, 6H), 7.33-7.42 (m, 2H), 7.12-7.27 (m, 2H), 7.03-7.12 (m, 2H), 4.32 (dd, J=2.20, 5.49 Hz, 1H), 3.87 (dd, J=3.78, 13.30 Hz, 1H), 2.39 (td, J=5.74, 11.72 Hz, 2H), 1.64-1.95 (m, 2H).

LCMS (HPLC Method 2): m/z 366 [M+H]$^+$@r.t. 3.92 min.
HRMS (ESI) calcd for C$_{21}$H$_{20}$ClN$_3$O [M+H]$^+$ 366.1368 found 366.1370.

Example 12

4-(2-aminoethyl)-7-[3-(trifluoromethoxy)phenyl]-3,4-dihydropyrrolo[1,2-a]pyrazin-1(2H)-one hydrochloride [(I), R2=3-(trifluoromethoxy)phenyl, R3=R4=H, A=—CH$_2$CH$_2$—NH$_2$](cpd 18)

Conv. r

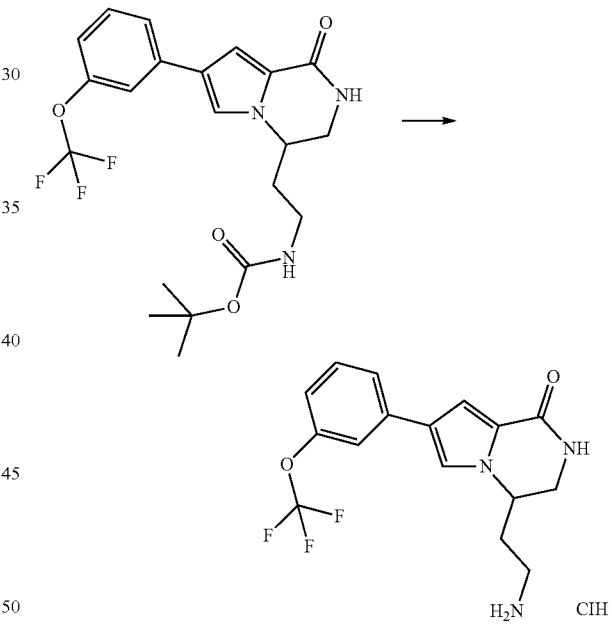

10 mg (0,022 mmol) of tert-butyl(2-{1-oxo-7-[3-(trifluoromethoxy)phenyl]-1,2,3,4-tetrahydropyrrolo[1,2-a]pyrazin-4-yl}ethyl)carbamate were dissolved with 4M HCl in 1,4-dioxane (1 ml). The solution was stirred at r.t. for 1 hour, and evaporated to dryness. The solid was triturated with diethyl ether, filtered and dried in vacuo to give the desired product 8 mg (94%).

$^1$H NMR (400 MHz, DMSO-d6) δ 7.77-7.89 (m, 3H), 7.75 (d, J=3.54 Hz, 1H), 7.71 (d, J=1.83 Hz, 1H), 7.63 (td, J=1.10, 8.06 Hz, 1H), 7.55 (s, 1H), 7.44-7.50 (m, 1H), 7.12-7.20 (m, 2H), 4.39-4.47 (m, 1H), 3.69-3.75 (m, 1H), 3.41 (m, 1H), 2.84-2.98 (m, 1H), 2.68-2.79 (m, 1H), 1.87-2.17 (m, 2H).

LCMS (HPLC Method 2): m/z 340 [M+H]$^+$@r.t. 4.48 min.
HRMS (ESI) calcd for C$_{16}$H$_{17}$F$_3$N$_3$O$_2$[M+H]$^+$ 340.1268 found 340.1242.

Working according to the same method, the following compound was prepared:

4-(2-aminoethyl)-7-(5-chloro-2-fluorophenyl)-3,4-dihydropyrrolo[1,2-a]pyrazin-1(2H)-one hydrochloride [(I), R2=5-chloro-2-fluorophenyl, R3=R4=H, A=—CH$_2$CH$_2$—NH$_2$](cpd 19)

$^1$H NMR (400 MHz, DMSO-d6) δ 7.71-7.82 (m, 5H), 7.64 (s, 1H), 7.24-7.33 (m, 2H), 7.17 (s, 1H), 4.49 (d, J=3.30 Hz, 1H), 3.73 (dd, J=3.66, 13.00 Hz, 1H), 2.91 (dd, J=5.86, 10.44 Hz, 1H), 2.72 (dd, J=5.86, 9.89 Hz, 1H), 1.93-2.12 (m, 2H).

LCMS (HPLC Method 2): m/z 308 [M+H]$^+$@r.t. 4.48 min.
HRMS (ESI) calcd for C$_{15}$H$_{16}$ClFN$_3$O [M+H]$^+$ 308.0961 found 308.0973.

4-(2-aminoethyl)-7-[3-(trifluoromethyl)phenyl]-3,4-dihydropyrrolo[1,2-a]pyrazin-1(2H)-one hydrochloride [(I), R2=3-(trifluoromethyl)phenyl, R3=R4=H, A=—CH$_2$CH$_2$—NH$_2$](cpd 20)

$^1$H NMR (400 MHz, DMSO-d6) δ 7.88-7.92 (m, 2H), 7.81 (br. s., 2H), 7.74-7.77 (m, 2H), 7.56-7.60 (m, 1H), 7.52 (d, J=7.69 Hz, 1H), 7.20 (d, J=1.83 Hz, 1H), 4.44 (br. s., 1H), 3.72 (dd, J=4.21, 13.00 Hz, 1H), 2.68-2.96 (m, 2H), 1.98-2.15 (m, 2H).

LCMS (HPLC Method 2): m/z 324 [M+H]$^+$@r.t. 4.4 min.
HRMS (ESI) calcd for C$_{16}$H$_{17}$F$_3$N$_3$O [M+H]$^+$ 324.1318 found 324.1317.

Working according to the same method the following compounds were prepared:

4-(2-aminoethyl)-7-(3-methoxyphenyl)-3,4-dihydropyrrolo[1,2-a]pyrazin-1(2H)-one hydrochloride [(I), R2=3-methoxyphenyl, R3=R4=H, A=—CH$_2$CH$_2$—NH$_2$](cpd 21)

$^1$H NMR (600 MHz, DMSO-d6) δ 7.73-7.79 (m, 3H), 7.7 (m, 1H), 7.57 (d, J=1.65 Hz, 1H), 7.22-7.28 (m, 1H), 7.15 (d, J=7.51 Hz, 1H), 7.09-7.13 (m, 1H), 7.08 (d, J=1.65 Hz, 1H), 6.74-6.78 (m, 1H), 4.37-4.47 (m, J=4.21 Hz, 1H), 4.07-4.17 (m, 1H), 3.79 (s, 3H), 3.72-3.66 (m, 1H), 2.84-2.96 (m, J=5.31 Hz, 1H), 2.72 (tt, J=5.77, 11.36 Hz, 1H), 2.14-1.95 (m, 2H).

LCMS (HPLC Method 2): m/z 286 [M+H]$^+$@r.t. 2.84 min.
HRMS (ESI) calcd for C$_{16}$H$_{20}$N$_3$O$_2$ [M+H]$^+$ 286.155 found 286.1553.

7-(3-acetylphenyl)-4-(2-aminoethyl)-3,4-dihydropyrrolo[1,2-a]pyrazin-1(2H)-one hydrochloride [(I), R2=3-acetylphenyl, R3=R4=H, A=—CH$_2$CH$_2$—NH$_2$](cpd 22)

$^1$H NMR (600 MHz, DMSO-d6) δ 8.11 (s, 1H), 7.85 (d, J=7.88 Hz, 1H), 7.72-7.83 (m, 5H), 7.70-7.72 (m, 1H), 7.48-7.52 (m, 1H), 7.18 (d, J=1.65 Hz, 1H), 4.45 (t, J=6.32 Hz, 1H), 3.63-3.76 (m, 1H), 3.44-3.54 (m, 1H), 2.92 (dt, J=5.49, 11.36 Hz, 1H), 2.68-2.81 (m, 1H), 2.62-2.65 (m, 3H), 1.92-2.15 (m, 2H).

LCMS (HPLC Method 2): m/z 298 [M+H]$^+$@r.t. 2.58 min.
HRMS (ESI) calcd for C$_{17}$H$_{20}$N$_3$O$_2$ [M+H]$^+$ 298.155 found 298.1547.

3-[4-(2-aminoethyl)-1-oxo-1,2,3,4-tetrahydropyrrolo[1,2-a]pyrazin-7-yl]benzonitrile hydrochloride [(I), R2=3-benzonitrile, R3=R4=H, A=—CH$_2$CH$_2$—NH$_2$](cpd 23)

$^1$H NMR (600 MHz, DMSO-d6) δ 8.04-8.11 (m, 1H), 7.90-7.97 (m, 1H), 7.75-7.83 (d, J=3.66 Hz, 4H), 7.74 (d, J=1.65 Hz, 1H), 7.60-7.64 (m, 1H), 7.51-7.57 (m, 1H), 7.21 (d, J=1.83 Hz, 1H), 4.35-4.49 (m, 1H), 3.63-3.74 (m, 1H), 3.43-3.53 (m, 1H), 2.83-2.99 (m, 1H), 2.68-2.82 (m, 1H), 1.95-2.14 (m, 2H).

LCMS (HPLC Method 2): m/z 281 [M+H]$^+$@r.t. 2.71 min.
HRMS (ESI) calcd for C$_{16}$H$_{17}$N$_4$O [M+H]$^+$ 281.1397 found 281.1398.

4-(2-aminoethyl)-7-(2-chloropyridin-4-yl)-3,4-dihydropyrrolo[1,2-a]pyrazin-1(2H)-one hydrochloride [(I), R2=2-chloropyridin-4-yl, R3=R4=H, A=—CH$_2$CH$_2$—NH$_2$](cpd 24)

$^1$H NMR (600 MHz, DMSO-d6) δ 8.30 (d, J=5.13 Hz, 1H), 7.93-7.96 (m, 2H), 7.78-7.9 (m, 3H), 7.73 (s, 1H), 7.62 (d, J=5.31 Hz, 1H), 7.33 (s, 1H), 4.46 (br. s., 1H), 3.68-3.75 (m, 1H), 3.35-3.46 (m, 1H), 2.70-2.97 (m, 2H), 2.00-2.14 (m, 2H).

LCMS (HPLC Method 2): m/z 291 [M+H]$^+$@r.t. 2.5 min.

4-(2-aminoethyl)-7-(3,4-difluorophenyl)-3,4-dihydropyrrolo[1,2-a]pyrazin-1(2H)-one hydrochloride [(I), R2=3,4-difluorophenyl, R3=R4=H, A=—CH$_2$CH$_2$—NH$_2$](cpd 25)

$^1$H NMR (600 MHz, DMSO-d6) δ 7.78 (br. s., 3H), 7.74 (d, J=3.85 Hz, 1H), 7.66 (ddd, J=1.74, 7.78, 12.27 Hz, 1H), 7.62 (d, J=1.65 Hz, 1H), 7.32-7.47 (m, 2H), 7.12 (d, J=1.65 Hz, 1H), 4.32-4.49 (m, J=3.11 Hz, 1H), 3.63-3.74 (m, 2H), 2.90 (br. s., 1H), 2.73 (br. s., 1H), 1.94-2.14 (m, 2H).

LCMS (HPLC Method 2): m/z 292 [M+H]$^+$@r.t. 3.17 min.
HRMS (ESI) calcd for C$_{15}$H$_{16}$F$_2$N$_3$O [M+H]$^+$ 292.1256 found 292.1255.

4-(2-aminoethyl)-7-(3-bromophenyl)-3,4-dihydropyrrolo[1,2-a]pyrazin-1(2H)-one hydrochloride
[(I), R2=3-bromophenyl, R3=R4=H, A=—CH$_2$CH$_2$—NH$_2$]

$^1$H NMR (600 MHz, DMSO-d6) δ 7.76 (m, 1H), 7.72-7.75 (m, 3H), 7.65 (m, 1H), 7.56-7.59 (m, 2H), 7.32-7.34 (m, 1H), 7.27 (m, 1H), 7.09 (m, 1H), 4.39 (bs, 1H), 3.67-3.70 (m, 1H), 2.80-2.85 (m, 1H), 2.65-2.68 (m, 1H), 1.95-2.01 (m, 1H)
LCMS (HPLC Method 2): m/z 334 [M+H]$^+$@r.t. 4.35 min.
HRMS (ESI) calcd for C$_{15}$H$_{16}$BrN$_3$O [M+H]$^+$ 334.055 found 334.0548.

4-(2-aminoethyl)-7-(3-phenoxyphenyl)-3,4-dihydropyrrolo[1,2-a]pyrazin-1(2H)-one hydrochloride
[(I), R2=3-bromophenyl, R3=R4=H, A=—CH$_2$CH$_2$—NH$_2$]

$^1$H NMR (600 MHz, DMSO-d6) δ 7.76 (br. s., 3H), 7.68-7.70 (m, 1H), 7.56 (s, 1H), 7.28-7.40 (m, 4H), 7.21 (s, 1H), 7.12 (t, J=7.33 Hz, 1H), 6.98-7.02 (m, 3H), 6.77 (td, J=1.95, 7.46 Hz, 1H), 4.39 (br. s., 1H), 3.65-3.72 (m, 1H), 3.35-3.37 (m, 1H), 2.81-2.91 (m, 1H), 2.63-2.73 (m, 1H), 1.93-2.10 (m, 2H).

LCMS (HPLC Method 2): m/z 348 [M+H]$^+$@r.t. 4.94 min.
HRMS (ESI) calcd for C$_{21}$H$_{22}$N$_3$O [M+H]$^+$ 348.1707 found 348.1706.

4-(2-aminoethyl)-7-[4-(trifluoromethoxy)phenyl]-3,4-dihydropyrrolo[1,2-a]pyrazin-1(2H)-one hydrochloride
[(I), R2=4-(trifluoromethoxy)phenyl, R3=R4=H, A=—CH$_2$CH$_2$—NH$_2$]

$^1$H NMR (600 MHz, DMSO-d6) δ 7.81 (br. s., 3H), 7.74 (d, J=3.85 Hz, 1H), 7.70 (d, J=8.06 Hz, 2H), 7.62 (d, J=1.47 Hz, 1H), 7.33 (d, J=8.06 Hz, 2H), 7.10 (d, J=1.47 Hz, 1H), 4.32-4.55 (m, 1H), 3.72 (dd, J=3.66, 13.00 Hz, 1H), 3.35-3.38 (m, J=3.66 Hz, 1H), 2.85-2.96 (m, 1H), 2.69-2.78 (m, 1H), 1.92-2.13 (m, 3H).

LCMS (HPLC Method 2): m/z 340 [M+H]$^+$@r.t. 4.72 min.
HRMS (ESI) calcd for C$_{16}$H$_{17}$F$_3$N$_3$O$_2$[M+H]$^+$ 340.1268 found 340.126.

4-(2-aminoethyl)-7-[3-(propan-2-yloxy)phenyl]-3,4-dihydropyrrolo[1,2-a]pyrazin-1(2H)-one hydrochloride
[(I), R2=3-(propan-2-yloxy)phenyl, R3=R4=H, A=—CH$_2$CH$_2$—NH$_2$]

LCMS (HPLC Method 2): m/z 314 [M+H]$^+$@r.t. 4.43 min.
HRMS (ESI) calcd for C$_{18}$H$_{24}$N$_3$O$_2$ [M+H]$^+$ 314.1863 found 314.1861.

Example 13

Tert-butyl {2-[6-bromo-7-(3-chlorophenyl)-1-oxo-1,2,3,4-tetrahydropyrrolo[1,2-a]pyrazin-4-yl]ethyl}carbamate [(I), R2=3-chlorophenyl, R3=Br, R4=H, A=—CH₂CH₂—NH—CO—OtBu]

Conv. e

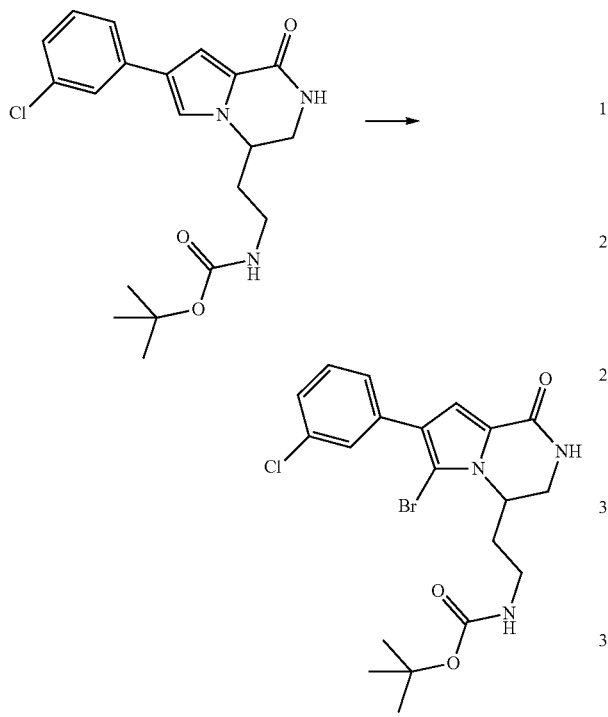

To a solution of tert-butyl{2-[6-bromo-7-(3-chlorophenyl)-1-oxo-1,2,3,4-tetrahydropyrrolo[1,2-a]pyrazin-4-yl]ethyl}carbamate (50 mg 0.13 mmol) in 5 ml of DCM, 25 mg (0.141 mmol) of NBS was added. The solution was stirred at room temperature for 1 hour; afterwards the volatiles were removed under vacuo. The crude was purified by column chromatography eluting with DCM/EtOAc/EtOH 8/1/1 to provide the desired compound as a pale yellow solid 36 mg (60%).

$^1$H NMR (400 MHz, DMSO-d6) δ 7.81 (d, J=5.00 Hz, 1H), 7.64 (t, J=1.83 Hz, 1H), 7.57 (td, J=1.25, 7.87 Hz, 1H), 7.44 (t, J=7.87 Hz, 1H), 7.36 (ddd, J=0.98, 2.04, 7.96 Hz, 1H), 7.03 (s, 1H), 6.97 (t, J=5.43 Hz, 1H), 4.38-4.50 (m, 1H), 3.72 (dd, J=3.48, 13.49 Hz, 1H), 3.46 (dd, J=5.07, 13.49 Hz, 1H), 2.87-3.14 (m, 12H), 1.77-1.93 (m, 1H), 1.64-1.78 (m, 1H), 1.38 (s, 9H).

LCMS (HPLC Method 2): m/z 468 [M+H]⁺@r.t. 6.55 min.

HRMS (ESI) calcd for C₂₀H₂₄BrClN₃O₃[M+H]⁺ 308.0961 found 308.0973.

Operating in an analogous way, the following compound was prepared:

tert-butyl(2-{6-bromo-1-oxo-7-[3-(trifluoromethoxy)phenyl]-1,2,3,4-tetrahydropyrrolo[1,2-a]pyrazin-4-yl}ethyl)carbamate [(I), R2=3-(trifluoromethoxy)phenyl, R3=Br, R4=H, A=—CH₂CH₂—NH—CO—OtBu]

LCMS (HPLC Method 2): m/z 519 [M+H]⁺@r.t. 6.95 min.

Example 14

4-(2-aminoethyl)-6-bromo-7-(3-chlorophenyl)-3,4-dihydropyrrolo[1,2-a]pyrazin-1(2H)-one hydrochloride [(I), R2=3-chlorophenyl, R3=Br, R4=H, A=—CH₂CH₂—NH₂](cpd 26)

Conv. r

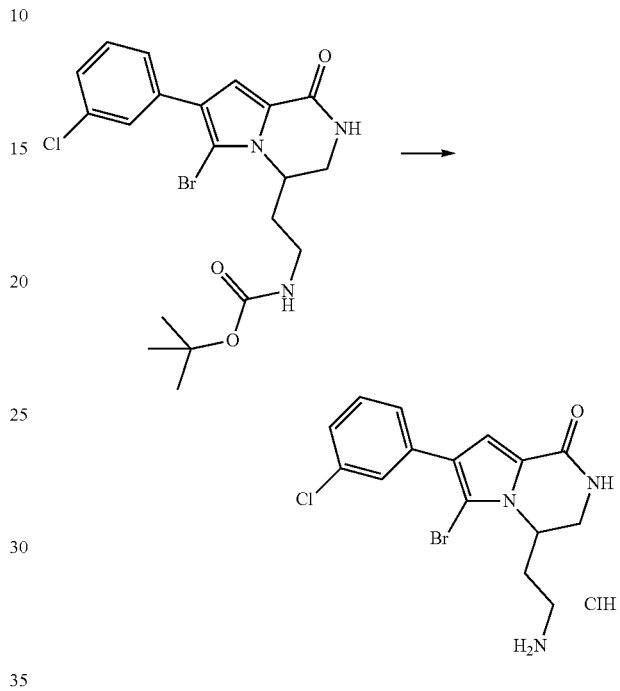

18 mg (0.038 mmol) of tert-butyl{2-[6-bromo-7-(3-chlorophenyl)-1-oxo-1,2,3,4-tetrahydropyrrolo[1,2-a]pyrazin-4-yl]ethyl}carbamate were dissolved with 4M HCl in 1,4-dioxane (1 ml). The solution was stirred at r.t. for 1 hour, and evaporated to dryness. The solid was triturated with diethyl ether, filtered and dried in vacuo to give the desired product 14 mg (93%).

$^1$H NMR (400 MHz, DMSO-d6) δ 7.88 (d, J=5.00 Hz, 1H), 7.79 (br. s., 3H), 7.65 (t, J=1.83 Hz, 1H), 7.57 (td, J=1.34, 7.81 Hz, 1H), 7.46 (t, J=7.87 Hz, 1H), 7.35-7.39 (m, 1H), 7.08 (s, 1H), 4.54-4.63 (m, 1H), 3.77 (dd, J=4.21, 13.61 Hz, 1H), 3.44 (dd, J=5.13, 13.06 Hz, 1H), 2.74-2.95 (m, 2H), 1.84-2.15 (m, 2H).

LCMS (HPLC Method 2): m/z 368 [M+H]⁺@r.t. 4.52 min.

HRMS (ESI) calcd for C₁₅H₁₆BrClN₃O [M+H]⁺ 368.016 found 368.0155.

According to the same methodology, but employing suitable starting material, the following compound was prepared:

4-(2-aminoethyl)-6-bromo-7-[3-(trifluoromethoxy)phenyl]-3,4-dihydropyrrolo[1,2-a]pyrazin-1(2H)-one hydrochloride [(I), R2=3-(trifluoromethoxy)phenyl, R3=Br, R4=H, A=—CH₂CH₂—NH₂](cpd 27)

$^1$H NMR (400 MHz, DMSO-d6) δ 7.89 (d, J=5.25 Hz, 1H), 7.78 (br. s., 3H), 7.62-7.67 (m, 1H), 7.53-7.59 (m, 2H), 7.31 (td, J=1.16, 8.30 Hz, 1H), 7.11 (s, 1H), 4.52-4.63 (m, 1H), 3.77 (dd, J=4.09, 13.73 Hz, 1H), 3.44 (dd, J=5.31, 13.24 Hz, 1H), 2.85 (br. s., 2H), 2.03-2.11 (m, 1H), 1.88-2.03 (m, 1H).

LCMS (HPLC Method 2): m/z 418 [M+H]⁺@r.t. 4.75 min.

HRMS (ESI) calcd for C₁₆H₁₆BrF₃N₃O₂ [M+H]⁺ 418.0373 found 418.0356.

Example 15 tert-butyl(2-{6-iodo-1-oxo-7-[3-(trifluoromethoxy)phenyl]-1,2,3,4-tetrahydropyrrolo[1,2-a]pyrazin-4-yl}ethyl)carbamate

[(I), R2=3-(trifluoromethoxy)phenyl, R3=I, R4=H, A=—CH$_2$CH$_2$—NH—CO—OtBu]
Conv. e

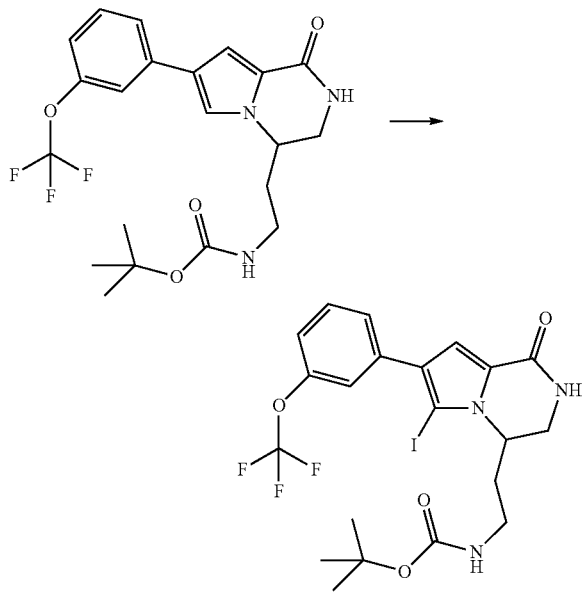

Iodine (450 mg 1.77 mmol) was added portion wise to a solution of tert-butyl(2-{1-oxo-7-[3-(trifluoromethoxy)phenyl]-1,2,3,4-tetrahydropyrrolo[1,2-a]pyrazin-4-yl}ethyl)carbamate (780 mg 1.77 mmol) and silver trifluoroacetate (392 mg, 1.77 mmol) in dry DCM (100 ml), at 5° C. The reaction mixture was stirred at the same temperature for 1 hour, then the ice bath removed and left to warm to rt (1 h). The solid was filtered, the organic phase washed with Na$_2$S$_2$O$_5$ (5% aq. solution) until decolouration occurred and finally washed with water. The organic was dried over Na$_2$SO$_4$ to obtain the title compound 1.0 g (99%) as a white solid.

$^1$H NMR (400 MHz, DMSO-d6) δ 7.78 (d, J=5.25 Hz, 1H), 7.56-7.60 (m, 1H), 7.51-7.56 (m, 2H), 7.29 (td, J=1.14, 7.72 Hz, 1H), 6.99 (s, 1H), 6.97 (t, J=5.49 Hz, 1H), 4.35-4.43 (m, 1H), 3.70 (dd, J=3.48, 13.61 Hz, 1H), 3.49 (dd, J=5.00, 13.43 Hz, 1H), 2.93-3.15 (m, 2H), 1.61-1.90 (m, 2H), 1.35-1.42 (m, 9H).

LCMS (HPLC Method 2): m/z 566 [M+H]$^+$@r.t. 6.00 min.

According to the same methodology, but employing suitable starting material, the following compounds were prepared:

tert-butyl{2-[7-(5-chloro-2-fluorophenyl)-6-iodo-1-oxo-1,2,3,4-tetrahydropyrrolo[1,2-a]pyrazin-4-yl]ethyl}carbamate [(I), R2=5-chloro-2-fluorophenyl, R3=I, R4=H, A=—CH$_2$CH$_2$—NH—CO—OtBu]

$^1$H NMR (400 MHz, DMSO-d6) δ 7.79 (d, J=5.13 Hz, 1H), 7.47-7.51 (m, 1H), 7.45 (ddd, J=2.75, 4.21, 8.79 Hz, 1H), 7.31-7.36 (m, 1H), 6.97 (t, J=5.40 Hz, 1H), 6.87 (d, J=1.28 Hz, 1H), 4.33-4.39 (m, 1H), 3.68-3.74 (m, 1H), 3.45-3.51 (m, 1H), 3.04-3.12 (m, 1H), 2.92-3.02 (m, 1H), 1.83 (d, J=7.88 Hz, 1H), 1.63-1.72 (m, 1H), 1.38 (s, 9H).

LCMS (HPLC Method 2): m/z 534 [M+H]$^+$@r.t. 5.83 min.
HRMS (ESI) calcd for C$_{20}$H$_{23}$ClFIN$_3$O$_3$[M+H]$^+$ 534.0451 found 534.0438.

tert-butyl{2-[6-iodo-7-(3-methoxyphenyl)-1-oxo-1,2,3,4-tetrahydropyrrolo[1,2-a]pyrazin-4-yl]ethyl}carbamate [(I), R2=3-methoxyphenyl, R3=I, R4=H, A=—CH$_2$CH$_2$—NH—CO—OtBu]

$^1$H NMR (400 MHz, DMSO-d6) δ 7.74 (d, J=5.13 Hz, 1H), 7.31 (t, J=7.97 Hz, 1H), 7.10 (d, J=7.69 Hz, 1H), 7.08 (s, 1H), 6.95-6.99 (m, J=4.21 Hz, 1H), 6.92 (s, 1H), 6.85-6.88 (m, J=2.20, 7.88 Hz, 1H), 4.34-4.43 (m, 1H), 3.79 (s, 3H), 3.70 (dd, J=3.48, 13.55 Hz, 1H), 3.48 (dd, J=5.04, 13.28 Hz, 1H), 3.03-3.14 (m, J=4.58, 8.24 Hz, 1H), 3.00 (td, J=6.91, 13.65 Hz, 1H), 1.76-1.87 (m, J=7.42, 13.28 Hz, 1H), 1.61-1.71 (m, J=4.58 Hz, 1H), 1.38 (s, 9H).

LCMS (HPLC Method 2): m/z 534 [M+Na]$^+$@r.t. 5.45 min.
HRMS (ESI) calcd for C$_{21}$H$_{26}$IN$_3$NaO$_4$ [M+Na]$^+$ 534.086 found 534.0853.

tert-butyl{2-[7-(3-acetylphenyl)-6-iodo-1-oxo-1,2,3,4-tetrahydropyrrolo[1,2-a]pyrazin-4-yl]ethyl}carbamate [(I), R2=3-acetylphenyl, R3=I, R4=H, A=—CH$_2$CH$_2$—NH—CO—OtBu]

$^1$H NMR (400 MHz, DMSO-d6) δ 8.13 (s, 1H), 7.86-7.89 (m, 1H), 7.78-7.80 (m, 1H), 7.76-7.78 (m, 1H), 7.57 (t, J=7.69 Hz, 1H), 7.02 (s, 1H), 6.98 (t, J=5.40 Hz, 1H), 4.32-4.43 (m, 1H), 3.68-3.73 (m, 1H), 3.49 (dd, J=4.95, 13.19 Hz, 1H), 2.95-3.15 (m, 2H), 2.58-2.66 (m, 3H), 1.62-1.90 (m, 2H), 1.36-1.42 (m, 9H).

LCMS (HPLC Method 2): m/z 546 [M+Na]$^+$@r.t. 5.07 min.
HRMS (ESI) calcd for C$_{22}$H$_{26}$IN$_3$NaO$_4$ [M+Na]$^+$ 546.086 found 534.0859.

tert-butyl{2-[7-(3-cyanophenyl)-6-iodo-1-oxo-1,2,3,4-tetrahydropyrrolo[1,2-a]pyrazin-4-yl]ethyl}carbamate [(I), R2=3-cyanophenyl, R3=I, R4=H, A=—CH$_2$CH$_2$—NH—CO—OtBu]

$^1$H NMR (400 MHz, DMSO-d6) δ 7.97 (s, 1H), 7.89 (d, J=7.88 Hz, 1H), 7.79 (d, J=4.95 Hz, 1H), 7.76 (d, J=7.88 Hz, 1H), 7.62 (t, J=7.78 Hz, 1H), 7.04 (s, 1H), 6.97 (br. s., 1H), 4.39 (d, J=9.52 Hz, 1H), 3.70 (d, J=10.99 Hz, 1H), 3.49 (dd, J=4.49, 12.73 Hz, 1H), 2.97-3.12 (m, 2H), 1.64-1.88 (m, 2H), 1.39 (s, 9H).

LCMS (HPLC Method 2): m/z 529 [M+Na]$^+$@r.t. 5.25 min.
HRMS (ESI) calcd for C$_{21}$H$_{23}$IN$_4$NaO$_3$ [M+Na]$^+$ 529.0707 found 529.0702.

tert-butyl{2-[7-(2-chloropyridin-4-yl)-6-iodo-1-oxo-1,2,3,4-tetrahydropyrrolo[1,2-a]pyrazin-4-yl]ethyl}carbamate [(I), R2=2-chloropyridin-4-yl, R3=I, R4=H, A=—CH$_2$CH$_2$—NH—CO—OtBu]

$^1$H NMR (400 MHz, DMSO-d6) δ 8.40 (d, J=5.13 Hz, 1H), 7.84 (d, J=5.13 Hz, 1H), 7.75 (s, 1H), 7.67 (d, J=5.31 Hz, 1H), 7.17 (s, 1H), 6.98 (br. s., 1H), 4.43 (br. s., 1H), 3.70 (d, J=12.82 Hz, 1H), 3.46-3.51 (m, 1H), 2.93-3.12 (m, 2H), 1.83 (d, J=8.24 Hz, 1H), 1.67 (d, J=8.24 Hz, 1H), 1.39 (s, 9H).

LCMS (HPLC Method 2): m/z 517 [M+Na]$^+$@r.t. 4.98 min.
HRMS (ESI) calcd for C$_{19}$H$_{22}$IN$_4$NaO$_3$ [M+Na]$^+$ 517.0498 found 517.0495.

tert-butyl{2-[7-(3,4-difluorophenyl)-6-iodo-1-oxo-1,2,3,4-tetrahydropyrrolo[1,2-a]pyrazin-4-yl]ethyl}carbamate [(I), R2=3,4-difluorophenyl, R3=I, R4=H, A=—CH$_2$CH$_2$—NH—CO—OtBu]

$^1$H NMR (400 MHz, DMSO-d6) δ 7.77 (d, J=5.13 Hz, 1H), 7.54-7.60 (m, 1H), 7.43-7.49 (m, 1H), 7.39 (br. s., 1H), 6.93-

6.99 (m, 2H), 4.33-4.42 (m, 1H), 3.63-3.73 (m, 1H), 3.48 (dd, J=4.76, 13.19 Hz, 1H), 2.93-3.14 (m, 2H), 1.62-1.86 (m, 2H), 1.36-1.40 (m, 9H).

LCMS (HPLC Method 2): m/z 540 [M+Na]⁺@r.t. 6.59 min.

HRMS (ESI) calcd for $C_{20}H_{22}F_2IN_4NaO_3$ [M+Na]⁺ 540.0566 found 540.0566.

tert-butyl{2-[7-(2-fluoropyridin-4-yl)-6-iodo-1-oxo-1,2,3,4-tetrahydropyrrolo[1,2-a]pyrazin-4-yl]ethyl}carbamate [(I), R2=2-fluoropyridin-4-yl, R3=I, R4=H, A=—CH₂CH₂—NH—CO—OtBu]

HRMS (ESI) calcd for $C_{19}H_{23}FIN_4O_3$[M+H]⁺ 501.0794 found 501.0786.

Example 16 tert-butyl(2-{1-oxo-6-phenyl-7-[3-(trifluoromethoxy)phenyl]-1,2,3,4-tetrahydropyrrolo[1,2-a]pyrazin-4-yl}ethyl)carbamate [(I), R2=3-(trifluoromethoxy)phenyl, R3=phenyl, R4=H, A=—CH₂CH₂—NH—CO—OtBu]

Conv. g

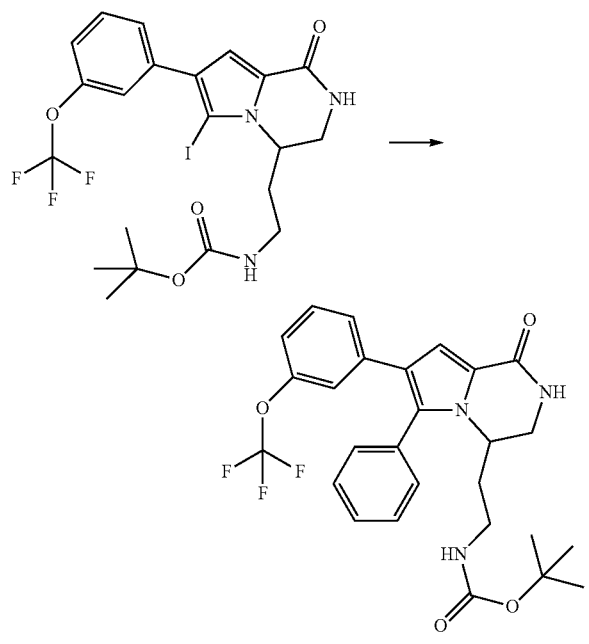

To a solution of tert-butyl(2-{6-iodo-1-oxo-7-[3-(trifluoromethoxy)phenyl]-1,2,3,4-tetrahydropyrrolo[1,2-a]pyrazin-4-yl}ethyl)carbamate (100 mg, 0.177 mmol) in 3 ml of 1,4-dioxane and 1 ml of water, under argon atmosphere, 64.7 mg (0.531 mmol) of phenyboronic acid, 7.2 mg (0.009 mmol) of 1,1'-bis(diphenylphosphino)ferrocenepaladium complex with dichloromethane and 172 mg (0.531 mmol) of cesium carbonate, were subsequently added. The mixture was heated at 80° for 1 hour in a sealed vial. The reaction was filtered through a celite pad and the solvent evaporated to dryness. The crude was then portioned between ethyl acetate and water, the organic layer dried over sodium sulphate and the solvent removed in vacuo. After purification by flash chromatography on silica gel column (DCM/EtOAc/EtOH 6/4/0.5), and further purification by HPLC/MS preparative method 1, 50 mg (54%) of tert-butyl(2-{1-oxo-6-phenyl-7-[3-(trifluoromethoxy)phenyl]-1,2,3,4-tetrahydropyrrolo[1,2-a]pyrazin-4-yl}ethyl)carbamate were obtained.

LCMS (HPLC Method 4): m/z 516 [M+H]⁺@r.t. 2.70 min.

Operating in an analogous way, the following compounds were prepared:

tert-butyl{2-[7-(3-methoxyphenyl)-6-(3-methylphenyl)-1-oxo-1,2,3,4-tetrahydropyrrolo[1,2-a]pyrazin-4-yl] ethyl}carbamate [(I), R2=3-methoxyphenyl, R3=3-methylphenyl, R4=H, A=—CH₂CH₂—NH—CO—OtBu]

Purification by HPLC preparative method 2 gave the title compound (60%).

LCMS (HPLC Method 3): m/z 476 [M+H]⁺@r.t. 6.41 min.

tert-butyl{2-[7-(3-acetylphenyl)-6-(3-methylphenyl)-1-oxo-1,2,3,4-tetrahydropyrrolo[1,2-a]pyrazin-4-yl] ethyl}carbamate [(I), R2=3-acetylphenyl, R3=3-methylphenyl, R4=H, A=—CH₂CH₂—NH—CO—OtBu]

Purification by HPLC preparative method 2 gave the title compound (77%).

LCMS (HPLC Method 3): m/z 488 [M+H]⁺@r.t. 6.03 min.

tert-butyl{2-[7-(3-cyanophenyl)-6-(3-methyl phenyl)-1-oxo-1,2,3,4-tetrahydropyrrolo[1,2-a]pyrazin-4-yl] ethyl}carbamate [(I), R2=3-cyanophenyl, R3=3-methylphenyl, R4=H, A=—CH₂CH₂—NH—CO—OtBu]

Purification by HPLC preparative method 2 gave the title compound (57%).

LCMS (HPLC Method 3): m/z 471 [M+H]⁺@r.t. 6.2 min.

tert-butyl{2-[7-(3,4-difluorophenyl)-6-(3-methylphenyl)-1-oxo-1,2,3,4-tetrahydropyrrolo[1,2-a]pyrazin-4-yl] ethyl}carbamate [(I), R2=3,4-difluorophenyl, R3=3-methylphenyl, R4=H, A=—CH₂CH₂—NH—CO—OtBu]

Purification by HPLC preparative method 2 gave the title compound (45%).

LCMS (HPLC Method 3): m/z 482 [M+H]⁺@r.t. 6.4 min.

tert-butyl{2-[6-(4-cyanophenyl)-7-(3,4-difluorophenyl)-1-oxo-1,2,3,4-tetrahydropyrrolo[1,2-a]pyrazin-4-yl] ethyl}carbamate [(I), R2=3,4-difluorophenyl, R3=4-cyanophenyl, R4=H, A=—CH₂CH₂—NH—CO—OtBu]

Purification by HPLC preparative method 2 gave the title compound (47%).

LCMS (HPLC Method 3): m/z 493 [M+H]⁺@r.t. 5.9 min.

tert-butyl{2-[7-(3,4-difluorophenyl)-1-oxo-6-(thiophen-3-yl)-1,2,3,4-tetrahydropyrrolo[1,2-a]pyrazin-4-yl] ethyl}carbamate [(I), R2=3,4-difluorophenyl, R3=thiophen-3-yl, R4=H, A=—CH₂CH₂—NH—CO—OtBu]

Purification by HPLC preparative method 2 gave the title compound (57%).

LCMS (HPLC Method 3): m/z 474 [M+H]⁺@r.t. 6.13 min.

tert-butyl{2-[7-(3,4-difluorophenyl)-1-oxo-6-phenyl-1,2,3,4-tetrahydropyrrolo[1,2-a]pyrazin-4-yl]ethyl}carbamate [(I), R2=3,4-difluorophenyl, R3=phenyl, R4=H, A=—CH₂CH₂—NH—CO—OtBu]

Purification by HPLC preparative method 2 gave the title compound (51%).

¹H NMR (600 MHz, DMSO-d6) δ 7.71 (d, J=4.95 Hz, 1H), 7.43-7.52 (m, 3H), 7.35 (dd, J=2.38, 7.14 Hz, 2H), 7.20-7.26 (m, 1H), 7.05-7.10 (m, 1H), 7.02 (s, 1H), 6.90 (d, J=8.43 Hz, 1H), 6.54 (t, J=5.31 Hz, 1H), 4.17 (d, J=4.03 Hz, 1H), 3.76 (dd, J=3.30, 13.19 Hz, 1H), 3.35-3.40 (m, 1H), 2.61-2.72 (m, 2H), 1.43-1.82 (m, 2H), 1.29 (s, 9H).

LCMS (HPLC Method 2): m/z 468 [M+H]⁺@r.t. 6.88 min.

HRMS (ESI) calcd for $C_{26}H_{28}F_2N_3O_3$[M+H]⁺ 468.2093 found 468.2097.

tert-butyl(2-{7-(2-chloropyridin-4-yl)-6-[4-(hydroxymethyl)phenyl]-1-oxo-1,2,3,4-tetrahydropyrrolo[1,2-a]pyrazin-4-yl}ethyl)carbamate [(I), R2=2-chloropyridin-4-yl, R3=4-(hydroxymethyl)phenyl, R4=H, A=—CH₂CH₂—NH—CO—OtBu]

Purification by HPLC/preparative method 1 gave the title compound (36%).

LCMS (HPLC Method 3): m/z 497 [M+H]$^+$@r.t. 4.49 min.

tert-butyl{2-[7-(2-chloropyridin-4-yl)-6-(3-methylphenyl)-1-oxo-1,2,3,4-tetrahydropyrrolo[1,2-a]pyrazin-4-yl]ethyl}carbamate [(I), R2=2-chloropyridin-4-yl, R3=3-methylphenyl, R4=H, A=—CH$_2$CH$_2$—NH—CO—OtBu]

Purification by HPLC/preparative method 1 gave the title compound (56%).

LCMS (HPLC Method 3): m/z 481 [M+H]$^+$@r.t. 5.73 min.

tert-butyl{2-[7-(2-chloropyridin-4-yl)-1-oxo-6-(pyridin-4-yl)-1,2,3,4-tetrahydropyrrolo[1,2-a]pyrazin-4-yl]ethyl}carbamate [(I), R2=2-chloropyridin-4-yl, R3=pyridin-4-yl, R4=H, A=—CH$_2$CH$_2$—NH—CO—OtBu]

Purification by HPLC/preparative method 1 gave the title compound (15%).

LCMS (HPLC Method 3): m/z 468 [M+H]$^+$@r.t. 4.14 min.

Example 17

4-(2-aminoethyl)-6-phenyl-7-[3-(trifluoromethoxy)phenyl]-3,4-dihydropyrrolo[1,2-a]pyrazin-1(2H)-one hydrochloride [(I), R2=3-(trifluoromethoxy)phenyl, R3=pyridin-4-yl, R4=H, A=—CH$_2$CH$_2$—NH$_2$](cpd 28)

Conv. r

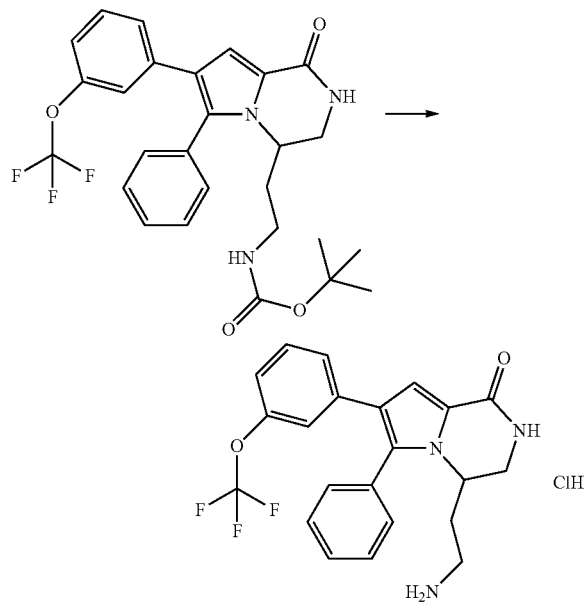

The product was dissolved in DCM (2 ml) and 4M HCl in 1,4-dioxane (2 ml) was added. The reaction was stirred at room temperature for 1 hour, the solvent was evaporated to dryness. The solid was treated with diethyl ether and the precipitate collected by filtration to give the title compound as a pale yellow solid 42 mg (97%).

$^1$H NMR (600 MHz, DMSO-d6) δ 7.80 (d, J=4.76 Hz, 1H), 7.54-7.65 (m, 3H), 7.46-7.54 (m, 4H), 7.36-7.42 (m, 2H), 7.34 (d, J=8.06 Hz, 1H), 7.25 (td, J=1.17, 8.03 Hz, 1H), 7.06-7.11 (m, 2H), 6.87 (s, 1H), 4.25-4.38 (m, 1H), 3.86 (dd, J=3.72, 13.37 Hz, 1H), 2.31-2.45 (m, 2H), 1.66-1.99 (m, 2H).

LCMS (HPLC Method 2): m/z 416 [M+H]$^+$@r.t. 5.04 min.

HRMS (ESI) calcd for C$_{22}$H$_{21}$F$_3$N$_3$O$_2$[M+H]$^+$ 416.1181 found 416.1168.

Operating in an analogous way, the following compounds were prepared:

4-(2-aminoethyl)-6-(thiophen-3-yl)-7-[3-(trifluoromethoxy)phenyl]-3,4-dihydropyrrolo[1,2-a]pyrazin-1(2H)-one hydrochloride [(I), R2=3-(trifluoromethoxy)phenyl, R3=thiophen-3-yl, R4=H, A=—CH$_2$CH$_2$—NH$_2$](cpd 29)

$^1$H NMR (400 MHz, DMSO-d6) δ 7.74-7.83 (m, 3H), 7.64-7.73 (m, 3H), 7.34-7.41 (m, 1H), 7.24-7.32 (m, 1H), 7.04-7.17 (m, 3H), 6.96 (s, 1H), 4.24-4.37 (m, 1H), 3.80 (dd, J=3.66, 13.30 Hz, 1H), 3.31-3.37 (m, 1H), 2.38-2.49 (m, 2H), 1.75-2.02 (m, 2H).

LCMS (HPLC Method 2): m/z 422 [M+H]$^+$@r.t. 5.04 min.

HRMS (ESI) calcd for C$_{20}$H$_{19}$F$_3$N$_3$O$_2$S [M+H]$^+$ 422.1145 found 422.1147.

4-(2-aminoethyl)-6-(2,3-dimethyl phenyl)-7-[3-(trifluoromethoxy)phenyl]-3,4-dihydropyrrolo[1,2-a]pyrazin-1(2H)-one hydrochloride [(I), R2=3-(trifluoromethoxy)phenyl, R3=2,3-dimethylphenyl, R4=H, A=—CH$_2$CH$_2$—NH$_2$] (cpd 30)

$^1$H NMR (600 MHz, DMSO-d6) δ 7.76 (d, J=4.95 Hz, 1H), 7.53-7.60 (m, 3H), 7.28-7.38 (m, 5H), 7.17 (s, 1H), 7.07 (d, J=8.06 Hz, 1H), 6.75 (s, 1H), 4.18-4.23 (m, J=6.04 Hz, 1H), 4.09-4.17 (m, 2H), 3.84 (dd, J=4.03, 13.37 Hz, 1H), 3.79-3.87 (m, 1H), 2.21-2.24 (m, 3H), 1.77 (s, 3H).

LCMS (HPLC Method 2): m/z 444 [M+H]$^+$@r.t. 4.51 min.

HRMS (ESI) calcd for C$_{24}$H$_{25}$F$_3$N$_3$O$_2$[M+H]$^+$ 444.1894 found 444.188.

4-(2-aminoethyl)-6-(3-methylphenyl)-7-[3-(trifluoromethoxy)phenyl]-3,4-dihydropyrrolo[1,2-a]pyrazin-1(2H)-one hydrochloride [(I), R2=3-(trifluoromethoxy)phenyl, R3=3-methylphenyl, R4=H, A=—CH$_2$CH$_2$—NH$_2$](cpd 31)

$^1$H NMR (600 MHz, DMSO-d6) δ 7.79 (d, J=4.95 Hz, 1H), 7.58 (br. s., 3H), 7.37-7.41 (m, 1H), 7.33-7.37 (m, 1H), 7.32 (d, J=7.51 Hz, 1H), 7.27 (d, J=8.06 Hz, 1H), 7.21 (s, 1H), 7.16 (d, J=7.14 Hz, 1H), 7.05-7.11 (m, 2H), 6.87 (s, 1H), 4.23-4.37 (m, 1H), 3.85 (dd, J=3.85, 13.55 Hz, 1H), 2.35-2.46 (m, 2H), 2.33 (s, 3H), 1.57-1.94 (m, 2H).

LCMS (HPLC Method 2): m/z 430 [M+H]$^+$@r.t. 4.41 min.

HRMS (ESI) calcd for C$_{23}$H$_{23}$F$_3$N$_3$O$_2$[M+H]$^+$ 430.1737 found 430.1735.

4-(2-aminoethyl)-6-(3-aminophenyl)-7-[3-(trifluoromethoxy)phenyl]-3,4-dihydropyrrolo[1,2-a]pyrazin-1(2H)-one hydrochloride [(I), R2=3-(trifluoromethoxy)phenyl, R3=3-aminophenyl, R4=H, A=—CH$_2$CH$_2$—NH$_2$](cpd 32)

$^1$H NMR (600 MHz, DMSO-d6) δ 7.79 (d, J=5.13 Hz, 1H), 7.71 (br. s., 3H), 7.33-7.38 (m, 1H), 7.31 (br. s., 1H), 7.27 (d, J=7.88 Hz, 1H), 7.06-7.12 (m, 2H), 6.98 (s, 1H), 6.95 (br. s., 1H), 6.75-6.88 (m, 2H), 4.30 (t, J=8.52 Hz, 1H), 3.79 (dd, J=3.75, 13.28 Hz, 1H), 2.41-2.49 (m, 2H), 1.87-1.99 (m, 1H), 1.71-1.86 (m, 1H).

LCMS (HPLC Method 2): m/z 431 [M+H]$^+$@r.t. 3.88 min.

HRMS (ESI) calcd for C$_{22}$H$_{22}$F$_3$N$_4$O$_2$[M+H]$^+$ 431.169 found 431.1699.

4-(2-aminoethyl)-6-[4-(hydroxymethyl)phenyl]-7-[3-(trifluoromethoxy)phenyl]-3,4-dihydropyrrolo[1,2-a]pyrazin-1(2H)-one hydrochloride [(I), R2=3-(trifluoromethoxy)phenyl, R3=4-(hydroxymethyl)phenyl, R4=H, A=—CH$_2$CH$_2$—NH$_2$](cpd 33)

$^1$H NMR (600 MHz, DMSO-d6) δ 7.79 (d, J=4.94 Hz, 1H), 7.58 (br. s., 3H), 7.44 (d, J=8.24 Hz, 2H), 7.30-7.37 (m, 3H), 7.20 (d, J=7.88 Hz, 1H), 7.04-7.12 (m, 2H), 6.95 (s, 1H), 5.35 (t, J=5.59 Hz, 1H), 4.59 (d, J=5.68 Hz, 2H), 4.25-4.39 (m, 1H), 3.85 (dd, J=3.75, 13.28 Hz, 1H), 2.29-2.47 (m, 2H), 1.81-1.94 (m, 1H), 1.69-1.81 (m, 1H).

LCMS (HPLC Method 2): m/z 446 [M+H]⁺@r.t. 4.72 min.
HRMS (ESI) calcd for $C_{23}H_{23}F_3N_3O_3$ [M+H]⁺ 446.1686 found 446.1678.

4-(2-aminoethyl)-7-(3-methoxyphenyl)-6-(3-methylphenyl)-3,4-dihydropyrrolo[1,2-a]pyrazin-1(2H)-one hydrochloride [(I), R2=3-methoxyphenyl, R3=3-methylphenyl, R4=H, A=—CH₂CH₂—NH₂](cpd 34)

¹H NMR (600 MHz, DMSO-d6) δ 7.74 (d, J=5.13 Hz, 1H), 7.57 (br. s., 3H), 7.34-7.40 (m, 1H), 7.29 (d, J=7.69 Hz, 1H), 7.23 (s, 1H), 7.14 (d, J=7.51 Hz, 1H), 7.10 (t, J=7.88 Hz, 1H), 7.02 (s, 1H), 6.72 (d, J=8.06 Hz, 1H), 6.67 (dd, J=1.92, 8.15 Hz, 1H), 6.60-6.64 (m, 1H), 4.22-4.38 (m, J=3.66 Hz, 1H), 3.85 (dd, J=3.85, 13.37 Hz, 1H), 3.56 (s, 3H), 2.39-2.45 (m, 1H), 2.34 (s, 3H), 1.81-1.90 (m, 1H), 1.77 (dt, J=6.50, 12.41 Hz, 1H).

LCMS (HPLC Method 2): m/z 376 [M+H]⁺@r.t. 4.71 min.
HRMS (ESI) calcd for $C_{23}H_{26}N_3O_2$ [M+H]⁺ 376.202 found 376.2013.

7-(3-acetylphenyl)-4-(2-aminoethyl)-6-(3-methylphenyl)-3,4-dihydropyrrolo[1,2-a]pyrazin-1(2H)-one hydrochloride [(I), R2=3-acetylphenyl, R3=3-methylphenyl, R4=H, A=—CH₂CH₂—NH₂](cpd 35)

¹H NMR (600 MHz, DMSO-d6) δ 7.78 (d, J=5.13 Hz, 1H), 7.64-7.70 (m, 2H), 7.58 (br. s., 3H), 7.36-7.41 (m, 2H), 7.32-7.36 (m, 1H), 7.30 (d, J=7.51 Hz, 1H), 7.25 (s, 1H), 7.15 (d, J=7.33 Hz, 1H), 7.12 (s, 1H), 4.28-4.40 (m, J=3.85 Hz, 1H), 3.87 (dd, J=3.75, 13.28 Hz, 1H), 2.42 (dt, J=5.68, 11.36 Hz, 2H), 2.37 (s, 3H), 2.34 (s, 3H), 1.84-1.94 (m, 1H), 1.78 (tt, J=5.98, 12.52 Hz, 1H).

LCMS (HPLC Method 2): m/z 388 [M+H]⁺@r.t. 4.48 min.
HRMS (ESI) calcd for $C_{24}H_{26}N_3O_2$ [M+H]⁺ 388.202 found 388.2013.

3-[4-(2-aminoethyl)-6-(3-methylphenyl)-1-oxo-1,2,3,4-tetrahydropyrrolo[1,2-a]pyrazin-7-yl]benzonitrile hydrochloride [(I), R2=3-benzonitrile, R3=3-methylphenyl, R4=H, A=—CH₂CH₂—NH₂](cpd 36)

¹H NMR (600 MHz, DMSO-d6) δ 7.80 (d, J=4.95 Hz, 1H), 7.54-7.65 (m, 4H), 7.51 (s, 1H), 7.35-7.43 (m, 3H), 7.33 (d, J=7.51 Hz, 1H), 7.23 (s, 1H), 7.12-7.16 (m, 2H), 4.34 (d, J=3.48 Hz, 1H), 3.86 (dd, J=3.94, 13.28 Hz, 1H), 2.37-2.45 (m, 2H), 2.35 (s, 3H), 1.71-1.92 (m, 2H).

LCMS (HPLC Method 2): m/z 371 [M+H]⁺@r.t. 4.6 min.
HRMS (ESI) calcd for $C_{23}H_{23}N_4O$ [M+H]⁺ 371.1867 found 371.1861.

4-(2-aminoethyl)-6-phenyl-7-[3-(trifluoromethyl)phenyl]-3,4-dihydropyrrolo[1,2-a]pyrazin-1(2H)-one hydrochloride [(I), R2=3-(trifluoromethyl)phenyl, R3=phenyl, R4=H, A=—CH₂CH₂—NH₂](cpd 37)

¹H NMR (600 MHz, DMSO-d6) δ 7.81 (d, J=4.94 Hz, 1H), 7.63 (br. s., 3H), 7.42-7.55 (m, 7H), 7.36-7.42 (m, 2H), 7.27 (s, 1H), 7.14 (s, 1H), 4.24-4.44 (m, J=3.48 Hz, 1H), 3.87 (dd, J=4.12, 13.28 Hz, 1H), 2.30-2.48 (m, 2H), 1.83-1.94 (m, 1H), 1.70-1.83 (m, 1H).

LCMS (HPLC Method 2): m/z 400 [M+H]⁺@r.t. 4.22 min.
HRMS (ESI) calcd for $C_{22}H_{21}F_3N_3O$ [M+H]⁺ 400.1631 found 400.1642.

4-(2-aminoethyl)-6-[4-(hydroxymethyl)phenyl]-7-[3-(trifluoromethyl)phenyl]-3,4-dihydropyrrolo[1,2-a]pyrazin-1(2H)-one hydrochloride [(I), R2=3-(trifluoromethyl)phenyl, R3=4-(hydroxymethyl)phenyl, R4=H, A=—CH₂CH₂—NH₂](cpd 38)

¹H NMR (600 MHz, DMSO-d6) δ 7.79 (d, J=4.95 Hz, 1H), 7.60 (br. s., 3H), 7.39-7.47 (m, 5H), 7.37 (s, 1H), 7.34 (d, J=7.88 Hz, 2H), 7.12 (s, 1H), 5.17-5.50 (m, J=12.64 Hz, 1H), 4.58 (s, 2H), 4.27-4.40 (m, J=3.30 Hz, 1H), 3.86 (dd, J=3.85, 13.37 Hz, 1H), 2.27-2.47 (m, 2H), 1.82-1.93 (m, 1H), 1.71-1.82 (m, 1H).

LCMS (HPLC Method 2): m/z 430 [M+H]⁺@r.t. 3.8 min.
HRMS (ESI) calcd for $C_{23}H_{23}F_3N_3O_2$ [M+H]⁺ 430.1737 found 430.1737.

4-(2-aminoethyl)-6-(3-methylphenyl)-7-[3-(trifluoromethyl)phenyl]-3,4-dihydropyrrolo[1,2-a]pyrazin-1(2H)-one hydrochloride [(I), R2=3-(trifluoromethyl)phenyl, R3=3-methylphenyl, R4=H, A=—CH₂CH₂—NH₂](cpd 39)

¹H NMR (600 MHz, DMSO-d6) δ 7.80 (d, J=5.13 Hz, 1H), 7.61 (br. s., 3H), 7.43-7.50 (m, 3H), 7.37-7.41 (m, 1H), 7.32 (d, J=7.69 Hz, 1H), 7.30 (s, 1H), 7.23 (s, 1H), 7.16 (d, J=7.51 Hz, 1H), 7.14 (s, 1H), 4.29-4.40 (m, 1H), 3.87 (dd, J=3.85, 13.37 Hz, 1H), 2.35-2.47 (m, 2H), 2.34 (s, 3H), 1.83-1.93 (m, 1H), 1.72-1.82 (m, 1H).

LCMS (HPLC Method 2): m/z 414 [M+H]⁺@r.t. 4.38 min.
HRMS (ESI) calcd for $C_{23}H_{23}F_3N_3O$ [M+H]⁺ 414.1788 found 414.1795.

4-(2-aminoethyl)-6-(thiophen-3-yl)-7-[3-(trifluoromethyl)phenyl]-3,4-dihydropyrrolo[1,2-a]pyrazin-1(2H)-one hydrochloride [(I), R2=3-(trifluoromethyl)phenyl, R3=thiophen-3-yl, R4=H, A=—CH₂CH₂—NH₂](cpd 40)

¹H NMR (600 MHz, DMSO-d6) δ 7.80 (d, J=4.95 Hz, 1H), 7.77 (dd, J=2.93, 4.95 Hz, 1H), 7.75 (d, J=0.92 Hz, 1H), 7.64 (br. s., 3H), 7.51-7.55 (m, 1H), 7.45-7.50 (m, 2H), 7.33 (s, 1H), 7.12 (s, 1H), 7.08 (dd, J=1.10, 4.95 Hz, 1H), 4.25-4.43 (m, 1H), 3.81 (dd, J=3.94, 13.46 Hz, 1H), 3.33-3.39 (m, 1H), 1.93 (dt, J=6.41, 12.82 Hz, 1H), 1.84 (dt, J=5.86, 12.27 Hz, 1H).

LCMS (HPLC Method 2): m/z 406 [M+H]⁺@r.t. 4.14 min.
HRMS (ESI) calcd for $C_{20}H_{19}F_3N_3OS$ [M+H]⁺ 406.1196 found 406.1197.

4-{4-(2-aminoethyl)-1-oxo-7-[3-(trifluoromethyl)phenyl]-1,2,3,4-tetrahydropyrrolo[1,2-a]pyrazin-6-yl}benzonitrile hydrochloride [(I), R2=3-(trifluoromethyl)phenyl, R3=4-benzonitrile, R4=H, A=—CH₂CH₂—NH₂] (cpd 41)

¹H NMR (600 MHz, DMSO-d6) δ 7.98 (d, J=8.42 Hz, 2H), 7.88 (d, J=4.94 Hz, 1H), 7.54-7.63 (m, 5H), 7.50-7.53 (m, 1H), 7.45-7.50 (m, 1H), 7.42 (d, J=7.69 Hz, 1H), 7.30 (s, 1H), 7.15 (s, 1H), 4.40 (t, J=8.43 Hz, 1H), 3.91 (dd, J=4.03, 13.37 Hz, 1H), 2.40-2.47 (m, 2H), 1.80-1.92 (m, 1H), 1.70 (dt, J=6.04, 12.45 Hz, 1H).

LCMS (HPLC Method 2): m/z 425 [M+H]⁺@r.t. 4.18 min.
HRMS (ESI) calcd for $C_{23}H_{20}F_3N_4O$ [M+H]⁺ 425.1584 found 425.1584.

4-(2-aminoethyl)-6-(pyridin-4-yl)-7-[3-(trifluoromethyl)phenyl]-3,4-dihydropyrrolo[1,2-a]pyrazin-1(2H)-one hydrochloride [(I), R2=3-(trifluoromethyl)phenyl, R3=pyridin-4-yl, R4=H, A=—CH₂CH₂—NH₂](cpd 42)

¹H NMR (600 MHz, DMSO-d6) δ 8.76 (d, J=5.31 Hz, 2H), 7.94 (d, J=4.95 Hz, 1H), 7.67 (br. s., 3H), 7.57 (br. s., 2H), 7.55 (d, J=8.06 Hz, 1H), 7.47-7.51 (m, 1H), 7.42-7.46 (m, 1H), 7.39 (s, 1H), 7.16 (s, 1H), 4.50 (br. s., 1H), 3.92 (dd, J=3.57, 13.46 Hz, 1H), 2.40-2.48 (m, 2H), 1.82-1.94 (m, 1H), 1.62-1.76 (m, 1H).

LCMS (HPLC Method 2): m/z 401 [M+H]⁺@r.t. 3.65 min.
HRMS (ESI) calcd for $C_{21}H_{20}F_3N_4O$ [M+H]⁺ 401.1584 found 401.1584.

4-(2-aminoethyl)-6-(4-hydroxyphenyl)-7-[3-(trifluoromethyl)phenyl]-3,4-dihydropyrrolo[1,2-a]pyrazin-1(2H)-one hydrochloride [(I), R2=3-(trifluoromethyl)phenyl, R3=4-hydroxyphenyl, R4=H, A=—CH₂CH₂—NH₂](cpd 43)

¹H NMR (600 MHz, DMSO-d6) δ 9.81 (s, 1H), 7.72 (d, J=4.95 Hz, 1H), 7.56 (br. s., 3H), 7.43-7.47 (m, 1H), 7.41 (d, J=5.31 Hz, 2H), 7.32 (s, 1H), 7.15 (d, J=8.24 Hz, 2H), 7.08 (s, 1H), 6.85 (d, J=8.61 Hz, 2H), 4.20-4.35 (m, J=3.85 Hz, 1H), 3.80 (dd, J=3.85, 13.37 Hz, 1H), 2.36-2.44 (m, 2H), 1.80-1.90 (m, J=6.04, 12.09 Hz, 1H), 1.67-1.79 (m, J=6.23, 12.36, 12.36 Hz, 1H).

LCMS (HPLC Method 2): m/z 416 [M+H]$^+$@r.t. 3.76 min. HRMS (ESI) calcd for $C_{22}H_{21}F_3N_3O_2$[M+H]$^+$ 425.1581 found 425.1582.

4-(2-aminoethyl)-7-(2-chloropyridin-4-yl)-6-[4-(hydroxymethyl)phenyl]-3,4-dihydropyrrolo[1,2-a]pyrazin-1(2H)-one hydrochloride [(I), R2=2-chloropyridin-4-yl, R3=4-(hydroxymethyl)phenyl, R4=H, A=—CH$_2$CH$_2$—NH$_2$](cpd 44)

$^1$H NMR (600 MHz, DMSO-d6) δ 8.11-8.15 (m, 1H), 7.85 (d, J=5.13 Hz, 1H), 7.63 (br. s., 3H), 7.47-7.52 (m, 2H), 7.39 (d, J=7.69 Hz, 2H), 7.28 (s, 1H), 7.17 (s, 1H), 7.05 (dd, J=1.47, 5.31 Hz, 1H), 4.62 (s, 2H), 4.18-4.35 (m, 1H), 3.83 (dd, J=3.85, 13.55 Hz, 1H), 3.45-3.47 (m, 1H), 2.27-2.47 (m, 2H), 1.83-1.92 (m, 1H), 1.71-1.81 (ddd, J=5.49, 12.64, 12.64 Hz, 1H).

LCMS (HPLC Method 2): m/z 397[M+H]$^+$@r.t. 2.91 min. HRMS (ESI) calcd for $C_{21}H_{22}ClN_4O_2$[M+H]$^+$ 397.1426 found 397.1432.

4-(2-aminoethyl)-7-(2-chloropyridin-4-yl)-6-(3-methylphenyl)-3,4-dihydropyrrolo[1,2-a]pyrazin-1(2H)-one hydrochloride [(I), R2=2-chloropyridin-4-yl, R3=3-methylphenyl, R4=H, A=—CH$_2$CH$_2$—NH$_2$](cpd 45)

$^1$H NMR (600 MHz, DMSO-d6) δ 8.15 (d, J=5.31 Hz, 1H), 7.86 (d, J=5.13 Hz, 1H), 7.56-7.70 (m, 3H), 7.42-7.47 (m, 1H), 7.38 (d, J=7.51 Hz, 1H), 7.29 (s, 1H), 7.27 (s, 1H), 7.20 (d, J=7.33 Hz, 1H), 7.12 (d, J=1.10 Hz, 1H), 7.07 (dd, J=1.47, 5.31 Hz, 1H), 4.25-4.36 (m, 1H), 3.84 (dd, J=3.94, 13.46 Hz, 1H), 3.39 (m, 1H), 2.39-2.47 (m, 2H), 2.38 (s, 3H), 1.84-1.93 (m, 1H), 1.72-1.81 (m, 1H).

LCMS (HPLC Method 2): m/z 381[M+H]$^+$@r.t. 3.47 min. HRMS (ESI) calcd for $C_{21}H_{22}ClN_4O$ [M+H]$^+$ 381.1477 found 381.1482.

4-(2-aminoethyl)-7-(2-chloropyridin-4-yl)-6-(pyridin-4-yl)-3,4-dihydropyrrolo[1,2-a]pyrazin-1(2H)-one hydrochloride [(I), R2=2-chloropyridin-4-yl, R3=pyridin-4-yl, R4=H, A=—CH$_2$CH$_2$—NH$_2$](cpd 46)

$^1$H NMR (600 MHz, DMSO-d6) δ 8.82 (d, J=5.13 Hz, 2H), 8.21 (d, J=5.31 Hz, 1H), 7.98 (d, J=4.94 Hz, 1H), 7.58-7.80 (m, 5H), 7.30 (s, 1H), 7.25 (s, 1H), 7.06 (dd, J=1.37, 5.22 Hz, 1H), 4.46 (br. s., 1H), 3.89 (dd, J=3.66, 13.55 Hz, 1H), 3.57 (m, 1H), 2.43-2.48 (m, J=5.86 Hz, 2H), 1.85-1.97 (m, 1H), 1.64-1.73 (m, 1H).

LCMS (HPLC Method 2): m/z 368[M+H]$^+$@r.t. 2.76 min. HRMS (ESI) calcd for $C_{19}H_{19}ClN_5O$ [M+H]$^+$ 368.1273 found 368.1262.

4-(2-aminoethyl)-7-(2-fluoropyridin-4-yl)-6-(3-methylphenyl)-3,4-dihydropyrrolo[1,2-a]pyrazin-1(2H)-one hydrochloride [(I), R2=2-fluoropyridin-4-yl, R3=3-methylphenyl, R4=H, A=—CH$_2$CH$_2$—NH$_2$](cpd 47)

$^1$H NMR (600 MHz, DMSO-d6) δ 7.98 (d, J=5.31 Hz, 1H), 7.86 (d, J=5.13 Hz, 1H), 7.49 (s, 3H), 7.43-7.47 (m, 1H), 7.36-7.40 (m, 1H), 7.27 (s, 1H), 7.20 (d, J=7.33 Hz, 1H), 6.99 (d, J=5.31 Hz, 1H), 6.80 (s, 1H), 4.22-4.34 (m, 1H), 3.84 (dd, J=3.75, 13.65 Hz, 1H), 2.38 (s, 4H), 1.82-1.94 (m, 1H), 1.75 (td, J=6.32, 12.64 Hz, 1H).

LCMS (HPLC Method 2): m/z 365 [M+H]$^+$@r.t. 4.24 min. HRMS (ESI) calcd for $C_{21}H_{22}FN_4O$ [M+H]$^+$ 365.1772 found 365.1762.

4-(2-aminoethyl)-7-(6-fluoropyridin-3-yl)-6-phenyl-3,4-dihydropyrrolo[1,2-a]pyrazin-1(2H)-one [(I), R2=6-fluoropyridin-3-yl, R3=phenyl, R4=H, A=—CH$_2$CH$_2$—NH$_2$](cpd 48)

$^1$H NMR (400 MHz, DMSO-d6) δ 7.89-7.97 (m, J=2.69 Hz, 1H), 7.71 (d, J=5.25 Hz, 1H), 7.65 (dt, J=2.62, 8.27 Hz, 1H), 7.43-7.53 (m, 3H), 7.34-7.40 (m, 2H), 7.05 (s, 1H), 6.99-7.04 (m, J=2.75, 8.73 Hz, 1H), 4.25-4.38 (m, 1H), 3.81 (dd, J=4.03, 13.18 Hz, 1H), 2.20-2.28 (m, 2H), 1.62-1.75 (m, J=6.84, 14.89 Hz, 1H), 1.37-1.48 (m, 1H).

LCMS (HPLC Method 2): m/z 351 [M+H]$^+$@r.t. 4.21 min. HRMS (ESI) calcd for $C_{29}H_{20}FN_4O$ [M+H]$^+$ 351.1616 found 351.1627.

4-(2-aminoethyl)-7-(3,4-difluorophenyl)-6-(3-methylphenyl)-3,4-dihydropyrrolo[1,2-a]pyrazin-1(2H)-one hydrochloride [(I), R2=3,4-difluorophenyl, R3=3-methylphenyl, R4=H, A=—CH$_2$CH$_2$—NH$_2$](cpd 49)

$^1$H NMR (600 MHz, DMSO-d6) δ 7.78 (d, J=4.76 Hz, 1H), 7.59 (br. s., 3H), 7.37-7.41 (m, 1H), 7.31 (d, J=7.51 Hz, 1H), 7.21-7.28 (m, 2H), 7.14 (d, J=7.33 Hz, 1H), 7.07-7.12 (m, 1H), 7.06 (s, 1H), 6.90 (d, J=7.69 Hz, 1H), 4.30 (br. s., 1H), 3.84 (dd, J=3.66, 13.55 Hz, 1H), 3.38-3.25 (m, 1H), 2.38-2.45 (m, 2H), 2.33-2.37 (m, 3H), 1.70-1.91 (m, 2H).

LCMS (HPLC Method 2): m/z 382 [M+H]$^+$@r.t. 5.01 min. HRMS (ESI) calcd for $C_{22}H_{22}F_2N_3O$ [M+H]$^+$ 382.1726 found 382.1730.

4-[4-(2-aminoethyl)-7-(3,4-difluorophenyl)-1-oxo-1,2,3,4-tetrahydropyrrolo[1,2-a]pyrazin-6-yl]benzonitrile hydrochloride [(I), R2=3,4-difluorophenyl, R3=4-benzonitrile, R4=H, A=—CH$_2$CH$_2$—NH$_2$](cpd 50)

$^1$H NMR (600 MHz, DMSO-d6) δ 7.95-8.00 (m, 2H), 7.86 (d, J=4.58 Hz, 1H), 7.58 (d, J=8.24 Hz, 5H), 7.23-7.32 (m, 1H), 7.13-7.19 (m, 1H), 7.07 (d, J=1.47 Hz, 1H), 6.84 (d, J=6.78 Hz, 1H), 4.37 (br. s., 1H), 3.83-3.92 (m, 1H), 3.3 (m, 1H), 2.35-2.44 (m, 2H), 1.60-1.91 (m, 2H).

LCMS (HPLC Method 2): m/z 393[M+H]$^+$@r.t. 4.78 min. HRMS (ESI) calcd for $C_{22}H_{19}F_2N_4O$ [M+H]$^+$ 393.1522 found 393.1528.

4-(2-aminoethyl)-7-(3,4-difluorophenyl)-6-(thiophen-3-yl)-3,4-dihydropyrrolo[1,2-a]pyrazin-1(2H)-one hydrochloride [(I), R2=3,4-difluorophenyl, R3=thiophen-3-yl, R4=H, A=—CH$_2$CH$_2$—NH$_2$](cpd 51)

$^1$H NMR (600 MHz, DMSO-d6) δ 7.73-7.81 (m, 3H), 7.63 (br. s., 3H), 7.24-7.32 (m, 1H), 7.12 (ddd, J=2.11, 7.88, 12.36 Hz, 1H), 7.08 (dd, J=1.19, 4.85 Hz, 1H), 7.05 (s, 1H), 6.97 (d, J=7.88 Hz, 1H), 4.28-4.37 (m, 1H), 3.79 (dd, J=3.85, 13.37 Hz, 1H), 3.38-3.33 (m, 1H), 2.40-2.49 (m, 2H), 1.74-1.97 (m, 2H).

LCMS (HPLC Method 2): m/z 374 [M+H]$^+$@r.t. 4.71 min. HRMS (ESI) calcd for $C_{19}H_{18}F_2N_3OS$ [M+H]$^+$ 374.1133 found 374.1147.

4-(2-aminoethyl)-7-(3,4-difluorophenyl)-6-phenyl-3,4-dihydropyrrolo[1,2-a]pyrazin-1(2H)-one hydrochloride [(I), R2=3,4-difluorophenyl, R3=phenyl, R4=H, A=—CH$_2$CH$_2$—NH$_2$](cpd 52)

$^1$H NMR (600 MHz, DMSO-d6) δ 7.79 (d, J=5.13 Hz, 1H), 7.62 (br. s., 3H), 7.49-7.56 (m, 3H), 7.35-7.41 (m, 2H), 7.21-7.29 (m, 1H), 7.05-7.10 (m, 2H), 6.90 (d, J=8.43 Hz, 1H), 4.30 (d, J=3.11 Hz, 1H), 3.84 (dd, J=3.94, 13.28 Hz, 1H), 3.31-3.35 (m, 1H), 2.31-2.45 (m, 2H), 1.68-1.93 (m, 2H).

LCMS (HPLC Method 2): m/z 368 [M+H]$^+$@r.t. 4.79 min. HRMS (ESI) calcd for $C_{20}H_{20}ClN_4O$ [M+H]$^+$ 368.1569 found 368.1580.

According to the same methodology used for example 11, but employing a purification with HPLC/MS method 2 the following compounds were prepared:

4-(2-aminoethyl)-7-[2-chloro-5-(trifluoromethoxy)phenyl]-6-(3-methylphenyl)-3,4-dihydropyrrolo[1,2-a]pyrazin-1(2H)-one trifluoroacetate [(I), R2=2-chloro-5-(trifluoromethoxy)phenyl, R3=3-methylphenyl, R4=H, A=—CH$_2$CH$_2$—NH$_2$](cpd 53)

$^1$H NMR (600 MHz, DMSO-d6) δ 7.84 (d, J=4.95 Hz, 1H), 7.58 (d, J=8.79 Hz, 1H), 7.50 (d, J=6.96 Hz, 3H), 7.27-7.33

(m, 1H), 7.24 (dd, J=2.47, 8.88 Hz, 1H), 7.21 (d, J=7.88 Hz, 1H), 7.07 (s, 1H), 7.03 (d, J=7.33 Hz, 1H), 6.97 (s, 1H), 6.90 (d, J=2.01 Hz, 1H), 4.38-4.57 (m, J=3.11 Hz, 1H), 3.92 (dd, J=3.94, 13.46 Hz, 1H), 2.31-2.43 (m, 2H), 2.26 (s, 3H), 1.68-1.92 (m, 2H).

LCMS (HPLC Method 2): m/z 464 [M+H]$^+$@r.t. 4.41 min.

HRMS (ESI) calcd for C$_{23}$H$_{22}$ClF$_3$N$_3$O$_2$ [M+H]$^+$ 464.1347 found 464.1362.

4-(2-aminoethyl)-6-cyclopropyl-7-[3-(trifluoromethoxy)phenyl]-3,4-dihydropyrrolo[1,2-a]pyrazin-1(2H)-one trifluoroacetate [(I), R2=3-(trifluoromethoxy)phenyl, R3=cyclopropyl, R4=H, A=—CH$_2$CH$_2$—NH$_2$](cpd 54)

$^1$H NMR (400 MHz, DMSO-d6) δ 7.65-7.77 (m, 4H), 7.43-7.57 (m, 4H), 7.19-7.25 (m, 1H), 6.87 (s, 1H), 4.65-4.74 (m, 1H), 3.71 (dd, J=4.03, 13.30 Hz, 1H), 3.38-3.45 (m, 1H), 2.88 (d, J=4.76 Hz, 2H), 1.83-2.15 (m, 2H), 0.87-1.12 (m, 2H), 0.51 (dd, J=4.27, 9.52 Hz, 1H), 0.15 (dd, J=4.15, 9.76 Hz, 1H).

LCMS (HPLC Method 2): m/z 380 [M+H]$^+$@r.t. 4.87 min.

HRMS (ESI) calcd for C$_{19}$H$_{21}$F$_3$N$_3$O$_2$[M+H]$^+$ 380.1581 found 380.1582.

Example 18 tert-butyl{2-[7-(5-chloro-2-fluorophenyl)-1-oxo-6-(thiophen-3-yl)-1,2,3,4-tetrahydropyrrolo[1,2-a]pyrazin-4-yl]ethyl}carbamate [(I), R2=5-chloro-2-fluorophenyl, R3=thiophen-3-yl, R4=H, A=—CH$_2$CH$_2$—NH—COOtBu] and tert-butyl{2-[7-(5-chloro-2-fluorophenyl)-1-oxo-8-(thiophen-3-yl)-1,2,3,4-tetrahydropyrrolo[1,2-a]pyrazin-4-yl]ethyl}carbamate [(I), R2=5-chloro-2-fluorophenyl, R4=thiophen-3-yl, R3=H, A=—CH$_2$CH$_2$—NH—COOtBu]

Conv. g

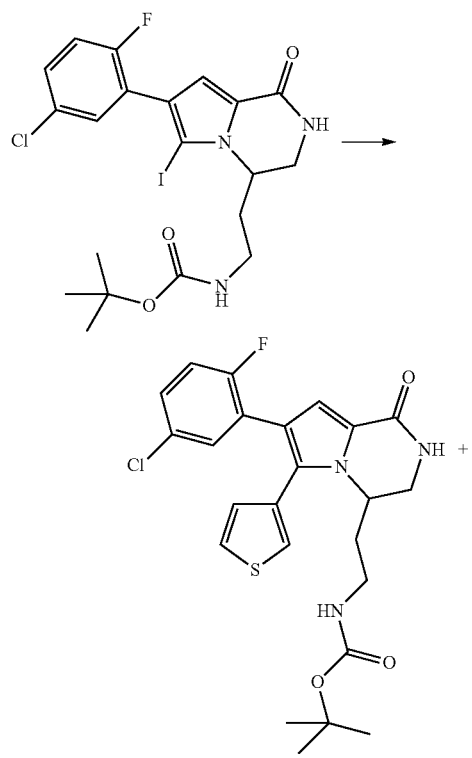

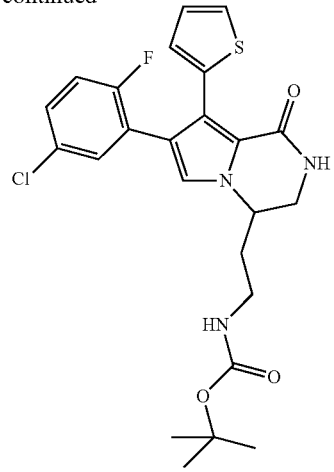

Thiophen-3-ylboronic acid (0.016 g, 0.12 mmol), cesium carbonate (0.092 g, 0.28 mmol) and 1,1'-bis(diphenylphosphino)ferrocenepaladium (0.0038 g, 0.0046 mmol) complex with dichloromethane, were subsequently added to a solution of tert-butyl{2-[7-(5-chloro-2-fluorophenyl)-6-iodo-1-oxo-1,2,3,4-tetrahydropyrrolo[1,2-a]pyrazin-4-yl]ethyl}carbamate (0.050 g, 0.093 mmol) in 1.5 ml of 1,4-dioxane and 0.5 ml of water, under argon atmosphere. The mixture was heated at 80° for 2 hours in a sealed vial. The reaction was filtered through a celite pad and the solvent evaporated to dryness. The crude was portioned between ethyl acetate and water, the organic layer dried over sodium sulphate and the solvent removed in vacuo. Purification by flash chromatography on silica gel column (DCM/MeOH 9:0.5), and further purification by HPLC/MS preparative method 1, afforded:

tert-butyl{2-[7-(5-chloro-2-fluorophenyl)-1-oxo-6-(thiophen-3-yl)-1,2,3,4-tetrahydropyrrolo[1,2-a]pyrazin-4-yl]ethyl}carbamate (0.027 g, 0.055 mmol, 59%)

LCMS (HPLC Method 3): m/z 490 [M+H]$^+$@r.t. 6.50 min. and tert-butyl{2-[7-(5-chloro-2-fluorophenyl)-1-oxo-8-(thiophen-3-yl)-1,2,3,4-tetrahydropyrrolo[1,2-a]pyrazin-4-yl]ethyl}carbamate (0.007 g, 0.014 mmol, 15%).

LCMS (HPLC Method 3): m/z 490 [M+H]$^+$@r.t. 6.68 min.

According to the same methodology, but employing suitable starting material, the following compounds were prepared:

tert-butyl{2-[7-(5-chloro-2-fluorophenyl)-1-oxo-6-phenyl-1,2,3,4-tetrahydropyrrolo[1,2-a]pyrazin-4-yl]ethyl}carbamate [(I), R2=5-chloro-2-fluorophenyl, R3=phenyl, R4=H, A=—CH$_2$CH$_2$—NH—COOtBu]

Purification by HPLC preparative method 2 gave the title compound (0.023 g, 0.047 mmol, 45%).

LCMS (HPLC Method 3): m/z 484 [M+H]$^+$@r.t. 6.45 min.

tert-butyl{2-[7-(5-chloro-2-fluorophenyl)-1-oxo-8-phenyl-1,2,3,4-tetrahydropyrrolo[1,2-a]pyrazin-4-yl]ethyl}carbamate [(I), R2=5-chloro-2-fluorophenyl, R4=phenyl, R3=H, A=—CH$_2$CH$_2$—NH—COOtBu]

Purification by HPLC preparative method 2 gave the title compound (0.004 g, 0.008 mmol, 9%).

LCMS (HPLC Method 3): m/z 484 [M+H]$^+$@r.t. 6.60 min.

tert-butyl{2-[7-(5-chloro-2-fluorophenyl)-6-(3-methylphenyl)-1-oxo-1,2,3,4-tetrahydropyrrolo[1,2-a]pyrazin-4-yl]ethyl}carbamate [(I), R2=5-chloro-2-fluorophenyl, R3=3-methylphenyl, R4=H, A=—CH$_2$CH$_2$—NH—COOtBu]

Purification by HPLC/MS preparative method 1 gave the title compound (0.022 g, 0.044 mmol, 69%).

LCMS (HPLC Method 3): m/z 498 [M+H]+@r.t. 6.9 min.

tert-butyl{2-[7-(5-chloro-2-fluorophenyl)-8-(3-methylphenyl)-1-oxo-1,2,3,4-tetrahydropyrrolo[1,2-a]pyrazin-4-yl]ethyl}carbamate [(I), R2=5-chloro-2-fluorophenyl, R4=3-methylphenyl, R3=H, A=—CH$_2$CH$_2$—NH—COOtBu]

Purification by HPLC/MS preparative method 1 gave the title compound (0.006 g, 0.012 mmol, 19%).

LCMS (HPLC Method 3): m/z 498 [M+H]+@r.t. 7.1 min.

Example 19

4-(2-aminoethyl)-7-(5-chloro-2-fluorophenyl)-6-(thiophen-3-yl)-3,4-dihydropyrrolo[1,2-a]pyrazin-1(2H)-one hydrochloride [(I), R2=5-chloro-2-fluorophenyl, R3=thiophen-3-yl, R4=H, A=—CH$_2$CH$_2$—NH$_2$](cpd 55)

Conv. R

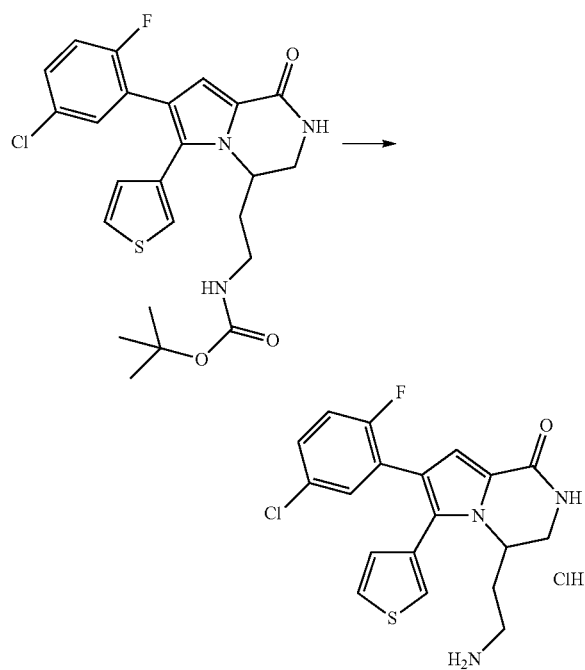

Tert-butyl {2-[7-(5-chloro-2-fluorophenyl)-1-oxo-6-(thiophen-3-yl)-1,2,3,4-tetrahydropyrrolo[1,2-a]pyrazin-4-yl]ethyl}carbamate (0.027 g, 0.055 mmol) was dissolved in 4M HCl in 1,4-dioxane (2 ml) and the reaction was stirred at room temperature for 1 hour. The solvent was evaporated to dryness, giving the title compound (0.018 g, 0.046 mmol, 98%).

$^1$H NMR (600 MHz, DMSO-d6) δ 7.80 (d, J=4.95 Hz, 1H), 7.68 (dd, J=2.93, 4.95 Hz, 1H), 7.62 (d, J=1.65 Hz, 4H), 7.23-7.28 (m, 1H), 7.16-7.20 (m, 1H), 6.97-7.04 (m, 2H), 6.92 (d, J=1.83 Hz, 1H), 4.45 (br. s., 1H), 3.81 (dd, J=3.85, 13.55 Hz, 1H), 3.3 (m, 1H), 2.37-2.45 (m, 2H), 1.75-1.96 (m, 2H).

LCMS (HPLC Method 2): m/z 390 [M+H]+@r.t. 3.73 min.
HRMS (ESI) calcd for C$_{19}$H$_{18}$ClFN$_3$OS [M+H]+ 390.0838 found 390.085.

According to the same methodology, but employing suitable starting material, the following compounds were prepared:

4-(2-aminoethyl)-7-(5-chloro-2-fluorophenyl)-8-(thiophen-3-yl)-3,4-dihydropyrrolo[1,2-a]pyrazin-1(2H)-one hydrochloride [(I), R2=5-chloro-2-fluorophenyl, R4=thiophen-3-yl, R3=H, A=—CH$_2$CH$_2$—NH$_2$](cpd 56) (5.4 mg 98% Y)

$^1$H NMR (600 MHz, DMSO-d6) δ 7.65-7.86 (m, 4H), 7.63 (d, J=1.83 Hz, 1H), 7.40 (s, 1H), 7.38 (dd, J=3.02, 4.85 Hz, 1H), 7.31 (td, J=3.50, 8.56 Hz, 1H), 7.17-7.25 (m, 3H), 7.00-7.06 (m, 1H), 6.94 (dd, J=1.10, 4.95 Hz, 1H), 4.49 (br. s., 1H), 3.74 (dd, J=3.94, 12.91 Hz, 1H), 3.47 (m, 1H), 1.95-2.16 (m, 2H).

LCMS (HPLC Method 2): m/z 390 [M+H]+@r.t. 3.85 min.
HRMS (ESI) calcd for C$_{19}$H$_{18}$ClFN$_3$OS [M+H]+ 390.0838 found 390.084.

According to the same methodology, but employing suitable starting material, the following compounds were prepared:

4-(2-aminoethyl)-7-(5-chloro-2-fluorophenyl)-6-phenyl-3,4-dihydropyrrolo[1,2-a]pyrazin-1(2H)-one hydrochloride [(I), R2=5-chloro-2-fluorophenyl, R3=phenyl, R4=H, A=—CH$_2$CH$_2$—NH$_2$](cpd 57)

$^1$H NMR (600 MHz, DMSO-d6) δ 7.83 (d, J=4.95 Hz, 1H), 7.57 (br. s., 3H), 7.41-7.50 (m, 3H), 7.31-7.35 (m, 2H), 7.25-7.29 (m, 1H), 7.15-7.19 (m, 1H), 7.01 (dd, J=2.66, 6.50 Hz, 1H), 6.97 (d, J=1.47 Hz, 1H), 4.45 (d, J=3.85 Hz, 1H), 3.90 (dd, J=3.75, 13.28 Hz, 1H), 2.28-2.41 (m, 2H), 1.70-1.91 (m, 2H).

LCMS (HPLC Method 2): m/z 384 [M+H]+@r.t. 3.78 min.
HRMS (ESI) calcd for C$_{21}$H$_{20}$ClFN$_3$O [M+H]+ 384.1274 found 384.1271.

4-(2-aminoethyl)-7-(5-chloro-2-fluorophenyl)-8-phenyl-3,4-dihydropyrrolo[1,2-a]pyrazin-1(2H)-one hydrochloride [(I), R2=5-chloro-2-fluorophenyl, R4=phenyl, R3=H, A=—CH$_2$CH$_2$—NH$_2$](cpd 58)

$^1$H NMR (600 MHz, DMSO-d6) δ 7.77 (br. s., 3H), 7.66 (d, J=4.03 Hz, 1H), 7.40 (s, 1H), 7.24 (dt, J=8.75, 3.41 Hz, 1H), 7.17-7.22 (m, 4H), 7.11-7.15 (m, 3H), 6.92 (dd, J=6.32, 2.66 Hz, 1H), 4.48 (br. s., 1H), 3.74 (dd, J=12.82, 3.66 Hz, 1H), 2.69-2.99 (m, 2H), 1.98-2.16 (m, 2H).

LCMS (HPLC Method 2): m/z 384 [M+H]+@r.t. 3.84 min.
HRMS (ESI) calcd for C$_{21}$H$_{20}$ClFN$_3$O [M+H]+ 384.1274 found 384.1279.

4-(2-aminoethyl)-7-(5-chloro-2-fluorophenyl)-6-(3-methylphenyl)-3,4-dihydropyrrolo[1,2-a]pyrazin-1(2H)-one hydrochloride [(I), R2=5-chloro-2-fluorophenyl, R3=3-methylphenyl, R4=H, A=—CH$_2$CH$_2$—NH$_2$](cpd 59)

$^1$H NMR (600 MHz, DMSO-d6) δ 7.83 (d, J=4.94 Hz, 1H), 7.56 (br. s., 3H), 7.32-7.35 (m, 1H), 7.23-7.29 (m, 2H), 7.15-7.20 (m, 2H), 7.07 (d, J=7.33 Hz, 1H), 7.02 (dd, J=2.56, 6.41 Hz, 1H), 6.96 (s, 1H), 4.46 (d, J=3.30 Hz, 1H), 3.90 (dd, J=3.66, 13.37 Hz, 1H), 3.69 (dd, J=5.86, 19.78 Hz, 1H), 2.33-2.44 (m, 2H), 2.32 (s, 3H), 1.70-1.92 (m, 2H).

LCMS (HPLC Method 2): m/z 398 [M+H]+@r.t. 4.1 min.
HRMS (ESI) calcd for C$_{22}$H$_{22}$ClFN$_3$O [M+H]+ 398.143 found 398.1434.

4-(2-aminoethyl)-7-(5-chloro-2-fluorophenyl)-8-(3-methylphenyl)-3,4-dihydropyrrolo[1,2-a]pyrazin-1(2H)-one hydrochloride [(I), R2=5-chloro-2-fluorophenyl, R4=3-methylphenyl, R3=H, A=—CH$_2$CH$_2$—NH$_2$](cpd 60)

$^1$H NMR (600 MHz, DMSO-d6) δ 7.80 (br. s., 3H), 7.64-7.7 (m, 1H), 7.41 (s, 1H), 7.27 (d, J=8.61 Hz, 1H), 7.17 (t, J=9.25 Hz, 1H), 7.07-7.12 (m, 1H), 6.98-7.04 (m, 2H), 6.95 (d, J=4.03 Hz, 1H), 6.90 (d, J=7.51 Hz, 1H), 4.50 (br. s., 1H), 3.71-3.78 (m, 1H), 3.40-3.49 (m, 1H), 2.96 (d, J=11.36 Hz,

1H), 2.71-2.82 (m, 1H), 2.19-2.23 (m, 3H), 2.00-2.16 (m, 2H).

LCMS (HPLC Method 2): m/z 398 [M+H]+@r.t. 4.17 min.
HRMS (ESI) calcd for $C_{22}H_{22}ClFN_3O$ [M+H]+ 398.143 found 398.1445.

Example 20

4-(2-aminoethyl)-6-ethynyl-7-[3-(trifluoromethoxy) phenyl]-3,4-dihydropyrrolo[1,2-a]pyrazin-1(2H)-one [(I), R2=3-(trifluoromethoxy)phenyl, R3=ethynyl, R4=H, A=—CH$_2$CH$_2$—NH$_2$](cpd 61)

Conv. h

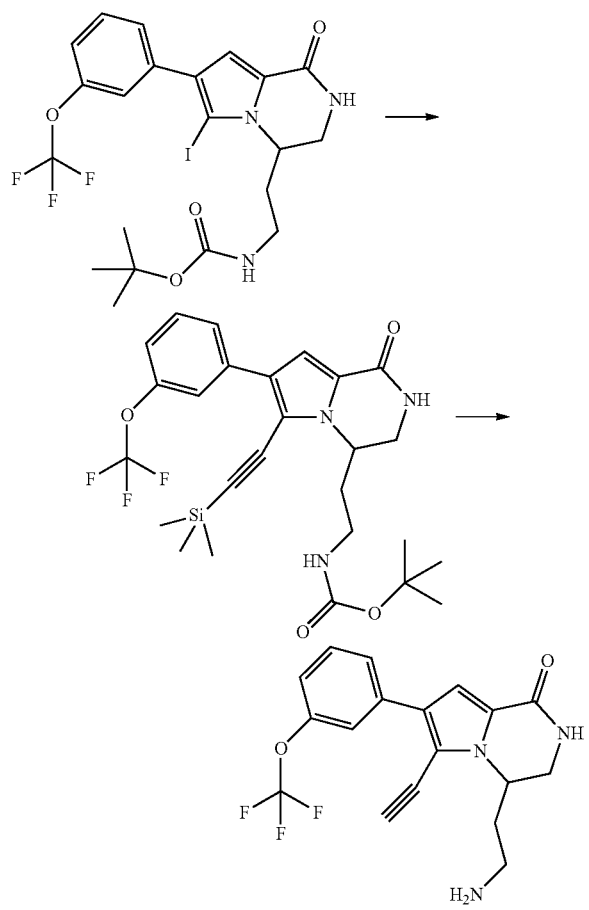

A mixture of tert-butyl(2-{6-iodo-1-oxo-7-[3-(trifluoromethoxy)phenyl]-1,2,3,4-tetrahydropyrrolo[1,2-a]pyrazin-4-yl}ethyl)carbamate (100 mg, 0.177 mmol), bis(triphenylphosphine)palladium(II) dichloride (24.8 mg, 0.035 mmol), copper(I) iodide (33.7 mg, 0.177 mmol), 1-chloro-4-ethynylbenzene (0.29 g, 2.15 mmol) and triethylamine (0.204 mL, 1.415 mmol) in dry 1,4 dioxane (4 mL) was degassed and stirred at 70° C. for 24 hours, under an argon atmosphere. The solvent was evaporated under vacuum and the residue purified by flash chromatography (DCM/EtOAc/EtOH 7/3/0.4), to obtain compound tert-butyl(2-{1-oxo-7-[3-(trifluoromethoxy)phenyl]-6-[(trimethylsilyl)ethynyl]-1,2,3,4-tetrahydropyrrolo[1,2-a]pyrazin-4-yl}ethyl)carbamate (37 mg g, 40% yield).

The product was dissolved in DCM (2 ml) and 4M HCl in 1,4-dioxane (1 ml) was added. The reaction was stirred at room temperature for 1 hour, after that the solvent was evaporated to dryness. The solid was dissolved with MeOH and treated with $K_2CO_3$ (30 mg 0.21 mmol), and mixture stirred at room temperature for 1 hour. The volatiles were removed under vacuum and the residue purified by flash chromatography (DCM/MeOH/NH$_4$OH 8/2/0.5), to give the title compound as a green solid 7 mg (28%).

$^1$H NMR (400 MHz, DMSO-d6) δ 7.90 (d, J=5.00 Hz, 1H), 7.76-7.84 (m, 2H), 7.54 (t, J=8.06 Hz, 1H), 7.27 (d, J=7.93 Hz, 1H), 7.12 (s, 1H), 4.53-4.66 (m, 1H), 3.77 (dd, J=4.21, 13.49 Hz, 1H), 3.42 (dd, J=5.31, 13.00 Hz, 2H), 2.61-2.86 (m, 2H), 1.80-2.05 (m, 2H).

LCMS (HPLC Method 2): m/z 364 [M+H]+@r.t. 4.75 min.
HRMS (ESI) calcd for $C_{18}H_{16}F_3N_3O$ [M+H]+ 364.1267 found 364.1273.

Example 21

4-(2-chloroethyl)-7-[3-(trifluoromethoxy)phenyl]-3, 4-dihydropyrrolo[1,2-a]pyrazin-1(2H)-one [(I), R2=3-(trifluoromethoxy)phenyl, R3=R4=H, A=—CH$_2$CH$_2$—Cl](cpd 62)

Conv. c

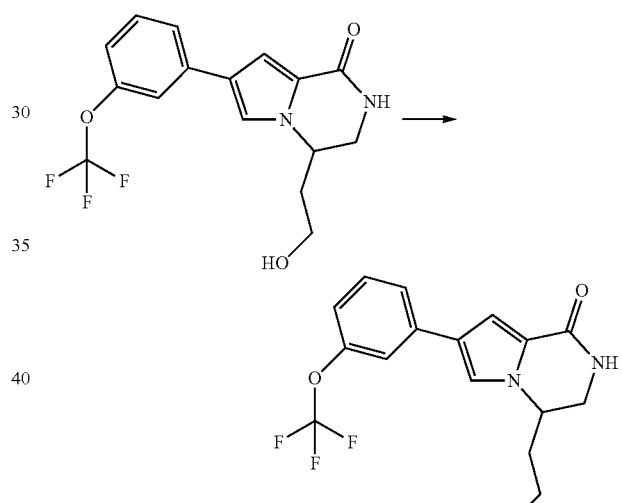

To a solution of 4-(2-hydroxyethyl)-7-[3-(trifluoromethoxy)phenyl]-3,4-dihydropyrrolo[1,2-a]pyrazin-1(2H)-one (723 mg, 1.929 mmol) in DCM (10 ml), mesyl chloride (300 ul, 3.859 mmol) and TEA (600 ul, 8.17 mmol), were added. The resulting solution was stirred at room temperature for 48 h. The reaction mixture was washed twice with sodium bicarbonate aqueous solution, and the organic phase was dried over anhydrous Na$_2$SO$_4$ and concentrated in vacuo. The crude was purified by flash chromatography (DCM/EtOAc/EtOH 6:4:0.5) to give the title compound as a solid 260 mg (37%).

$^1$H NMR (600 MHz, DMSO-d6) δ 7.73 (d, J=2.93 Hz, 1H), 7.67 (d, J=1.65 Hz, 1H), 7.65 (d, J=8.24 Hz, 1H), 7.57-7.60 (m, 1H), 7.45 (t, J=7.97 Hz, 1H), 7.06-7.17 (m, 2H), 4.40-4.48 (m, 1H), 3.68-3.77 (m, 2H), 3.65 (td, J=6.87, 11.17 Hz, 1H), 3.40 (td, J=4.03, 13.00 Hz, 1H), 2.31 (qd, J=6.90, 14.10 Hz, 1H), 2.19 (qd, J=6.96, 14.10 Hz, 1H).

LCMS (HPLC Method 2): m/z 359 [M+H]+@r.t. 5.65 min.
HRMS (ESI) calcd for $C_{16}H_{15}ClF_3N_2O_2$ [M+H]+ 359.0769 found 359.0765.

Example 22

4-(2-chloroethyl)-6-iodo-7-[3-(trifluoromethoxy)phenyl]-3,4-dihydropyrrolo[1,2-a]pyrazin-1(2H)-one [(I), R2=3-(trifluoromethoxy)phenyl, R3=iodo, R4=H, A=—CH₂CH₂—Cl]

Conv. e

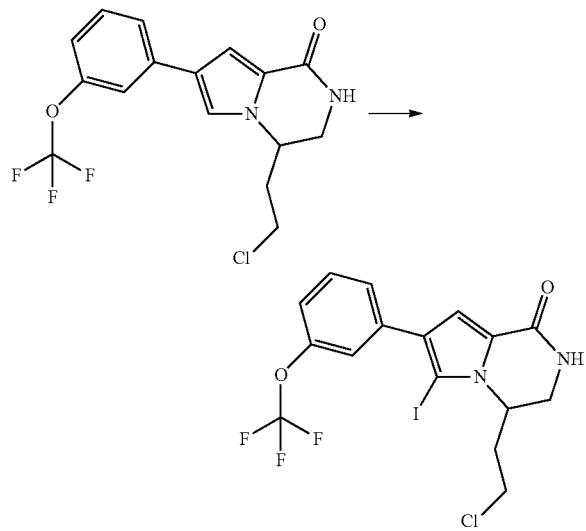

Iodine (183.94 mg, 0.725 mmol) was added portion wise to a solution of 4-(2-chloroethyl)-7-[3-(trifluoromethoxy)phenyl]-3,4-dihydropyrrolo[1,2-a]pyrazin-1(2H)-one (260 mg, 0.0.725 mmol) and silver trifluoroacetate (160 mg, 0.725 mmol) in dry dichloromethane (10 mL), at 5° C. The reaction mixture was stirred at the same temperature for 1 h, then the ice bath removed and left to warm to rt and left under stirring until HPLC analysis revealed the desappearence of the starting material (1 h). The solid was filtered, the organic phase washed with Na₂S₂O₅ (5% aq. solution) until decolouration occurred and finally washed with H₂O (1×20 mL). The organic phase was dried over Na₂SO₄ and purified by flash chromatography using DCM/EtOAc/EtOH 7/3/0.2 as eluent to give the title compound (300 mg, 73% yield) as a brown solid.

LCMS (HPLC Method 3): m/z 485 [M+H]⁺@r.t. 4.65 min.

Example 23

4-(2-chloroethyl)-6-(3-methylphenyl)-7-[3-(trifluoromethoxy)phenyl]-3,4-dihydropyrrolo[1,2-a]pyrazin-1(2H)-one [(I), R2=3-(trifluoromethoxy)phenyl, R3=3-methylphenyl, R4=H, A=—CH₂CH₂—Cl](cpd 63)

Conv. g

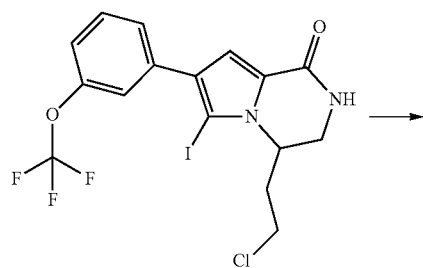

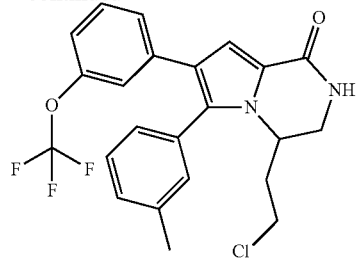

To a solution of 4-(2-chloroethyl)-6-iodo-7-[3-(trifluoromethoxy)phenyl]-3,4-dihydropyrrolo[1,2-a]pyrazin-1(2H)-one (50 mg, 0.103 mmol) in 3 ml of 1,4-dioxane and 1 ml of water, under argon atmosphere, 18.2 mg (0.134 mmol) of (3-methylphenyl)boronic acid, 8.4 mg (0.010 mmol) of 1,1'-bis(diphenylphosphino)ferrocenepaladium, complex with dichloromethane and 100 mg (0.310 mmol) of cesium carbonate, were subsequently added. The mixture was heated at 80° for 6 hour in a sealed vial. The reaction was filtered through a celite pad and the solvent evaporated to dryness. The crude was then portioned between ethyl acetate and water, the organic layer dried over sodium sulphate and the solvent removed in vacuo. After purification by flash chromatography on silica gel column (DCM/EtOAc/EtOH 6/4/0.5), and further purification by HPLC/MS preparative method 1, 15 mg (32%) of title compound were obtained.

¹H NMR (600 MHz, DMSO-d6) δ 7.72 (d, J=4.95 Hz, 1H), 7.32-7.38 (m, 2H), 7.26-7.31 (m, 2H), 7.24 (s, 1H), 7.16 (d, J=7.33 Hz, 1H), 7.03-7.11 (m, 2H), 6.92 (s, 1H), 4.20-4.42 (m, J=4.03 Hz, 1H), 3.85 (dd, J=3.66, 13.37 Hz, 1H), 3.40-3.46 (m, 2H), 3.35-3.39 (m, 1H), 2.31 (s, 3H), 2.04-2.18 (m, 1H), 1.59-1.80 (m, 1H).

LCMS (HPLC Method 2): m/z 449 [M+H]⁺@r.t. 7.43 min.

HRMS (ESI) calcd for C₂₃H₂₁ClF₃N₂O₂ [M+H]⁺ 449.1238 found 449.124.

Working according to the same method, and using the appropriate boronic acid, the following compound were prepared:

methyl 4-{4-(2-chloroethyl)-1-oxo-7-[3-(trifluoromethoxy)phenyl]-1,2,3,4-tetrahydropyrrolo[1,2-a]pyrazin-6-yl}benzoate [(I), R2=3-(trifluoromethoxy)phenyl, R3=methyl 4-benzoate, R4=H, A=—CH₂CH₂—Cl) (cpd 64)

The title compound was isolated as a yellow solid (0.132 g, 0.268 mmol, 87%).

¹H NMR (600 MHz, DMSO-d6) δ 8.27 (s, 1H), 8.03 (d, J=7.88 Hz, 2H), 7.80 (d, J=2.75 Hz, 1H), 7.57 (d, J=7.88 Hz, 2H), 7.33-7.38 (m, 1H), 7.22 (d, J=7.69 Hz, 1H), 7.04-7.13 (m, 2H), 6.92 (s, 1H), 4.45 (dt, J=7.97, 3.89 Hz, 1H), 3.87-3.94 (m, 4H), 3.42-3.48 (m, 2H), 1.99-2.16 (m, 1H), 1.59-1.78 (m, 1H).

LCMS (HPLC Method 2): m/z 493 [M+H]⁺@r.t. 6.77 min.

4-{4-(2-chloroethyl)-1-oxo-7-[3-(trifluoromethoxy)phenyl]-1,2,3,4-tetrahydropyrrolo[1,2-a]pyrazin-6-yl}benzaldehyde [(I), R2=3-(trifluoromethoxy)phenyl, R3=4-benzaldehyde, R4=H, A=—CH₂CH₂—Cl) (cpd 65)

The title compound was isolated as an orange solid (75%).

¹H NMR (600 MHz, DMSO-d6) δ 10.08 (s, 1H), 7.99 (d, J=8.24 Hz, 2H), 7.82 (d, J=4.94 Hz, 1H), 7.65 (d, J=7.88 Hz, 2H), 7.35-7.38 (m, 1H), 7.24 (d, J=7.88 Hz, 1H), 7.07-7.13 (m, 3H), 6.92 (s, 1H), 4.45-4.51 (m, 1H), 3.92 (dd, J=13.46, 3.75 Hz, 1H), 3.40-3.50 (m, 3H), 2.11 (d, J=5.68 Hz, 1H), 1.71 (d, J=5.31 Hz, 1H).

LCMS (HPLC Method 2): m/z 463 [M+H]⁺@r.t. 6.48 min.
HRMS (ESI) calcd for $C_{23}H_{19}ClF_3N_2O_3$ [M+H]⁺ 463.1031 found 463.1022.

4-{4-(2-chloroethyl)-1-oxo-7-[3-(trifluoromethoxy)phenyl]-1,2,3,4-tetrahydropyrrolo[1,2-a]pyrazin-8-yl}benzaldehyde [(I), R2=3-(trifluoromethoxy)phenyl, R3=H, R4=4-benzaldehyde, A=—CH₂CH₂—Cl) (cpd 66)
LCMS (HPLC Method 2): m/z 463 [M+H]⁺@r.t. 6.78 min.

Example 24

4-{4-(2-chloroethyl)-1-oxo-7-[3-(trifluoromethoxy)phenyl]-1,2,3,4-tetrahydropyrrolo[1,2-a]pyrazin-6-yl}benzoic acid [(I), R2=3-(trifluoromethoxy)phenyl, R3=4-benzoic acid, R4=H, A=—CH₂CH₂—Cl) (cpd 67)

Conv. l

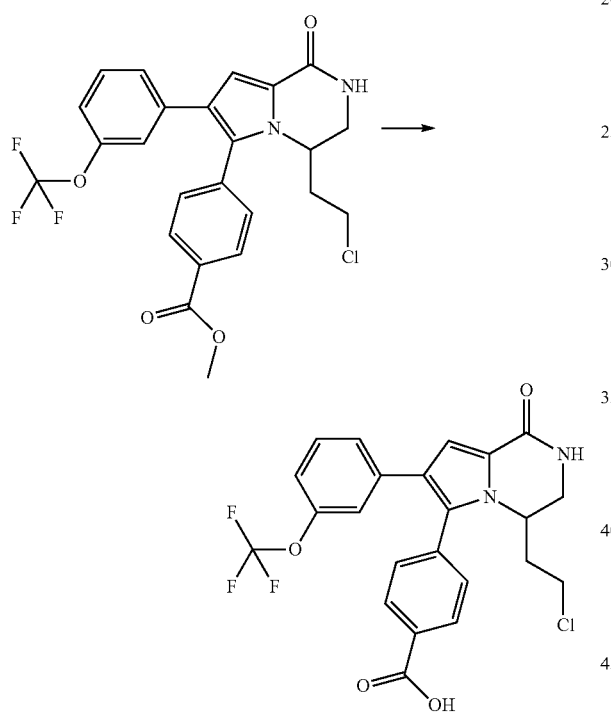

Lithium hydroxyde (0.022 g, 0.52 mmol) was added to a a solution of methyl 4-{4-(2-chloroethyl)-1-oxo-7-[3-(trifluoromethoxy)phenyl]-1,2,3,4-tetrahydropyrrolo[1,2-a]pyrazin-6-yl}benzoate (0.130 g, 0.26 mmol) in THF-water (1:1, 4 ml) and the reaction mixture was stirred at room temperature for 12 h. The solvent (THF) was removed under reduced pressure and the aqueous residue was diluted with water. The aqueous phase was acidified with hydrochloric acid (1M) until a precipitation occurred, the solid was filtered, washed with water and dried under vacuum, to give the title compound as a white solid (0.080 g, 63%).

¹H NMR (600 MHz, DMSO-d6) δ 8.01 (d, J=8.43 Hz, 2H), 7.76-7.81 (m, 1H), 7.53 (d, J=7.88 Hz, 2H), 7.33-7.39 (m, 1H), 7.24 (d, J=8.24 Hz, 1H), 7.05-7.12 (m, 2H), 6.91 (s, 1H), 4.38-4.49 (m, 1H), 3.90 (dd, J=13.37, 3.66 Hz, 1H), 3.40-3.48 (m, 3H), 2.03-2.16 (m, 1H), 1.64-1.74 (m, 1H).
LCMS (HPLC Method 2): m/z 479 [M+H]⁺@r.t. 5.14 min.
HRMS (ESI) calcd for $C_{23}H_{19}ClF_3N_2O_4$ [M+H]⁺ 479.0980 found 479.0992.

Example 25

4-{4-(2-chloroethyl)-1-oxo-7-[3-(trifluoromethoxy)phenyl]-1,2,3,4-tetrahydropyrrolo[1,2-a]pyrazin-6-yl}benzamide [(I), R2=3-(trifluoromethoxy)phenyl, R3=4-benzamide, R4=H, A=—CH₂CH₂—Cl) (cpd 68)

Conv. j

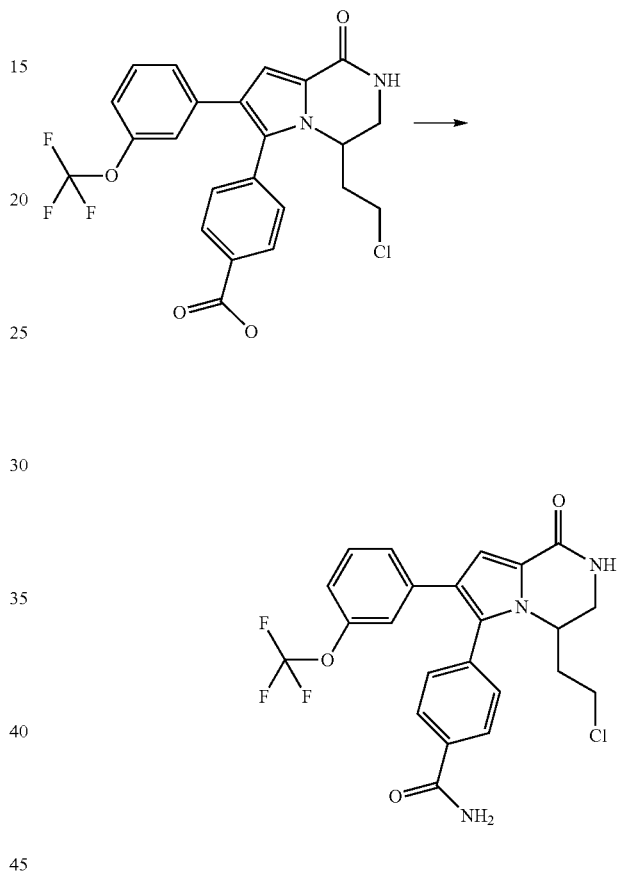

Ammonium chloride (0.025 g, 0.48 mmol) was added to a solution of 4-{4-(2-chloroethyl)-1-oxo-7-[3-(trifluoromethoxy)phenyl]-1,2,3,4-tetrahydropyrrolo[1,2-a]pyrazin-6-yl}benzoic acid (0.040 g, 0.080 mmol), DIPEA (0.062 g, 0.48 mmol) and TBTU (0.040 g, 0.125 mmol) in DMF (2 ml). The reaction mixture was stirred at room temperature for 12 hours, concentrated to dryness and the residue was dissolved with DCM and washed with water. The organic layer was dried (Na₂SO₄) and the crude was purified by HPLC preparative method 2, providing the title compound as a yellow solid (0.010 g, 25%).

¹H NMR (600 MHz, DMSO-d6) δ 8.06 (br. s., 1H), 7.97 (d, J=8.61 Hz, 2H), 7.77 (d, J=5.13 Hz, 1H), 7.45-7.52 (m, 2H), 7.44 (br. s., 1H), 7.30-7.37 (m, 1H), 7.22 (d, J=8.06 Hz, 1H), 7.10 (dd, J=8.61, 1.83 Hz, 1H), 7.08 (s, 1H), 6.93 (s, 1H), 4.44 (dt, J=8.24, 4.30 Hz, 1H), 3.89 (dd, J=13.46, 3.94 Hz, 1H), 3.38-3.49 (m, 3H), 2.04-2.16 (m, 1H), 1.63-1.77 (m, 1H).
LCMS (HPLC Method 2): m/z 478 [M+H]⁺@r.t. 5.44 min.
HRMS (ESI) calcd for $C_{23}H_{20}ClF_3N_3O_3$[M+H]⁺ 478.1140 found 478.1139.

Example 26

4-{4-(2-chloroethyl)-1-oxo-7-[3-(trifluoromethoxy)phenyl]-1,2,3,4-tetrahydropyrrolo[1,2-a]pyrazin-6-yl}-N-(1-methylpiperidin-4-yl)benzamide trifluoroacetate [(I), R2=3-(trifluoromethoxy)phenyl, R3=4-N-(1-methylpiperidin-4-yl)benzamide, R4=H, A=—CH$_2$CH$_2$—Cl) (cpd 69)

Conv. j

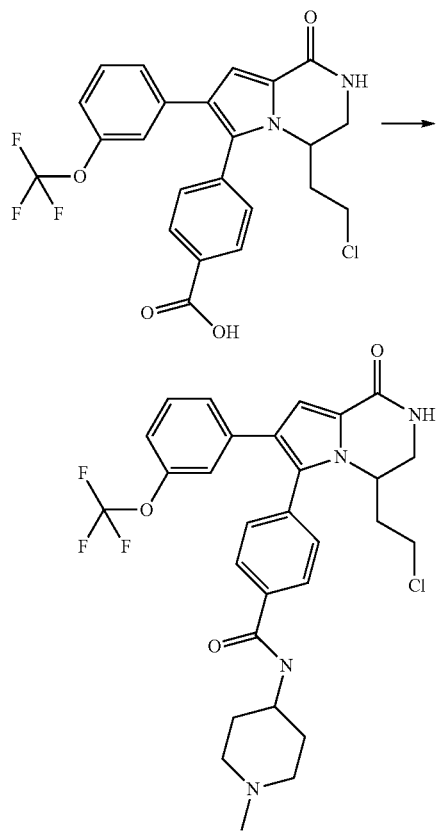

A solution of EDCl (0.024 g, 0.125 mmol) in DCM (1 ml) was added to a a solution of 4-{4-(2-chloroethyl)-1-oxo-7-[3-(trifluoromethoxy)phenyl]-1,2,3,4-tetrahydropyrrolo[1,2-a]pyrazin-6-yl}benzoic acid (0.040 g, 0.080 mmol), DIPEA (0.080 g, 0.625 mmol), HOBT (0.0168 g, 0.125 mmol) and 1-methylpiperidin-4-amine (0.029 g, 0.25 mmol) in DMF (1 ml). The reaction mixture was stirred at room temperature for 12 hours, the solvents were removed under vacuo, the residue was partitioned between DCM and water, the organic layer was dried and HPLC preparative method 2 purification of the crude provided the title compound (0.014 g, 29%).

$^1$H NMR (600 MHz, DMSO-d6) δ 9.15-9.41 (m, 1H), 8.29-8.62 (m, 1H), 7.89-8.03 (m, 2H), 7.79 (d, J=4.94 Hz, 1H), 7.45-7.58 (m, 2H), 7.28-7.38 (m, 1H), 7.15-7.22 (m, 1H), 7.03-7.13 (m, 2H), 6.81-7.01 (m, 1H), 4.43 (m, J=3.48 Hz, 1H), 3.98-4.21 (m, 1H), 3.86-3.93 (m, 1H), 3.43-3.52 (m, 5H), 3.04-3.15 (m, 2H), 2.74-2.84 (m, 3H), 2.11 (ddt, J=14.29, 8.65, 5.56, 5.56 Hz, 1H), 2.00-2.08 (m, 2H), 1.63-1.84 (m, 3H).

LCMS (HPLC Method 2): m/z 575 [M+H]$^+$@r.t. 4.99 min.
HRMS (ESI) calcd for C$_{29}$H$_{31}$ClF$_3$N$_4$O$_3$[M+H]$^+$ 575.2032 found 575.2036.

Example 27

4-(2-chloroethyl)-6-{4-[(dimethylamino)methyl]phenyl}-7-[3-(trifluoromethoxy)phenyl]-3,4-dihydropyrrolo[1,2-a]pyrazin-1(2H)-one trifluoroacetate [(I), R2=3-(trifluoromethoxy)phenyl, R3=4-[(dimethylamino)methyl]phenyl, R4=H, A=—CH$_2$CH$_2$—Cl) (cpd 70)

Conv. k

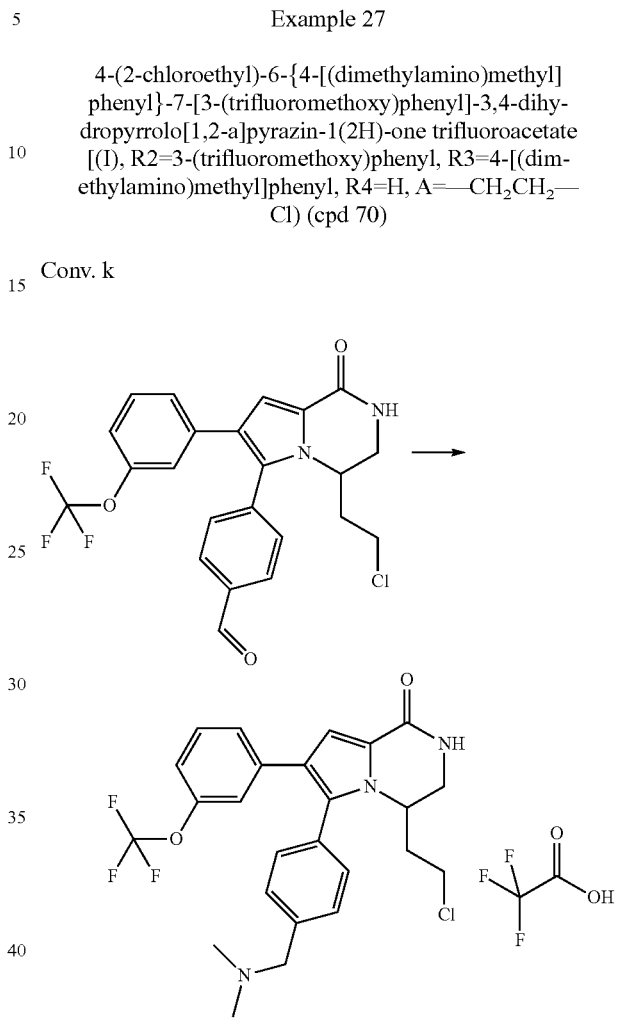

A solution of 4-{4-(2-chloroethyl)-1-oxo-7-[3-(trifluoromethoxy)phenyl]-1,2,3,4-tetrahydropyrrolo[1,2-a]pyrazin-6-yl}benzaldehyde (0.050 g, 0.108 mmol), dimethylamine (0.160 ml, 0.324 mmol) and acetic acid (6 µl, 0.108 mmol) in dry THF (1 ml) was stirred at room temperature for 11 h. Sodium cyanoborohydride (0.020 g, 0.324 mmol) was then added and the reaction mixture was stirred at room temperature for 12 hours. The solvent was evaporated, the residue was partioned between DCM and water, the organic layer was dried over Na$_2$SO$_4$, filtered and concentrated to dryness. Purification of the crude by HPLC preparative method 2 provided the title compound:
(0.039 g, 58%).

$^1$H NMR (600 MHz, DMSO-d6) δ 9.73 (br. s., 1H), 7.79 (d, J=4.94 Hz, 1H), 7.58-7.62 (m, 2H), 7.53-7.56 (m, 2H), 7.34-7.39 (m, 1H), 7.28 (d, J=8.24 Hz, 1H), 7.08-7.12 (m, 2H), 6.89 (s, 1H), 4.41-4.45 (m, 1H), 4.30-4.40 (m, 2H), 3.89 (dd, J=13.37, 3.85 Hz, 1H), 3.41-3.51 (m, 3H), 2.74 (dd, J=11.26, 4.49 Hz, 6H), 2.13 (ddt, J=13.99, 9.32, 4.83, 4.83 Hz, 1H), 1.70 (ddt, J=14.38, 9.57, 5.06, 5.06 Hz, 1H).

LCMS (HPLC Method 2): m/z 492 [M+H]$^+$@r.t. 5.21 min.
HRMS (ESI) calcd for C$_{25}$H$_{26}$ClF$_3$N$_3$O$_2$ [M+H]$^+$ 492.1660 found 492.1651.

Working according to the same method, and using the appropriate amine, the following compounds were prepared:

4-(2-chloroethyl)-6-{4-[(4-methylpiperazin-1-yl)methyl]phenyl}-7-[3-(trifluoromethoxy)phenyl]-3,4-dihydropyrrolo[1,2-a]pyrazin-1(2H)-one trifluoroacetate [(I), R2=3-(trifluoromethoxy)phenyl, R3=4-[(4-methylpiperazin-1-yl)methyl]phenyl, R4=H, A=—CH$_2$CH$_2$—Cl) (cpd 71)

(0.035 g, 59%).

$^1$H NMR (600 MHz, DMSO-d6) δ 8.98-9.83 (brs, 1H), 7.76 (d, J=4.76 Hz, 1H), 7.43-7.46 (m, 2H), 7.38-7.42 (m, 2H), 7.34-7.37 (m, 1H), 7.29-7.32 (m, 1H), 7.04-7.11 (m, 2H), 6.89 (s, 1H), 4.36-4.43 (m, 1H), 3.87 (dd, J=13.28, 3.94 Hz, 1H), 3.69 (m, 2H), 3.29-3.47 (m, 3H), 2.84-3.13 and (m, 4H), 2.79 (s, 3H), 2.35-2.47 (m, 4H), 2.12 (td, J=9.16, 4.95 Hz, 1H), 1.69 (td, J=9.57, 4.67 Hz, 1H).

LCMS (HPLC Method 2): m/z 547 [M+H]$^+$@r.t. 5.34 min.
HRMS (ESI) calcd for C$_{28}$H$_{31}$ClF$_3$N$_4$O$_2$ [M+H]$^+$ 547.2082 found 547.2073.

4-(2-chloroethyl)-8-{4-[(dimethylamino)methyl]phenyl}-7-[3-(trifluoromethoxy)phenyl]-3,4-dihydropyrrolo[1,2-a]pyrazin-1(2H)-one trifluoroacetate [(I), R2=3-(trifluoromethoxy)phenyl, R3=H, R4=4-[(dimethylamino)methyl]phenyl, A=—CH$_2$CH$_2$—Cl) (cpd 72)

(0.00195 g, 3.7%).

LCMS (HPLC Method 3): m/z 492 [M+H]$^+$@r.t. 5.0 min.
HRMS (ESI) calcd for C$_{25}$H$_{26}$ClF$_3$N$_3$O$_2$ [M+H]$^+$ 492.1660 found 492.1659.

4-(2-chloroethyl)-8-{4-[(4-methyl piperazin-1-yl)methyl]phenyl}-7-[3-(trifluoromethoxy)phenyl]-3,4-dihydropyrrolo[1,2-a]pyrazin-1(2H)-one trifluoroacetate [(I), R2=3-(trifluoromethoxy)phenyl, R3=H, R4=4-[(4-methylpiperazin-1-yl)methyl]phenyl, A=—CH$_2$CH$_2$—Cl) (cpd 73)

LCMS (HPLC Method 3): m/z 547 [M+H]$^+$@r.t. 5.1 min.
HRMS (ESI) calcd for C$_{28}$H$_{31}$ClF$_3$N$_4$O$_2$ [M+H]$^+$ 547.2082 found 547.2086.

Example 28

4-(2-hydroxyethyl)-6-iodo-7-[3-(trifluoromethoxy)phenyl]-3,4-dihydropyrrolo[1,2-a]pyrazin-1(2H)-one [(I), R2=3-(trifluoromethoxy)phenyl, R3=iodo, R4=H, A=—CH$_2$CH$_2$—OH]

Conv. e

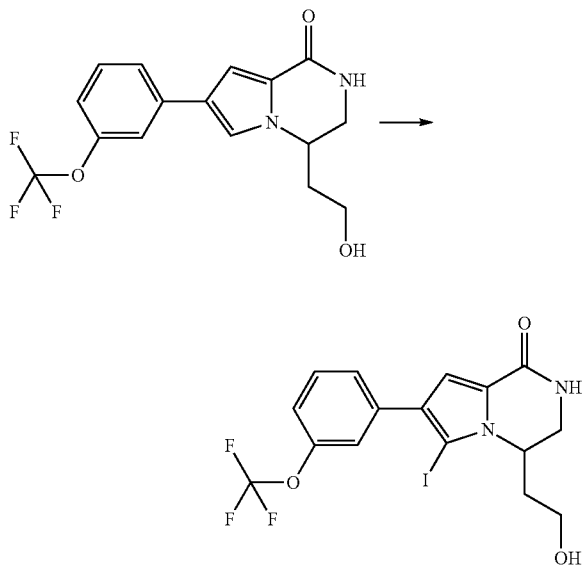

Iodine (0.298 g, 1.17 mmol) was added portion wise to a solution of 4-(2-hydroxyethyl)-7-[3-(trifluoromethoxy)phenyl]-3,4-dihydropyrrolo[1,2-a]pyrazin-1(2H)-one (0.400 g, 1.176 mmol) and silver trifluoroacetate in dry DCM (15 ml) at 5° C. The reaction mixture was stirred at the same temperature for 1 hour, then the ice bath was removed and left to warm to room temperature (1 h). The solid was filtered, the organic phase washed with Na$_2$S$_2$O$_5$ (5% aq. solution) until decolouration occurred and finally washed with water. The organic layer was dried over Na$_2$SO$_4$ to obtain the title compound (0.427 g, 78%) as a white solid.

$^1$H NMR (600 MHz, DMSO-d6) δ 7.77 (d, J=4.95 Hz, 1H), 7.56-7.60 (m, 1H), 7.52-7.56 (m, 1H), 7.53 (d, J=2.20 Hz, 1H), 7.29 (d, J=8.06 Hz, 1H), 6.99 (s, 1H), 4.76 (t, J=5.13 Hz, 1H), 4.41-4.50 (m, 1H), 3.72 (dd, J=3.85, 13.37 Hz, 1H), 3.50-3.60 (m, 3H), 1.82-1.90 (m, 1H), 1.72 (qd, J=6.89, 10.83 Hz, 1H).

LCMS (HPLC Method 2): m/z 467 [M+H]$^+$@r.t. 4.67 min.
HRMS (ESI) calcd for C$_{16}$H$_{15}$F$_3$IN$_2$O$_3$[M+H]$^+$ 467.0074 found 467.0085.

Example 29

Methyl 4-{4-(2-hydroxyethyl)-1-oxo-7-[3-(trifluoromethoxy)phenyl]-1,2,3,4-tetrahydropyrrolo[1,2-a]pyrazin-6-yl}benzoate [(I), R2=3-(trifluoromethoxy)phenyl, R3=4-methylcarboxyphenyl, R4=H, A=—CH$_2$CH$_2$—OH](cpd 74)

Conv. g

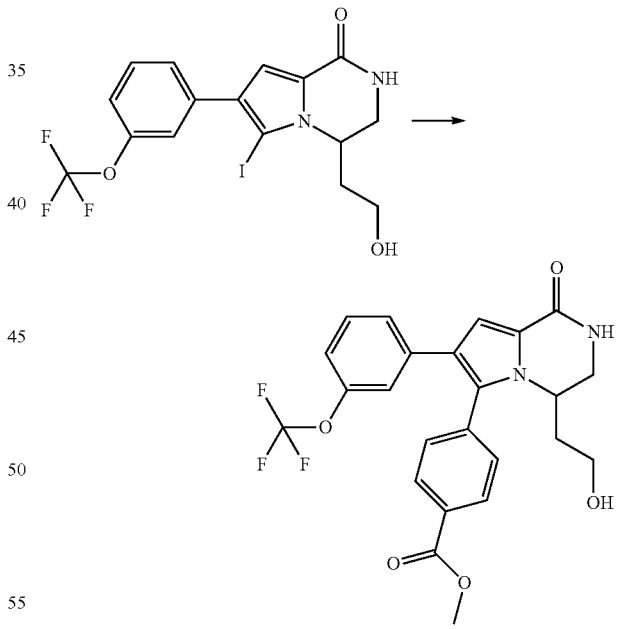

Cesium carbonate (0.567 g, 1.73 mmol), [4-(methoxycarbonyl)phenyl]boronic acid (0.135 g, 0.75 mmol), and 1,1'-bis(diphenylphosphino)ferrocenepaladium (0.023 g, 0.029 mmol) complex with dichloromethane, were subsequently added to a solution of 4-(2-hydroxyethyl)-6-iodo-7-[3-(trifluoromethoxy)phenyl]-3,4-dihydropyrrolo[1,2-a]pyrazin-1(2H)-one (0.270 g, 0.579 mmol) in 1.5 ml of 1,4-dioxane and 0.5 ml of water, under argon atmosphere. The mixture was heated at 80° for 2 hours in a sealed vial. The reaction was filtered through a celite pad and the solvent evaporated to dryness. The crude was portioned between ethyl acetate and water, the organic layer dried over sodium sulphate and the solvent removed in vacuo. Purification by flash chromatography on silica gel column (DCM/MeOH, 9/0.4) afforded the title compound as a yellow solid (0.211 g, 77%).

$^1$H NMR (600 MHz, DMSO-d6) δ 8.03 (d, J=8.24 Hz, 2H), 7.77 (d, J=4.76 Hz, 1H), 7.53 (d, J=8.24 Hz, 2H), 7.33-7.37 (m, 1H), 7.22 (d, J=7.69 Hz, 1H), 7.11 (s, 1H), 7.06 (s, 1H), 6.90 (s, 1H), 4.31-4.40 (m, 2H), 3.89 (s, 3H), 3.81-3.86 (m, 1H), 3.42 (dd, J=5.13, 13.19 Hz, 1H), 3.07-3.22 (m, 2H), 1.72-1.83 (m, 1H), 1.37-1.49 (m, 1H).

LCMS (HPLC Method 2): m/z 475 [M+H]$^+$@r.t. 6.15 min.

HRMS (ESI) calcd for $C_{24}H_{22}F_3N_2O_5$[M+H]$^+$ 475.1476 found 475.1470.

Working according to the same method, and using the appropriate boronic acid, the following compound was prepared:

4-{4-(2-hydroxyethyl)-1-oxo-7-[3-(trifluoromethoxy)phenyl]-1,2,3,4-tetrahydropyrrolo[1,2-a]pyrazin-6-yl}benzaldehyde [(I), R2=3-(trifluoromethoxy)phenyl, R3=4-formylphenyl, R4=H, A=—CH$_2$CH$_2$—OH](cpd 75)

The title compound was obtained in a 59% yield.

$^1$H NMR (600 MHz, DMSO-d6) δ 10.08 (s, 1H), 7.99 (d, J=8.24 Hz, 2H), 7.78 (d, J=5.13 Hz, 1H), 7.56-7.68 (m, 2H), 7.31-7.43 (m, 1H), 7.23 (d, J=8.06 Hz, 1H), 7.11 (d, J=8.79 Hz, 1H), 7.06 (s, 1H), 6.90 (s, 1H), 4.17-4.46 (m, 2H), 3.85 (dd, J=3.85, 13.19 Hz, 1H), 3.38-3.49 (m, 1H), 3.15-3.23 (m, 1H), 3.11 (qd, J=5.64, 11.10 Hz, 1H), 1.65-1.86 (m, 1H), 1.27-1.56 (m, 1H).

LCMS (HPLC Method 2): m/z 445 [M+H]$^+$@r.t. 5.85 min.

HRMS (ESI) calcd for $C_{23}H_{20}F_3N_2O_4$[M+H]$^+$ 445.137 found 445.1358.

Example 30

4-{4-(2-hydroxyethyl)-1-oxo-7-[3-(trifluoromethoxy)phenyl]-1,2,3,4-tetrahydropyrrolo[1,2-a]pyrazin-6-yl}benzoic acid [(I), R2=3-(trifluoromethoxy)phenyl, R3=4-benzoic acid, R4=H, A=—CH$_2$CH$_2$—OH](cpd 76)

Conv. i

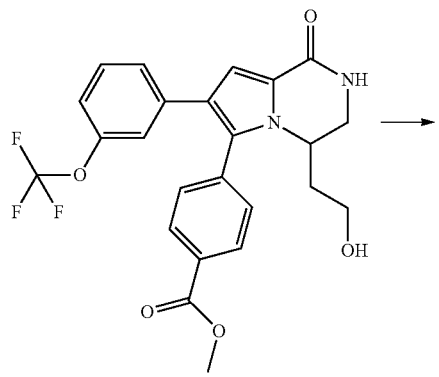

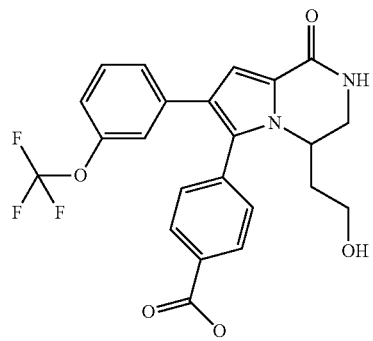

Lithium hydroxyde (0.053 g, 1.26 mmol) was added to a a solution of methyl 4-{4-(2-hydroxyethyl)-1-oxo-7-[3-(trifluoromethoxy)phenyl]-1,2,3,4-tetrahydropyrrolo[1,2-a]pyrazin-6-yl}benzoate (0.200 g, 0.42 mmol) in THF-water (1:1, 4 ml) and the reaction mixture was stirred at room temperature for 12 h. The THF was removed under reduced pressure and the aqueous residue was diluted with water. The aqueous phase was acidified with hydrochloric acid (1 M) until a precipitation occurred, the solid was filtered, washed with water and dried under vacuum, to give the title compound as a white brown solid (0.169 g, 87%).

$^1$H NMR (500 MHz, DMSO-d6) δ 13.17 (br. s., 1H), 8.00 (d, J=8.39 Hz, 2H), 7.77-7.82 (m, 1H), 7.47-7.52 (m, 2H), 7.33-7.38 (m, 1H), 7.23 (d, J=8.08 Hz, 1H), 7.10 (d, J=8.85 Hz, 1H), 7.06 (s, 1H), 6.89 (s, 1H), 4.40 (t, J=4.88 Hz, 1H), 4.29-4.38 (m, 1H), 3.83 (dd, J=13.04, 3.74 Hz, 1H), 3.39-3.46 (m, 1H), 3.06-3.24 (m, 2H), 1.72-1.84 (m, 1H), 1.36-1.49 (m, 1H).

LCMS (HPLC Method 2): m/z 461 [M+H]$^+$@r.t. 4.78 min.

HRMS (ESI) calcd for $C_{23}H_{20}F_3N_2O_5$ [M+H]$^+$ 461.1319 found 461.1327.

Example 31

4-{4-(2-hydroxyethyl)-1-oxo-7-[3-(trifluoromethoxy)phenyl]-1,2,3,4-tetrahydropyrrolo[1,2-a]pyrazin-6-yl}benzamide [(I), R2=3-(trifluoromethoxy)phenyl, R3=4-benzamide, R4=H, A=—CH$_2$CH$_2$—OH](cpd 77)

Conv. j

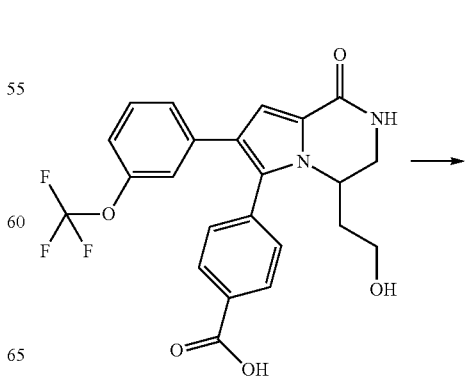

-continued

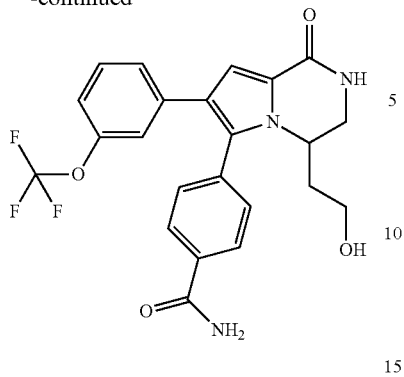

Ammonium chloride (0.027 g, 0.52 mmol) was added to a solution of 4-{4-(2-hydroxyethyl)-1-oxo-7-[3-(trifluoromethoxy)phenyl]-1,2,3,4-tetrahydropyrrolo[1,2-a]pyrazin-6-yl}benzoic acid (0.040 g, 0.087 mmol), DIPEA (0.067 g, 0.52 mmol) and TBTU (0.042 g, 0.13 mmol) in DMF (2 ml). The reaction mixture was stirred at room temperature for 12 hours, concentrated to dryness and the residue was taken into DCM and washed with water. The organic layer was dried (Na$_2$SO$_4$) and the crude was purified by HPLC preparative method 2, providing the title compound as a orange solid (0.030 g, 0.065 mmol, 75%).

$^1$H NMR (600 MHz, DMSO-d6) δ 8.06 (br. s., 1H), 7.96 (d, J=8.43 Hz, 2H), 7.74 (d, J=5.13 Hz, 1H), 7.45 (d, J=8.24 Hz, 3H), 7.32-7.37 (m, 1H), 7.21 (d, J=8.06 Hz, 1H), 7.09 (d, J=8.79 Hz, 1H), 7.05 (s, 1H), 6.91 (s, 1H), 4.21-4.43 (m, 2H), 3.82 (dd, J=3.85, 13.00 Hz, 1H), 3.42 (dd, J=5.68, 12.45 Hz, 1H), 3.16-3.24 (m, 1H), 3.07-3.15 (m, 1H), 1.71-1.82 (m, 1H), 1.38-1.51 (m, 1H).

LCMS (HPLC Method 2): m/z 460 [M+H]$^+$@r.t. 5.02 min.

HRMS (ESI) calcd for C$_{23}$H$_{21}$F$_3$N$_3$O$_4$[M+H]$^+$ 460.1479 found 460.1479.

Example 32

N-[2-(dimethylamino)ethyl]-4-{4-(2-hydroxyethyl)-1-oxo-7-[3-(trifluoromethoxy)phenyl]-1,2,3,4-tetrahydropyrrolo[1,2-a]pyrazin-6-yl}benzamide trifluoroacetate [(I), R2=3-(trifluoromethoxy)phenyl, R3=N-[2-(dimethylamino)ethyl]-4-benzamide, R4=H, A=—CH$_2$CH$_2$—OH](cpd 78)

Conv. j

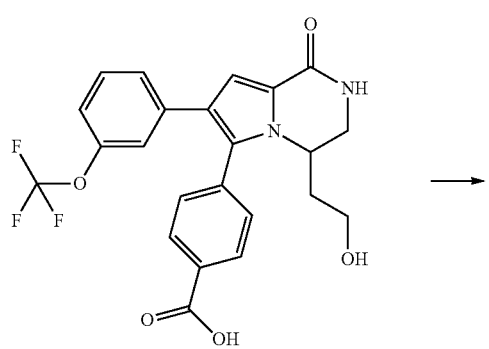

-continued

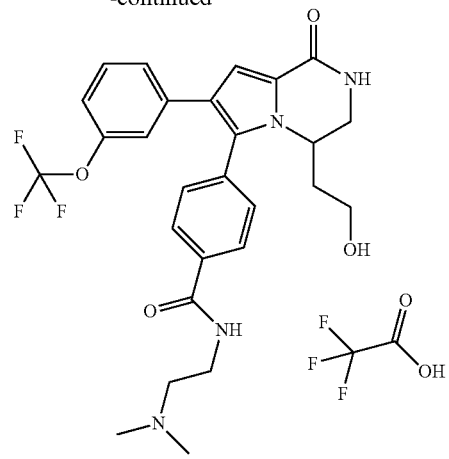

A solution of EDC HCl (0.025 g, 0.13 mmol) in DCM (1 ml) was added to a a solution of 4-{4-(2-hydroxyethyl)-1-oxo-7-[3-(trifluoromethoxy)phenyl]-1,2,3,4-tetrahydropyrrolo[1,2-a]pyrazin-6-yl}benzoic acid (0.040 g, 0.087 mmol), DIPEA (0.056 g, 0.435 mmol), HOBT (0.017 g, 0.13 mmol) and dimethylethylamine (0.023 g, 0.261 mmol) in DMF (2 ml). The reaction mixture was stirred at room temperature for 12 hours; the solvents were removed under vacuo, the residue was partitioned between DCM and water, the organic layer was dried and HPLC preparative method 2 purification of the crude provided the title compound (0.008 g, 0.014 mmol, 17%).

$^1$H NMR (600 MHz, DMSO-d6) δ 9.30 (br. s., 1H), 8.77 (t, J=5.49 Hz, 1H), 7.94 (d, J=8.24 Hz, 2H), 7.77 (d, J=5.13 Hz, 1H), 7.51 (d, J=8.24 Hz, 2H), 7.30-7.36 (m, 1H), 7.19 (d, J=8.06 Hz, 1H), 7.10 (d, J=9.71 Hz, 1H), 7.06 (s, 1H), 6.96 (s, 1H), 4.25-4.36 (m, 1H), 3.83 (dd, J=3.66, 13.19 Hz, 1H), 3.58-3.65 (m, 2H), 3.43 (dd, J=5.13, 13.00 Hz, 1H), 3.25-3.31 (m, 2H), 3.17-3.24 (m, 1H), 3.07-3.14 (m, 1H), 2.86 (d, J=4.58 Hz, 6H), 1.69-1.82 (m, 1H), 1.45 (dt, J=7.33, 12.73 Hz, 1H).

LCMS (HPLC Method 2): m/z 531 [M+H]$^+$@r.t. 4.51 min.

HRMS (ESI) calcd for C$_{27}$H$_{29}$F$_3$N$_4$O$_4$[M+H]$^+$ 460.2214 found 460.2291.

Working according to the same method, and using the appropriate amine, the following compounds were prepared:

4-{4-(2-hydroxyethyl)-1-oxo-7-[3-(trifluoromethoxy)phenyl]-1,2,3,4-tetrahydropyrrolo[1,2-a]pyrazin-6-yl}-N,N-dimethylbenzamide [(I), R2=3-(trifluoromethoxy)phenyl, R3=N,N-dimethylbenzamide, R4=H, A=—CH$_2$CH$_2$—OH] (cpd 79)

The title compound was obtained after HPLC preparative method 2 purification (40%).

$^1$H NMR (600 MHz, DMSO-d6) δ 7.73 (d, J=5.13 Hz, 1H), 7.46-7.50 (m, 2H), 7.41-7.44 (m, 2H), 7.34-7.39 (m, 1H), 7.30 (d, J=7.88 Hz, 1H), 7.09 (d, J=8.06 Hz, 1H), 7.06 (s, 1H), 6.88 (s, 1H), 4.32 (td, J=4.42, 8.93 Hz, 1H), 3.82 (dd, J=3.85, 13.00 Hz, 1H), 3.41 (dd, J=5.49, 13.00 Hz, 1H), 3.21 (ddd, J=6.14, 7.46, 10.94 Hz, 1H), 3.09-3.15 (m, 1H), 3.00 (br. s., 3H), 2.92 (s, 3H), 1.75-1.86 (m, 1H), 1.40-1.52 (m, 1H).

LCMS (HPLC Method 2): m/z 488 [M+H]$^+$@r.t. 5.5 min.

HRMS (ESI) calcd for C$_{25}$H$_{25}$F$_3$N$_3$O$_4$[M+H]$^+$ 488.1792 found 488.1793.

4-{4-(2-hydroxyethyl)-1-oxo-7-[3-(trifluoromethoxy)phenyl]-1,2,3,4-tetrahydropyrrolo[1,2-a]pyrazin-6-yl}-N-methylbenzamide

[(I), R2=3-(trifluoromethoxy)phenyl, R3=N-methylbenzamide, R4=H, A=—CH$_2$CH$_2$—OH](cpd 80)

The title compound was obtained after HPLC preparative method 2 purification (58%).

$^1$H NMR (600 MHz, DMSO-d6) δ 8.53 (q, J=4.33 Hz, 1H), 7.92 (d, J=8.43 Hz, 2H), 7.72-7.76 (m, 1H), 7.43-7.48 (m, 2H), 7.30-7.36 (m, 1H), 7.20 (d, J=8.24 Hz, 1H), 7.09 (d, J=6.41 Hz, 1H), 7.05 (s, 1H), 6.91-6.98 (m, 1H), 4.25-4.36 (m, 1H), 3.82 (dd, J=3.75, 13.10 Hz, 1H), 3.42 (dd, J=5.31, 13.00 Hz, 1H), 3.15-3.23 (m, 1H), 3.04-3.15 (m, 1H), 2.81 (d, J=4.58 Hz, 3H), 1.68-1.85 (m, 1H), 1.36-1.51 (m, 1H).).

LCMS (HPLC Method 2): m/z 474 [M+H]$^+$@r.t. 5.2 min.

HRMS (ESI) calcd for C$_{24}$H$_{23}$F$_3$N$_3$O$_4$[M+H]$^+$ 474.1635 found 474.1641.

4-{4-(2-hydroxyethyl)-1-oxo-7-[3-(trifluoromethoxy)phenyl]-1,2,3,4-tetrahydropyrrolo[1,2-a]pyrazin-6-yl}-N-(1-methylpiperidin-4-yl)benzamide trifluoroacetate [(I), R2=3-(trifluoromethoxy)phenyl, R3=N-(1-methylpiperidin-4-yl)benzamide, R4=H, A=—CH$_2$CH$_2$—OH](cpd 81)

The title compound was obtained after HPLC preparative method 2 purification (87%).

$^1$H NMR (600 MHz, DMSO-d6) δ 9.23 (br. s., 1H), 8.56 (d, J=7.51 Hz, 1H), 7.94 (d, J=8.24 Hz, 2H), 7.76 (d, J=4.76 Hz, 1H), 7.45-7.50 (m, 2H), 7.34 (quind, J=3.97, 7.93 Hz, 1H), 7.19 (d, J=7.69 Hz, 1H), 7.08-7.12 (m, 1H), 7.05 (s, 1H), 6.95 (s, 1H), 4.32 (td, J=4.42, 8.93 Hz, 1H), 4.12-4.20 (m, 1H), 3.99-4.09 (m, 1H), 3.82 (dd, J=3.94, 13.28 Hz, 1H), 3.06-3.55 (m, 8H), 2.78 (d, J=4.58 Hz, 3H), 1.98-2.10 (m, 2H), 1.68-1.86 (m, 2H).

LCMS (HPLC Method 2): m/z 557 [M+H]$^+$@r.t. 4.52 min.

HRMS (ESI) calcd for C$_{29}$H$_{32}$F$_3$N$_4$O$_4$[M+H]$^+$ 557.237 found 557.237.

Example 33

4-(2-hydroxyethyl)-6-{4-[(4-methyl piperazin-1-yl)methyl]phenyl}-7-[3-(trifluoromethoxy)phenyl]-3,4-dihydropyrrolo[1,2-a]pyrazin-1(2H)-one trifluoroacetate [(I), R2=3-(trifluoromethoxy)phenyl, R3=4-[(4-methylpiperazin-1-yl)methyl]phenyl, R4=H, A=—CH$_2$CH$_2$—OH](cpd 82)

Conv. k

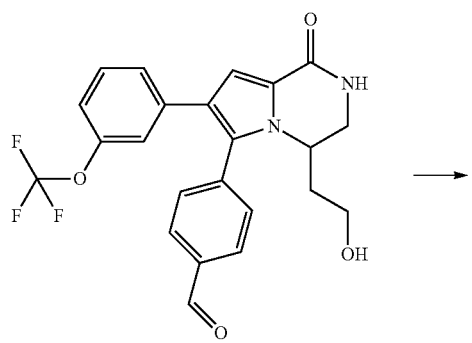

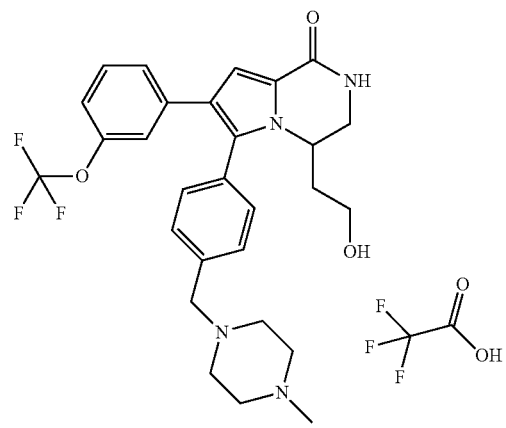

A solution of 4-{4-(2-hydroxyethyl)-1-oxo-7-[3-(trifluoromethoxy)phenyl]-1,2,3,4-tetrahydropyrrolo[1,2-a]pyrazin-6-yl}benzaldehyde (0.037 g, 0.083 mmol), 1-methylpiperazine (0.025 g, 0.249 mmol) and acetic acid (0.005 g, 0.083 mmol) in dry THF was stirred at room temperature for 1 h. Sodium cyanoborohydride (0.0157 g, 0.25 mmol) was then added and the reaction mixture was stirred at room temperature for 12 hours. The solvent was evaporated, the residue was partioned between DCM and water, the organic layer was dried over Na$_2$SO$_4$, filtered and concentrated to dryness. Purification of the crude by HPLC preparative method 2 provided the title compound (0.026 g, 0.049 mmol, 59%).

$^1$H NMR (600 MHz, DMSO-d6) δ 9.46 (br. s., 1H), 7.72 (d, J=4.94 Hz, 1H), 7.44 (d, J=7.69 Hz, 2H), 7.33-7.39 (m, 3H), 7.29-7.32 (m, 1H), 7.06-7.10 (m, 1H), 7.06 (s, 1H), 6.85 (s, 1H), 4.21-4.30 (m, 1H), 3.79 (dd, J=3.85, 13.19 Hz, 1H), 3.69 (br. s., 2H), 3.21 (ddd, J=6.04, 7.60, 10.90 Hz, 2H), 3.11 (td, J=5.91, 11.26 Hz, 2H), 2.90-3.07 (m, 4H), 2.79 (br. s., 3H), 2.27-2.47 (m, 2H), 1.71-1.82 (m, 1H), 1.40-1.51 (m, 1H).

LCMS (HPLC Method 2): m/z 529 [M+H]$^+$@r.t. 4.76 min.

HRMS (ESI) calcd for =C$_{28}$H$_{32}$F$_3$N$_4$O$_3$[M+H]$^+$ 529.2421 found 529.2413.

Working according to the same method, and using the appropriate amine, the following compound were prepared:

6-{4-[(dimethylamino)methyl]phenyl}-4-(2-hydroxyethyl)-7-[3-(trifluoromethoxy)phenyl]-3,4-dihydropyrrolo[1,2-a]pyrazin-1(2H)-one trifluoroacetate [(I), R2=3-(trifluoromethoxy)phenyl, R3=4-[(dimethylamino)methyl]phenyl, R4=H, A=—CH$_2$CH$_2$—OH](cpd 83)

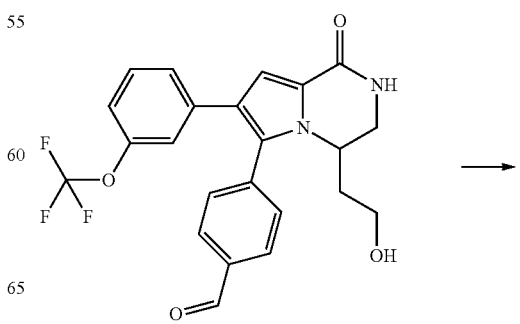

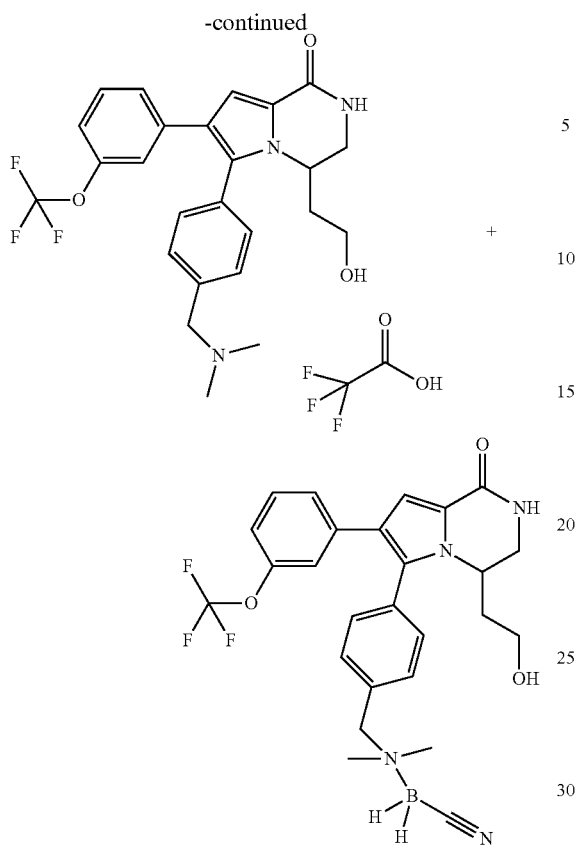

6-{4-[(dimethylamino)methyl]phenyl}-4-(2-hydroxyethyl)-7-[3-(trifluoromethoxy)phenyl]-3,4-dihydropyrrolo[1,2-a]pyrazin-1(2H)-one trifluoroacetate was obtained after purification by HPLC preparative method 2 (17%).

$^1$H NMR (500 MHz, DMSO-d6) δ 9.70 (br. s., 1H), 7.78 (d, J=4.88 Hz, 1H), 7.59 (d, J=8.24 Hz, 2H), 7.47-7.53 (m, 2H), 7.34-7.38 (m, 1H), 7.27-7.31 (m, 1H), 7.09 (d, J=7.93 Hz, 1H), 7.07 (s, 1H), 6.87 (s, 1H), 4.24-4.48 (m, 4H), 3.82 (dd, J=3.74, 13.19 Hz, 1H), 3.04-3.23 (m, 2H), 2.74 (dd, J=4.58, 13.57 Hz, 6H), 1.70-1.86 (m, 1H), 1.34-1.51 (m, 1H).

LCMS (HPLC Method 2): m/z 474[M+H]$^+$@r.t. 4.64 min.
HRMS (ESI) calcd for $C_{25}H_{27}F_3N_3O_3$[M+H]$^+$ 474.1999 found 474.1998.

(cyano)[6-{4-[(dimethylamino)methyl]phenyl}-4-(2-hydroxyethyl)-7-[3-(trifluoromethoxy)phenyl]-3,4-dihydropyrrolo[1,2-a]pyrazin-1(2H)-one]dihydridoboron was obtained after purification by HPLC preparative method 2 (9%).

$^1$H NMR (600 MHz, DMSO-d6) δ 7.73 (d, J=5.13 Hz, 1H), 7.61 (d, J=8.06 Hz, 2H), 7.42-7.47 (m, 2H), 7.33-7.37 (m, 1H), 7.29 (d, J=7.88 Hz, 1H), 7.01-7.11 (m, 2H), 6.88 (s, 1H), 4.33 (t, J=4.95 Hz, 1H), 4.25-4.32 (m, 1H), 4.09 (s, 2H), 3.81 (dd, J=3.94, 13.10 Hz, 1H), 3.40 (dd, J=5.22, 12.73 Hz, 1H), 3.16-3.24 (m, 1H), 3.10 (qd, J=5.73, 11.01 Hz, 1H), 2.54 (d, J=4.03 Hz, 6H), 1.56-1.96 (m, 3H), 1.44 (qd, J=6.44, 12.36 Hz, 1H).

LCMS (HPLC Method 2): m/z 512[M+H]$^+$@r.t. 5.99 min.
HRMS (ESI) calcd for $C_{26}H_{29}BF_3N_4O_3$ [M+H]$^+$ 512.2316 found 512.2305.

4-(2-hydroxyethyl)-6-[4-(hydroxymethyl)phenyl]-7-[3-(trifluoromethoxy)phenyl]-3,4-dihydropyrrolo[1,2-a]pyrazin-1(2H)-one [(I), R2=3-(trifluoromethoxy)phenyl, R3=4-(hydroxymethyl)phenyl, R4=H, A=—CH$_2$CH$_2$—OH] (cpd 84)

$^1$H NMR (600 MHz, DMSO-d6) δ 7.70 (d, J=5.31 Hz, 1H), 7.41 (d, J=8.06 Hz, 2H), 7.32 (td, J=4.03, 8.06 Hz, 3H), 7.20 (d, J=8.06 Hz, 1H), 7.06 (d, J=7.51 Hz, 1H), 7.03 (s, 1H), 6.95 (s, 1H), 5.30 (t, J=5.68 Hz, 1H), 4.57 (d, J=5.68 Hz, 2H), 4.42 (t, J=5.04 Hz, 1H), 4.28 (td, J=4.24, 8.93 Hz, 1H), 3.78 (dd, J=3.94, 13.10 Hz, 1H), 3.41 (dd, J=5.13, 12.45 Hz, 1H), 3.18-3.24 (m, 1H), 3.07-3.16 (m, 1H), 1.71-1.82 (m, 1H), 1.41-1.54 (m, 1H).

LCMS (HPLC Method 2): m/z 447 [M+H]$^+$@r.t. 5.39 min.
HRMS (ESI) calcd for $C_{23}H_{22}F_3N_2O_4$[M+H]$^+$ 447.1526 found 447.1518.

Example 34 tert-butyl(2-{(4S)-1-oxo-6-(thiophen-3-yl)-7-[3-(trifluoromethoxy)phenyl]-1,2,3,4-tetrahydropyrrolo[1,2-a]pyrazin-4-yl}ethyl)carbamate [(I), R2=3-(trifluoromethoxy)phenyl, R3=thiophen-3-yl, R4=H, A=—CH$_2$CH$_2$—NH—CO—OtBu] and tert-butyl(2-{(4R)-1-oxo-6-(thiophen-3-yl)-7-[3-(trifluoromethoxy)phenyl]-1,2,3,4-tetrahydropyrrolo[1,2-a]pyrazin-4-yl}ethyl)carbamate [(I), R2=3-(trifluoromethoxy)phenyl, R3=thiophen-3-yl, R4=H, A=—CH$_2$CH$_2$—NH—CO—OtBu]

Conv. g

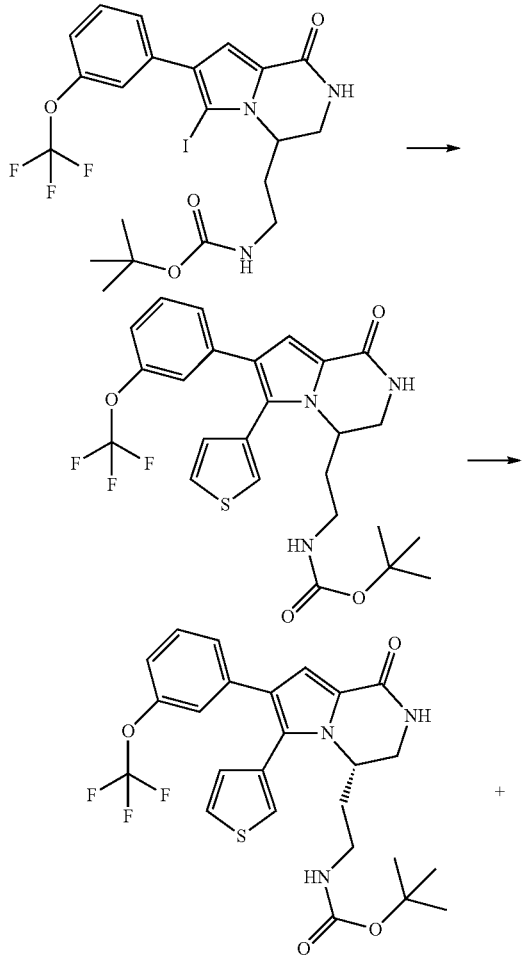

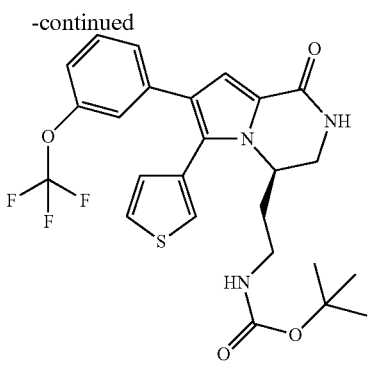

To a solution of tert-butyl(2-{6-iodo-1-oxo-7-[3-(trifluoromethoxy)phenyl]-1,2,3,4-tetrahydropyrrolo[1,2-a]pyrazin-4-yl}ethyl)carbamate (100 mg, 0.177 mmol) in 3 ml of 1,4-dioxane and 1 ml of water, under argon atmosphere, (67.9 mg, 0.531 mmol) of 3-thienylboronic acid, 7.2 mg (0.009 mmol) of 1,1'-bis(diphenylphosphino)ferrocenepalladium, complex with dichloromethane and 172 mg (0.531 mmol) of cesium carbonate, were subsequently added. The mixture was heated at 80° for 1 hour in a sealed vial. The reaction was filtered through a celite pad and the solvent evaporated to dryness. The crude was then portioned between ethyl acetate and water, the organic layer dried over sodium sulphate and the solvent removed in vacuo. After purification by flash chromatography on silica gel column (DCM/EtOAc/EtOH 6/4/0.5), and further purification by HPLC/MS preparative method 1, 50 mg (54%) of tert-butyl(2-{1-oxo-6-(thiophen-3-yl)-7-[3-(trifluoromethoxy)phenyl]-1,2,3,4-tetrahydropyrrolo[1,2-a]pyrazin-4-yl}ethyl)carbamate were obtained.

LCMS (HPLC Method 4): m/z 522 [M+H]$^+$@r.t. 2.75 min.

Single enantiomers (99% e.e.) have been obtained by preparative chiral-HPLC by using ChiralPack AD 250×20 mm 10 um as column system and n-hexane/ethanol 85:15 as eluents. Configuration of the stereogenic center was assigned by comparison with the compound of example 39 synthesized starting from optically pure L-aspartic acid (scheme 5 preparations K, L, M, N, O, P, Q and examples 6, and 38).

tert-butyl(2-{(4S)-1-oxo-6-(thiophen-3-yl)-7-[3-(trifluoromethoxy)phenyl]-1,2,3,4-tetrahydropyrrolo[1,2-a]pyrazin-4-yl}ethyl)carbamate [(I), R2=3-(trifluoromethoxy)phenyl, R3=thiophen-3-yl, R4=H, A=—CH$_2$CH$_2$—NH—CO—OtBu]

First eluting peak: $^1$H NMR (400 MHz, DMSO-d6) δ 7.62-7.80 (m, 3H), 7.21-7.40 (m, 2H), 7.09 (td, J=1.14, 8.21 Hz, 1H), 7.00-7.06 (m, 2H), 6.96 (s, 1H), 6.64 (t, J=5.80 Hz, 1H), 4.11-4.28 (m, 1H), 3.65-3.80 (m, 1H), 3.36-3.44 (m, 1H), 2.75 (d, J=6.10 Hz, 2H), 1.69-1.91 (m, 1H), 1.56 (dd, J=4.88, 13.18 Hz, 1H), 1.33 (s, 9H).

LCMS (HPLC Method 2): m/z 522 [M+H]$^+$@r.t. 6.3 min.

HRMS (ESI) calcd for C$_{25}$H$_{26}$F$_3$N$_3$NaO$_4$S [M+Na]$^+$ 544.1488 found 544.1474.

tert-butyl(2-{(4R)-1-oxo-6-(thiophen-3-yl)-7-[3-(trifluoromethoxy)phenyl]-1,2,3,4-tetrahydropyrrolo[1,2-a]pyrazin-4-yl}ethyl)carbamate [(I), R2=3-(trifluoromethoxy)phenyl, R3=thiophen-3-yl, R4=H, A=—CH$_2$CH$_2$—NH—CO—OtBu]

Second eluting peak: $^1$H NMR (400 MHz, DMSO-d6) δ 7.63-7.75 (m, 3H), 7.33-7.40 (m, 1H), 7.20-7.31 (m, 1H), 7.09 (td, J=1.25, 8.12 Hz, 1H), 7.00-7.05 (m, 2H), 6.96 (s, 1H), 6.64 (t, J=5.61 Hz, 1H), 4.08-4.28 (m, 1H), 3.72 (dd, J=3.17, 13.30 Hz, 1H), 3.36-3.44 (m, 1H), 2.69-2.83 (m, J=5.49 Hz, 2H), 1.70-1.93 (m, 1H), 1.47-1.68 (m, 1H), 1.33 (s, 9H).

LCMS (HPLC Method 2): m/z 522 [M+H]$^+$@r.t. 6.28 min.

HRMS (ESI) calcd for C$_{25}$H$_{26}$F$_3$N$_3$NaO$_4$S [M+Na]$^+$ 544.1488 found 544.1487.

Example 35

(4S)-4-(2-aminoethyl)-6-(thiophen-3-yl)-7-[3-(trifluoromethoxy)phenyl]-3,4-dihydropyrrolo[1,2-a]pyrazin-1(2H)-one hydrochloride [(I), R2=3-(trifluoromethoxy)phenyl, R3=thiophen-3-yl, R4=H, A=—CH$_2$CH$_2$—NH$_2$](cpd 85)

Conv. r

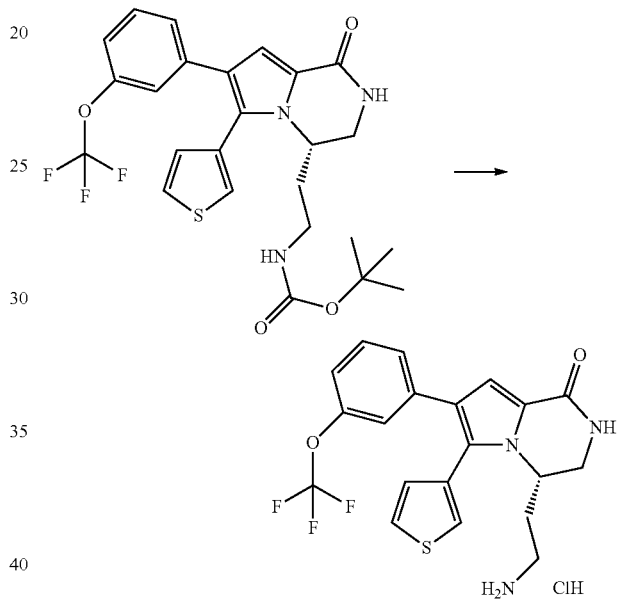

A solution of tert-butyl(2-{(4S)-1-oxo-6-(thiophen-3-yl)-7-[3-(trifluoromethoxy)phenyl]-1,2,3,4-tetrahydropyrrolo[1,2-a]pyrazin-4-yl}ethyl)carbamate (25 mg, 0.038 mmol) 4M HCl in 1,4-dioxane (4 ml) was stirred at room temperature until HPLC analysis revealed the disappearance of the starting material. The solvent was evaporated to dryness under reduced pressure and the product was treated with diethyl ether and decanted to give the title compound as a white solid 15 mg (88%).

$^1$H NMR (400 MHz, DMSO-d6) δ 7.70-7.82 (m, 3H), 7.63 (t, J=4.88 Hz, 3H), 7.34-7.42 (m, 1H), 7.29 (td, J=1.19, 8.00 Hz, 1H), 7.11 (td, J=1.21, 8.09 Hz, 1H), 7.05-7.09 (m, 2H), 6.95 (s, 1H), 4.28-4.37 (m, 1H), 3.80 (dd, J=3.78, 13.43 Hz, 1H), 1.68-2.03 (m, 2H).

LCMS (HPLC Method 2): m/z 422 [M+H]$^+$@r.t. 4.11 min.

HRMS (ESI) calcd for C$_{20}$H$_{20}$F$_3$N$_3$O$_2$S [M+H]$^+$ 422.1145 found 422.1156.

Operating in an analogous way, the following compound was obtained:

(4R)-4-(2-aminoethyl)-6-(thiophen-3-yl)-7-[3-(trifluoromethoxy)phenyl]-3,4-dihydropyrrolo[1,2-a]pyrazin-1(2H)-one hydrochloride [(I), R2=3-(trifluoromethoxy)phenyl, R3=thiophen-3-yl, R4=H, A=—CH$_2$CH$_2$—NH$_2$](cpd 86)

$^1$H NMR (400 MHz, DMSO-d6) δ 7.72-7.82 (m, 3H), 7.61 (t, J=5.80 Hz, 3H), 7.34-7.41 (m, 1H), 7.23-7.32 (m, 1H), 7.11 (td, J=1.17, 8.03 Hz, 1H), 7.06-7.09 (m, 2H), 6.93-6.98 (m, J=0.73 Hz, 1H), 4.23-4.39 (m, 1H), 3.77-3.85 (m, 1H), 1.71-2.03 (m, 2H).

LCMS (HPLC Method 2): m/z 422 [M+H]$^+$@r.t. 4.08 min.
HRMS (ESI) calcd for $C_{20}H_{20}F_3N_3O_2S$ [M+H]$^+$ 422.1145 found 422.1160.

Example 36

(4S)-4-(2-aminoethyl)-6-phenyl-7-[3-(trifluoromethoxy)phenyl]-3,4-dihydropyrrolo[1,2-a]pyrazin-1(2H)-one [(I), R2=3-(trifluoromethoxy)phenyl, R3=phenyl, R4=H, A=—CH$_2$CH$_2$—NH$_2$] (cpd 87) and (4R)-4-(2-aminoethyl)-6-phenyl-7-[3-(trifluoromethoxy)phenyl]-3,4-dihydropyrrolo[1,2-a]pyrazin-1(2H)-one [(I), R2=3-(trifluoromethoxy)phenyl, R3=phenyl, R4=H, A=—CH$_2$CH$_2$—NH$_2$] (cpd 88)

The compound 4-(2-aminoethyl)-6-phenyl-7-[3-(trifluoromethoxy)phenyl]-3,4-dihydropyrrolo[1,2-a]pyrazin-1 (2H)-one hydrochloride prepared according to example 11 was resolved by preparative chiral-HPLC by using Chiral-Pack AD 250×20 mm 10 um as column system and n-hexane/ethanol 85:15 as eluents. Configuration of the stereogenic center was assigned by comparison with the compound of example 40 synthesized starting from optically pure L aspartic acid (scheme 5 preparations K, L, M, N, O, P, Q and examples 6, 38 and 39).

(4S)-4-(2-aminoethyl)-6-phenyl-7-[3-(trifluoromethoxy) phenyl]-3,4-dihydropyrrolo[1,2-a]pyrazin-1(2H)-one
First eluting peak, $^1$H NMR (400 MHz, DMSO-d6) δ 7.70 (d, J=4.88 Hz, 1H), 7.45-7.51 (m, 4H), 7.31-7.40 (m, 4H), 7.23-7.28 (m, 1H), 7.07 (s, 1H), 7.04 (s, 1H), 6.89 (s, 1H), 4.26-4.34 (m, 1H), 3.80 (dd, J=4.09, 13.00 Hz, 1H), 2.24 (t, J=7.14 Hz, 2H), 1.64-1.75 (m, 1H), 1.36-1.47 (m, 1H).

LCMS (HPLC Method 2): m/z 416 [M+H]$^+$@r.t. 5.09 min.
HRMS (ESI) calcd for $C_{22}H_{21}F_3N_3O_2$[M+H]$^+$ 416.158 found 416.160.

(4R)-4-(2-aminoethyl)-6-phenyl-7-[3-(trifluoromethoxy) phenyl]-3,4-dihydropyrrolo[1,2-a]pyrazin-1(2H)-one
Second eluting peak, $^1$H NMR (400 MHz, DMSO-d$_6$) δ 7.71 (d, J=4.76 Hz, 1H), 7.45-7.53 (m, 2H), 7.19-7.41 (m, 3H), 6.99-7.11 (m, 2H), 6.88 (s, 1H), 4.24-4.37 (m, 1H), 3.81 (dd, J=3.78, 12.69 Hz, 1H), 1.93-2.40 (m, 1H), 1.40-1.81 (m, 2H).

LCMS (HPLC Method 2): m/z 416 [M+H]$^+$@r.t. 5.11 min.
HRMS (ESI) calcd for $C_{22}H_{21}F_3N_3O_2$[M+H]$^+$ 416.158 found 416.160.

(4R)-4-(2-chloroethyl)-6-{4-[(4-methyl piperazin-1-yl) methyl]phenyl}-7-[3-(trifluoromethoxy)phenyl]-3,4-dihydropyrrolo[1,2-a]pyrazin-1(2H)-one [(I), R2=3-(trifluoromethoxy)phenyl, R3=4-[(4-methylpiperazin-1-yl)methyl] phenyl, R4=H, A=—CH$_2$CH$_2$—Cl]

$^1$H NMR (600 MHz, DMSO-d6) δ 7.72 (d, J=4.95 Hz, 2H), 7.37-7.45 (m, 2H), 7.27-7.37 (m, 4H), 7.04-7.09 (m, 2H), 6.87 (s, 1H), 4.36-4.42 (m, 1H), 3.86 (dd, J=3.94, 13.28 Hz, 1H), 3.46-3.53 (m, 2H), 3.36-3.45 (m, 3H), 2.19-2.47 (m, 8H), 2.14 (s, 3H), 2.07-2.12 (m, 1H), 1.64-1.75 (m, 1H).

LCMS (HPLC Method 2): m/z 547 [M+H]$^+$@r.t. 5.33 min.
HRMS (ESI) calcd for $C_{28}H_{31}ClF_3N_4O_2$ [M+H]$^+$ 547.2082 found 547.2086.

(4S)-4-(2-chloroethyl)-6-{4-[(4-methyl piperazin-1-yl) methyl]phenyl}-7-[3-(trifluoromethoxy)phenyl]-3,4-dihydropyrrolo[1,2-a]pyrazin-1(2H)-one [(I), R2=3-(trifluoromethoxy)phenyl, R3=4-[(4-methylpiperazin-1-yl)methyl] phenyl, R4=H, A=—CH$_2$CH$_2$—Cl](cpd 106)

LCMS (HPLC Method 2): m/z 547 [M+H]$^+$@r.t. 5.34 min.
HRMS (ESI) calcd for $C_{28}H_{31}ClF_3N_4O_2$ [M+H]$^+$ 547.2082 found 547.2088.

Example 37

(4S)-4-(2-aminoethyl)-7-[3-(trifluoromethoxy)phenyl]-3,4-dihydropyrrolo[1,2-a]pyrazin-1(2H)-one hydrochloride [(I), R2=3-(trifluoromethoxy)phenyl, R3=R4=H, A=—CH$_2$CH$_2$—NH$_2$](cpd 89)

Conv. r

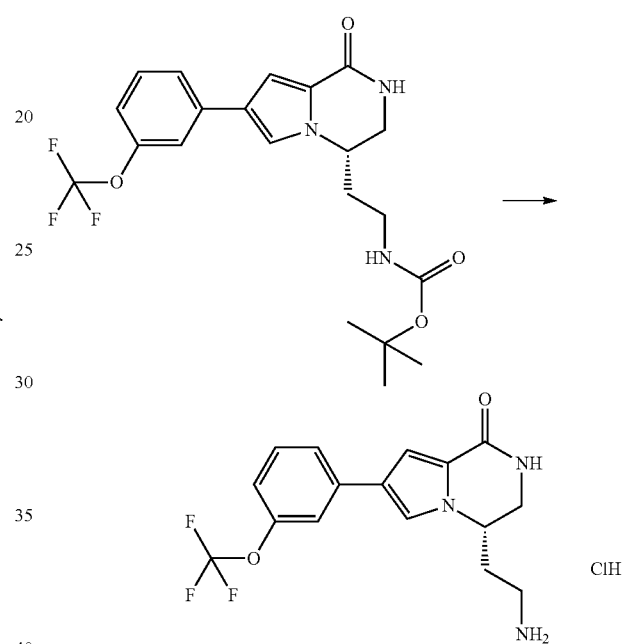

A solution of tert-butyl(2-{(4S)-1-oxo-7-[3-(trifluoromethoxy)phenyl]-1,2,3,4-tetrahydropyrrolo[1,2-a] pyrazin-4-yl}ethyl)carbamate (0.036 g, 0.08 mmol) in 4M HCl in 1,4-dioxane (1 ml) was stirred at room temperature for 1 h. The solvent was removed under vacuo, giving the title compound as a white solid (0.027 g, 97%).

$^1$H NMR (600 MHz, DMSO-d$_6$) δ 7.85 (br. s., 3H), 7.75 (d, J=3.48 Hz, 1H), 7.72 (s, 1H), 7.63 (d, J=8.42 Hz, 1H), 7.55 (s, 1H), 7.47 (t, J=7.97 Hz, 1H), 7.09-7.18 (m, 2H), 4.37-4.51 (m, J=3.66 Hz, 1H), 3.71 (dd, J=3.75, 12.73 Hz, 1H), 3.30-3.38 (m, 1H), 2.85-2.97 (m, 1H), 2.68-2.80 (m, 1H), 1.97-2.14 (m, 2H).

LCMS (HPLC Method 2): m/z 340 [M+H]$^+$@r.t. 4.51 min.
HRMS (ESI) calcd for $C_{16}H_{17}F_3N_3O_2$[M+H]$^+$ 340.1268 found 340.1267.

According to the same methodology, the following compounds were prepared:

(4S)-4-(2-aminoethyl)-7-(6-aminopyridin-3-yl)-3,4-dihydropyrrolo[1,2-a]pyrazin-1(2H)-one hydrochloride [(I), R2=6-aminopyridin-3-yl, R3=R4=H, A=—CH$_2$CH$_2$—NH$_2$]

$^1$H NMR (600 MHz, DMSO-d$_6$) δ 8.22 (d, J=2.20 Hz, 2H), 7.85-8.06 (m, 5H), 7.77 (m, 1H), 7.65-7.69 (m, 1H), 7.12 (d, J=1.83 Hz, 1H), 7.03 (d, J=9.71 Hz, 1H), 4.38-4.50 (m, 1H), 3.68 (dd, J=3.11, 13.37 Hz, 1H), 2.83-2.94 (m, 1H), 2.69-2.80 (m, 1H), 1.98-2.13 (m, 2H).

LCMS (HPLC Method 2): m/z 272 [M+H]⁺@r.t. 3.21 min.
HRMS (ESI) calcd for $C_{14}H_{18}N_5O$ [M+H]⁺ 272.1506 found 272.1508.

(4S)-4-(3-aminopropyl)-7-[3-(trifluoromethoxy)phenyl]-3,4-dihydropyrrolo[1,2-a]pyrazin-1(2H)-one hydrochloride [(I), R2=3-(trifluoromethoxy)phenyl, R3=R4=H, A=—CH₂—CH₂CH₂—NH₂](cpd 90)

¹H NMR (600 MHz, DMSO-d₆) δ 7.69-7.78 (m, J=12.09 Hz, 3H), 7.66-7.68 (m, 1H), 7.63 (d, J=7.69 Hz, 1H), 7.55 (br. s., 1H), 7.46 (t, J=7.97 Hz, 1H), 7.04-7.17 (m, 2H), 4.31 (br. s., 1H), 3.68 (dd, J=3.39, 12.55 Hz, 1H), 2.69-2.90 (m, 2H), 1.84-1.96 (m, J=10.99 Hz, 1H), 1.77 (dt, J=5.31, 10.26 Hz, 1H), 1.59-1.67 (m, J=8.97 Hz, 1H), 1.54 (dd, J=6.23, 10.62 Hz, 1H).

LCMS (HPLC Method 2): m/z 354 [M+H]⁺@r.t. 4.86 min.
HRMS (ESI) calcd for $C_{17}H_{19}N_3O_2F_3Cl$ [M+H]⁺ 354.1424 found 354.1424.

(4S)-4-(3-aminopropyl)-7-(3-chlorophenyl)-3,4-dihydro-pyrrolo[1,2-a]pyrazin-1(2H)-one hydrochloride
[(I), R2=3-chlorophenyl, R3=R4=H, A=—CH₂—CH₂CH₂—NH₂](cpd 91)

¹H NMR (600 MHz, DMSO-d₆) δ 7.67-7.85 (m, 7H), 7.65 (d, J=7.33 Hz, 1H), 7.56 (d, J=8.06 Hz, 1H), 7.36 (t, J=7.60 Hz, 1H), 7.21 (d, J=8.97 Hz, 1H), 7.10 (s, 1H), 4.30 (br. s., 1H), 3.68 (dd, J=3.21, 12.36 Hz, 2H), 2.72-2.88 (m, J=7.88, 17.40 Hz, 2H), 1.84-1.97 (m, 1H), 1.72-1.82 (m, 1H), 1.47-1.67 (m, 2H).

LCMS (HPLC Method 2): m/z 304 [M+H]⁺@r.t. 4.42 min.
HRMS (ESI) calcd for $C_{16}H_{19}N_3OCl_2$ [M+H]⁺ 304.1211 found 304.1209.

Example 37a (4S)-4-(1H-imidazol-4-ylmethyl)-7-[3-(trifluoromethoxy)phenyl]-3,4-dihydropyrrolo[1,2-a]pyrazin-1(2H)-one [(I), R2=3-(trifluoromethoxy)phenyl, R3=R4=H, A=CH₂-1H-imidazol-4-yl](cpd 107)

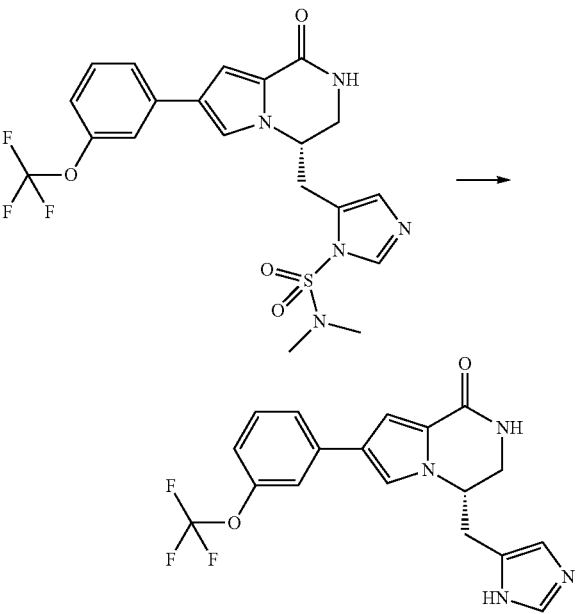

N,N-dimethyl-4-({(4S)-1-oxo-7-[3-(trifluoromethoxy)phenyl]-1,2,3,4-tetrahydropyrrolo[1,2-a]pyrazin-4-yl}methyl)-1H-imidazole-1-sulfonamide was dissolved in a mixture 1:1 of water (2 ml) and 4N HCl in dioxane (2 ml) and heated at 75° C. until deprotection was completed. After evaporation under vacuo, purification by RP-HPLC afforded the title compound as a white solid.

¹H NMR (600 MHz, DMSO-d6) δ 9.00 (br. s., 1H), 7.72 (d, J=3.30 Hz, 1H), 7.58 (d, J=8.43 Hz, 1H), 7.50 (s, 1H), 7.42-7.47 (m, 2H), 7.38 (s, 1H), 7.14 (d, J=1.65 Hz, 2H), 4.67 (m, 1H), 3.68 (m, 1H), 3.47 (m, 1H), 3.17-3.27 (m, 2H). LCMS (HPLC Method 2): m/z 377 [M+H]⁺@r.t. 5.02 min.
HRMS (ESI) calcd for $C_{18}H_{16}F_3N_4O_2$[M+H]⁺ 377.122. found 377.1213.

Example 38 tert-butyl(2-{(4S)-6-iodo-1-oxo-7-[3-(trifluoromethoxy)phenyl]-1,2,3,4-tetrahydropyrrolo[1,2-a]pyrazin-4-yl}ethyl)carbamate [(I), R2=3-(trifluoromethoxy)phenyl, R3=I, R4=H, A=—CH₂CH₂—NH—CO—OtBu]

Conv. e

Iodine (0.488 g, 1.92 mmol) was added portion wise to a solution of tert-butyl(2-{(4S)-1-oxo-7-[3-(trifluoromethoxy)phenyl]-1,2,3,4-tetrahydropyrrolo[1,2-a]pyrazin-4-yl}ethyl)carbamate (0.845 g, 1.92 mmol) and silver trifluoroacetate (0.425 g, 1.92 mmol) in dry DCM (20 ml), at 5° C. The reaction mixture was stirred at the same temperature for 1 hour, then the ice bath removed and left to warm to rt (1 h). The solid was filtered, the organic phase washed with Na₂S₂O₅ (5% aq. solution) until discoloration occurred and finally washed with water. The organic layer was dried over Na₂SO₄ to obtain the title compound as a brown solid (0.976 g, 1.72 mmol, 90%).

¹H NMR (600 MHz, DMSO-d6) δ 7.78 (d, J=5.31 Hz, 1H), 7.56-7.60 (m, 1H), 7.54 (t, J=7.97 Hz, 1H), 7.52 (br. S., 1H), 7.29 (d, J=8.06 Hz, 1H), 6.99 (s, 1H), 6.97 (t, J=5.49 Hz, 1H), 4.36-4.44 (m, 1H), 3.68-3.73 (m, 1H), 3.49 (dd, J=4.85, 13.46 Hz, 1H), 2.95-3.13 (m, 2H), 1.79-1.88 (m, 1H), 1.63-1.72 (m, 1H), 1.39 (s, 9H).

LCMS (HPLC Method 2): m/z 588 [M+Na]+r.t. 6.98 min.

HRMS (ESI) calcd for C₂₁H₂₃F₃IN₃NaO₄ [M+Na]⁺ 588.0577 found 588.0571.

According to the same methodology but employing tert-butyl(3-{(4S)-1-oxo-7-[3-(trifluoromethoxy)phenyl]-1,2,3,4-tetrahydropyrrolo[1,2-a]pyrazin-4-yl}propyl)carbamate, the following compound was prepared:

tert-butyl(3-{(4S)-6-iodo-1-oxo-7-[3-(trifluoromethoxy)phenyl]-1,2,3,4-tetrahydropyrrolo[1,2-a]pyrazin-4-yl}propyl)carbamate [(I), R2=3-(trifluoromethoxy)phenyl, R3=I, R4=H, A=—CH₂—CH₂CH₂—NH—CO—OtBu]

¹H NMR (600 MHz, DMSO-d₆) δ 7.76 (d, J=4.58 Hz, 1H), 7.42-7.60 (m, 3H), 7.29 (d, J=7.88 Hz, 1H), 6.99 (s, 1H), 6.81-6.88 (m, 1H), 4.27-4.36 (m, 1H), 3.71 (dd, J=3.85, 13.55 Hz, 1H), 3.41 (dd, J=5.49, 13.37 Hz, 1H), 2.80-3.02 (m, 2H), 1.69 (dt, J=4.85, 9.02 Hz, 1H), 1.52-1.59 (m, 1H), 1.42-1.51 (m, 2H), 1.36 (s, 9H).

LCMS (HPLC Method 2): m/z 580 [M+H]⁺@r.t. 6.90 min.

HRMS (ESI) calcd for C₂₂H₂₅N₃O₄F₃I [M+H]⁺ 580.0915 found 580.0909.

(4S)-6-iodo-4-(propan-2-yl)-7-[3-(trifluoromethoxy)phenyl]-3,4-dihydropyrrolo[1,2-a]pyrazin-1(2H)-one

[(I), R2=3-(trifluoromethoxy)phenyl, R3=Hal=I, R4=H, A=—CH₂(CH₃)₂]

LCMS (HPLC Method 2): m/z 465 [M+H]⁺@r.t. 6.87 min.

HRMS (ESI) calcd for C₁₇H₁₇F₃IN₂O₂[M+H]⁺ 465.0282 found 465.0273.

4-({(4S)-6-iodo-1-oxo-7-[3-(trifluoromethoxy)phenyl]-1,2,3,4-tetrahydropyrrolo[1,2-a]pyrazin-4-yl}methyl)-N,N-dimethyl-1H-imidazole-1-sulfonamide

[(I), R2=3-(trifluoromethoxy)phenyl, R3=Hal=I, R4=H, A=CH₂-1-(dimethylsulfamoyl)-1H-imidazol-4-yl]

LCMS (HPLC Method 2): m/z 610 [M+H]⁺@r.t. 6.29 min.

HRMS (ESI) calcd for C₂₀H₁₉F₃IN₅O₄S [M+H]⁺ 610.0228 found 610.0233.

Example 39 tert-butyl(2-{(4S)-1-oxo-6-(thiophen-3-yl)-7-[3-(trifluoromethoxy)phenyl]-1,2,3,4-tetrahydropyrrolo[1,2-a]pyrazin-4-yl}ethyl)carbamate [(I), R2=3-(trifluoromethoxy)phenyl, R3=thiophen-3-yl, R4=H, A=—CH₂CH₂—NH—CO—OtBu]

Conv. g

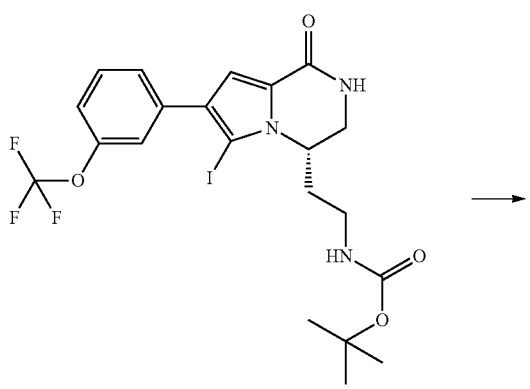

→

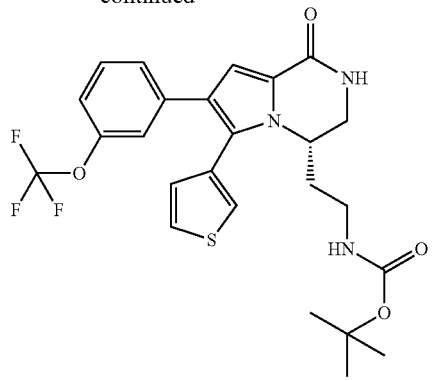

Cesium carbonate (0.173 g, 0.53 mmol), thiophen-3-yl boronic acid (0.034 g, 0.265 mmol), and 1,1'-bis(diphenylphosphino)ferrocenepaladium (0.0076 g, 0.008 mmol) complex with dichloromethane, were subsequently added to a solution of tert-butyl(2-{(4S)-6-iodo-1-oxo-7-[3-(trifluoromethoxy)phenyl]-1,2,3,4-tetrahydropyrrolo[1,2-a]pyrazin-4-yl}ethyl)carbamate (0.100 g, 0.177 mmol) in 3 ml of 1,4-dioxane and 1 ml of water, under argon atmosphere. The mixture was heated at 80° for 2 hours in a sealed vial. The reaction was filtered through a celite pad and the solvent evaporated to dryness. The crude was portioned between ethyl acetate and water, the organic layer dried over sodium sulphate and the solvent removed in vacuo. Purification by flash chromatography on silica gel column (DCM/MeOH, 9/0.3), followed by HPLC preparative method 2 purification, afforded the title compound (0.056 g, 0.11 mmol, 61%).

¹H NMR (600 MHz, DMSO d6) δ 7.71 (dd, J=2.84, 4.85 Hz, 2H), 7.68 (dd, J=1.28, 2.93 Hz, 1H), 7.34-7.40 (m, 1H), 7.28 (d, J=8.06 Hz, 1H), 7.07-7.11 (m, 1H), 7.01-7.05 (m, 2H), 6.96 (s, 1H), 6.64 (t, J=5.59 Hz, 1H), 4.20 (td, J=4.28, 8.47 Hz, 1H), 3.72 (dd, J=3.30, 13.55 Hz, 1H), 3.41 (d, J=5.13 Hz, 1H), 2.65-2.82 (m, 2H), 1.80 (dt, J=7.05, 13.87 Hz, 1H), 1.47-1.62 (m, 1H), 1.33 (s, 9H).

LCMS (HPLC Method 2): m/z 522 [M+H]⁺@r.t. 6.3 min.

HRMS (ESI) calcd for C₂₅H₂₇F₃N₃O₄S [M+H]⁺ 522.1669 found 522.1666.

Working according to the same procedure, and using the appropriate boronic acid, the following compounds were prepared:

tert-butyl(2-{(4S)-1-oxo-6-phenyl-7-[3-(trifluoromethoxy)phenyl]-1,2,3,4-tetrahydropyrrolo[1,2-a]pyrazin-4-yl}ethyl)carbamate [(I), R2=3-(trifluoromethoxy)phenyl, R3=phenyl, R4=H, A=—CH₂CH₂—NH—CO—OtBu]

The title compound was obtained after HPLC preparative method 2 purification (56%).

¹H NMR (600 MHz, DMSO-d6) δ 7.72 (d, J=5.13 Hz, 1H), 7.45-7.52 (m, 3H), 7.30-7.39 (m, 3H), 7.25 (d, J=7.51 Hz, 1H), 7.03-7.08 (m, 2H), 6.88 (s, 1H), 6.52-6.58 (m, 1H), 4.18 (br. s., 1H), 3.73-3.82 (m, 1H), 3.39 (dd, J=12.55, 5.04 Hz, 1H), 2.65-2.72 (m, 2H), 1.68-1.82 (m, 1H), 1.49 (dd, J=12.73, 4.85 Hz, 1H), 1.29 (s, 9H).

LCMS (HPLC Method 2): m/z 538 [M+Na]⁺@r.t. 7.06 min.

HRMS (ESI) calcd for C₂₇H₂₈F₃NaN₃O₄[M+Na]⁺ 538.1924 found 538.1924.

tert-butyl(2-{(4S)-6-(3-methylphenyl)-1-oxo-7-[3-(trifluoromethoxy)phenyl]-1,2,3,4-tetrahydropyrrolo[1,2-a]

pyrazin-4-yl}ethyl)carbamate [(I), R2=3-(trifluoromethoxy)phenyl, R3=3-methylphenyl, R4=H, A=—CH$_2$CH$_2$—NH—CO—OtBu]

The title compound was obtained after HPLC preparative method 2 purification (47%).

$^1$H NMR (600 MHz, DMSO-d6) δ 7.71 (d, J=4.95 Hz, 1H), 7.32-7.37 (m, 2H), 7.26-7.30 (m, 2H), 7.18 (s, 1H), 7.13 (d, J=7.33 Hz, 1H), 7.04-7.09 (m, 2H), 6.89 (s, 1H), 6.54 (t, J=5.31 Hz, 1H), 4.17 (br. s., 1H), 3.72-3.79 (m, 1H), 3.39 (dd, J=13.00, 4.95 Hz, 1H), 2.66-2.71 (m, 2H), 2.32 (s, 3H), 1.75 (d, J=7.14 Hz, 1H), 1.45-1.54 (m, 1H), 1.29 (s, 9H).

LCMS (HPLC Method 2): m/z 530 [M+H]$^+$@r.t. 7.32 min.
HRMS (ESI) calcd for C$_{28}$H$_{31}$F$_3$N$_3$O$_4$[M+H]$^+$ 530.2261 found 530.2272.

tert-butyl(2-{(4S)-6-(4-hydroxyphenyl)-1-oxo-7-[3-(trifluoromethoxy)phenyl]-1,2,3,4-tetrahydropyrrolo[1,2-a]pyrazin-4-yl}ethyl)carbamate [(I), R2=3-(trifluoromethoxy)phenyl, R3=4-hydroxyphenyl, R4=H, A=—CH$_2$CH$_2$—NH—CO—OtBu]

The title compound was obtained after HPLC preparative method 2 purification (49%).

$^1$H NMR (600 MHz, DMSO-d6) δ 9.73 (s, 1H), 7.66 (d, J=4.95 Hz, 1H), 7.29-7.36 (m, 1H), 7.25 (d, J=7.69 Hz, 1H), 7.13 (d, J=8.43 Hz, 2H), 7.05 (d, J=8.24 Hz, 1H), 7.02 (s, 1H), 6.94 (s, 1H), 6.85 (d, J=8.61 Hz, 2H), 6.57 (t, J=5.04 Hz, 1H), 4.07-4.20 (m, 1H), 3.73 (dd, J=13.74, 3.11 Hz, 1H), 3.36-3.41 (m, 1H), 2.65-2.75 (m, 2H), 1.74 (m, J=7.69 Hz, 1H) 1.50 (m, J=13.19, 4.95 Hz, 1H), 1.31 (s, 9H).

LCMS (HPLC Method 2): m/z 532 [M+H]$^+$@r.t. 6.17 min.
HRMS (ESI) calcd for C$_{27}$H$_{29}$F$_3$N$_3$O$_5$[M+H]$^+$ 532.2054 found 532.2045.

tert-butyl(2-{(4S)-6-(4-fluorophenyl)-1-oxo-7-[3-(trifluoromethoxy)phenyl]-1,2,3,4-tetrahydropyrrolo[1,2-a]pyrazin-4-yl}ethyl)carbamate [(I), R2=3-(trifluoromethoxy)phenyl, R3=4-fluorophenyl, R4=H, A=—CH$_2$CH$_2$—NH—CO—OtBu]

The title compound was obtained after HPLC preparative method 2 purification (50%).

$^1$H NMR (600 MHz, DMSO-d6) δ 7.72 (d, J=4.40 Hz, 1H), 7.41 (dd, J=7.88, 5.68 Hz, 2H), 7.33-7.38 (m, 1H), 7.30 (t, J=8.70 Hz, 2H), 7.25 (d, J=7.51 Hz, 1H), 7.08 (d, J=7.69 Hz, 1H), 7.04 (s, 1H), 6.88 (s, 1H), 6.57 (t, J=5.49 Hz, 1H), 4.14 (m, J=4.03 Hz, 1H), 3.77 (dd, J=13.10, 3.02 Hz, 1H), 3.37-3.42 (m, 1H), 2.64-2.79 (m, 2H), 1.75 (m, J=6.59 Hz, 1H), 1.45 (m, J=8.43 Hz, 1H), 1.29 (s, 9H).

LCMS (HPLC Method 2): m/z 534 [M+H]$^+$@r.t. 7.08 min.
HRMS (ESI) calcd for C$_{27}$H$_{28}$F$_4$N$_3$O$_4$[M+H]$^+$ 534.2011 found 534.2008.

tert-butyl(2-{(4S)-6-(4-acetylphenyl)-1-oxo-7-[3-(trifluoromethoxy)phenyl]-1,2,3,4-tetrahydropyrrolo[1,2-a]pyrazin-4-yl}ethyl)carbamate [(I), R2=3-(trifluoromethoxy)phenyl, R3=4-acetylphenyl, R4=H, A=—CH$_2$CH$_2$—NH—CO—OtBu]

The title compound was obtained after HPLC preparative method 2 purification (38%).

$^1$H NMR (600 MHz, DMSO-d6) δ 8.03 (d, J=8.06 Hz, 2H), 7.77 (d, J=4.94 Hz, 1H), 7.44-7.55 (m, 2H), 7.30-7.40 (m, 1H), 7.21 (d, J=7.88 Hz, 1H), 7.10 (d, J=7.88 Hz, 1H), 7.06 (s, 1H), 6.91 (br. s., 1H), 6.58 (t, J=5.49 Hz, 1H), 4.25 (d, J=8.06 Hz, 1H), 3.81 (dd, J=13.46, 2.84 Hz, 1H), 3.42 (dd, J=12.64, 4.40 Hz, 1H), 2.69 (m, J=5.68 Hz, 2H), 2.60 (s, 3H), 1.75 (m, J=5.86 Hz, 1H), 1.38-1.51 (m, 1H), 1.26 (s, 9H).

LCMS (HPLC Method 2): m/z 558 [M+H]$^+$@r.t. 6.66 min.
HRMS (ESI) calcd for C$_{29}$H$_{31}$F$_3$N$_3$O$_5$[M+H]$^+$ 558.2211 found 558.2216.

tert-butyl(2-{(4S)-6-[4-(methylsulfonyl)phenyl]-1-oxo-7-[3-(trifluoromethoxy)phenyl]-1,2,3,4-tetrahydropyrrolo[1,2-a]pyrazin-4-yl}ethyl)carbamate [(I), R2=3-(trifluoromethoxy)phenyl, R3=4-(methylsulfonyl)phenyl, R4=H, A=—CH$_2$CH$_2$—NH—CO—OtBu]

The title compound was obtained after HPLC preparative method 2 purification (50%).

$^1$H NMR (600 MHz, DMSO-d6) δ 8.00 (d, J=8.06 Hz, 2H), 7.80 (d, J=4.76 Hz, 1H), 7.63 (d, J=8.24 Hz, 2H), 7.33-7.41 (m, 1H), 7.26 (d, J=7.51 Hz, 1H), 7.12 (d, J=8.06 Hz, 1H), 7.07 (s, 1H), 6.84 (br. s., 1H), 6.61 (t, J=5.31 Hz, 1H), 4.23 (m, J=4.03 Hz, 1H), 3.82 (dd, J=14.01, 3.21 Hz, 1H), 3.39-3.45 (m, 1H), 3.23 (s, 3H), 2.62-2.76 (m, 2H), 1.76 (m, J=7.14 Hz, 1H), 1.45 (m, J=13.46, 5.77 Hz, 1H), 1.30 (s, 9H).

LCMS (HPLC Method 2): m/z 616 [M+Na]+r.t. 6.26 min.
HRMS (ESI) calcd for C$_{28}$H$_{31}$F$_3$N$_3$NaO$_6$S [M+Na]$^+$ 616.1699 found 616.1696.

tert-butyl(2-{(4S)-6-(4-formylphenyl)-1-oxo-7-[3-(trifluoromethoxy)phenyl]-1,2,3,4-tetrahydropyrrolo[1,2-a]pyrazin-4-yl}ethyl)carbamate [(I), R2=3-(trifluoromethoxy)phenyl, R3=4-formylphenyl, R4=H, A=—CH$_2$CH$_2$—NH—CO—OtBu]

The title compound was obtained after HPLC preparative method 2 purification, as a yellow oil (93%).

$^1$H NMR (600 MHz, DMSO-d6) δ 10.09 (s, 1H), 7.99 (d, J=7.88 Hz, 2H), 7.59 (d, J=8.06 Hz, 2H), 7.34-7.38 (m, 1H), 7.23 (d, J=7.88 Hz, 1H), 7.11 (d, J=8.06 Hz, 1H), 7.06 (s, 1H), 6.90 (s, 1H), 6.57 (br. s., 1H), 4.26 (d, J=4.03 Hz, 1H), 3.82 (d, J=10.07 Hz, 1H), 3.39-3.44 (m, 1H), 2.69 (br. s., 2H), 1.75 (d, J=5.49 Hz, 1H), 1.45 (dd, J=13.10, 4.85 Hz, 1H), 1.25 (s, 9H).

LCMS (HPLC Method 2): m/z 544 [M+H]$^+$@r.t. 6.63 min.
HRMS (ESI) calcd for C$_{28}$H$_{29}$F$_3$N$_3$O$_5$[M+H]$^+$ 544.2054 found 544.2034.

tert-butyl(3-{(4S)-1-oxo-6-(thiophen-3-yl)-7-[3-(trifluoromethoxy)phenyl]-1,2,3,4-tetrahydropyrrolo[1,2-a]pyrazin-4-yl}propyl) carbamate [(I), R2=3-(trifluoromethoxy)phenyl, R3=thiophen-3-yl, R4=H, A=—CH$_2$CH$_2$CH$_2$—NH—CO—OtBu]

Purification by HPLC preparative method 2 gave the title compound.

$^1$H NMR (400 MHz, DMSO-d$_6$) δ 7.66-7.74 (m, 3H), 7.33-7.39 (m, 1H), 7.25-7.31 (m, J=1.2 Hz, 1H), 7.04-7.11 (m, 2H), 7.02 (s, 1H), 6.92-6.97 (m, 1H), 6.69 (t, J=5.55 Hz, 1H), 3.99-4.24 (m, J=3.7 Hz, 1H), 3.76 (dd, J=3.9, 13.1 Hz, 1H), 3.25-3.32 (m, 1H), 2.61-2.69 (m, 2H), 1.56-1.68 (m, 1H), 1.37-1.46 (m, 1H), 1.34 (s, 9H), 1.05-1.19 (m, 2H).

LCMS (HPLC Method 2): m/z 536 [M+H]$^+$@r.t. 7.05 min.
HRMS (ESI) calcd for C$_{26}$H$_{28}$N$_3$O$_4$F$_3$S [M+H]$^+$ 536.1826 found 536.1835.

Purification by HPLC preparative method 2 gave the title compound.

tert-butyl(3-{(4S)-1-oxo-6-phenyl-7-[3-(trifluoromethoxy)phenyl]-1,2,3,4-tetrahydropyrrolo[1,2-a]pyrazin-4-yl}propyl) carbamate [(I), R2=3-(trifluoromethoxy)phenyl, R3=phenyl, R4=H, A=—CH$_2$CH$_2$CH$_2$—NH—CO—OtBu]

LCMS (HPLC Method 1): m/z 530 [M+H]$^+$@r.t. 1.75 min.
Purification by HPLC preparative method 2 gave the title compound.

tert-butyl(3-{(4S)-6-(4-hydroxyphenyl)-1-oxo-7-[3-(trifluoromethoxy)phenyl]-1,2,3,4-tetrahydropyrrolo[1,2-a]pyrazin-4-yl}propyl)carbamate [(I), R2=3-(trifluoromethoxy)phenyl, R3=4-hydroxyphenyl, R4=H, A=—CH$_2$CH$_2$CH$_2$—NH—CO—OtBu]

LCMS (HPLC Method 1): m/z 545 [M+H]$^+$@r.t. 1.45 min.
Purification by HPLC preparative method 2 gave the title compound.

tert-butyl(3-{(4S)-6-[4-(hydroxymethyl)phenyl]-1-oxo-7-[3-(trifluoromethoxy)phenyl]-1,2,3,4-tetrahydropyrrolo

[1,2-a]pyrazin-4-yl}propyl)carbamate [(I), R2=3-(trifluoromethoxy)phenyl, R3=4-(hydroxymethyl)phenyl, R4=H, A=—CH$_2$CH$_2$CH$_2$—NH—CO—OtBu]

LCMS (HPLC Method 1): m/z 560 [M+H]$^+$@r.t. 1.55 min.

4-{(4S)-1-oxo-4-(propan-2-yl)-7-[3-(trifluoromethoxy)phenyl]-1,2,3,4-tetrahydropyrrolo[1,2-a]pyrazin-8-yl}benzonitrile [(I), R2=3-(trifluoromethoxy)phenyl, R3=H, R4=benzonitrile, A=—CH$_2$(CH$_3$)$_2$]

$^1$H NMR (400 MHz, DMSO-d$_6$) δ 7.70-7.75 (m, 2H), 7.68 (d, J=4.40 Hz, 1H), 7.49-7.50 (m, 1H), 7.33-7.42 (m, 3H), 7.13 (dd, J=1.56, 7.97 Hz, 2H), 6.79 (s, 1H), 4.04 (td, J=3.50, 7.46 Hz, 1H), 3.67 (dd, J=3.30, 13.37 Hz, 1H), 3.44-3.53 (m, 1H), 2.17 (qd, J=6.85, 14.06 Hz, 1H), 0.99 (d, J=6.78 Hz, 3H), 0.91 (d, J=6.78 Hz, 3H).

LCMS (HPLC Method 2): m/z 440 [M+H]$^+$@r.t. 6.98 min.
HRMS (ESI) calcd for C$_{24}$H$_{21}$F$_3$N$_3$O$_2$[M+H]$^+$ 440.1581 found 440.159.

(4S)-6-(4-hydroxyphenyl)-4-(propan-2-yl)-7-[3-(trifluoromethoxy)phenyl]-3,4-dihydropyrrolo[1,2-a]pyrazin-1(2H)-one [(I), R2=3-(trifluoromethoxy)phenyl, R3=4-hydroxyphenyl, R4=H, A=—CH$_2$(CH$_3$)$_2$](cpd 108)

$^1$H NMR (600 MHz, DMSO-d$_6$) δ 9.38-9.97 (m, 1H), 7.64 (d, J=5.13 Hz, 1H), 7.31-7.38 (m, 1H), 7.25 (d, J=8.24 Hz, 1H), 7.12 (d, J=7.88 Hz, 2H), 7.06 (d, J=8.24 Hz, 1H), 6.99 (s, 1H), 6.93 (s, 1H), 6.84 (d, J=8.61 Hz, 2H), 3.96 (dd, J=3.85, 7.51 Hz, 1H), 3.80 (dd, J=4.03, 13.37 Hz, 1H), 3.46 (dd, J=5.49, 13.19 Hz, 1H), 1.85 (qd, J=6.98, 14.06 Hz, 1H), 0.73 (d, J=6.78 Hz, 3H), 0.46 (d, J=6.96 Hz, 3H).

LCMS (HPLC Method 2): m/z 431 [M+H]$^+$@r.t. 6.11 min.
HRMS (ESI) calcd for C$_{23}$H$_{22}$F$_3$N$_2$O$_3$[M+H]$^+$ 431.1577 found 431.1567.

(4S)-8-(4-hydroxyphenyl)-4-(propan-2-yl)-7-[3-(trifluoromethoxy)phenyl]-3,4-dihydropyrrolo[1,2-a]pyrazin-1(2H)-one [(I), R2=3-(trifluoromethoxy)phenyl, R3=H, R4=4-hydroxyphenyl, A=—CH$_2$(CH$_3$)$_2$]

$^1$H NMR (600 MHz, DMSO-d$_6$) δ 9.25 (br. s., 1H), 7.47 (d, J=4.40 Hz, 1H), 7.40 (s, 1H), 7.32 (t, J=7.97 Hz, 1H), 7.14 (d, J=8.43 Hz, 1H), 7.06 (d, J=8.42 Hz, 1H), 6.97 (d, J=8.61 Hz, 2H), 6.88 (s, 1H), 6.60-6.66 (m, 2H), 3.92-4.00 (m, 1H), 3.63 (dd, J=3.57, 13.10 Hz, 1H), 3.42-3.47 (m, 1H), 2.10-2.20 (m, 1H), 0.99 (d, J=6.78 Hz, 3H), 0.89 (d, J=6.78 Hz, 3H). LCMS (HPLC Method 2): m/z 431 [M+H]$^+$@r.t. 6.45 min.
HRMS (ESI) calcd for C$_{23}$H$_{22}$F$_3$N$_2$O$_3$[M+H]$^+$ 431.1577 found 431.1576.

Example 40

(4S)-4-(2-aminoethyl)-6-(thiophen-3-yl)-7-[3-(trifluoromethoxy)phenyl]-3,4-dihydropyrrolo[1,2-a]pyrazin-1(2H)-one hydrochloride [(I), R2=3-(trifluoromethoxy)phenyl, R3=thiophen-3-yl, R4=H, A=—CH$_2$CH$_2$—NH$_2$](cpd 85)

Conv. r

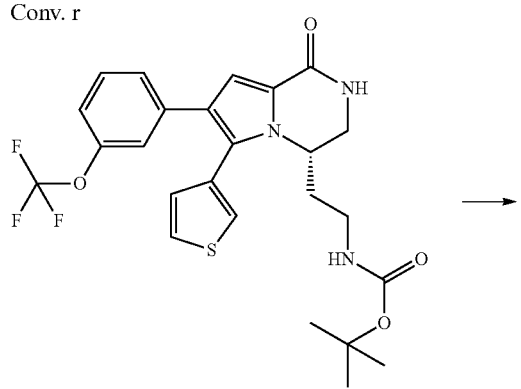

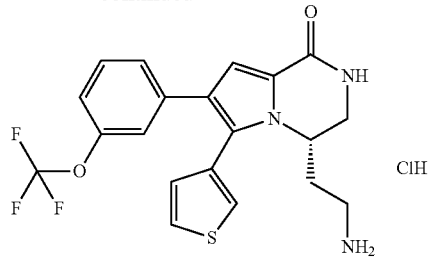

A solution of tert-butyl(2-{(4S)-1-oxo-6-(thiophen-3-yl)-7-[3-(trifluoromethoxy)phenyl]-1,2,3,4-tetrahydropyrrolo[1,2-a]pyrazin-4-yl}ethyl)carbamate (0.012 g, 0.023 mmol) in 4M HCl in 1,4-dioxane (1 ml) was stirred at room temperature for 1 h. The solvent was removed under vacuo, giving the title compound (9.6 g, 99%).

$^1$H NMR (600 MHz, DMSO-d6) δ 7.79 (d, J=4.76 Hz, 1H), 7.77 (dd, J=4.85, 2.84 Hz, 1H), 7.73-7.75 (m, 1H), 7.64 (br. s., 3H), 7.35-7.40 (m, 1H), 7.29 (d, J=7.88 Hz, 1H), 7.11 (d, J=8.24 Hz, 1H), 7.06-7.09 (m, 2H), 6.95 (s, 1H), 4.17-4.43 (m, 1H), 3.80 (dd, J=13.28, 3.94 Hz, 1H), 3.35 (m, J=5.13 Hz, 1H), 2.41-2.48 (m, 2H), 1.89-1.98 (m, 1H), 1.83 (td, J=12.27, 6.23 Hz, 1H).

LCMS (HPLC Method 2): m/z 422 [M+H]$^+$@r.t. 5.06 min.
HRMS (ESI) calcd for C$_{20}$H$_{19}$F$_3$N$_3$O$_2$S [M+H]$^+$ 422.1145 found 422.1145.

Working according to the same procedure, the following compounds were prepared:

(4S)-4-(2-aminoethyl)-6-phenyl-7-[3-(trifluoromethoxy)phenyl]-3,4-dihydropyrrolo[1,2-a]pyrazin-1(2H)-one hydrochloride [(I), R2=3-(trifluoromethoxy)phenyl, R3=phenyl, R4=H, A=—CH$_2$CH$_2$—NH$_2$](cpd 87)

$^1$H NMR (600 MHz, DMSO-d6) δ 7.80 (d, J=4.95 Hz, 1H), 7.59 (br. s., 3H), 7.46-7.54 (m, 3H), 7.37-7.41 (m, 2H), 7.32-7.37 (m, 1H), 7.25 (d, J=8.06 Hz, 1H), 7.03-7.15 (m, 2H), 6.87 (s, 1H), 4.32 (m, J=3.48 Hz, 1H), 3.86 (dd, J=13.37, 3.85 Hz, 1H), 3.20-3.47 (m, 1H), 2.24-2.47 (m, 2H), 1.83-1.92 (m, 1H), 1.77 (tt, J=12.45, 5.95 Hz, 1H).

LCMS (HPLC Method 2): m/z 416 [M+H]$^+$@r.t. 5.32 min.
HRMS (ESI) calcd for C$_{22}$H$_{21}$F$_3$N$_3$O$_2$[M+H]$^+$ 416.1581 found 416.1578.

(4S)-4-(2-aminoethyl)-6-(3-methylphenyl)-7-[3-(trifluoromethoxy)phenyl]-3,4-dihydropyrrolo[1,2-a]pyrazin-1(2H)-one hydrochloride [(I), R2=3-(trifluoromethoxy)phenyl, R3=3-methylphenyl, R4=H, A=—CH$_2$CH$_2$—NH$_2$](cpd 92)

$^1$H NMR (600 MHz, DMSO-d6) δ 7.79 (d, J=4.94 Hz, 1H), 7.60 (br. s., 3H), 7.37-7.42 (m, 1H), 7.33-7.37 (m, 1H), 7.32 (d, J=7.69 Hz, 1H), 7.27 (d, J=7.88 Hz, 1H), 7.21 (s, 1H), 7.17 (d, J=7.51 Hz, 1H), 7.02-7.12 (m, 2H), 6.88 (s, 1H), 4.32 (m, J=3.85 Hz, 1H), 3.85 (dd, J=13.28, 3.94 Hz, 1H), 3.28-3.38 (m, 1H), 2.45-2.36 (m, 2H), 2.33 (s, 3H), 1.81-1.92 (m, 1H), 1.71-1.81 (m, 1H).

LCMS (HPLC Method 2): m/z 430 [M+H]$^+$@r.t. 5.56 min.
HRMS (ESI) calcd for C$_{23}$H$_{23}$F$_3$N$_3$O$_2$[M+H]$^+$ 430.1737 found 430.1734.

(4S)-4-(2-aminoethyl)-6-(4-hydroxyphenyl)-7-[3-(trifluoromethoxy)phenyl]-3,4-dihydropyrrolo[1,2-a]pyrazin-1(2H)-one hydrochloride [(I), R2=3-(trifluoromethoxy)phenyl, R3=4-hydroxyphenyl, R4=H, A=—CH$_2$CH$_2$—NH$_2$](cpd 93)

$^1$H NMR (600 MHz, DMSO-d6) δ 9.83 (br. s., 1H), 7.74 (d, J=5.13 Hz, 1H), 7.53-7.67 (m, 3H), 7.32-7.37 (m, 1H), 7.25 (d, J=8.06 Hz, 1H), 7.17 (d, J=8.42 Hz, 2H), 7.03-7.10 (m,

2H), 6.94 (s, 1H), 6.88 (d, J=8.61 Hz, 2H), 4.28 (m, J=3.85 Hz, 1H), 3.82 (dd, J=13.37, 4.03 Hz, 1H), 2.36-2.47 (m, 2H), 1.82-1.93 (m, 1H), 1.64-1.81 (m, 1H).

LCMS (HPLC Method 2): m/z 432 [M+H]$^+$@r.t. 4.88 min.

HRMS (ESI) calcd for $C_{22}H_{21}F_3N_3O_3$[M+H]$^+$ 432.1530 found 432.1535.

(4S)-4-(2-aminoethyl)-6-(4-fluorophenyl)-7-[3-(trifluoromethoxy)phenyl]-3,4-dihydropyrrolo[1,2-a]pyrazin-1(2H)-one hydrochloride [(I), R2=3-(trifluoromethoxy)phenyl, R3=4-fluorophenyl, R4=H, A=—CH$_2$CH$_2$—NH$_2$](cpd 94)

$^1$H NMR (600 MHz, DMSO-d6) δ 7.80 (d, J=5.13 Hz, 1H), 7.59 (br. s., 3H), 7.42-7.47 (m, 2H), 7.36 (dt, J=12.27, 8.43 Hz, 3H), 7.25 (d, J=7.88 Hz, 1H), 7.05-7.14 (m, 2H), 6.87 (s, 1H), 4.23-4.36 (m, 1H), 3.86 (dd, J=13.37, 4.03 Hz, 1H), 2.37-2.48 (m, 2H), 1.82-1.94 (m, 1H), 1.64-1.79 (m, 1H).

LCMS (HPLC Method 2): m/z 434 [M+H]$^+$@r.t. 5.43 min.

HRMS (ESI) calcd for $C_{22}H_{20}F_4N_3O_2$[M+H]$^+$ 434.1486 found 434.1487.

(4S)-6-(4-acetyl phenyl)-4-(2-aminoethyl)-7-[3-(trifluoromethoxy)phenyl]-3,4-dihydropyrrolo[1,2-a]pyrazin-1(2H)-one hydrochloride [(I), R2=3-(trifluoromethoxy)phenyl, R3=4-acetylphenyl, R4=H, A=—CH$_2$CH$_2$—NH$_2$](cpd 95)

$^1$H NMR (600 MHz, DMSO-d6) δ 8.05 (d, J=8.43 Hz, 2H), 7.85 (d, J=5.13 Hz, 1H), 7.56 (br. s., 3H), 7.54 (d, J=8.06 Hz, 2H), 7.34-7.39 (m, 1H), 7.21 (d, J=7.88 Hz, 1H), 7.05-7.16 (m, 2H), 6.91 (s, 1H), 4.39 (d, J=3.48 Hz, 1H), 3.90 (dd, J=13.55, 3.85 Hz, 1H), 2.62 (s, 3H), 2.30-2.46 (m, 2H), 1.69-1.91 (m, 2H).

LCMS (HPLC Method 2): m/z 458 [M+H]$^+$@r.t. 5.21 min.

HRMS (ESI) calcd for $C_{24}H_{23}F_3N_3O_3$[M+H]$^+$ 458.1686 found 458.1671.

(4S)-4-(2-aminoethyl)-6-[4-(methylsulfonyl)phenyl]-7-[3-(trifluoromethoxy)phenyl]-3,4-dihydropyrrolo[1,2-a]pyrazin-1(2H)-one hydrochloride [(I), R2=3-(trifluoromethoxy)phenyl, R3=4-(methylsulfonyl)phenyl, R4=H, A=—CH$_2$CH$_2$—NH$_2$](cpd 96)

$^1$H NMR (600 MHz, DMSO-d6) δ 8.03 (d, J=8.43 Hz, 2H), 7.88 (d, J=5.13 Hz, 1H), 7.66 (d, J=8.24 Hz, 2H), 7.55 (br. s., 3H), 7.38-7.42 (m, 1H), 7.26 (d, J=8.06 Hz, 1H), 7.14 (d, J=8.43 Hz, 1H), 7.11 (s, 1H), 6.84 (br.s., 1H), 4.40 (br. s., 1H), 3.90 (dd, J=13.55, 3.85 Hz, 1H), 3.26 (s, 3H), 2.39-2.47 (m, 2H), 1.68-1.92 (m, 2H).

LCMS (HPLC Method 2): m/z 494 [M+H]$^+$@r.t. 4.98 min.

HRMS (ESI) calcd for $C_{23}H_{23}F_3N_3O_4S$ [M+H]$^+$ 494.1356 found 494.1345.

4-{(4S)-4-(2-aminoethyl)-1-oxo-7-[3-(trifluoromethoxy)phenyl]-1,2,3,4-tetrahydropyrrolo[1,2-a]pyrazin-6-yl}benzaldehyde hydrochloride [(I), R2=3-(trifluoromethoxy)phenyl, R3=4-formylphenyl, R4=H, A=—CH$_2$CH$_2$—NH$_2$](cpd 97)

$^1$H NMR (600 MHz, DMSO-d6) δ 10.11 (s, 1H), 8.02 (d, J=8.24 Hz, 2H), 7.87 (d, J=4.94 Hz, 1H), 7.62 (d, J=8.06 Hz, 2H), 7.52-7.60 (m, 3H), 7.34-7.42 (m, 1H), 7.22 (d, J=7.69 Hz, 1H), 7.09-7.14 (m, 2H), 6.90 (s, 1H), 4.41 (br. s., 1H), 3.91 (dd, J=13.37, 3.85 Hz, 1H), 3.35-3.38 (m, 1H), 2.33-2.46 (m, 2H), 1.68-1.91 (m, 2H).

LCMS (HPLC Method 2): m/z 444 [M+H]$^+$@r.t. 5.17 min.

HRMS (ESI) calcd for $C_{23}H_{21}F_3N_3O_3$[M+H]$^+$ 444.1530 found 444.1543.

4-{(4S)-4-(2-aminoethyl)-1-oxo-7-[3-(trifluoromethoxy)phenyl]-1,2,3,4-tetrahydropyrrolo[1,2-a]pyrazin-8-yl}benzaldehyde hydrochloride [(I), R2=3-(trifluoromethoxy)phenyl, R3=H, R4=4-formylphenyl, A=—CH$_2$CH$_2$—NH$_2$](cpd 98)

LCMS (HPLC Method 2): m/z 444 [M+H]$^+$@r.t. 5.56 min.

(4S)-4-(3-aminopropyl)-6-phenyl-7-[3-(trifluoromethoxy)phenyl]-3,4-dihydropyrrolo[1,2-a]pyrazin-1(2H)-one hydrochloride [(I), R2=3-(trifluoromethoxy)phenyl, R3=phenyl, R4=H, A=—CH$_2$CH$_2$CH$_2$—NH$_2$](cpd 102)

$^1$H NMR (400 MHz, DMSO-d$_6$) δ 7.75 (d, J=5.0 Hz, 1H), 7.57 (d, J=2.9 Hz, 3H), 7.47-7.52 (m, 3H), 7.39-7.43 (m, 2H), 7.35 (m, 1H), 7.25 (m, 2H), 7.02-7.11 (m, 2H), 6.87 (m, 1H), 4.14-4.28 (m, 1H), 3.86 (dd, J=3.91, 13.3 Hz, 1H), 3.29-3.41 (m, 1H), 2.45 (br. s., 2H), 1.57-1.73 (m, 1H), 1.38-1.52 (m, 1H), 1.13-1.30 (m, 2H).

LCMS (HPLC Method 2): m/z 430 [M+H]$^+$@r.t. 5.61 min.

HRMS (ESI) calcd for $C_{23}H_{23}F_3N_3O_2$[M+H]$^+$ 430.1737 found 430.1741.

(4S)-4-(3-aminopropyl)-6-(thiophen-3-yl)-7-[3-(trifluoromethoxy)phenyl]-3,4-dihydropyrrolo[1,2-a]pyrazin-1(2H)-one hydrochloride [(I), R2=3-(trifluoromethoxy)phenyl, R3=thiophen-yl, R4=H, A=—CH$_2$CH$_2$CH$_2$—NH$_2$](cpd 103)

$^1$H NMR (400 MHz, DMSO-d$_6$) δ 7.71-7.77 (m, 3H), 7.61 (br. s., 3), 7.34-7.42 (m, 1H), 7.25-7.32 (m, 1H), 7.08-7.13 (m, 2H), 7.06 (s, 1H), 6.95 (s, 1H), 4.19 (m, 1H), 3.80 (dd, J=3.91, 13.30 Hz, 1H), 2.53-2.62 (m, 2H), 1.64-1.79 (m, 1H), 1.44-1.60 (m, 1H), 1.17-1.40 (m, 2H).

LCMS (HPLC Method 2): m/z 436 [M+H]$^+$@r.t. 5.51 min.

HRMS (ESI) calcd for $C_{21}H_{21}F_3N_3O_2S$ [M+H]$^+$ 436.1301 found 436.1307.

(4S)-4-(3-aminopropyl)-6-(4-hydroxyphenyl)-7-[3-(trifluoromethoxy)phenyl]-3,4-dihydropyrrolo[1,2-a]pyrazin-1(2H)-one hydrochloride [(I), R2=3-(trifluoromethoxy)phenyl, R3=4-hydroxyphenyl, R4=H, A=—CH$_2$CH$_2$CH$_2$—NH$_2$](cpd 104)

$^1$H NMR (400 MHz, DMSO-d$_6$) δ 9.80 (br. s., 1H), 7.66-7.72 (m, 1H), 7.59 (br. s., 3H), 7.31-7.37 (m, 1H), 7.25 (d, J=8.06 Hz, 1H), 7.18 (d, J=8.54 Hz, 2H), 7.05-7.09 (m, 1H), 7.04 (s, 1H), 6.91-6.95 (m, 1H), 6.87 (d, J=8.67 Hz, 2H), 4.17 (m, 1H), 3.82 (dd, J=3.78, 13.06 Hz, 1H), 3.29-3.42 (m, 1H), 2.42-2.56 (m, 2H), 1.59-1.74 (m, 1H), 1.39-1.52 (m, 1H), 1.24 (quin, J=7.75 Hz, 2H).

LCMS (HPLC Method 2): m/z 446 [M+H]$^+$@r.t. 5.12 min.

HRMS (ESI) calcd for $C_{23}H_{23}F_3N_3O_3$[M+H]$^+$ 446.1686 found 446.1702.

(4S)-4-(3-aminopropyl)-6-[4-(hydroxymethyl)phenyl]-7-[3-(trifluoromethoxy)phenyl]-3,4-dihydropyrrolo[1,2-a]pyrazin-1(2H)-one hydrochloride
[(I), R2=3-(trifluoromethoxy)phenyl, R3=4-(hydroxymethyl)phenyl, R4=H, A=—CH$_2$CH$_2$CH$_2$—NH$_2$](cpd 105)

$^1$H NMR (400 MHz, DMSO-d$_6$) δ 7.74 (d, J=4.88 Hz, 1H), 7.60 (br. s., 3H), 7.40-7.46 (m, 2H), 7.26-7.38 (m, 3H), 7.18-7.24 (m, 1H), 7.08 (td, J=1.08, 8.33 Hz, 1H), 7.06 (s, 1H), 6.95 (br. s., 1H), 4.58 (s, 2H), 4.20 (m, 1H), 3.85 (dd, J=4.03, 13.43 Hz, 1H), 3.30-3.45 (m, 1H) 2.41-2.49 (m, 1H), 1.56-1.70 (m, 1H), 1.40-1.53 (m, 1H), 1.14-1.30 (m, 2H).

LCMS (HPLC Method 2): m/z 460 [M+H]$^+$@r.t. 5.06 min.

HRMS (ESI) calcd for $C_{24}H_{25}F_3N_3O_3$[M+H]$^+$ 460.1843 found 460.1847.

(4S)-4-(3-aminopropyl)-6-[4-(methylsulfonyl)phenyl]-7-[3-(trifluoromethoxy)phenyl]-3,4-dihydropyrrolo[1,2-a]pyrazin-1(2H)-one hydrochloride [(I), R2=3-(trifluoromethoxy)phenyl, R3=4-(methylsulfonyl)phenyl, R4=H, A=—CH$_2$CH$_2$CH$_2$NH$_2$](cpd 109)

¹H NMR (600 MHz, DMSO-d6) δ 8.02 (d, J=8.43 Hz, 2H), 7.84 (d, J=4.95 Hz, 1H), 7.67 (d, J=8.24 Hz, 2H), 7.57 (br. s., 3H), 7.36-7.42 (m, 2H), 7.22-7.29 (m, 2H), 7.13 (d, J=7.69 Hz, 1H), 7.09 (s, 1H), 6.72-6.93 (m, 1H), 4.23-4.30 (m, J=4.03 Hz, 1H), 3.90 (dd, J=3.75, 12.91 Hz, 1H), 3.26 (s, 3H), 1.60-1.70 (m, 1H), 1.44-1.53 (m, 1H), 1.11-1.28 (m, 2H). LCMS (HPLC Method 2): m/z 508 [M+H]⁺@r.t. 4.17 min.

HRMS (ESI) calcd for $C_{24}H_{25}F_3N_3O_4S$ [M+H]⁺ 508.1513 found 508.1517.

(4S)-6-(4-acetyl phenyl)-4-(3-aminopropyl)-7-[3-(trifluoromethoxy)phenyl]-3,4-dihydropyrrolo[1,2-a]pyrazin-1 (2H)-one hydrochloride [(I), R2=3-(trifluoromethoxy)phenyl, R3=4-acetylphenyl, R4=H, A=—CH₂CH₂CH₂NH₂] (cpd 110)

¹H NMR (600 MHz, DMSO-d6) δ 8.04 (d, J=8.42 Hz, 2H), 7.82 (d, J=4.95 Hz, 1H), 7.55 (d, J=8.24 Hz, 5H), 7.36 (t, J=8.06 Hz, 1H), 7.21 (d, J=7.69 Hz, 1H), 7.12 (dd, J=0.73, 8.24 Hz, 1H), 7.08 (s, 1H), 6.91 (s, 1H), 4.22-4.31 (m, J=3.48 Hz, 1H), 3.90 (dd, J=4.03, 13.19 Hz, 1H), 2.63 (s, 3H), 2.41-2.48 (m, 1H), 1.57-1.70 (m, J=5.77, 10.90 Hz, 1H), 1.41-1.51 (m, 1H), 1.11-1.26 (m, 2H).

LCMS (HPLC Method 2): m/z 472 [M+H]⁺@r.t. 4.38 min.

HRMS (ESI) calcd for $C_{25}H_{25}F_3N_3O_3$[M+H]⁺ 472.1843 found 472.1847.

(4S)-4-(3-aminopropyl)-6-(4-fluorophenyl)-7-[3-(trifluoromethoxy)phenyl]-3,4-dihydropyrrolo[1,2-a]pyrazin-1 (2H)-one hydrochloride [(I), R2=3-(trifluoromethoxy)phenyl, R3=4-fluorophenyl, R4=H, A=—CH₂CH₂CH₂NH₂] (cpd 111)

¹H NMR (600 MHz, DMSO-d6) δ 7.76 (d, J=4.52 Hz, 1H), 7.58 (br. s., 3H), 7.42-7.48 (m, 2H), 7.30-7.40 (m, 3H), 7.22-7.28 (m, 1H), 7.09 (d, J=8.42 Hz, 1H), 7.06 (s, 1H), 6.87 (s, 1H), 4.12-4.22 (m, 1H), 3.82-3.90 (m, 1H), 3.37-3.40 (m, 2H) 1.57-1.71 (m, 1H), 1.40-1.52 (m, 1H), 1.14-1.29 (m, J=8.79 Hz, 2H).

LCMS (HPLC Method 2): m/z 448 [M+H]⁺@r.t. 5.68 min.

HRMS (ESI) calcd for $C_{23}H_{22}F_4N_3O_2$[M+H]⁺ 448.1643 found 448.1657.

(4S)-4-(2-aminoethyl)-6-(1H-indol-5-yl)-7-[3-(trifluoromethoxy)phenyl]-3,4-dihydropyrrolo[1,2-a]pyrazin-1 (2H)-one trifluoroacetate [(I), R2=3-(trifluoromethoxy)phenyl, R3=1H-indol-5-yl, R4=H, A=—CH₂CH₂CH₂—NH₂]

LCMS (HPLC Method 2): m/z 455 [M+H]⁺@r.t. 5.32 min.

HRMS (ESI) calcd for $C_{24}H_{21}F_3N_4O_2$[M+H]⁺ 455.169 found 455.1678.

(4S)-4-(2-aminoethyl)-6-(1,3-benzodioxol-5-yl)-7-[3-(trifluoromethoxy)phenyl]-3,4-dihydropyrrolo[1,2-a]pyrazin-1(2H)-one hydrochloride [(I), R2=3-(trifluoromethoxy)phenyl, R3=1,3-benzodioxol-5-yl, R4=H, A=—CH₂CH₂CH₂—NH₂](cpd 112)

¹H NMR (600 MHz, DMSO-d₆) δ 7.77 (d, J=4.76 Hz, 1H), 7.57 (br. s., 3H), 7.35-7.39 (m, 1H), 7.26 (d, J=7.88 Hz, 1H), 7.10 (d, J=7.14 Hz, 1H), 7.07 (s, 1H), 7.04 (d, J=8.06 Hz, 1H), 6.92-6.98 (m, 2H), 6.85 (d, J=8.06 Hz, 1H), 6.10 (d, J=13.92 Hz, 1H), 4.35 (d, J=3.85 Hz, 1H), 3.85 (dd, J=3.94, 13.46 Hz, 1H), 2.40-2.47 (m, 1H), 1.71-1.95 (m, 2H). LCMS (HPLC Method 2): m/z 460 [M+H]⁺@r.t. 5.42 min.

HRMS (ESI) calcd for $C_{23}H_{21}F_3N_3O_4$[M+H]⁺ 460.1479 found 460.148.

(4S)-4-(2-aminoethyl)-6-(3-fluoro-4-methoxyphenyl)-7-[3-(trifluoromethoxy)phenyl]-3,4-dihydropyrrolo[1,2-a]pyrazin-1(2H)-one hydrochloride

[(I), R2=3-(trifluoromethoxy)phenyl, R3=3-fluoro-4-methoxyphenyl, R4=H, A=—CH₂CH₂CH₂—NH₂](cpd 113)

¹H NMR (600 MHz, DMSO-d₆) δ 7.79 (d, J=4.95 Hz, 1H), 7.56 (br. s., 3H), 7.36 (dd, J=7.88, 7.88 Hz, 1H), 7.22-7.31 (m, 3H), 7.16 (d, J=7.88 Hz, 1H), 7.11 (d, J=7.88 Hz, 1H), 7.07 (s, 1H), 6.91 (s, 1H), 4.35 (t, J=7.60 Hz, 1H), 3.89 (s, 3H), 3.87 (dd, J=3.94, 13.46 Hz, 1H), 3.34-3.36 (m, 1H), 2.38-2.48 (m, 2H), 1.81-1.91 (m, 1H), 1.69-1.80 (m, 1H). LCMS (HPLC Method 2): m/z 464 [M+H]⁺@r.t. 5.56 min.

HRMS (ESI) calcd for $C_{23}H_{22}F_4N_3O_3$[M+H]⁺ 464.1592 found 464.1578.

(4S)-4-(2-aminoethyl)-6-[4-(2-methylpropoxy)phenyl]-7-[3-(trifluoromethoxy)phenyl]-3,4-dihydropyrrolo[1,2-a]pyrazin-1(2H)-one hydrochloride

[(I), R2=3-(trifluoromethoxy)phenyl, R3=4-(2-methylpropoxy)phenyl, R4=H, A=—CH₂CH₂CH₂—NH₂](cpd 114)

¹H NMR (600 MHz, DMSO-d₆) δ 7.76 (d, J=5.13 Hz, 1H), 7.59 (br. s., 3H), 7.32-7.38 (m, 1H), 7.29 (d, J=8.24 Hz, 2H), 7.25 (d, J=7.88 Hz, 1H), 7.01-7.11 (m, 4H), 6.90 (s, 1H), 4.23-4.39 (m, 1H), 3.84 (dd, J=3.85, 13.37 Hz, 1H), 3.76-3.82 (m, 2H), 3.34-3.36 (m, 1H), 2.38-2.47 (m, 2H), 2.05 (td, J=7.03, 13.60 Hz, 1H), 1.62-1.93 (m, 2H), 1.00 (d, J=6.59 Hz, 6H). LCMS (HPLC Method 2): m/z 488 [M+H]⁺@r.t. 6.55 min.

HRMS (ESI) calcd for $C_{26}H_{29}F_3N_3O_3$[M+H]⁺ 464.1592 found 464.1578.

(4S)-4-(2-aminoethyl)-6-[4-(dimethylamino)phenyl]-7-[3-(trifluoromethoxy)phenyl]-3,4-dihydropyrrolo[1,2-a]pyrazin-1(2H)-one hydrochloride

[(I), R2=3-(trifluoromethoxy)phenyl, R3=4-(dimethylamino)phenyl, R4=H, A=—CH₂CH₂CH₂—NH₂](cpd 115)

¹H NMR (600 MHz, DMSO-d₆) δ 7.73 (d, J=4.88 Hz, 1H), 7.63 (br. s., 3H), 7.31-7.36 (m, 1H), 7.21-7.26 (m, 1H), 7.17 (d, J=8.67 Hz, 2H), 7.04-7.09 (m, 2H), 6.97 (s, 1H), 6.83 (d, J=8.67 Hz, 2H), 4.27-4.36 (m, 1H), 3.83 (dd, J=3.78, 13.18 Hz, 1H), 3.33 (dd, J=5.13, 13.18 Hz, 2H), 2.97 (s, 6H), 2.41 (ddd, J=6.04, 11.60, 17.52 Hz, 1H), 1.76-1.93 (m, 1H). LCMS (HPLC Method 2): m/z 459 [M+H]⁺@r.t. 4.78 min.

HRMS (ESI) calcd for $C_{24}H_{26}F_3N_4O_2$[M+H]⁺ 459.2003 found 459.2009.

(4S)-4-(2-aminoethyl)-6-(4-methoxyphenyl)-7-[3-(trifluoromethoxy)phenyl]-3,4-dihydropyrrolo[1,2-a]pyrazin-1(2H)-one hydrochloride [(I), R2=3-(trifluoromethoxy)phenyl, R3=4-methoxyphenyl, R4=H, A=—CH₂CH₂CH₂—NH₂](cpd 116)

¹H NMR (600 MHz, DMSO-d6) δ 7.77 (d, J=4.95 Hz, 1H), 7.49 (br. s., 3H), 7.33-7.37 (m, 1H), 7.31 (d, J=8.43 Hz, 2H), 7.23 (d, J=7.88 Hz, 1H), 7.03-7.11 (m, 4H), 6.92 (s, 1H), 4.28-4.33 (m, 1H), 3.85 (dd, J=3.85, 13.37 Hz, 1H), 3.81 (s, 3H), 2.38-2.48 (m, 2H), 1.70-1.90 (m, 2H). LCMS (HPLC Method 2): m/z 446 [M+H]⁺@r.t. 4.55 min.

HRMS (ESI) calcd for $C_{23}H_{23}F_3N_3O_2$[M+H]⁺ 446.1686 found 446.1693.

(4S)-4-(2-aminoethyl)-8-[4-(methylsulfonyl)phenyl]-7-[3-(trifluoromethoxy)phenyl]-3,4-dihydropyrrolo[1,2-a]pyrazin-1(2H)-one hydrochloride

[(I), R2=3-(trifluoromethoxy)phenyl, R3=H, R4=4-(methylsulfonyl)phenyl, A=—CH₂CH₂CH₂—NH₂]

¹H NMR (600 MHz, DMSO-d₆) δ 7.81 (d, J=8.42 Hz, 5H), 7.56 (s, 1H), 7.44 (d, J=8.42 Hz, 2H), 7.39 (t, J=8.06 Hz, 1H), 7.14 (t, J=8.06 Hz, 2H), 6.79 (s, 1H), 4.52 (m, 1H), 3.77 (dd, J=3.94, 12.18 Hz, 1H), 3.20 (s, 3H), 2.77-3.04 (m, 2H), 2.36-2.39 (m, 1H), 2.02-2.20 (m, 2H). LCMS (HPLC Method 2): m/z 494 [M+H]⁺@r.t. 3.86 min.

HRMS (ESI) calcd for $C_{23}H_{23}F_3N_3O_4S$ [M+H]⁺ 494.1356 found 446.1361.

(4S)-4-(2-aminoethyl)-6-(2-aminopyrimidin-5-yl)-7-[3-(trifluoromethoxy)phenyl]-3,4-dihydropyrrolo[1,2-a]pyrazin-1(2H)-one dihydrochloride

[(I), R2=3-(trifluoromethoxy)phenyl, R3=2-aminopyrimidin-5-yl, R4=H, A=—CH₂CH₂CH₂—NH₂](cpd 117)

¹H NMR (600 MHz, DMSO-d₆) δ 8.19 (m, 2H), 7.76 (d, J=4.94 Hz, 1H), 7.37-7.43 (m, 1H), 7.27 (d, J=7.88 Hz, 1H), 7.12 (d, J=8.61 Hz, 1H), 7.01-7.05 (m, 2H), 6.98 (s, 2H), 4.31 (br. s., 1H), 3.80 (dd, J=3.75, 13.28 Hz, 1H), 3.32-3.34 (m, 1H), 2.49-2.52 (m, 2H), 1.68-1.93 (m, 2H). LCMS (HPLC Method 2): m/z 433 [M+H]⁺@r.t. 3.49 min.

HRMS (ESI) calcd for $C_{20}H_{21}F_3N_6O_2$[M+H]⁺ 433.4112 found 433.4110.

(4S)-4-(2-aminoethyl)-6-(naphthalen-2-yl)-7-[3-(trifluoromethoxy)phenyl]-3,4-dihydropyrrolo[1,2-a]pyrazin-1(2H)-one hydrochloride [(I), R2=3-(trifluoromethoxy)phenyl, R3=naphthalen-2-yl, R4=H, A=—CH₂CH₂CH₂—NH₂] (cpd 118)

¹H NMR (600 MHz, DMSO-d₆) δ 7.99-8.07 (m, 3H), 7.96 (d, J=7.69 Hz, 1H), 7.83 (d, J=5.13 Hz, 1H), 7.52-7.65 (m, 5H), 7.40-7.45 (m, 1H), 7.29-7.35 (dd, J=8.06, 8.05 Hz, 1H), 7.23 (d, J=8.06 Hz, 1H), 7.15 (s, 1H), 7.05-7.09 (dd, J=1.01, 8.05 Hz, 1H), 6.93 (s, 1H), 4.43-4.53 (m, J=3.66 Hz, 1H), 3.91 (dd, J=5.13, 13.37 Hz, 1H), 2.29-2.46 (m, 2H), 1.83-1.96 (m, 1H), 1.69-1.82 (m, 1H).

LCMS (HPLC Method 2): m/z 466 [M+H]⁺@r.t. 5.92 min.
HRMS (ESI) calcd for $C_{26}H_{23}F_3N_3O_2$[M+H]⁺ 466.1737 found 466.1738.

(4S)-4-(2-aminoethyl)-6-(biphenyl-3-yl)-7-[3-(trifluoromethoxy)phenyl]-3,4-dihydropyrrolo[1,2-a]pyrazin-1(2H)-one hydrochloride [(I), R2=3-(trifluoromethoxy)phenyl, R3=biphenyl-3-yl, R4=H, A=—CH₂CH₂CH₂—NH₂] (cpd 119)

¹H ¹H NMR (600 MHz, DMSO-d₆) δ 7.81 (d, J=5.13 Hz, 1H), 7.79 (d, J=8.43 Hz, 1H), 7.52-7.67 (m, 7H), 7.45 (dd, J=8.06, 7.69 Hz, 2H), 7.34-7.42 (m, 3H), 7.30 (d, J=8.06 Hz, 1H), 7.12 (s, 1H), 7.10 (d, J=8.07 Hz, 1H), 6.92 (s, 1H), 4.28-4.53 (m, 1H), 3.93 (dd, J=5.13, 13.28 Hz, 1H), 3.39 (m, 1H), 2.30-2.48 (m, 2H), 1.74-1.93 (m, 2H). LCMS (HPLC Method 2): m/z 492 [M+H]⁺@r.t. 6.21 min.

HRMS (ESI) calcd for $C_{26}H_{23}F_3N_3O_2$[M+H]⁺ 492.1894 found 492.1898.

4-{(4S)-4-(2-aminoethyl)-1-oxo-7-[3-(trifluoromethoxy)phenyl]-1,2,3,4-tetrahydropyrrolo[1,2-a]pyrazin-6-yl}benzenesulfonamide hydrochloride

[(I), R2=3-(trifluoromethoxy)phenyl, R3=4-phenylsulfonamide, R4=H, A=—CH₂CH₂CH₂—NH₂](cpd 120)

¹H NMR (600 MHz, DMSO-d₆) δ 7.90 (d, J=8.61 Hz, 2H), 7.86 (d, J=4.95 Hz, 1H), 7.55-7.67 (m, 5H), 7.53 (s, 2H), 7.29-7.39 (m, 1H), 7.16 (d, J=8.04 Hz, 1H), 7.14 (d, J=8.08 Hz, 1H), 7.09 (s, 1H), 6.97 (s, 1H), 4.29-4.43 (m, 1H), 3.88 (dd, J=4.95, 13.28 Hz, 1H), 3.42 (m, 1H), 2.29-2.47 (m, 2H), 1.82-1.94 (m, 1H), 1.65-1.81 (m, 1H).

LCMS (HPLC Method 2): m/z 495 [M+H]⁺@r.t. 4.79 min.
HRMS (ESI) calcd for $C_{22}H_{22}F_3N_4O_4S$ [M+H]⁺ 495.1309 found 495.131.

(4S)-4-(2-aminoethyl)-6-(3-fluorophenyl)-7-[3-(trifluoromethoxy)phenyl]-3,4-dihydropyrrolo[1,2-a]pyrazin-1(2H)-one hydrochloride [(I), R2=3-(trifluoromethoxy)phenyl, R3=3-fluorophenyl, R4=H, A=—CH₂CH₂CH₂—NH₂] (cpd 121)

¹H NMR (600 MHz, DMSO-d6) δ 7.83 (d, J=4.95 Hz, 1H), 7.60 (br. s., 3H), 7.51-7.57 (m, 1H), 7.37-7.41 (m, 1H), 7.35 (dt, J=2.29, 8.65 Hz, 1H), 7.27 (d, J=8.24 Hz, 2H), 7.23 (d, J=7.51 Hz, 1H), 7.12 (d, J=8.24 Hz, 1H), 7.10 (s, 1H), 6.87 (s, 1H), 4.28-4.46 (m, 1H), 3.88 (dd, J=4.95, 13.37 Hz, 2H), 3.44-3.50 (m, 1H), 2.33-2.48 (m, 2H), 1.82-1.93 (m, 1H), 1.68-1.80 (m, 1H). LCMS (HPLC Method 2): m/z 434 [M+H]⁺@r.t. 5.49 min.

HRMS (ESI) calcd for $C_{22}H_{21}F_4N_3O_2$[M+H]⁺ 434.1486 found 434.1491.

(4S)-4-(2-aminoethyl)-6-(4-fluoro-3-methylphenyl)-7-[3-(trifluoromethoxy)phenyl]-3,4-dihydropyrrolo[1,2-a]pyrazin-1(2H)-one hydrochloride

[(I), R2=3-(trifluoromethoxy)phenyl, R3=4-fluoro-3-methylphenyl, R4=H, A=—CH₂CH₂CH₂—NH₂](cpd 122)

¹H NMR (600 MHz, DMSO-d6) δ 7.80 (d, J=5.13 Hz, 1H), 7.60 (br. s., 3H), 7.35-7.40 (m, 1H), 7.34 (d, J=6.59 Hz, 1H), 7.25-7.29 (m, 2H), 7.23 (d, J=3.11 Hz, 1H), 7.03-7.13 (m, 2H), 6.87 (s, 1H), 4.24-4.40 (m, 1H), 3.85 (dd, J=4.03, 13.37 Hz, 1H), 3.39 (m, 1H), 2.36-2.48 (m, 2H), 2.25 (s, 3H), 1.81-1.95 (m, 1H), 1.75 (dt, J=5.95, 12.50 Hz, 1H). LCMS (HPLC Method 2): m/z 448 [M+H]⁺@r.t. 5.75 min.

HRMS (ESI) calcd for $C_{23}H_{22}F_4N_3O_2$[M+H]⁺ 448.1643 found 448.1643.

(4S)-4-(2-aminoethyl)-8-(4-fluoro-3-methylphenyl)-7-[3-(trifluoromethoxy)phenyl]-3,4-dihydropyrrolo[1,2-a]pyrazin-1(2H)-one hydrochloride

[(I), R2=3-(trifluoromethoxy)phenyl, R3=H, R4=4-fluoro-3-methylphenyl, A=—CH₂CH₂CH₂—NH₂]

LCMS (HPLC Method 2): m/z 448 [M+H]⁺@r.t. 5.86 min.
HRMS (ESI) calcd for $C_{23}H_{22}F_4N_3O_2$[M+H]⁺ 448.1643 found 448.1642.

(4S)-4-(2-aminoethyl)-6-[4-(methylsulfanyl)phenyl]-7-[3-(trifluoromethoxy)phenyl]-3,4-dihydropyrrolo[1,2-a]pyrazin-1(2H)-one hydrochloride

[(I), R2=3-(trifluoromethoxy)phenyl, R3=4-(methylsulfanyl)phenyl, R4=H, A=—CH₂CH₂CH₂—NH₂](cpd 123)

¹H NMR (600 MHz, DMSO-d₆) δ 7.79 (d, J=5.13 Hz, 1H), 7.60 (br. s., 3H), 7.34-7.40 (m, 3H), 7.29-7.33 (m, 2H), 7.23 (d, J=8.24 Hz, 1H), 7.10 (d, J=8.24 Hz, 1H), 7.08 (s, 1H), 6.93 (s, 1H), 4.30-4.36 (m, 1H), 3.86 (dd, J=3.75, 13.28 Hz, 1H), 3.36-3.43 (m, 1H), 2.39-2.47 (m, 2H), 1.71-1.86 (m, 2H).

LCMS (HPLC Method 2): m/z 462 [M+H]⁺@r.t. 5.72 min.
HRMS (ESI) calcd for $C_{23}H_{23}F_3N_3O_2S$ [M+H]⁺ 462.1458 found 462.1455.

(4S)-4-(2-aminoethyl)-6-(4-tert-butylphenyl)-7-[3-(trifluoromethoxy)phenyl]-3,4-dihydropyrrolo[1,2-a]pyrazin-1(2H)-one hydrochloride [(I), R2=3-(trifluoromethoxy)phenyl, R3=4-tert-butylphenyl, R4=H, A=—CH₂CH₂CH₂—NH₂](cpd 124)

¹H NMR (600 MHz, DMSO-d₆) δ 7.79 (d, J=5.13 Hz, 1H), 7.61 (br. s., 3H), 7.52 (d, J=8.42 Hz, 2H), 7.33-7.39 (m, 2H), 7.31 (d, J=8.42 Hz, 2H), 7.09 (s, 1H), 7.07 (d, J=7.69 Hz, 1H), 6.71 (s, 1H), 4.30-4.36 (m, 1H), 3.84 (dd, J=3.94, 13.28 Hz, 1H), 3.36-3.44 (m, 1H), 2.33-2.44 (m, 2H), 1.74-1.93 (m, 2H), 1.32 (s, 9H).

LCMS (HPLC Method 2): m/z 472 [M+H]⁺@r.t. 6.42 min.
HRMS (ESI) calcd for $C_{26}H_{29}F_3N_3O_2$[M+H]⁺ 472.2207 found 472.2206.

(4S)-4-(2-aminoethyl)-7-[3-(trifluoromethoxy)phenyl]-6-[3-(trifluoromethyl)phenyl]-3,4-dihydropyrrolo[1,2-a]pyrazin-1(2H)-one hydrochloride

[(I), R2=3-(trifluoromethoxy)phenyl, R3=3-(trifluoromethyl)phenyl, R4=H, A=—CH₂CH₂CH₂—NH₂](cpd 125)

¹H NMR (600 MHz, DMSO-d₆) δ 7.86 (d, J=5.68 Hz, 2H), 7.71-7.78 (m, 2H), 7.69 (s, 1H), 7.62 (br. s., 3H), 7.37-7.43 (m, 1H), 7.29 (d, J=8.24 Hz, 1H), 7.10-7.15 (m, 2H), 6.75 (s, 1H), 4.36 (br. s., 1H), 3.91 (dd, J=3.85, 13.37 Hz, 1H), 3.36-3.45 (m, 1H), 2.33-2.46 (m, 2H), 1.71-1.92 (m, 2H).

LCMS (HPLC Method 2): m/z 484 [M+H]⁺@r.t. 5.87 min.
HRMS (ESI) calcd for $C_{23}H_{20}F_6N_3O_2$[M+H]⁺ 484.1454 found 472.1465.

(4S)-4-(2-aminoethyl)-6-(3-chlorophenyl)-7-[3-(trifluoromethoxy)phenyl]-3,4-dihydropyrrolo[1,2-a]pyrazin-1(2H)-one hydrochloride

[(I), R2=3-(trifluoromethoxy)phenyl, R3=3-chlorophenyl, R4=H, A=—CH₂CH₂CH₂—NH₂](cpd 126)

¹H NMR (600 MHz, DMSO-d₆) δ 7.84 (d, J=5.13 Hz, 1H), 7.60 (br. s., 3H), 7.56-7.58 (m, 1H), 7.51-7.55 (m, 1H), 7.47 (s, 1H), 7.38-7.41 (m, 1H), 7.37 (d, J=7.51 Hz, 1H), 7.26 (d, J=8.24 Hz, 1H), 7.13 (d, J=7.33 Hz, 1H), 7.10 (s, 1H), 6.86 (s, 1H), 4.32-4.42 (m, 1H), 3.89 (dd, J=3.94, 13.28 Hz, 1H), 3.36-3.43 (m, 1H), 2.39-2.47 (m, 1H), 1.67-1.95 (m, 2H). LCMS (HPLC Method 2): m/z 450 [M+H]⁺@r.t. 5.67 min.

HRMS (ESI) calcd for $C_{22}H_{20}ClF_3N_3O_2$ [M+H]⁺ 450.1191 found 472.1192.

(4S)-4-(2-aminoethyl)-6-(4-ethoxy-3-fluorophenyl)-7-[3-(trifluoromethoxy)phenyl]-3,4-dihydropyrrolo[1,2-a]pyrazin-1(2H)-one hydrochloride

[(I), R2=3-(trifluoromethoxy)phenyl, R3=4-ethoxy-3-fluorophenyl, R4=H, A=—CH₂CH₂CH₂—NH₂](cpd 127)

¹H NMR (600 MHz, DMSO-d₆) δ 7.79 (d, J=4.95 Hz, 1H), 7.61 (br. s., 3H), 7.35-7.40 (m, 1H), 7.18-7.31 (m, 3H), 7.09-7.15 (m, 2H), 7.07 (s, 1H), 6.91 (s, 1H), 4.35 (d, J=3.66 Hz, 1H), 4.16 (q, J=7.14 Hz, 2H), 3.86 (dd, J=3.94, 13.46 Hz, 1H), 3.36-3.42 (m, 1H), 2.39-2.49 (m, 2H), 1.69-1.92 (m, 2H), 1.38 (t, J=7.14 Hz, 3H).

LCMS (HPLC Method 2): m/z 478 [M+H]⁺@r.t. 5.79 min.

HRMS (ESI) calcd for $C_{24}H_{24}F_4N_3O_3$[M+H]⁺ 478.1749 found 478.1755.

4S)-4-(2-aminoethyl)-6-(4-methoxy-3,5-dimethyl phenyl)-7-[3-(trifluoromethoxy)phenyl]-3,4-dihydropyrrolo[1,2-a]pyrazin-1(2H)-one hydrochloride

[(I), R2=3-(trifluoromethoxy)phenyl, R3=4-methoxy-3,5-dimethylphenyl, R4=H, A=—CH₂CH₂CH₂—NH₂](cpd 128)

¹H NMR (600 MHz, DMSO-d₆) δ 7.78 (d, J=4.95 Hz, 1H), 7.63 (br. s., 3H), 7.31-7.42 (m, 2H), 7.06-7.10 (m, 2H), 7.04 (s, 2H), 6.81 (s, 1H), 4.33 (d, J=3.66 Hz, 1H), 3.83 (dd, J=3.94, 13.46 Hz, 1H), 3.71 (s, 3H), 3.43-3.47 (m, 1H), 2.40-2.49 (m, 2H), 2.23 (s, 6H), 1.75-1.92 (m, 2H). LCMS (HPLC Method 2): m/z 474 [M+H]⁺@r.t. 5.85 min HRMS (ESI) calcd for $C_{25}H_{27}F_3N_3O_3$[M+H]⁺ 474.1999 found 474.1998.

(4S)-4-(2-aminoethyl)-6-(3-chloro-4-methoxyphenyl)-7-[3-(trifluoromethoxy)phenyl]-3,4-dihydropyrrolo[1,2-a]pyrazin-1(2H)-one hydrochloride

[(I), R2=3-(trifluoromethoxy)phenyl, R3=3-chloro-4-methoxyphenyl, R4=H, A=—CH₂CH₂CH₂—NH₂](cpd 129)

¹H NMR (600 MHz, DMSO-d₆) δ 7.80 (d, J=4.95 Hz, 1H), 7.60 (br. s., 3H), 7.46 (s, 1H), 7.36-7.40 (m, 1H), 7.33 (d, J=8.24 Hz, 1H), 7.22-7.29 (m, 2H), 7.11 (d, J=7.69 Hz, 1H), 7.07 (s, 1H), 6.90 (s, 1H), 4.30-4.37 (m, 1H), 3.91 (s, 3H), 3.88 (dd, J=4.03, 13.55 Hz, 1H), 2.41-2.47 (m, 2H), 1.70-1.94 (m, 2H).

LCMS (HPLC Method 2): m/z 480 [M+H]⁺@r.t. 5.66 min.

HRMS (ESI) calcd for $C_{23}H_{22}ClF_3N_3O_3$ [M+H]⁺ 480.1297 found 474.1298.

(4S)-6-[4-(1-aminocyclopropyl)phenyl]-4-(2-aminoethyl)-7-[3-(trifluoromethoxy)phenyl]-3,4-dihydropyrrolo[1,2-a]pyrazin-1(2H)-one hydrochloride

[(I), R2=3-(trifluoromethoxy)phenyl, R3=4-(1-aminocyclopropyl)phenyl, R4=H, A=—CH₂CH₂CH₂—NH₂](cpd 130)

¹H NMR (600 MHz, DMSO-d₆) δ 8.94 (br. s., 3H), 7.82 (m, 1H), 7.80 (m, 3H), 7.47-7.49 (m, 2H), 7.42-7.44 (m, 2H), 7.34 (t, J=8.05 Hz, 1H), 7.20 (d, J=8.06 Hz, 1H), 7.11 (d, J=8.06 Hz, 1H), 7.08 (s, 1H), 6.91 (s, 1H), 4.26-4.28 (m, 1H), 3.85-3.89 (m, 1H), 2.36-2.42 (m, 1H), 2.05-2.12 (m, 1H), 1.85-1.9 (m, 1H), 1.45 (m, 2H), 1.22-1.25 (m, 2H). LCMS (HPLC Method 2): m/z 471 [M+H]⁺@r.t. 4.56 min.

HRMS (ESI) calcd for $C_{25}H_{26}F_3N_4O_2$[M+H]⁺ 471.2003 found 471.201.

Example 40a (4S)-6-[4-(1-aminocyclopropyl)phenyl]-4-(propan-2-yl)-7-[3-(trifluoromethoxy)phenyl]-3,4-dihydropyrrolo[1,2-a]pyrazin-1(2H)-one hydrochloride [(I), R2=3-(trifluoromethoxy)phenyl, R3=4-(1-aminocyclopropyl)phenyl, R4=H, A=—CH₂(CH₃)₂](cpd 131)

Prepared as described in Example 39, using (4-{1-[(tert-butoxycarbonyl)amino]cyclopropyl}phenyl)boronic acid, followed by Boc group removal as described in Example 40.

¹H NMR (600 MHz, DMSO-d₆) δ 8.79 (br. s., 3H), 7.73 (d, J=4.95 Hz, 1H), 7.44-7.47 (m, 2H), 7.38-7.42 (m, 2H), 7.34 (t, J=8.06 Hz, 1H), 7.22 (d, J=7.88 Hz, 1H), 7.10 (d, J=8.24 Hz, 1H), 7.01 (s, 1H), 6.87 (s, 1H), 3.98 (dd, J=3.48, 7.69 Hz, 1H), 3.87 (dd, J=3.94, 13.46 Hz, 1H), 3.64-3.72 (m, 1H), 3.43-3.54 (m, 2H), 1.85 (d, J=7.14 Hz, 1H), 1.43 (br. s., 2H), 1.24 (d, J=7.51 Hz, 2H), 0.72 (d, J=6.78 Hz, 3H), 0.43 (d, J=6.96 Hz, 3H).

LCMS (HPLC Method 2): m/z 470 [M+H]⁺@r.t. 5.59 min.

HRMS (ESI) calcd for $C_{26}H_{26}F_3N_3O_2$[M+H]⁺ 470.2050 found 470.2044.

Example 40b (4S)-6-(4-ethoxy-3-fluorophenyl)-4-(1H-imidazol-4-ylmethyl)-7-[3-(trifluoromethoxy)phenyl]-3,4-dihydropyrrolo[1,2-a]pyrazin-1(2H)-one

[(I), R2=3-(trifluoromethoxy)phenyl, R3=4-ethoxy-3-fluorophenyl, R4=H, A=CH₂-1H-imidazol-4-yl](cpd 132)

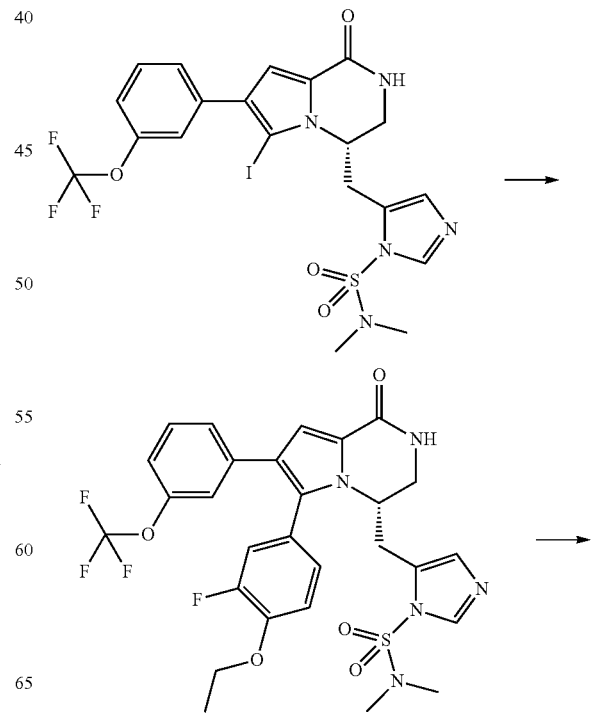

-continued

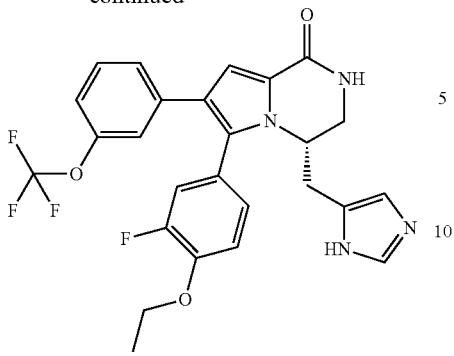

(4-ethoxy-3-fluorophenyl)boronic acid (0.072 g, 0.39 mmol), cesium carbonate (0.096 g, 0.3 mmol) and 1,1'-bis(diphenylphosphino)ferrocenepalladium (0.008 g, 0.010 mmol) complex with dichloromethane, were subsequently added to a degassed solution of 4-({(4S)-6-iodo-1-oxo-7-[3-(trifluoromethoxy)phenyl]-1,2,3,4-tetrahydropyrrolo[1,2-a]pyrazin-4-yl}methyl)-N,N-dimethyl-1H-imidazole-1-sulfonamide (0.06 g, 0.1 mmol) in 3 ml of 1,4-dioxane and 1 ml of water, under argon. The mixture was heated at 100° for 3 hours in a sealed vial. The reaction was portioned between ethyl acetate and water, the organic layer dried over sodium sulphate and the solvent removed in vacuo. 4-({(4S)-6-(4-ethoxy-3-fluorophenyl)-1-oxo-7-[3-(trifluoromethoxy)phenyl]-1,2,3,4-tetrahydropyrrolo[1,2-a]pyrazin-4-yl}methyl)-N,N-dimethyl-1H-imidazole-1-sulfonamide was submitted to the next step without purification. The crude was dissolved in a mixture 1:1 of water (2 ml) and 4N HCl in dioxane (2 ml) and heated at 75° C. until deprotection was completed. After evaporation under vacuo, purification by RP-HPLC afforded the title compound as a white solid.

$^1$H NMR (600 MHz, DMSO-d6) δ 11.77 (br. s., 1H), 7.71 (d, J=5.13 Hz, 1H), 7.44 (s, 1H), 7.34-7.41 (m, 1H), 7.19-7.30 (m, 3H), 7.08 (d, J=7.88 Hz, 2H), 7.06 (s, 1H), 6.94 (s, 1H), 6.63 (s, 1H), 4.33-4.46 (m, 1H), 4.16 (dq, J=0.73, 6.84 Hz, 2H), 3.72 (dd, J=3.75, 12.73 Hz, 1H), 3.33-3.37 (m, 1H), 2.79-2.87 (m, 1H), 1.38 (t, J=6.96 Hz, 3H). LCMS (HPLC Method 2): m/z 515 [M+H]$^+$@r.t. 5.03 min.

HRMS (ESI) calcd for $C_{26}H_{23}F_4N_4O_3$[M+H]$^+$ 515.1701 found 515.1701.

According to the same method, but employing the appropriate boronic acid, the following compound was prepared:

(4S)-4-(1H-imidazol-4-ylmethyl)-6-(3-methylphenyl)-7-[3-(trifluoromethoxy)phenyl]-3,4-dihydropyrrolo[1,2-a]pyrazin-1(2H)-one

[(I), R2=3-(trifluoromethoxy)phenyl, R3=3-methylphenyl, R4=H, A=CH2-1H-imidazol-4-yl](cpd 133)

$^1$H NMR (600 MHz, DMSO-d6) δ 11.77 (br. s., 1H), 7.71 (d, J=4.58 Hz, 1H), 7.43 (br. s., 2H), 7.31-7.39 (m, 3H), 7.29 (d, J=7.33 Hz, 3H), 7.16 (br. s., 3H), 7.08 (s, 1H), 7.06 (d, J=7.88 Hz, 1H), 6.91 (br. s., 1H), 6.58 (br. s., 1H), 4.24-4.49 (m, J=4.03 Hz, 1H), 3.64-3.76 (m, J=9.34 Hz, 1H), 2.81-2.89 (m, 2H), 2.30 (s, 3H).

LCMS (HPLC Method 2): m/z 467 [M+H]$^+$@r.t. 5.03 min.

HRMS (ESI) calcd for $C_{25}H_{22}F_4N_4O_2$[M+H]$^+$ 467.1690 found 467.1691.

Example 41 tert-butyl(2-{(4S)-6-[4-(morpholin-4-ylmethyl)phenyl]-1-oxo-7-[3-(trifluoromethoxy)phenyl]-1,2,3,4-tetrahydropyrrolo[1,2-a]pyrazin-4-yl}ethyl)carbamate trifluoroacetate [(I), R2=3-(trifluoromethoxy)phenyl, R3=4-4-(morpholin-4-ylmethyl)phenyl, R4=H, A=—CH$_2$CH$_2$—NH—CO—O-tBu] Conv. k

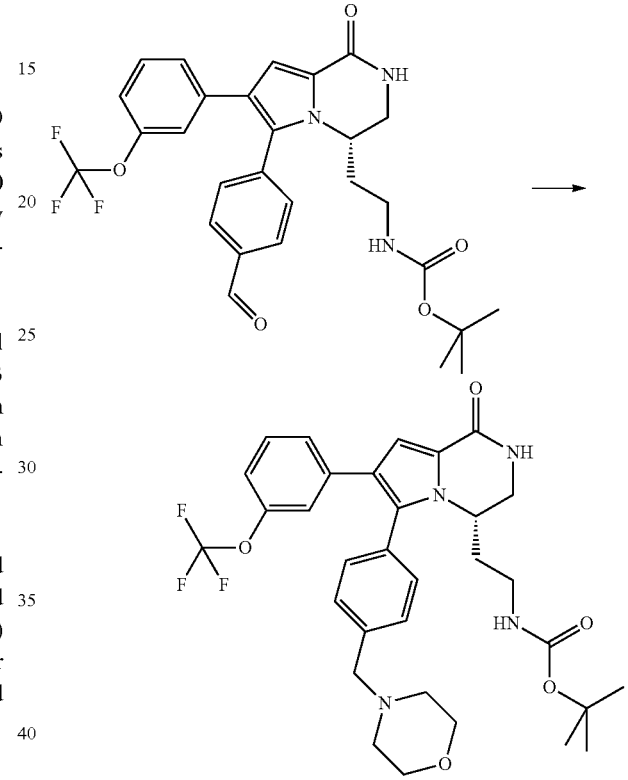

A solution of tert-butyl(2-{(4S)-6-(4-formylphenyl)-1-oxo-7-[3-(trifluoromethoxy)phenyl]-1,2,3,4-tetrahydropyrrolo[1,2-a]pyrazin-4-yl}ethyl)carbamate (0.050 g, 0.092 mmol), morpholine (24 µl, 0.276 mmol) and acetic acid (0.005 g, 0.092 mmol) in dry THF (2 ml) was stirred at room temperature for 1 h. Sodium cyanoborohydride (0.017 g, 0.276 mmol) was then added and the reaction mixture was stirred at room temperature for 12 hours. The solvent was evaporated, the residue was partitioned between DCM and water, the organic layer was dried over Na$_2$SO$_4$, filtered and concentrated to dryness. Purification of the crude by HPLC preparative method 1 provided the title compound (0.030 g, 59%)

$^1$H NMR (600 MHz, DMSO-d6) δ 9.55-10.37 (m, 1H), 7.79 (d, J=4.15 Hz, 1H), 7.59 (d, J=7.20 Hz, 2H), 7.44-7.52 (m, 3H), 7.32-7.39 (m, 1H), 7.25-7.31 (m, 1H), 7.10 (d, J=6.10 Hz, 2H), 7.07 (s, 1H), 6.86 (s, 1H), 6.46-6.67 (m, 1H), 3.01-4.47 (m, 13H), 1.73 (m, J=13.18, 6.35 Hz, 1H), 1.43-1.57 (m, 1H), 1.30 (s, 9H).

LCMS (HPLC Method 2): m/z 615 [M+H]$^+$@r.t. 6.67 min.

HRMS (ESI) calcd for $C_{32}H_{38}F_3N_4O_5$[M+H]$^+$ 615.2789 found 615.2811.

Working according to the same method, the following compounds were prepared after HPLC preparative method 1 purification:

tert-butyl(2-{(4S)-6-{4-[(4-methylpiperazin-1-yl)methyl]phenyl}-1-oxo-7-[3-(trifluoromethoxy)phenyl]-1,2,3,4-tetrahydropyrrolo[1,2-a]pyrazin-4-yl}ethyl)carbamate trifluoroacetate [(I), R2=3-(trifluoromethoxy)phenyl, R3=4-[(4-methylpiperazin-1-yl)methyl]phenyl, R4=H, A=—CH$_2$CH$_2$—NH—CO—O-tBu](0.034 g, 59%).

$^1$H NMR (600 MHz, DMSO-d6) δ 7.75 (d, J=4.39 Hz, 1H), 7.44 (d, J=7.81 Hz, 2H), 7.28-7.38 (m, 4H), 7.03-7.09 (m, 2H), 6.82 (s, 1H), 6.46-6.65 (m, 1H), 4.06-4.23 (m, 1H), 3.78 (d, J=13.30 Hz, 2H), 3.68 (br. s., 2H), 2.26-3.57 (m, 13H), 1.67-1.81 (m, 1H), 1.43-1.55 (m, 1H), 1.30 (s, 9H).

LCMS (HPLC Method 2): m/z 628 [M+H]$^+$@r.t. 5.61 min.
HRMS (ESI) calcd for C$_{33}$H$_{41}$F$_3$N$_5$O$_4$[M+H]$^+$ 628.3105 found 628.3104.

tert-butyl(2-{(4S)-6-{4-[(dimethylamino)methyl]phenyl}-1-oxo-7-[3-(trifluoromethoxy)phenyl]-1,2,3,4-tetrahydropyrrolo[1,2-a]pyrazin-4-yl}ethyl)carbamate trifluoroacetate [(I), R2=3-(trifluoromethoxy)phenyl, R3=4-[(dimethylamino)methyl]phenyl, R4=H, A=—CH$_2$CH$_2$—NH—CO—O-tBu](0.029 g, 62%).

$^1$H NMR (600 MHz, DMSO-d6) δ 9.72 (s, 1H), 7.78 (d, J=4.64 Hz, 1H), 7.59 (d, J=7.93 Hz, 2H), 7.45-7.52 (m, 2H), 7.33-7.39 (m, 1H), 7.24-7.31 (m, 1H), 7.08-7.12 (m, 1H), 7.07 (s, 1H), 6.84 (s, 1H), 6.59 (t, J=5.74 Hz, 1H), 4.29-4.43 (m, 2H), 4.09-4.26 (m, 1H), 3.81 (d, J=10.25 Hz, 1H), 2.76 (br. s., 6H), 2.56-2.65 (m, 2H), 1.73 (dd, J=13.79, 6.71 Hz, 1H), 1.41-1.57 (m, 1H), 1.29 (s, 9H).

LCMS (HPLC Method 2): m/z 573 [M+H]$^+$@r.t. 5.60 min.
HRMS (ESI) calcd for C$_{30}$H$_{36}$F$_3$N$_4$O$_4$[M+H]$^+$ 573.2683 found 573.2706.

tert-butyl(2-{(4S)-8-[4-(morpholin-4-ylmethyl)phenyl]-1-oxo-7-[3-(trifluoromethoxy)phenyl]-1,2,3,4-tetrahydropyrrolo[1,2-a]pyrazin-4-yl}ethyl)carbamate trifluoroacetate [(I), R2=3-(trifluoromethoxy)phenyl, R3=H, R4=4-(morpholin-4-ylmethyl)phenyl, A=—CH$_2$CH$_2$—NH—CO—O-tBu]

(0.0022 g, 4%)
LCMS (HPLC Method 5): m/z 615 [M+H]$^+$@r.t. 6.69 min.
HRMS (ESI) calcd for C$_{32}$H$_{38}$F$_3$N$_4$O$_5$[M+H]$^+$ 615.2789 found 615.2789.

tert-butyl(2-{(4S)-8-{4-[(4-methylpiperazin-1-yl)methyl]phenyl}-1-oxo-7-[3-(trifluoromethoxy)phenyl]-1,2,3,4-tetrahydropyrrolo[1,2-a]pyrazin-4-yl}ethyl)carbamate trifluoroacetate [(I), R2=3-(trifluoromethoxy)phenyl, R3=H, R4=4-[(4-methylpiperazin-1-yl)methyl]phenyl, A=—CH$_2$CH$_2$—NH—CO—O-tBu](0.0013 g, 2%)

LCMS (HPLC Method 5): m/z 628 [M+H]$^+$@r.t. 10.94 min.
HRMS (ESI) calcd for C$_{33}$H$_{41}$F$_3$N$_5$O$_4$[M+H]$^+$ 628.3105 found 628.3102.

tert-butyl(2-{(4S)-8-{4-[(dimethylamino)methyl]phenyl}-1-oxo-7-[3-(trifluoromethoxy)phenyl]-1,2,3,4-tetrahydropyrrolo[1,2-a]pyrazin-4-yl}ethyl)carbamate trifluoroacetate [(I), R2=3-(trifluoromethoxy)phenyl, R3=H, R4=4-[(dimethylamino)methyl]phenyl, A=—CH$_2$CH$_2$—NH—CO—O-tBu](0.001 g, 2%)

LCMS (HPLC Method 5): m/z 573 [M+H]$^+$@r.t. 10.69 min.
HRMS (ESI) calcd for C$_{30}$H$_{36}$F$_3$N$_4$O$_4$[M+H]$^+$ 573.2683 found 573.2386.

tert-butyl(3-{(4S)-6-{4-[(dimethylamino)methyl]phenyl}-1-oxo-7-[3-(trifluoromethoxy)phenyl]-1,2,3,4-tetrahydropyrrolo[1,2-a]pyrazin-4-yl}propyl)carbamate trifluoroacetate [(I), R2=3-(trifluoromethoxy)phenyl, R3=4-[(dimethylamino)methyl]phenyl, R4=H, A=—CH$_2$CH$_2$CH$_2$NH—CO—OtBu]

LCMS (HPLC Method 2): m/z 587 [M+H]$^+$@r.t. 4.53 min.
HRMS (ESI) calcd for C$_{31}$H$_{38}$F$_3$N$_4$O$_4$[M+H]$^+$ 587.284 found 587.2856.

tert-butyl(3-{(4S)-8-{4-[(dimethylamino)methyl]phenyl}-1-oxo-7-[3-(trifluoromethoxy)phenyl]-1,2,3,4-tetrahydropyrrolo[1,2-a]pyrazin-4-yl}propyl)carbamate trifluoroacetate [(I), R2=3-(trifluoromethoxy)phenyl, R3=H, R4=4-[(dimethylamino)methyl]phenyl, A=—CH$_2$CH$_2$CH$_2$NH—CO—OtBu]

LCMS (HPLC Method 2): m/z 587 [M+H]$^+$@r.t. 4.97 min.
HRMS (ESI) calcd for C$_{31}$H$_{38}$F$_3$N$_4$O$_4$[M+H]$^+$ 587.284 found 587.2853.

tert-butyl(3-{(4S)-6-{4-[(4-methylpiperazin-1-yl)methyl]phenyl}-1-oxo-7-[3-(trifluoromethoxy)phenyl]-1,2,3,4-tetrahydropyrrolo[1,2-a]pyrazin-4-yl}propyl)carbamate trifluoroacetate [(I), R2=3-(trifluoromethoxy)phenyl, R3=[(4-methylpiperazin-1-yl)methyl]phenyl, R4=H, A=—CH$_2$CH$_2$CH$_2$NH—CO—OtBu]

LCMS (HPLC Method 2): m/z 642 [M+H]$^+$@r.t. 4.55 min.
HRMS (ESI) calcd for C$_{34}$H$_{43}$F$_3$N$_5$O$_4$[M+H]$^+$ 642.3262 found 642.3283.

tert-butyl(3-{(4S)-8-{4-[(4-methylpiperazin-1-yl)methyl]phenyl}-1-oxo-7-[3-(trifluoromethoxy)phenyl]-1,2,3,4-tetrahydropyrrolo[1,2-a]pyrazin-4-yl}propyl)carbamate trifluoroacetate [(I), R2=3-(trifluoromethoxy)phenyl, R3=H, R4=[(4-methylpiperazin-1-yl)methyl]phenyl, A=—CH$_2$CH$_2$CH$_2$NH—CO—OtBu]

LCMS (HPLC Method 2): m/z 642 [M+H]$^+$@r.t. 5.08 min.
HRMS (ESI) calcd for C$_{34}$H$_{43}$F$_3$N$_5$O$_4$[M+H]$^+$ 642.3262 found 642.3267.

Example 42

(4S)-4-(2-aminoethyl)-6-[4-(morpholin-4-ylmethyl)phenyl]-7-[3-(trifluoromethoxy)phenyl]-3,4-dihydropyrrolo[1,2-a]pyrazin-1(2H)-one hydrochloride [(I), R2=3-(trifluoromethoxy)phenyl, R3=4-(morpholin-4-ylmethyl)phenyl, R4=H, A=—CH$_2$CH$_2$—NH$_2$]
(cpd 99) Conv. r

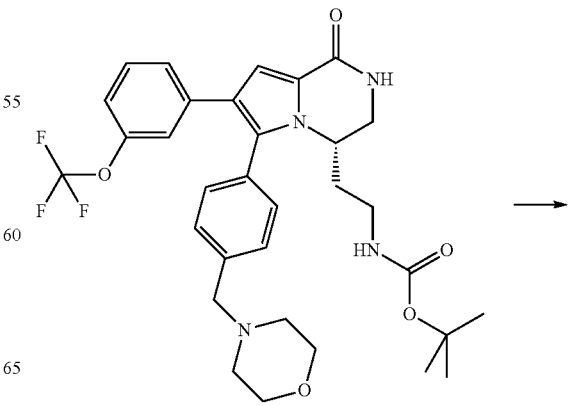

-continued

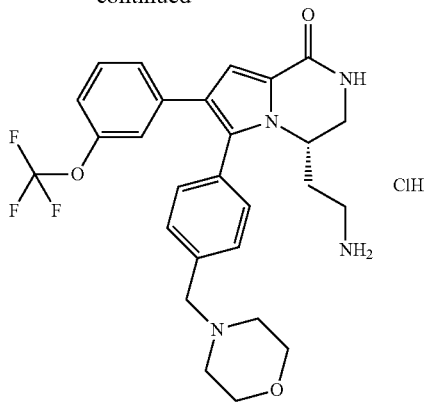

tert-butyl(2-{(4S)-6-[4-(morpholin-4-ylmethyl)phenyl]-1-oxo-7-[3-(trifluoromethoxy)phenyl]-1,2,3,4-tetrahydropyrrolo[1,2-a]pyrazin-4-yl}ethyl)carbamate trifluoroacetate (0.030 g, 0.049 mmol) was dissolved in 4M HCl in 1,4-dioxane (2 ml) and the reaction was stirred at room temperature for 1 hour. The solvent was evaporated to dryness, giving the title compound (98%).

$^1$H NMR (600 MHz, DMSO-d6) δ 7.83 (d, J=4.76 Hz, 1H), 7.74 (d, J=8.06 Hz, 2H), 7.64-7.72 (m, 2H), 7.46-7.51 (m, 2H), 7.32-7.41 (m, 1H), 7.23-7.30 (m, 1H), 7.07-7.13 (m, 2H), 6.87 (s, 1H), 4.38-4.46 (m, 2H), 4.23-4.35 (m, 1H), 3.78-3.86 (m, 1H), 3.44-2.99 (m, 10H), 2.34-2.46 (m, 2H), 1.82-1.96 (m, 1H), 1.69-1.83 (m, 1H).

LCMS (HPLC Method 2): m/z 515 [M+H]$^+$@r.t. 5.26 min.

HRMS (ESI) calcd for $C_{27}H_{30}F_3N_4O_3$[M+H]$^+$ 515.2265 found 515.2272.

Working according to the same method, using the appropriate carbamate, the following compounds were prepared:
(4S)-4-(2-aminoethyl)-6-{4-[(4-methyl piperazin-1-yl)methyl]phenyl}-7-[3-(trifluoromethoxy)phenyl]-3,4-dihydropyrrolo[1,2-a]pyrazin-1(2H)-one hydrochloride [(I), R2=3-(trifluoromethoxy)phenyl, R3=4-[(4-methylpiperazin-1-yl)methyl]phenyl, R4=H, A=—CH$_2$CH$_2$—NH$_2$) (cpd 100)

$^1$H NMR (600 MHz, DMSO-d6) δ 10.23-11.15 (m, 1H), 7.82 (d, J=4.76 Hz, 1H), 7.72 (br. s., 3H), 7.60 (br. s., 2H), 7.42 (d, J=7.81 Hz, 2H), 7.33-7.40 (m, 1H), 7.26 (d, J=7.81 Hz, 1H), 7.06-7.12 (m, 2H), 6.90 (br. s., 1H), 4.27-4.37 (m, 1H), 3.80-3.90 (m, 2H), 3.16-3.58 (brm, 10H), 2.79 (s, 3H), 2.35-2.46 (m, 2H), 1.83-1.96 (m, 1H), 1.69-1.83 (m, 1H). LCMS (HPLC Method 2): m/z 528 [M+H]$^+$@r.t. 2.86 min.

HRMS (ESI) calcd for $C_{28}H_{33}F_3N_5O_2$[M+H]$^+$ 528.2581 found 528.2567.

(4S)-4-(2-aminoethyl)-6-{4-[(dimethylamino)methyl]phenyl}-7-[3-(trifluoromethoxy)phenyl]-3,4-dihydropyrrolo[1,2-a]pyrazin-1(2H)-one hydrochloride [(I), R2=3-(trifluoromethoxy)phenyl, R3=4-[(dimethylamino)methyl]phenyl, R4=H, A=—CH$_2$CH$_2$—NH$_2$) (cpd 101)

$^1$H NMR (600 MHz, DMSO-d6) δ 10.68 (br. s., 1H), 7.84 (d, J=4.76 Hz, 1H), 7.73 (d, J=4.88 Hz, 3H), 7.70 (d, J=8.06 Hz, 2H), 7.46-7.53 (m, 2H), 7.33-7.41 (m, 1H), 7.24-7.31 (m, 1H), 7.06-7.14 (m, 2H), 6.85 (s, 1H), 4.27-4.34 (m, 1H), 3.86 (dd, J=13.61, 3.84 Hz, 1H), 3.35-3.50 (m, 3H), 2.73 (d, J=2.69 Hz, 6H), 2.35-2.46 (m, 2H), 1.90 (m, J=12.57, 6.23 Hz, 1H), 1.77 (m, J=11.90, 6.53 Hz, 1H).

LCMS (HPLC Method 2): m/z 473 [M+H]$^+$@r.t. 2.78 min.

HRMS (ESI) calcd for $C_{25}H_{28}F_3N_4O_2$[M+H]$^+$ 473.2159 found 473.2166.

(4S)-4-(3-aminopropyl)-6-{4-[(dimethylamino)methyl]phenyl}-7-[3-(trifluoromethoxy)phenyl]-3,4-dihydropyrrolo[1,2-a]pyrazin-1(2H)-one dihydrochloride [(I), R2=3-(trifluoromethoxy)phenyl, R3=4-[(dimethylamino)methyl]phenyl, R4=H, A=—CH$_2$CH$_2$CH$_2$NH$_2$](cpd 134)

$^1$H NMR (600 MHz, DMSO-d6) δ 10.66 (br. s., 1H), 7.79 (d, J=4.95 Hz, 1H), 7.70-7.75 (m, 3H), 7.66-7.70 (m, 2H), 7.51 (d, J=7.88 Hz, 2H), 7.32-7.39 (m, 1H), 7.27 (d, J=8.24 Hz, 1H), 7.10 (d, J=9.34 Hz, 1H), 7.08 (s, 1H), 6.86 (s, 1H), 4.16-4.22 (m, 1H), 3.87 (dd, J=4.12, 13.46 Hz, 1H), 3.31 (dd, J=5.31, 13.37 Hz, 1H), 2.74 (d, J=4.76 Hz, 3H), 2.72 (d, J=4.95 Hz, 3H), 2.39-2.48 (m, 2H), 1.60-1.70 (m, 1H), 1.40-1.48 (m, 1H), 1.14-1.25 (m, 2H) LCMS (HPLC Method 2): m/z 487 [M+H]$^+$@r.t. 2.74 min.

HRMS (ESI) calcd for $C_{26}H_{30}F_3N_4O_2$[M+H]$^+$ 487.2316 found 487.2321.

(4S)-4-(3-aminopropyl)-6-{4-[(4-methyl piperazin-1-yl)methyl]phenyl}-7-[3-(trifluoromethoxy)phenyl]-3,4-dihydropyrrolo[1,2-a]pyrazin-1(2H)-one dihydrochloride [(I), R2=3-(trifluoromethoxy)phenyl, R3=4-[(4-methylpiperazin-1-yl)methyl]phenyl, R4=H, A=—CH$_2$CH$_2$CH$_2$NH$_2$](cpd 135)

$^1$H NMR (600 MHz, DMSO-d6) δ 7.78 (d, J=4.94 Hz, 1H), 7.68-7.75 (m, 3H), 7.61 (br. s., 2H), 7.45 (br. s., 2H), 7.36 (t, J=8.06 Hz, 1H), 7.25 (d, J=7.88 Hz, 1H), 7.09 (d, J=7.88 Hz, 1H), 7.07 (s, 1H), 6.90 (br. s., 1H), 4.16-4.24 (m, J=3.11 Hz, 1H), 3.86 (dd, J=3.75, 13.10 Hz, 1H), 3.49-3.59 (m, 2H), 2.79 (br. s., 3H), 2.44 (d, J=6.23 Hz, 1H), 1.59-1.77 (m, 1H), 1.39-1.56 (m, 1H), 1.09-1.30 (m, 2H).

LCMS (HPLC Method 2): m/z 542 [M+H]$^+$@r.t. 2.88 min.

HRMS (ESI) calcd for $C_{29}H_{35}F_3N_5O_2$[M+H]$^+$ 542.2738 found 542.2746.

(4S)-6-{4-[(dimethylamino)methyl]phenyl}-4-(propan-2-yl)-7-[3-(trifluoromethoxy)phenyl]-3,4-dihydropyrrolo[1,2-a]pyrazin-1(2H)-one

[(I), R2=3-(trifluoromethoxy)phenyl, R3=4-[(dimethylamino)methyl]phenyl, R4=H, A=—CH$_2$(CH$_3$)$_2$](cpd 136)

$^1$H NMR (600 MHz, DMSO-d6) δ 7.69 (d, J=5.31 Hz, 1H), 7.38 (d, J=8.06 Hz, 2H), 7.33-7.37 (m, 1H), 7.30 (t, J=8.15 Hz, 3H), 7.07 (d, J=8.06 Hz, 1H), 7.02 (s, 1H), 6.81 (s, 1H), 4.00 (dd, J=3.66, 7.51 Hz, 1H), 3.84 (dd, J=4.21, 13.37 Hz, 1H), 3.39-3.50 (m, 4H), 2.15 (s, 6H), 1.84 (qd, J=6.95, 14.13 Hz, 1H), 0.71 (d, J=6.59 Hz, 3H), 0.43 (d, J=6.96 Hz, 3H). LCMS (HPLC Method 2): m/z 472 [M+H]$^+$@r.t. 5.23 min.

HRMS (ESI) calcd for $C_{26}H_{29}F_3N_3O_2$[M+H]$^+$ 472.2207 found 472.2213.

(4S)-6-{4-[(4-methyl piperazin-1-yl)methyl]phenyl}-4-(propan-2-yl)-7-[3-(trifluoromethoxy)phenyl]-3,4-dihydropyrrolo[1,2-a]pyrazin-1(2H)-one [(I), R2=3-(trifluoromethoxy)phenyl, R3=4-[(4-methylpiperazin-1-yl)methyl]phenyl, R4=H, A=—CH$_2$(CH$_3$)$_2$](cpd 137)

$^1$H NMR (600 MHz, DMSO-d6) δ 7.69 (d, J=5.13 Hz, 1H), 7.38 (d, J=8.24 Hz, 2H), 7.34-7.37 (m, 1H), 7.31-7.34 (m, 1H), 7.28 (d, J=7.51 Hz, 2H), 7.07 (d, J=7.88 Hz, 1H), 7.02 (s, 1H), 6.78 (s, 1H), 3.99 (dd, J=3.85, 7.33 Hz, 1H), 3.83 (dd, J=4.03, 13.37 Hz, 1H), 3.41-3.55 (m, 3H), 2.38 (dd, J=1.65, 3.66 Hz, 7H), 2.15 (s, 3H), 1.84 (qd, J=7.04, 14.22 Hz, 1H), 0.71 (d, J=6.78 Hz, 3H), 0.43 (d, J=6.96 Hz, 3H).

LCMS (HPLC Method 2): m/z 527 [M+H]$^+$@r.t. 5.35 min.

HRMS (ESI) calcd for $C_{29}H_{34}F_3N_4O_2$[M+H]$^+$ 527.2629 found 527.2641.

Example 43

(4S)-6-[4-(aminomethyl)phenyl]-4-(propan-2-yl)-7-[3-(trifluoromethoxy)phenyl]-3,4-dihydropyrrolo[1,2-a]pyrazin-1(2H)-one [(I), R2=3-(trifluoromethoxy)phenyl, R3=4-(aminomethyl)phenyl, R4=H, A=—CH$_2$(CH$_3$)$_2$](cpd 138)

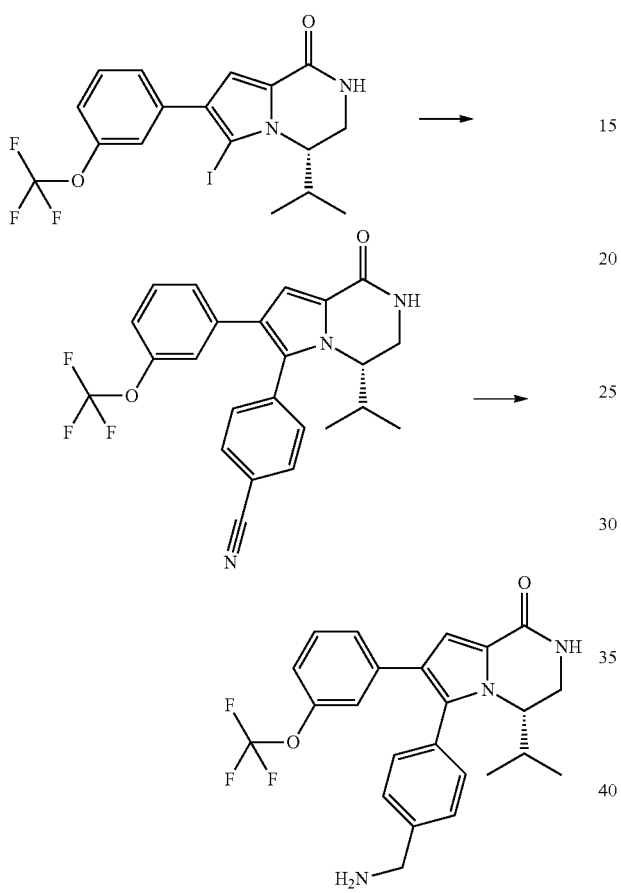

To a degassed solution of (4S)-6-iodo-4-(propan-2-yl)-7-[3-(trifluoromethoxy)phenyl]-3,4-dihydropyrrolo[1,2-a]pyrazin-1(2H)-one (68 mg, 0.15 mmol) in 5 ml of 1,4-dioxane and 0.5 ml of water, under argon atmosphere, (4-cyanophenyl)boronic acid (43 mg, 0.3 mmol), 1,1'-bis(diphenylphosphino)ferrocenepalladium complex with dichloromethane (12 mg, 0.013 mmol), cesium carbonate (126.0 mg, 0.45 mmol) were subsequently added. The mixture was heated at 85° C. for 3 hours in a sealed vial. The reaction was filtered through a celite pad and the solvent evaporated to dryness. The crude was then portioned between ethyl acetate and water, the organic layer dried over sodium sulphate and the solvent removed in vacuo. Purification by flash chromatography on silica gel column (EtOAc/Hex 8/2) led to a mixture of two regioisomers. 4-{(4S)-1-oxo-4-(propan-2-yl)-7-[3-(trifluoromethoxy)phenyl]-1,2,3,4-tetrahydropyrrolo[1,2-a]pyrazin-6-yl}benzonitrile was not characterized, but dissolved in 3 ml of methanol and reacted overnight at room temperature with NaBH$_4$ (14 mg, 0.36 mmol) in the presence of CoCl$_2$ (21 mg, 0.09 mmol) overnight. A further addition of NaBH$_4$ and CoCl$_2$ was necessary to complete the reaction, which was worked up with acqueous ammonia and extracted with ethyl acetate. The product was purified by silica chromatography (DCM/MeOH 9/1 NH$_3$ 0.2%) and isolated as a brownish solid.

$^1$H NMR (600 MHz, DMSO-d6) δ 7.68 (d, J=5.13 Hz, 1H), 7.39-7.45 (m, 2H), 7.30-7.35 (m, 1H), 7.24-7.30 (m, 2H), 7.20 (d, J=8.24 Hz, 1H), 7.07 (d, J=8.61 Hz, 1H), 6.97-7.01 (m, 1H), 6.92 (s, 1H), 4.00 (dd, J=3.48, 7.51 Hz, 1H), 3.84 (dd, J=4.03, 13.37 Hz, 1H), 3.80 (s, 2H), 3.47 (dd, J=4.95, 12.82 Hz, 1H), 1.85 (qd, J=6.94, 14.17 Hz, 1H), 0.72 (d, J=6.78 Hz, 3H), 0.44 (d, J=6.96 Hz, 3H). LCMS (HPLC Method 2): m/z 444 [M+H]$^+$@r.t. 4.89 min.

HRMS (ESI) calcd for C$_{24}$H$_{25}$F$_3$N$_3$O$_2$[M+H]$^+$ 444.1894 found 444.1891.

Example 44

(4S)-6-[3-(dimethylamino)prop-1-yn-1-yl]-4-(propan-2-yl)-7-[3-(trifluoromethoxy)phenyl]-3,4-dihydropyrrolo[1,2-a]pyrazin-1(2H)-one [(I), R2=3-(trifluoromethoxy)phenyl, R3=3-(dimethylamino)prop-1-yn-1-yl, R4=H, A=—CH$_2$(CH$_3$)$_2$-](cpd 139) conv. h

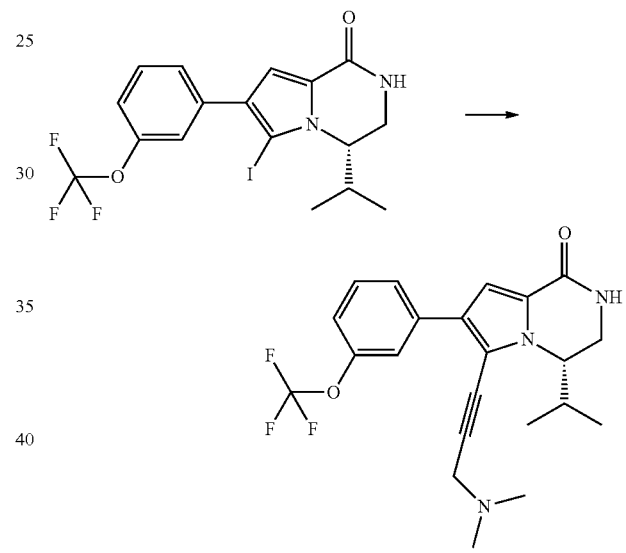

In a sealed vial under argon, (4S)-6-iodo-4-(propan-2-yl)-7-[3-(trifluoromethoxy)phenyl]-3,4-dihydropyrrolo[1,2-a]pyrazin-1(2H)-one (26 mg, 0.05 mmol) was reacted with 1,1-dimethylpropargyl-amine (12 µl, 0.1 mmol) in the presence of copper iodine (1.7 mg, 9.0 µmol), Pd(OAc)$_2$ (1 mg, 4 µmol), triphenylphosphine (2.3 mg, 8 µmol) and 800 µl of degassed piperidine as base and solvent. The reaction was let stir 24 h at room temperature, worked up with water and DCM and the crude was purified by RP-HPLC.

LCMS (HPLC Method 2): m/z 420 [M+H]$^+$@r.t. 3.90 min

Example 45

(4S)-6-(3-aminoprop-1-yn-1-yl)-4-(propan-2-yl)-7-[3-(trifluoromethoxy)phenyl]-3,4-dihydropyrrolo[1,2-a]pyrazin-1(2H)-one hydrochloride [(I), R2=3-(trifluoromethoxy)phenyl, R3=3-aminoprop-1-yn-1-yl, R4=H, A=—CH$_2$(CH$_3$)$_2$](cpd 140)

Prepared as described in Example 44, using tert-butyl prop-2-yn-1-ylcarbamate followed by boc removal, as described in Example 40

LCMS (HPLC Method 2): m/z 392 [M+H]$^+$@r.t. 2.75 min

Example 46

2,2-dimethyl-N-(2-{(4S)-6-(3-methylphenyl)-1-oxo-7-[3-(trifluoromethoxy)phenyl]-1,2,3,4-tetrahydropyrrolo[1,2-a]pyrazin-4-yl}ethyl)propanamide [(I), R2=3-(trifluoromethoxy)phenyl, R3=phenyl, R4=H, A=—CH₂CH₂—NH, R1=—COR5, R5=t-Bu](cpd 141) conv. m

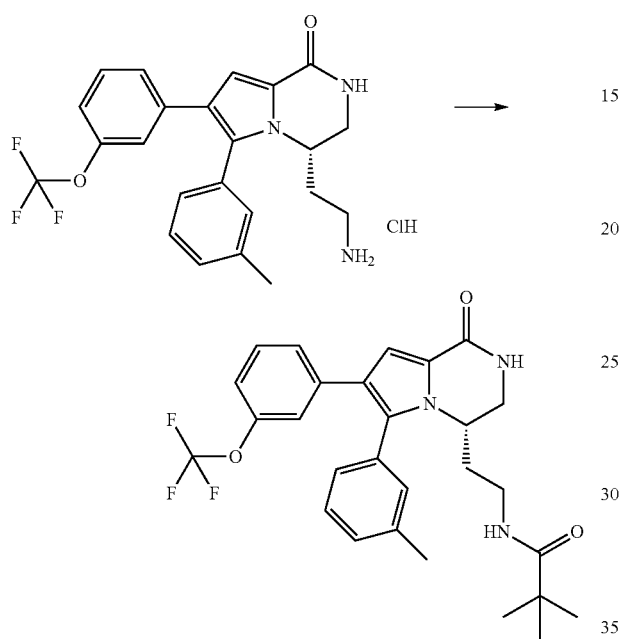

10 mg (0.023 mmol) of 1 (4S)-4-(2-aminoethyl)-6-(3-methylphenyl)-7-[3-(trifluoromethoxy)phenyl]-3,4-dihydropyrrolo[1,2-a]pyrazin-1(2H)-one hydrochloride were dissolved in 1.5 ml of DCM. To the obtained solution 20 µl (0.16 mmol) of pivaloyl chloride, 34 µl (0.2 mmol) of DIPEA, were added. The mixture was stirred at rt for 2 hours, the solution was portioned between ethyl acetate and saturated aqueous solution of NaHCO₃, the organic layer was washed with brine, dried over Na₂SO₄ and evaporated under vacuum. The product was purified by silica chromatography (DCM/MeOH 95/5) and isolated as a white solid 8.4 mg (74%).

¹H NMR (600 MHz, DMSO-d6) δ 7.72 (d, J=4.76 Hz, 1H), 7.31-7.38 (m, 2H), 7.22-7.29 (m, 3H), 7.18 (s, 1H), 7.12 (d, J=7.14 Hz, 1H), 7.03-7.07 (m, 2H), 6.85 (s, 1H), 4.06-4.15 (m, 1H), 3.77 (dd, J=3.75, 13.28 Hz, 1H), 3.53 (dd, J=3.75, 13.28 Hz, 1H), 2.75-2.93 (m, 2H), 2.31 (s, 3H), 1.72-1.83 (m, 1H), 1.43-1.52 (m, 1H), 0.91 (s, 9H).

LCMS (HPLC Method 2): m/z 514 [M+H]⁺@r.t. 6.01 min.
HRMS (ESI) calcd for C₂₈H₃₁F₃N₃O₃[M+H]⁺ 514.2312 found 514.2322.

Operating in an analogous way, the following compounds were obtained:

N-(2-{(4S)-1-oxo-6-phenyl-7-[3-(trifluoromethoxy)phenyl]-1,2,3,4-tetrahydropyrrolo[1,2-a]pyrazin-4-yl}ethyl)acetamide [(I), R2=3-(trifluoromethoxy)phenyl, R3=phenyl, R4=H, A=—CH₂CH₂—NH, R1=—COR5, R5=Me](cpd 142)

¹H NMR (600 MHz, DMSO-d6) δ 7.71 (d, J=5.13 Hz, 1H), 7.59-7.65 (m, 1H), 7.53-7.57 (m, 1H), 7.45-7.51 (m, 3H), 7.30-7.37 (m, 3H), 7.26 (d, J=8.24 Hz, 1H), 7.01-7.08 (m, 2H), 6.88 (s, 1H), 4.06-4.23 (m, 1H), 3.78 (dd, J=3.85, 13.19 Hz, 1H), 3.41 (dd, J=5.22, 12.55 Hz, 1H), 2.71-2.87 (m, 2H), 1.73-1.82 (m, 1H), 1.57 (s, 3H), 1.35-1.47 (m, 1H). LCMS (HPLC Method 2): m/z 458 [M+H]⁺@r.t. 4.86 min.
HRMS (ESI) calcd for C₂₄H₂₃F₃N₃O₃[M+H]⁺ 458.1686 found 458.1684.

2,2-dimethyl-N-(2-{(4S)-1-oxo-6-phenyl-7-[3-(trifluoromethoxy)phenyl]-1,2,3,4-tetrahydropyrrolo[1,2-a]pyrazin-4-yl}ethyl)propanamide
[(I), R2=3-(trifluoromethoxy)phenyl, R3=phenyl, R4=H, A=—CH₂CH₂—NH, R1=—COR5, R5=t-Bu](cpd 143)

¹H NMR (600 MHz, DMSO-d6) δ 7.73 (d, J=5.13 Hz, 1H), 7.44-7.52 (m, 3H), 7.30-7.38 (m, 2H), 7.22-7.27 (m, 1H), 6.99-7.08 (m, 2H), 6.84 (s, 1H), 4.04-4.18 (m, 1H), 3.78 (dd, J=3.75, 13.46 Hz, 1H), 3.53 (dd, J=5.49, 12.64 Hz, 1H), 2.76-2.91 (m, 2H), 1.70-1.83 (m, 1H), 1.40-1.53 (m, 1H), 0.88-0.92 (m, 9H).

LCMS (HPLC Method 2): m/z 500 [M+H]⁺@r.t. 5.76 min.
HRMS (ESI) calcd for C₂₄H₂₃F₃N₃O₃[M+H]⁺ 500.2156 found 500.215.

Example 47

1-tert-butyl-3-(2-{(4S)-6-(3-methylphenyl)-1-oxo-7-[3-(trifluoromethoxy)phenyl]-1,2,3,4-tetrahydropyrrolo[1,2-a]pyrazin-4-yl}ethyl)urea [(I), R2=3-(trifluoromethoxy)phenyl, R3=3-methylphenyl, R4=H, A=—CH₂CH₂—NH, R1=—CONHR7, R7=t-Bu] (cpd 144) Conv. o

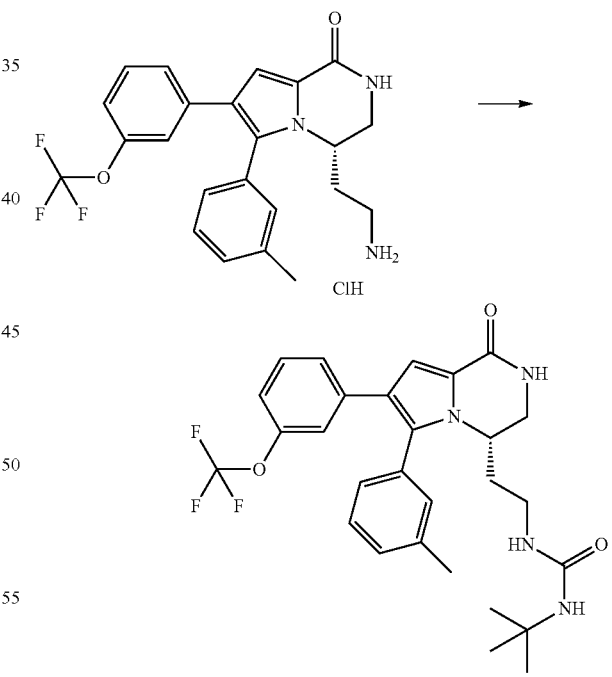

28 mg (0.065 mmol) of 1 (4S)-4-(2-aminoethyl)-6-(3-methylphenyl)-7-[3-(trifluoromethoxy)phenyl]-3,4-dihydropyrrolo[1,2-a]pyrazin-1(2H)-one hydrochloride were dissolved in 2 ml of DCM. To the obtained solution, 20 µl (0.20 mmol) of t-butyl isocyanate, 60 µl (0.33 mmol) of DIPEA, were added. The mixture was stirred at rt for 18 hours, the solution was portioned between ethyl acetate and saturated aqueous solution of NaHCO₃, the organic layer was washed with brine, dried over Na$_2$SO$_4$ and evaporated under vacuum. The crude was purified by HPLC preparative method 1, to provide 1-tert-butyl-3-(2-{(4S)-6-(3-methylphenyl)-1-oxo-7-[3-(trifluoromethoxy)phenyl]-1,2,3,4-tetrahydropyrrolo[1,2-a]pyrazin-4-yl}ethyl)urea 12 mg (35%) as a white solid.

$^1$H NMR (600 MHz, DMSO-d6) δ 7.71 (d, J=5.13 Hz, 1H), 7.32-7.38 (m, 2H), 7.28 (t, J=8.52 Hz, 2H), 7.18 (s, 1H), 7.14 (d, J=7.51 Hz, 1H), 7.06 (m, 1H), 6.89 (s, 1H), 5.36-5.53 (m, 2H), 4.13-4.21 (m, 1H), 3.76 (dd, J=3.85, 13.19 Hz, 1H), 3.41-3.44 (m, 1H), 2.65-2.80 (m, 2H), 2.32 (s, 3H), 1.65-1.83 (m, 1H), 1.35-1.52 (m, 1H), 1.14 (s, 9H). LCMS (HPLC Method 2): m/z 529 [M+H]$^+$@r.t. 5.96 min.

HRMS (ESI) calcd for C$_{28}$H$_{32}$F$_3$N$_4$O$_3$[M+H]$^+$ 529.2421 found 529.2426.

Operating in an analogous way, the following compounds were obtained:

1-tert-butyl-3-(2-{(4S)-1-oxo-6-phenyl-7-[3-(trifluoromethoxy)phenyl]-1,2,3,4-tetrahydropyrrolo[1,2-a]pyrazin-4-yl}ethyl)urea [(I), R2=3-(trifluoromethoxy)phenyl, R3=phenyl, R4=H, A=—CH$_2$CH$_2$—NH, R'=CONHR7, R7=t-Bu](cpd 145)

$^1$H NMR (600 MHz, DMSO-d6) δ 7.72 (d, J=4.95 Hz, 1H), 7.44-7.51 (m, 3H), 7.34-7.38 (m, 2H), 7.31-7.35 (m, 1H), 7.25 (d, J=8.06 Hz, 1H), 7.02-7.10 (m, 2H), 6.88 (s, 1H), 5.44 (t, J=5.86 Hz, 1H), 5.36 (s, 1H), 4.17 (td, J=4.21, 8.79 Hz, 1H), 3.77 (dd, J=3.75, 13.28 Hz, 1H), 3.42 (dd, J=5.22, 12.73 Hz, 1H), 2.63-2.77 (m, 2H), 1.65-1.80 (m, 1H), 1.37-1.49 (m, 1H), 1.14 (s, 9H). LCMS (HPLC Method 2): m/z 515 [M+H]$^+$ @r.t. 5.7 min.

HRMS (ESI) calcd for C$_{27}$H$_{30}$F$_3$N$_4$O$_3$[M+H]$^+$ 515.2265 found 515.226.

1-butan-2-yl-3-(2-{(4S)-1-oxo-6-phenyl-7-[3-(trifluoromethoxy)phenyl]-1,2,3,4-tetrahydropyrrolo[1,2-a]pyrazin-4-yl}ethyl)urea [(I), R2=3-(trifluoromethoxy)phenyl, R3=phenyl, R4=H, A=—CH$_2$CH$_2$—NH, R'=CONHR7, R7=1-butan-2-yl](cpd 146)

$^1$H NMR (600 MHz, DMSO-d6) δ 7.72 (d, J=4.95 Hz, 1H), 7.42-7.51 (m, 3H), 7.31-7.39 (m, 3H), 7.25 (d, J=7.88 Hz, 1H), 7.01-7.09 (m, 2H), 6.88 (s, 1H), 5.50 (t, J=5.77 Hz, 1H), 5.42 (dd, J=4.49, 8.15 Hz, 1H), 4.13-4.23 (m, J=4.40 Hz, 1H), 3.77 (dd, J=2.84, 13.64 Hz, 1H), 3.34-3.48 (m, 2H), 2.66-2.84 (m, 2H), 1.66-1.81 (m, 1H), 1.40-1.51 (m, 1H), 1.19-1.32 (m, 2H), 0.92 (dd, J=4.85, 6.50 Hz, 3H), 0.76 (dt, J=5.77, 7.37 Hz, 3H).

LCMS (HPLC Method 2): m/z 515 [M+H]$^+$@r.t. 5.57 min.
HRMS (ESI) calcd for C$_{27}$H$_{30}$F$_3$N$_4$O$_3$[M+H]$^+$ 515.2265 found 515.2264.

Example 48

N-(2-{(4S)-1-oxo-6-phenyl-7-[3-(trifluoromethoxy)phenyl]-1,2,3,4-tetrahydropyrrolo[1,2-a]pyrazin-4-yl}ethyl)methanesulfonamide

[(I), R2=(trifluoromethoxy)phenyl, R3=phenyl, R4=H, A=—CH$_2$CH$_2$—NH, R'=—S(O)$_2$R9, R9=Me](cpd 147) conv. s

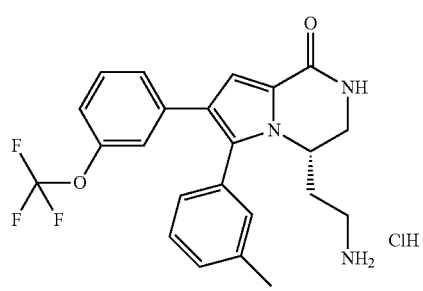

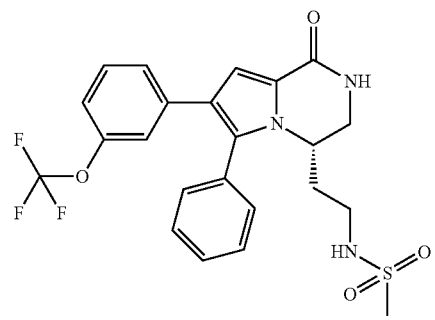

40 mg (0.096 mmol) of 1(4S)-4-(2-aminoethyl)-6-phenyl)-7-[3-(trifluoromethoxy)phenyl]-3,4-dihydropyrrolo[1,2-a]pyrazin-1(2H)-one hydrochloride were dissolved in 3 ml of DCM. To the obtained solution, 15 μl (0.192 mmol) of methanesulfonyl chloride, 57 μl (0.33 mmol) of DIPEA, were added. The mixture was stirred at rt for 2 hours, the solution was portioned between ethyl acetate and saturated aqueous solution of NaHCO$_3$, the organic layer was washed with brine, dried over Na$_2$SO$_4$ and evaporated under vacuum. The product was purified by HPLC preparative method 2 and isolated as a off-white solid 24 mg (51%) as a white solid.

$^1$H NMR (600 MHz, DMSO-d6) δ 7.74 (d, J=4.95 Hz, 1H), 7.45-7.55 (m, 3H), 7.38 (dd, J=2.56, 6.78 Hz, 2H), 7.32-7.36 (m, 1H), 7.26 (d, J=8.06 Hz, 1H), 7.01-7.10 (m, 2H), 6.88 (s, 1H), 6.82 (t, J=6.04 Hz, 1H), 4.27 (td, J=4.24, 8.20 Hz, 1H), 3.80 (dd, J=3.75, 13.28 Hz, 1H), 3.39 (dd, J=5.22, 13.10 Hz, 1H), 2.69 (s, 3H), 2.64-2.68 (m, 2H), 1.77-1.87 (m, 1H), 1.49-1.61 (m, 1H). LCMS (HPLC Method 2): m/z 494 [M+H]$^+$@r.t. 5.15 min.

HRMS (ESI) calcd for C$_{24}$H$_{23}$F$_3$N$_3$O$_4$S [M+H]$^+$ 494.1356 found 494.1356.

Example 49

1-(2-{(4S)-6-(3-methylphenyl)-1-oxo-7-[3-(trifluoromethoxy)phenyl]-1,2,3,4-tetrahydropyrrolo[1,2-a]pyrazin-4-yl}ethyl)guanidine hydrochloride

[(I), R2=3-(trifluoromethoxy)phenyl, R3=3-methylphenyl, R4=H, A=—CH$_2$CH$_2$—NH, R'=—C(NH)NH$_2$](cpd 148) conv. s

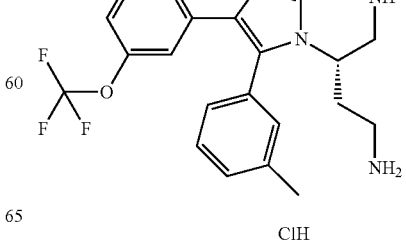

-continued

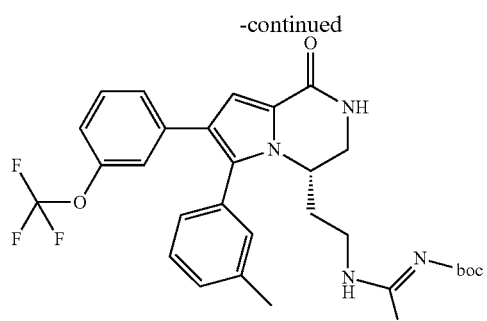

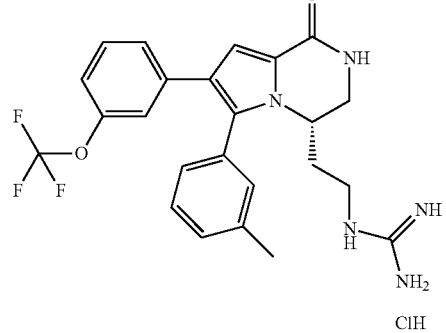

(S)-4-(2-Amino-ethyl)-6-(3-methyl-phenyl)-7-(3-trifluoromethoxy-phenyl)-3,4-dihydro-2H-pyrrolo[1,2-a]pyrazin-1-one hydrochloride (20 mg, 43 μmol) and diisopropylamine (20 uL, 120 μmol) were suspended in 20 ml of acetonitrile; N-Boc protected pyrazole-1-carboxyamidine hydrochloride (20 mg, 64 μmol) was added. The reaction was let stir overnight at room temperature and monitored through TLC (DCM/MeOH 98/2). At reaction completion the solvent was removed, the crude was dissolved with ethyl acetate and washed with water. The organic layer dried and evaporated, was chromatographated on silica (Cycloexane/EthylAcetate/Methanol 7:2.5:0.5) to obtain tert-butyl{(Z)-[(tert-butoxycarbonyl)amino][(2-{(4S)-6-(3-methylphenyl)-1-oxo-7-[3-(trifluoromethoxy)phenyl]-1,2,3,4-tetrahydropyrrolo[1,2-a]pyrazin-4-yl}ethyl)amino]methylidene}carbamate as a colorless oil.

LCMS (HPLC Method 2): m/z 672 [M+H]$^+$@r.t. 8.48 min.
HRMS (ESI) calcd for $C_{34}H_{41}F_3N_5O_6$[M+H]$^+$ 672.3004 found 672.2991.

The product obtained was suspended in a solution 4 N of hydrochloride acid in dioxane and stirred for 6 hours, the solvent was evaporated and the pure product 1-(2-{(4S)-6-(3-methylphenyl)-1-oxo-7-[3-(trifluoromethoxy)phenyl]-1,2,3,4-tetrahydropyrrolo[1,2-a]pyrazin-4-yl}ethyl)guanidine hydrochloride was isolated as a white solid.

$^1$H NMR (600 MHz, DMSO-d6) δ 7.73 (d, J=4.95 Hz, 1H), 7.33-7.40 (m, 2H), 7.28 (d, J=6.96 Hz, 3H), 7.12-7.20 (m, 2H), 7.06-7.10 (m, 2H), 6.89 (br. s., 1H), 4.30 (d, J=4.76 Hz, 1H), 3.85 (dd, J=3.85, 13.19 Hz, 1H), 3.38-3.42 (m, 1H), 2.79-2.91 (m, 2H), 2.32 (s, 3H), 1.74-1.83 (m, 1H), 1.61 (dt, J=6.96, 13.55 Hz, 1H).

LCMS (HPLC Method 2): m/z 472 [M+H]$^+$@r.t. 5.68 min.
HRMS (ESI) calcd for $C_{34}H_{41}F_3N_5O_6$[M+H]$^+$ 472.1955 found 472.1945.

Operating in an analogous way, the following compound was obtained:

1-(2-{(4S)-6-[4-(methylsulfonyl)phenyl]-1-oxo-7-[3-(trifluoromethoxy)phenyl]-1,2,3,4-tetrahydropyrrolo[1,2-a]pyrazin-4-yl}ethyl)guanidine hydrochloride [(I), R2=3-(trifluoromethoxy)phenyl, R3=4-(methylsulfonyl)phenyl, R4=H, A=—CH$_2$CH$_2$—NH, R'=—C(NH)NH$_2$](cpd 149)

$^1$H NMR (600 MHz, DMSO-d6) δ 7.93-8.04 (m, 2H), 7.84 (d, J=4.76 Hz, 1H), 7.62-7.68 (m, 2H), 7.36-7.42 (m, 1H), 7.35 (br. s., 1H), 7.24 (d, J=7.51 Hz, 1H), 7.13 (d, J=7.69 Hz, 1H), 7.09 (s, 1H), 6.84 (s, 1H), 4.31 (br. s., 1H), 3.91 (dd, J=3.39, 12.91 Hz, 1H), 3.43 (dd, J=4.85, 12.90 Hz, 1H), 3.26 (s, 3H), 2.76-2.92 (m, J=5.31 Hz, 2H), 1.82 (qd, J=7.00, 13.99 Hz, 1H), 1.62 (qd, J=7.00, 13.99 Hz, 1H).

LCMS (HPLC Method 2): m/z 536 [M+H]$^+$@r.t. 5.06 min.
HRMS (ESI) calcd for $C_{34}H_{41}F_3N_5O_6$[M+H]$^+$ 536.1574 found 536.1567.

Example 50

4-(piperidin-4-yl)-7-[3-(trifluoromethoxy)phenyl]-3,4-dihydropyrrolo[1,2-a]pyrazin-1(2H)-one [(I) A=piperidin-4-yl, R2=3-(trifluoromethoxy)phenyl, R3=R4=H]

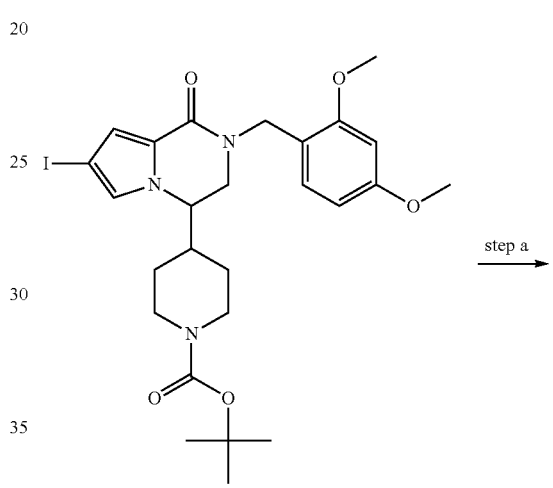

step a

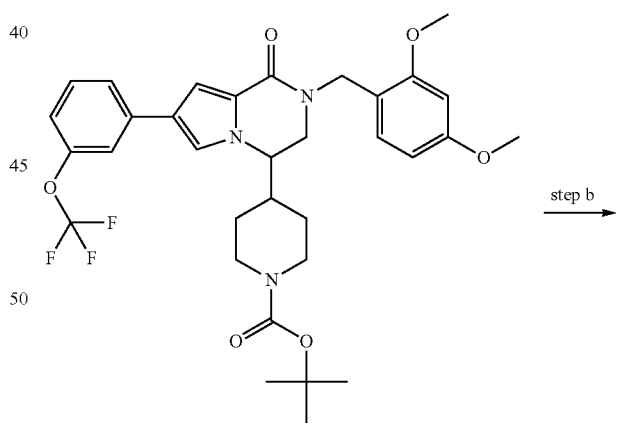

step b

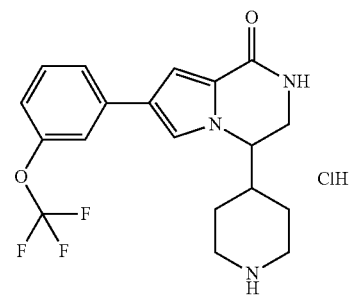

Step a

Cesium carbonate (32.6 mg, 0.1 mmol), [3-(trifluoromethoxy)phenyl]boronic acid (20 mg, 0.1 mmol), and 1,1'-bis(diphenylphosphino)ferrocenepaladium (4 mg, 0.005 mmol) complex with dichloromethane, were subsequently added to a solution of tert-butyl 4-[2-(2,4-dimethoxybenzyl)-7-iodo-1-oxo-1,2,3,4-tetrahydropyrrolo[1,2-a]pyrazin-4-yl]piperidine-1 carboxylate (30 mg, 0.05 mmol) in 3 ml of 1,4-dioxane and 1 ml of water, under argon atmosphere. The mixture was heated at 90° for 4 hours in a sealed vial. The reaction was filtered through a celite pad and the solvent evaporated to dryness. The crude was portioned between ethyl acetate and water, the organic layer dried over sodium sulphate and the solvent removed in vacuo. Purification by flash chromatography on silica gel column (Hex/EtOAc 8/2) afforded the compound tert-butyl 4-{2-(2,4-dimethoxybenzyl)-1-oxo-7-[3-(trifluoromethoxy)phenyl]-1,2,3,4-tetrahydropyrrolo[1,2-a]pyrazin-4-yl}piperidine-1-carboxylate as oil (10 mg, 32%).

LCMS (HPLC Method 2): m/z 630 [M+H]$^+$@r.t. 6.50 min.

Step b

The product obtained was suspended in a solution 4 N of hydrochloride acid in dioxane and stirred for 6 hours, the solvent was evaporated and the pure product 4-(piperidin-4-yl)-7-[3-(trifluoromethoxy)phenyl]-3,4-dihydropyrrolo[1,2-a]pyrazin-1(2H)-one hydrochloride was isolated as a white solid.

LCMS (HPLC Method 2): m/z 380 [M+H]$^+$@r.t. 3.57 min

Pharmacology

The compounds of formula (I) are active as protein kinase inhibitors and are therefore useful, for instance, to restrict the unregulated proliferation of tumour cells.

In therapy, they may be used in the treatment of various tumours, such as those formerly defined, as well as in the treatment of other cell proliferative disorders such as benign prostate hyperplasia, familial adenomatosis polyposis, neurofibromatosis, psoriasis, vascular smooth cell proliferation associated with atherosclerosis, pulmonary fibrosis, arthritis, glomerulonephritis and post-surgical stenosis and restenosis.

The short forms and abbreviations used herein have the following meaning:

| Ci | Curie | L | liter |
| DMSO | dimethylsulfoxide | mL | milliliter |
| KDa | kiloDalton | μL | microliter |
| microCi | microCurie | M | molar |
| mg | milligram | mM | millimolar |
| microg | microgram | μM | micromolar |
| ng | nanogram | nM | nanomolar |

Biochemical Assay for Inhibitors of PIM1 Kinase Activity

The inhibitory activity of putative kinase inhibitors and the potency of selected compounds were determined using a trans-phosphorylation assay.

Specific peptide or protein substrates were trans-phosphorylated by their specific ser-thr or tyr kinase in the presence of ATP traced with $^{33}$P-γ-ATP, and in the presence of their own optimal buffer and cofactors.

At the end of the phosphorylation reaction, more than 98% unlabeled ATP and radioactive ATP were captured by an excess of the ion exchange dowex resin; the resin then settled down to the bottom of the reaction plate by gravity. Supernatant was subsequently withdrawn and transferred into a counting plate, then evaluated by β-counting.

Reagents/Assay Conditions i. Dowex Resin Preparation 500 g of wet resin (SIGMA, custom prepared resin DOWEX 1×8 200-400 mesh, 2.5 Kg) were weighed out and diluted to 2 L in 150 mM sodium formate, pH 3.00.

The resin was allowed to settle down (some hours) and then the supernatant was discarded.

After three washes as above over a couple of days, the resin was allowed to settle and two volumes (wrt the resin volume) of 150 mM sodium formate buffer were added.

The pH was then measured and should have been around 3.00.

The washed resin was stable for more than one week; the stock resin was kept at 4° C. before use.

ii. Kinase Buffer (KB)

The buffer for PIM1 assay was composed of HEPES 50 mM, at pH 7.5, with 10 mM MgCl$_2$, 1 mM DTT, 3 μM NaVO$_3$, and 0.2 mg/mL BSA.

Full-length human PIM1 was expressed and purified as described in Bullock A N, et al., J. Biol. Chem. 2005, 280, 41675-82.

The enzyme showed a linear kinetic after a step of pre-activation by auto-phosphorylation in the following conditions:

1.7 μM PIM1 was incubated 1 h at 28° C. in the presence of 125 μM ATP.

iii. Assay Conditions

ATP concentration: 200 μM; $^{33}$P-γ-ATP: 6 nM; Enzyme concentration: 1 nM Substrate concentration Aktide (Chemical Abstract Service Registry Number 324029-01-8): 25 μM iv. Robotized Dowex Assay The test mix consisted of:

1) 3× Enzyme mix (done in Kinase Buffer 3×), 5 μL/well
2) 3× substrate and ATP mix (done in ddH$_2$O), together with $^{33}$P-γ-ATP, 5 μL/well
3) 3× test compounds (diluted into ddH$_2$O—3% DMSO)—5 μL/well See below for compound dilution and assay scheme v. Dilution of Compounds For IC$_{50}$ determination, test compounds were received as a 1 mM solution in 100% DMSO and distributed into 96-well plates: compounds were then plated into the first column of a new 96-well plate (A1 to G1), 100 μl/well.

An automated station (Biomek FX, Beckman) was used for serial dilutions, producing 1:3 dilutions in 100% DMSO, from line A1 to A10, for all the compounds in the column. Moreover, 4-5 copies of daughter plates were prepared by reformatting 5 μL of this first set of 100% DMSO dilution plates into 384-deep well plates: one copy of these serial dilution plates with the test compounds was thawed on the day of study, reconstituted at the working concentration (3-fold the final concentration) with 162 μL/well of water and used for IC$_{50}$ determination assays. In a standard experiment, the highest concentration (3×) of compounds was typically 30 μM, while the lowest one was typically 1.5 nM.

Each 384-well plate generated at least one curve of the standard inhibitor staurosporine and reference wells (total enzyme activity vs. no enzymatic activity) for evaluation of Z' and signal to background (S/B) ratio.

vi. Assay Scheme 384-well plates, V bottom (test plates) were prepared with 5 μl of compound diluted as previously described (3×) and then placed onto a PlateTrak 12 robotized station (Perkin Elmer; the robot has one 384-tip pipetting head for assay start, plus one 96-tip head for dispensing resin) together with one reservoir for Enzyme mix (3×) and one for ATP mix (3×).

Data were analyzed by an internally customized version of the "Assay Explorer" SW package, which provided sigmoidal fitting of the ten-dilution curves for IC$_{50}$ determination in secondary assay/hit confirmation routines.

Method for PIM2 Kinase Inhibition Assay: Dowex Technique i. Kinase Buffer (KB)

The buffer for PIM2 assay was composed of HEPES 50 mM, at pH 7.5, with 1 mM MgCl$_2$, 1 mM DTT, 3 µM Na$_3$VO$_4$, and 0.2 mg/mL BSA.

Full-length human PIM2 was expressed and purified as described in Fedorov O, et al., PNAS 2007 104, 51, 20523-28.

ii. Assay Conditions (Final Concentrations)

Enzyme concentration=1.5 nM; ATP=4 µM; $^{33}$P-γ-ATP=1 nM

Aktide substrate (Chemical Abstract Service Registry Number 324029-01-8)=5 µM iii. Robotized Dowex Assay See above: same procedure as described for PIM1.

In Vitro Cell Proliferation Assay

BaF3 cell line transfected with PIM1 was generated following the procedure described in Pogacic, V. et al Cancer Research 2007, 67, 6916-6924.

MV-4-11 (biphenotypic B myelomonocytic leukemia) cell line was obtained from ATCC.

Media for BaF3-PIM1 cell line contained RPMI 1640 plus 2 mM Glutamine and 10% Fetal bovine serum.

Media for MV-4-11 cell line contained RPMI 1640 or EMEM plus 2 mM Glutamine and 10% Fetal bovine serum.

BaF3-PIM1 and MV-4-11 cells were seeded at 125 cells/well and 1250 cells/well respectively in a 384-well white plates in complete medium and treated with compounds dissolved in 0.1% DMSO, 24 h after seeding.

The cells were incubated at 37° C. and 5% CO$_2$ and after 72 hours the plates were processed using CellTiter-Glo assay (Promega) following the manufacturer's instruction.

CellTiter-Glo was a homogenous method based on the quantification of the ATP present, an indicator of metabolitically active cells. ATP was quantified using a system based on luciferase and D-luciferin resulting into light generation. The luminescent signal was proportional to the number of cells present in culture.

Briefly 25 µl/well reagent solution were added to each wells and after 5 minutes shacking microplates were red by Envision (PerkinElmer) luminometer. The luminescent signal was proportional to the number of cells present in culture.

Inhibitory activity was evaluated comparing treated versus control data using Assay Explorer (MDL) program. IC$_{50}$ was calculated using sigmoidal interpolation curve.

Given the above inhibition assays, the compounds of the formula (I) of the invention resulted to possess a good PIM-1 inhibitory activity, typically with an IC$_{50}$ well below 0.05 microM and a good PIM-2 inhibitory activity, typically with an IC$_{50}$ well below 0.2 microM.

Moreover, the compounds of the formula (I) of the invention showed good cellular proliferation inhibitory activity, typically with an IC$_{50}$ in the range of from 1 to 7 microM in MV-4-11 and in the range of from 0.05 to 7 microM in BaF3-PIM1 cells.

The following Table A reports the experimental data of some representative compounds of the invention of formula (I) being tested in the specific in vitro kinase assay above described on the PIM-1 and PIM-2 enzyme in comparison with some Ref. compounds of the prior art.

Following Table A also reports the antiproliferative activity of some representative compounds of the invention of formula (I) being tested against MV-4-11 and BaF3-PIM1 cells in comparison with some Ref. compounds of the prior art.

The Ref. compounds are disclosed in the patent application WO2010/031816 cited above.

TABLE A

| Compound | PIM-1 IC$_{50}$ µM | PIM-2 IC$_{50}$ µM | BaF3-PIM1 IC$_{50}$ µM | MV4-11 IC$_{50}$ µM |
|---|---|---|---|---|
| Ref. cmp 1 (A157-M-B65 isomer S) | 0.01 | 0.10 | | >10 |
| Ref. cmp 2 (A127-M-B65 isomer S) | 0.01 | 0.18 | | >10 |
| Ref. cmp 3 (A127-M-B61 isomer S) | 0.02 | 0.25 | | >10 |
| 28 | 0.007 | 0.055 | 0.275 | 1.736 |
| 29 | 0.019 | 0.143 | 0.315 | 2.618 |
| 55 | 0.017 | 0.077 | 0.140 | 3.605 |
| 57 | 0.016 | 0.032 | 0.239 | 2.603 |
| 82 | 0.001 | 0.035 | 0.486 | 5.965 |
| 83 | 0.004 | 0.038 | 0.329 | 2.888 |
| 85 | 0.012 | 0.069 | 0.085 | 3.658 |
| 87 | 0.009 | 0.038 | 0.202 | 3.613 |
| 92 | 0.005 | 0.015 | 0.147 | 2.200 |
| 17 | 0.034 | 0.117 | 0.450 | |
| 31 | 0.023 | 0.051 | 0.326 | 2.593 |
| 32 | 0.008 | 0.069 | 2.025 | |
| 59 | 0.040 | 0.114 | 0.323 | 4.620 |
| 33 | 0.004 | 0.015 | 0.598 | |
| 38 | 0.020 | 0.102 | 3.030 | |
| 40 | 0.043 | 0.155 | 0.340 | 5.036 |
| 44 | 0.024 | 0.110 | 6.570 | |
| 45 | 0.041 | 0.102 | 3.960 | 3.170 |
| 43 | 0.012 | 0.021 | 7.000 | |
| 77 | 0.007 | 0.058 | 2.325 | |
| 79 | 0.013 | 0.093 | 1.223 | |
| 78 | 0.006 | 0.090 | 4.065 | |
| 81 | 0.011 | 0.069 | 6.050 | |
| 80 | 0.020 | 0.075 | 3.813 | |
| 84 | 0.011 | 0.090 | 0.224 | |
| 93 | 0.001 | 0.016 | 0.699 | |
| 70 | 0.016 | 0.113 | 0.418 | 1.500 |
| 71 | 0.014 | 0.044 | 0.273 | 3.140 |
| 94 | 0.020 | 0.027 | 0.428 | 5.425 |
| 95 | 0.006 | 0.017 | 0.573 | 1.260 |
| 96 | 0.001 | 0.003 | 5.470 | |
| 97 | 0.007 | 0.022 | 1.500 | 2.100 |
| 99 | 0.002 | 0.007 | 0.410 | 0.672 |
| 100 | 0.001 | 0.002 | 3.101 | 0.616 |
| 101 | 0.001 | 0.009 | 0.296 | 0.939 |
| 102 | 0.019 | 0.156 | 0.836 | 1.640 |
| 103 | 0.011 | 0.153 | 1.180 | 2.930 |
| 104 | 0.004 | 0.048 | 7.000 | |
| 105 | 0.016 | 0.109 | 6.950 | |
| 116 | 0.003 | 0.022 | 0.142 | 0.861 |
| 115 | 0.003 | 0.046 | 0.076 | 0.812 |
| 110 | 0.022 | 0.129 | 3.900 | 3.195 |
| 109 | 0.011 | 0.082 | 6.510 | |
| 134 | 0.002 | 0.066 | 4.325 | 7.055 |
| 135 | 0.001 | 0.013 | 6.450 | |
| 147 | 0.026 | 0.172 | 0.638 | 3.620 |
| 142 | 0.034 | 0.174 | 0.491 | 4.890 |
| 112 | 0.006 | 0.016 | 0.071 | 1.772 |
| 118 | 0.027 | 0.152 | 0.310 | 0.760 |
| 120 | 0.001 | 0.003 | 1.360 | 5.350 |
| 126 | 0.013 | 0.021 | 0.125 | 0.776 |
| 127 | 0.012 | 0.024 | 0.125 | 0.433 |
| 128 | 0.008 | 0.032 | 0.175 | 0.470 |
| 123 | 0.016 | 0.045 | 0.089 | 0.730 |
| 124 | 0.024 | 0.160 | 0.130 | 0.468 |
| 125 | 0.044 | 0.097 | 0.304 | 0.940 |
| 121 | 0.003 | 0.012 | 0.086 | 0.660 |
| 122 | 0.017 | 0.086 | 0.165 | 0.776 |
| 129 | 0.003 | 0.012 | 0.198 | 0.710 |
| 130 | 0.001 | 0.003 | 0.150 | |
| 106 | 0.027 | 0.099 | 0.210 | |
| 138 | 0.012 | 0.173 | 0.276 | |
| 148 | 0.008 | 0.012 | 0.110 | |
| 149 | 0.008 | 0.019 | 1.770 | |
| 113 | 0.023 | 0.036 | 0.053 | |

So far, the novel compounds of the invention are unexpectedly endowed with a potent PIM-1 and PIM-2 inhibitory activity resulting in an antiproliferative activity significantly higher than that of the structurally closest prior art compounds. Therefore, the compounds of the invention are particularly advantageous, in therapy, against cancer.

The invention claimed is:
1. A compound of formula (I):

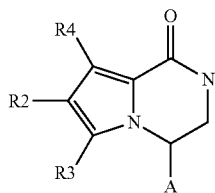

(I)

wherein
A is selected from straight or branched $C_1$-$C_6$ alkyl, heterocyclyl and —$(CH_2)_{1-3}$—X—R1;
R1 is hydrogen, halogen or an optionally substituted group selected from straight or branched $C_1$-$C_6$ alkyl, $C_3$-$C_7$ cycloalkyl, cycloalkyl-alkyl, $C_2$-$C_6$ alkenyl, $C_2$-$C_6$ alkynyl, aryl, arylalkyl, heterocyclyl and heterocyclylalkyl;
R2 is an optionally substituted group selected from straight or branched $C_1$-$C_6$ alkyl, $C_3$-$C_7$ cycloalkyl, cycloalkyl-alkyl, $C_2$-$C_6$ alkenyl, $C_2$-$C_6$ alkynyl, aryl, arylalkyl, heterocyclyl and heterocyclylalkyl;
R3 is hydrogen, halogen, cyano or an optionally substituted group selected from $C_3$-$C_7$ cycloalkyl, cycloalkyl-alkyl, $C_2$-$C_6$ alkenyl, and R4 is halogen, cyano or an optionally substituted group selected from $C_3$-$C_7$ cycloalkyl, cycloalkyl-alkyl, $C_2$-$C_6$ alkenyl, or R3 is halogen, cyano or an optionally substituted group selected from $C_3$-$C_7$ cycloalkyl, cycloalkyl-alkyl, $C_2$-$C_6$ alkenyl, and R4 is hydrogen, halogen, cyano or an optionally substituted group selected from $C_3$-$C_7$ cycloalkyl, cycloalkyl-alkyl, $C_2$-$C_6$ alkenyl,
$C_2$-$C_6$ alkynyl, aryl, arylalkyl, heterocyclyl and heterocyclylalkyl;
X is a single bond or a divalent radical selected from —NR'—, and —O—, wherein R' is hydrogen, COR5, C(NH)R5, S(O)$_2$R9, or an optionally substituted straight or branched $C_1$-$C_6$ alkyl, $C_3$-$C_7$ cycloalkyl, cycloalkyl-alkyl, aryl, arylalkyl, heterocyclyl and heterocyclylalkyl or, together with the nitrogen atom to which they are bound, R' and R1 may form a 5 to 7 membered heteroaryl or heterocyclyl group optionally containing one additional heteroatom selected from N, O and S;
wherein:
R5 is OR6, NR7R8 or an optionally substituted group selected from straight or branched $C_1$-$C_6$ alkyl, $C_3$-$C_7$ cycloalkyl, cycloalkyl-alkyl, $C_2$-$C_6$ alkenyl, $C_2$-$C_6$ alkynyl, aryl, arylalkyl, heterocyclyl and heterocyclylalkyl wherein:
R6 is an optionally substituted group selected from straight or branched $C_1$-$C_6$ alkyl, $C_3$-$C_7$ cycloalkyl, aryl and heterocyclyl;
R7 and R8 are each independently hydrogen or an optionally substituted group selected from straight or branched $C_1$-$C_6$ alkyl, $C_3$-$C_7$ cycloalkyl, aryl and heterocyclyl;
R9 is an optionally substituted group selected from straight or branched $C_1$-$C_6$ alkyl, $C_3$-$C_7$ cycloalkyl, aryl and heterocyclyl;
and a pharmaceutically acceptable salt thereof, wherein any of the above R1, R2, R3, R4, R5, R6, R7, R8, R9 and R' group may be optionally substituted, in any of their free positions, by one or more groups independently selected from: halogen atom, nitro, oxo, cyano, $C_1$-$C_6$ alkyl, polyfluorinated alkyl, polyfluorinated alkoxy, alkenyl, alkynyl, hydroxyalkyl, aryl, arylalkyl, heterocyclyl, $C_3$-$C_7$ cycloalkyl, hydroxy, alkoxy, aryloxy, heterocyclyloxy, methylenedioxy, alkylcarbonyloxy, arylcarbonyloxy, cycloalkenyloxy, heterocyclylcarbonyloxy, alkylideneaminooxy, carboxy, alkoxycarbonyl, aryloxycarbonyl, cycloalkyloxycarbonyl, heterocyclyloxycarbonyl, amino, ureido, alkylamino, dialkylamino, arylamino, diarylamino, heterocyclylamino, formylamino, alkylcarbonylamino, arylcarbonylamino, heterocyclylcarbonylamino, aminocarbonyl, alkylaminocarbonyl, dialkylaminocarbonyl, arylaminocarbonyl, heterocyclylaminocarbonyl, alkoxycarbonylamino, hydroxyaminocarbonyl, alkoxyimino, alkylsulfonylamino, arylsulfonylamino, heterocyclylsulfonylamino, formyl, alkylcarbonyl, arylcarbonyl, cycloalkylcarbonyl, heterocyclylcarbonyl, alkylsulfonyl, arylsulfonyl, aminosulfonyl, alkylaminosulfonyl, dialkylaminosulfonyl, arylaminosulfonyl, heterocyclylaminosulfonyl, arylthio, alkylthio, phosphonate and alkylphosphonate.

2. A compound of formula (I) as defined in claim 1 wherein:
R2 is an optionally substituted group selected from $C_2$-$C_6$ alkenyl, $C_2$-$C_6$ alkynyl, aryl, arylalkyl, heterocyclyl and heterocyclylalkyl.

3. A compound of formula (I) as defined in claim 1 wherein:
A is —$(CH_2)_{1-3}$—X—R1, wherein X is as defined in claim 1 and R1 is hydrogen, halogen or an optionally substituted group selected from straight or branched $C_1$-$C_6$ alkyl, $C_3$-$C_7$ cycloalkyl, cycloalkyl-alkyl, arylalkyl and heterocyclyl; and
R2 is an optionally substituted group selected from $C_2$-$C_6$ alkynyl, aryl and heterocyclyl.

4. A compound of formula (I) as defined in claim 1 wherein:
A is —$(CH_2)_{1-3}$—X—R1, wherein X is —NR'—; R' is COR5; and R5 is NR7R8 or an optionally substituted group selected from straight or branched $C_1$-$C_6$ alkyl, $C_3$-$C_7$ cycloalkyl, cycloalkyl-alkyl, $C_2$-$C_6$ alkenyl, $C_2$-$C_6$ alkynyl, aryl, arylalkyl, heterocyclyl and heterocyclylalkyl.

5. A compound of formula (I) as defined in claim 1 wherein:
A is —$(CH_2)_{1-3}$—X—R1, wherein X is —NR'—; R' is COR5; R5 is NR7R8 or an optionally substituted group selected from straight or branched $C_1$-$C_6$ alkyl, $C_3$-$C_7$ cycloalkyl, cycloalkyl-alkyl, aryl, arylalkyl, heterocyclyl and heterocyclylalkyl, wherein R7 and R8 are each independently hydrogen or an optionally substituted group selected from straight or branched $C_1$-$C_6$ alkyl, aryl and heterocyclyl; and
R4 is hydrogen, halogen, cyano or an optionally substituted group selected from straight or branched $C_1$-$C_6$ alkyl, $C_3$-$C_7$ cycloalkyl, $C_2$-$C_6$ alkenyl, $C_2$-$C_6$ alkynyl, aryl and heterocyclyl.

6. A compound of formula (I) or a pharmaceutically acceptable salt thereof as defined in claim 1 which is selected from the group consisting of:
7-(3-chlorophenyl)-4-(2-hydroxyethyl)-6-phenyl-3,4-dihydropyrrolo[1,2-c]pyrazin-1(2H)-one (cpd 2),
7-(3-chlorophenyl)-4-{2-[(1-methylpiperidin-4-yl)amino]ethyl}-6-phenyl-3,4-dihydropyrrolo[1,2-a]pyrazin-1(2H)-one (cpd 13),
4-(2-aminoethyl)-7-(3-chlorophenyl)-6-phenyl-3,4-dihydropyrrolo[1,2-a]pyrazin-1(2H)-one (cpd 17), 4-(2-aminoethyl)-6-bromo-7-[3-(trifluoromethoxy)phenyl]-3,4-dihydropyrrolo[1,2-a]pyrazin-1(2H)-one (cpd 27), 4-(2-aminoethyl)-6-phenyl-7-[3-(trifluoromethoxy)phenyl]-3,4-dihydropyrrolo[1,2-a]pyrazin-1(2H)-one (cpd 28), 4-(2-aminoethyl)-6-(thiophen-3-yl)-'7-[3-(trifluoromethoxy)phenyl]-3,4-dihydropyrrolo[1,2-a]pyrazin-1(2H)-one (cpd 29), 4-(2-aminoethyl)-6-(3-methylphenyl)-7-[3-(trifluoromethoxy)phenyl]-3,4-dihydropyrrolo[1,2-a]pyrazin-1(2H)-one (cpd 31), 4-(2-aminoethyl)-6-[4-(hydroxymethyl)phenyl]-7-[3-(trifluoromethoxy)phenyl]-3,4-dihydropyrrolo[1,2-a]pyrazin-1(2H)-one (cpd 33), 4-(2-aminoethyl)-6-phenyl-7-[3-(trifluoromethyl)phenyl]-3,4-dihydropyrrolo[1,2-a]pyrazin-1(2H)-one (cpd 37), 4-(2-aminoethyl)-6-[4-(hydroxymethyl)phenyl]-7-[3-(trifluoromethyl)phenyl]-3,4-dihydropyrrolo[1,2-a]pyrazin-1(2H)-one (cpd 38), 4-(2-aminoethyl)-6-(3-methylphenyl)-7-[3-(trifluoromethyl)phenyl]-3,4-dihydropyrrolo[1,2-a]pyrazin-1(2H)-one (cpd 39), 4-(2-aminoethyl)-6-(thiophen-3-yl)-'7-[3-(trifluoromethyl)phenyl]-3,4-dihydropyrrolo[1,2-a]pyrazin-1(2H)-one (cpd 40), 4-(2-aminoethyl)-6-(4-hydroxyphenyl)-7-[3-(trifluoromethyl)phenyl]-3,4-dihydropyrrolo[1,2-a]pyrazin-1(2H)-one (cpd 43), 4-(2-aminoethyl)-7-(2-chloropyridin-4-yl)-6-[4-(hydroxymethyl)phenyl]-3,4-dihydropyrrolo[1,2-a]pyrazin-1(2H)-one (cpd 44), 4-(2-aminoethyl)-7-(2-chloropyridin-4-yl)-6-(3-methylphenyl)-3,4-dihydropyrrolo[1,2-a]pyrazin-1(2H)-one (cpd 45), 4-(2-aminoethyl)-7-(2-fluoropyridin-4-yl)-6-(3-methylphenyl)-3,4-dihydropyrrolo[1,2-a]pyrazin-1(2H)-one (cpd 47), 4-(2-aminoethyl)-7-(6-fluoropyridin-3-yl)-6-phenyl-3,4-dihydropyrrolo[1,2-a]pyrazin-1(2H)-one (cpd 48), 4-(2-aminoethyl)-7-(3,4-difluorophenyl)-6-(3-methylphenyl)-3,4-dihydropyrrolo[1,2-a]pyrazin-1(2H)-one (cpd 49), 4-(2-aminoethyl)-7-(3,4-difluorophenyl)-6-(thiophen-3-yl)-3,4-dihydropyrrolo[1,2-a]pyrazin-1(2H)-one (cpd 51), 4-(2-aminoethyl)-7-(3,4-difluorophenyl)-6-phenyl-3,4-dihydropyrrolo[1,2-a]pyrazin-1(2H)-one (cpd 52), 4-(2-aminoethyl)-7-[2-chloro-5-(trifluoromethoxy)phenyl]-6-(3-methylphenyl)-3,4-dihydropyrrolo[1,2-a]pyrazin-1(2H)-one (cpd 53), 4-(2-aminoethyl)-6-cyclopropyl-7-[3-(trifluoromethoxy)phenyl]-3,4-dihydropyrrolo[1,2-a]pyrazin-1(2H)-one (cpd 54), 4-(2-aminoethyl)-7-(5-chloro-2-fluorophenyl)-6-(thiophen-3-yl)-3,4-dihydropyrrolo[1,2-a]pyrazin-1(2H)-one (cpd 55), 4-(2-aminoethyl)-7-(5-chloro-2-fluorophenyl)-6-phenyl-3,4-dihydropyrrolo[1,2-a]pyrazin-1(2H)-one (cpd 57), 4-(2-aminoethyl)-7-(5-chloro-2-fluorophenyl)-6-(3-methylphenyl)-3,4-dihydropyrrolo[1,2-a]pyrazin-1(2H)-one (cpd 59), 4-(2-aminoethyl)-6-ethynyl-7-[3-(trifluoromethoxy)phenyl]-3,4-dihydropyrrolo[1,2-a]pyrazin-1(2H)-one (cpd 61), 4-(2-chloroethyl)-6-(3-methylphenyl)-7-[3-(trifluoromethoxy)phenyl]-3,4-dihydropyrrolo[1,2-a]pyrazin-1(2H)-one (cpd 63), 4-{4-(2-chloroethyl)-1-oxo-7-[3-(trifluoromethoxy)phenyl]-1,2,3,4-tetrahydropyrrolo[1,2-c]pyrazin-6-yl}benzamide (cpd 68), 4-(2-chloroethyl)-6-{4-[(dimethylamino)methyl]phenyl}-7-[3-(trifluoromethoxy)phenyl]-3,4-dihydropyrrolo[1,2-c]pyrazin-1(2H)-one (cpd 70), 4-(2-chloroethyl)-6-{4-[(4-methylpiperazin-1-yl)methyl]phenyl}-7-[3-(trifluoromethoxy)phenyl]-3,4-dihydropyrrolo[1,2-a]pyrazin-1(2H)-one (cpd 71), 4-{4-(2-hydroxyethyl)-1-oxo-7-[3-(trifluoromethoxy)phenyl]-1,2,3,4-tetrahydropyrrolo[1,2-a]pyrazin-6-yl}benzamide (cpd 77), N-[2-(dimethylamino)ethyl]-4-{4-(2-hydroxyethyl)-1-oxo-7-[3-(trifluoromethoxy)phenyl]-1,2,3,4-tetrahydropyrrolo[1,2-a]pyrazin-6-yl}benzamide (cpd 78), 4-{4-(2-hydroxyethyl)-1-oxo-7-[3-(trifluoromethoxy)phenyl]-1,2,3,4-tetrahydropyrrolo[1,2-a]pyrazin-6-yl}-N,N-dimethylbenzamide (cpd 79), 4-{4-(2-hydroxyethyl)-1-oxo-7-[3-(trifluoromethoxy)phenyl]-1,2,3,4-tetrahydropyrrolo[1,2-a]pyrazin-6-yl}-N-methylbenzamide (cpd 80), 4-{4-(2-hydroxyethyl)-1-oxo-7-[3-(trifluoromethoxy)phenyl]-1,2,3,4-tetrahydropyrrolo[1,2-a]pyrazin-6-yl}-N-(1-methylpiperidin-4-yl)benzamide (cpd 81), 6-{4-[(dimethylamino)methyl]phenyl}-4-(2-hydroxyethyl)-7-[3-(trifluoromethoxy)phenyl]-3,4-dihydropyrrolo[1,2-a]pyrazin-1(2H)-one (cpd 83), 4-(2-hydroxyethyl)-6-[4-(hydroxymethyl)phenyl]-7-[3-(trifluoromethoxy)phenyl]-3,4-dihydropyrrolo[1,2-a]pyrazin-1(2H)-one (cpd 84), (4S)-4-(2-aminoethyl)-6-(thiophen-3-yl)-7-[3-(trifluoromethoxy)phenyl]-3,4-dihydropyrrolo[1,2-a]pyrazin-1(2H)-one (cpd 85), (4R)-4-(2-aminoethyl)-6-(thiophen-3-yl)-'7-[3-(trifluoromethoxy)phenyl]-3,4-dihydropyrrolo[1,2-a]pyrazin-1(2H)-one (cpd 86), (4S)-4-(2-aminoethyl)-6-phenyl-7-[3-(trifluoromethoxy)phenyl]-3,4-dihydropyrrolo[1,2-a]pyrazin-1(2H)-one (cpd 87), (4R)-4-(2-aminoethyl)-6-phenyl-7-[3-(trifluoromethoxy)phenyl]-3,4-dihydropyrrolo[1,2-a]pyrazin-1(2H)-one (cpd 88), (4S)-4-(2-aminoethyl)-6-(3-methylphenyl)-7-[3-(trifluoromethoxy)phenyl]-3,4-dihydropyrrolo[1,2-a]pyrazin-1(2H)-one (cpd 92), (4S)-4-(2-aminoethyl)-6-(4-fluorophenyl)-7-[3-(trifluoromethoxy)phenyl]-3,4-dihydropyrrolo[1,2-a]pyrazin-1(2H)-one (cpd 94), (4S)-6-(4-acetylphenyl)-4-(2-aminoethyl)-7-[3-(trifluoromethoxy)phenyl]-3,4-dihydropyrrolo[1,2-a]pyrazin-1(2H)-one (cpd 95), (4S)-4-(2-aminoethyl)-6-[4-(methylsulfonyl)phenyl]-7-[3-(trifluoromethoxy)phenyl]-3,4-dihydropyrrolo[1,2-a]pyrazin-1(2H)-one (cpd 96), (4S)-4-(2-aminoethyl)-6-[4-(morpholin-4-ylmethyl)phenyl]-7-[3-(trifluoromethoxy)phenyl]-3,4-dihydropyrrolo[1,2-a]pyrazin-1(2H)-one (cpd 99), (4S)-4-(2-amino ethyl)-6-{4-[(4-methylpiperazin-1-yl)methyl]phenyl}-7-[3-(trifluoromethoxy)phenyl]-3,4-dihydropyrrolo[1,2-a]pyrazin-1(2H)-one (cpd 100), (4S)-4-(2-aminoethyl)-6-{4-[(dimethylamino)methyl]phenyl-7-[3-(trifluoromethoxy)phenyl]-3,4-dihydropyrrolo[1,2-a]pyrazin-1(2H)-one (cpd 101), (4S)-4-(3-aminopropyl)-6-phenyl-7-[3-(trifluoromethoxy)phenyl]-3,4-dihydropyrrolo[1,2-a]pyrazin-1(2H)-one (cpd 102), (4S)-4-(3-aminopropyl)-6-(thiophen-3-yl)-7-[3-(trifluoromethoxy)phenyl]-3,4-dihydropyrrolo[1,2-a]pyrazin-1(2H)-one (cpd 103), (4S)-4-(3-aminopropyl)-6-(4-hydroxyphenyl)-7-[3-(trifluoromethoxy)phenyl]-3,4-dihydropyrrolo[1,2-a]pyrazin-1(2H)-one (cpd 104), (4S)-4-(3-aminopropyl)-6-[4-(hydroxymethyl)phenyl]-7-[3-(trifluoromethoxy)phenyl]-3,4-dihydropyrrolo[1,2-a]pyrazin-1(2H)-one (cpd 105), (4S)-4-(2-chloroethyl)-6-{4-[(4-methylpiperazin-1-yl)methyl]phenyl-7-[3-(trifluoromethoxy)phenyl]-3,4-dihydropyrrolo[1,2-a]pyrazin-1(2H)-one (cpd 106), (4S)-6-(4-acetylphenyl)-4-(3-aminopropyl)-7-[3-(trifluoromethoxy)phenyl]-3,4-dihydropyrrolo[1,2-c]pyrazin-1(2H)-one (cpd 110), (4S)-4-(3-aminopropyl)-6-(4-fluorophenyl)-7-[3-(trifluoromethoxy)phenyl]-3,4-dihydropyrrolo[1,2-c]pyrazin-1(2H)-one (cpd 111), (4S)-4-(2-aminoethyl)-6-(1,3-benzodioxol-5-yl)-7-[3-(trifluoromethoxy)phenyl]-3,4-dihydropyrrolo[1,2-a]pyrazin-1(2H)-one (cpd 112), (4S)-4-(2-aminoethyl)-6-(3-fluoro-4-methoxyphenyl)-7-[3-(trifluoromethoxy)phenyl]-3,4-dihydropyrrolo[1,2-a]pyrazin-1(2H)-one (cpd 113), (4S)-4-(2-aminoethyl)-6-[4-(2-methylpropoxyl)phenyl]-7-[3-(trifluoromethoxy)phenyl]-3,4-dihydropyrrolo[1,2-a]pyrazin-1(2H)-one (cpd 114), (4S)-4-(2-aminoethyl)-6-[4-(dimethylamino)phenyl]-7-[3-(trifluoromethoxy)phenyl]-3,4-dihydropyrrolo[1,2-a]pyrazin-1(2H)-one (cpd 115), (4S)-4-(2-aminoethyl)-6-(4-methoxyphenyl)-7-[3-(trifluoromethoxy)phenyl]-3,4-dihydropyrrolo[1,2-a]pyrazin-1(2H)-one (cpd 116), (4S)-4-(2-aminoethyl)-6-(2-aminopyrimidin-5-yl)-'7-[3-(trifluoromethoxy)phenyl]-3,4-dihydropyrrolo[1,2-a]pyrazin-1(2H)-one (cpd 117), (4S)-4-(2-aminoethyl)-6-(naphthalen-2-yl)-7-[3-(trifluoromethoxy)phenyl]-3,4-dihydropyrrolo[1,2-a]pyrazin-1(2H)-one (cpd 118), (4S)-4-(2-aminoethyl)-6-(biphenyl-3-yl)-'7-[3-(trifluoromethoxy)phenyl]-3,4-dihydropyrrolo[1,2-a]pyrazin-1(2H)-one (cpd 119), 4-{(4S)-4-(2-aminoethyl)-1-oxo-7-[3-(trifluoromethoxy)phenyl]-1,2,3,4-tetrahydropyrrolo[1,2-a]pyrazin-6-yl}benzenesulfonamide (cpd 120), (4S)-4-(2-aminoethyl)-6-(3-fluorophenyl)-7-[3-(trifluoromethoxy)phenyl]-3,4-dihydropyrrolo[1,2-a]pyrazin-1(2H)-one (cpd 121), (4S)-4-(2-aminoethyl)-6-(4-fluoro-3-methylphenyl)-7-[3-(trifluoromethoxy)phenyl]-3,4-dihydropyrrolo[1,2-a]pyrazin-1(2H)-one (cpd 122), (4S)-4-(2-aminoethyl)-6-[4-(methylsulfanyl)phenyl]-7-[3-(trifluoromethoxy)phenyl]-3,4-dihydropyrrolo[1,2-a]pyrazin-1(2H)-one (cpd 123), (4S)-4-(2-aminoethyl)-6-(4-tert-butylphenyl)-7-[3-(trifluoromethoxy)phenyl]-3,4-dihydropyrrolo[1,2-a]pyrazin-1(2H)-one (cpd 124), (4S)-4-(2-aminoethyl)-7-[3-(trifluoromethoxy)phenyl]-6-[3-(trifluoromethyl)phenyl]-3,4-dihydropyrrolo[1,2-a]pyrazin-1(2H)-one (cpd 125), (4S)-4-(2-aminoethyl)-6-(3-chlorophenyl)-7-[3-(trifluoromethoxy)phenyl]-3,4-dihydropyrrolo[1,2-a]pyrazin-1(2H)-one (cpd 126), (4S)-4-(2-aminoethyl)-6-(4-ethoxy-3-fluorophenyl)-7-[3-(trifluoromethoxy)phenyl]-3,4-dihydropyrrolo[1,2-a]pyrazin-1(2H)-one (cpd 127), (4S)-4-(2-aminoethyl)-6-(4-methoxy-3,5-dimethylphenyl)-7-[3-(trifluoromethoxy)phenyl]-3,4-dihydropyrrolo[1,2-a]pyrazin-1(2H)-one (cpd 128), (4S)-4-(2-aminoethyl)-6-(3-chloro-4-methoxyphenyl)-7-[3-(trifluoromethoxy)phenyl]-3,4-dihydropyrrolo[1,2-a]pyrazin-1(2H)-one (cpd 129), (4S)-6-[4-(1-aminocyclopropyl)phenyl]-4-(2-aminoethyl)-7-[3-(trifluoromethoxy)phenyl]-3,4-dihydropyrrolo[1,2-a]pyrazin-1(2H)-one (cpd 130), (4S)-6-[4-(1-aminocyclopropyl)phenyl]-4-(propan-2-yl)-7-[3-(trifluoromethoxy)phenyl]-3,4-dihydropyrrolo[1,2-c]pyrazin-1(2H)-one (cpd 131), (4S)-6-(4-ethoxy-3-fluorophenyl)-4-(1H-imidazol-4-ylmethyl)-7-[3-(trifluoromethoxy)phenyl]-3,4-dihydropyrrolo[1,2-a]pyrazin-1(2H)-one (cpd 132), (4S)-4-(1H-imidazol-4-ylmethyl)-6-(3-methylphenyl)-7-[3-(trifluoromethoxy)phenyl]-3,4-dihydropyrrolo[1,2-a]pyrazin-1(2H)-one (cpd 133), (45)-4-(3-aminopropyl)-6-{4-[(dimethylamino)methyl]phenyl}-7-[3-(trifluoromethoxy)phenyl]-3,4-dihydropyrrolo[1,2-a]pyrazin-1(2M-one (cpd 134), (45)-4-(3-aminopropyl)-6-{4-[(4-methylpiperazin-1-yl)methyl]phenyl}-7-[3-(trifluoromethoxy)phenyl]-3,4-dihydropyrrolo[1,2-a]pyrazin-1(2H)-one (cpd 135), (4S)-6-{4-[(dimethylamino)methyl]phenyl}-4-(propan-2-yl)-7-[3-(trifluoromethoxy)phenyl]-3,4dihydropyrrolo[1,2-a]pyrazin-1(2H)-one (cpd 136), (4S)-6-{4-[(4-methylpiperazin-1-yl)methyl]phenyl}-4-(propan-2-yl)-7-[3-(trifluoromethoxy)phenyl]-3,4-dihydropyrrolo[1,2-a]pyrazin-1(2H)-one (cpd 137), (4S)-6-[4-(aminomethyl)phenyl]-4-(propan-2-yl)-7-[3-(trifluoromethoxy)phenyl]-3,4-dihydropyrrolo[1,2-c]pyrazin-1(2M-one (cpd 138), (4S)-6-[3-(dimethylamino)prop-1-yn-1-yl]-4-(propan-2-yl)-7-[3-(trifluoromethoxy)phenyl]-3,4-dihydropyrrolo[1,2-a]pyrazin-1(2M-one (cpd 139), (4S)-6-(3-aminoprop-1-yn-1-yl)-4-(propan-2-yl)-7-[3-(trifluoromethoxy)phenyl]-3,4-dihydropyrrolo[1,2-a]pyrazin-1(2H)-one (cpd 140), 2,2-dimethyl-N-(2-{(4S)-6-(3-methylphenyl)-1-oxo-7-[3-(trifluoromethoxy)phenyl]-1,2,3,4-tetrahydropyrrolo[1,2-a]pyrazin-4-yl}ethyl)propanamide (cpd 141), N-(2-{(4S)-1-oxo-6-phenyl-7-[3-(trifluoromethoxy)phenyl]-1,2,3,4-tetrahydropyrrolo[1,2-a]pyrazin-4-yl}ethyl)acetamide (cpd 142), 2,2-dimethyl-N-(2-{(4S)-1-oxo-6-phenyl-7-[3-(trifluoromethoxy)phenyl]-1,2,3,4-tetrahydropyrrolo[1,2-a]pyrazin-4-yl}ethyl)propanamide (cpd 143), 1-tert-butyl-3-(2-{(4S)-6-(3-methylphenyl)-1-oxo-7-[3-(trifluoromethoxy)phenyl]-1,2,3,4-tetrahydropyrrolo[1,2-a]pyrazin-4-yl}ethyl)urea (cpd 144), 1-tert-butyl-3-(2-{(4S)-1-oxo-6-phenyl-7-[3-(trifluoromethoxy)phenyl]-1,2,3,4-tetrahydropyrrolo[1,2-a]pyrazin-4-yl}ethyl)urea (cpd 145), 1-butan-2-yl-3-(2-{(4S)-1-oxo-6-phenyl-7-[3-(trifluoromethoxy)phenyl]-1,2,3,4-tetrahydropyrrolo[1,2-a]pyrazin-4-yl}ethyl)urea (cpd 146), N-(2-{(4S)-1-oxo-6-phenyl-7-[3-(trifluoromethoxy)phenyl]-1,2,3,4-tetrahydropyrrolo[1,2-a]pyrazin-4-yl}ethyl)methanesulfonamide (cpd 147), 1-(2-{(4S)-6-(3-methylphenyl)-1-oxo-7-[3-(trifluoromethoxy)phenyl]-1,2,3,4-tetrahydropyrrolo[1,2-a]pyrazin-4-yl}ethyl)guanidine (cpd 148), and 1-(2-{(4S)-6-[4-(methylsulfonyl)phenyl]-1-oxo-7-[3-(trifluoromethoxy)phenyl]-1,2,3,4-tetrahydropyrrolo[1,2-a]pyrazin-4-yl}ethyl)guanidine (cpd 149).

7. A pharmaceutical composition comprising a therapeutically effective amount of a compound of formula (I) or a pharmaceutically acceptable salt thereof, as defined in claim 1, and at least one pharmaceutically acceptable excipient, carrier and/or diluent.

8. The pharmaceutical composition according to claim 7 further comprising one or more chemotherapeutic agents.

9. A product or kit comprising a compound of formula (I) or a pharmaceutically acceptable salt thereof, as defined in claim 1, or a pharmaceutical composition comprising a therapeutically effective amount of said compound of formula (1) or a pharmaceutically acceptable salt thereof and at least one pharmaceutically acceptable excipient, carrier and/or diluent and one or more chemotherapeutic agents.

10. A method for treating a disease caused by and/or associated with a dysregulated protein kinase activity, said disease selected from the group consisting of breast cancer, colon cancer, prostate cancer, leukemia, B-cell lymphoma, Burkitt's lymphoma and myeloma, which comprises administering to a mammal in need thereof an effective amount of a compound of formula (I) as defined in claim 1.

11. The method according to claim 10 further comprising subjecting the mammal in need thereof to a radiation therapy or chemotherapy regimen in combination with at least one cytostatic or cytotoxic agent.

12. The method according to claim 10 wherein the mammal in need thereof is a human.

13. An in vitro method for inhibiting PIM-1, PIM-2 and PIM-3 protein kinase activity which comprises contacting said protein with an effective amount of a compound of formula (I) as defined in claim 1.

14. A process for preparing a compound of formula (I) as defined in claim 1 or a pharmaceutically acceptable salt thereof, characterized in that the process comprises the following step of reacting a compound of formula (VI)

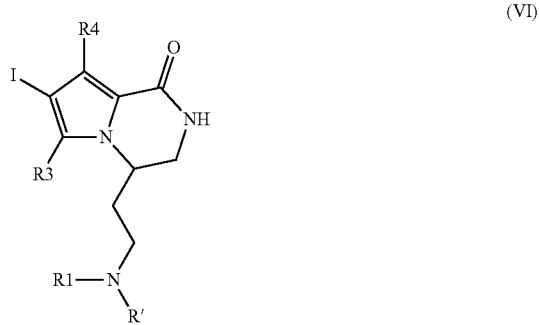

(VI)

wherein R' is hydrogen or a protecting group selected from the group consisting of tert-butylcarbamate and benzyloxycarbonyl, according to any one of the alternative steps:

Step 5a) with an organoboron of formula (XII):

R2'B(OZ')OZ"    (XII)

wherein R2' is selected from straight or branched $C_1$-$C_6$ alkyl, $C_3$-$C_7$ cycloalkyl, cycloalkyl-alkyl, $C_2$-$C_6$ alkenyl, aryl, arylalkyl, heterocyclyl and heterocyclylalkyl;

and Z' and Z" are either hydrogen, $C_1$-$C_6$ alkyl or, taken together with the oxygen atoms to which they are bonded, may form a 5 to 6 membered heterocyclyl, or Step 5b) with a terminal alkyne of formula (XIII):

$R^aC{\equiv}CH$    (XIII)

wherein $R^a$ is hydrogen, or selected from straight or branched $C_1$-$C_6$ alkyl, $C_3$-$C_7$ cycloalkyl, cycloalkyl-alkyl, $C_2$-$C_6$ alkenyl, $C_2$-$C_6$ alkynyl, aryl, arylalkyl, heterocyclyl and heterocyclylalkyl;

or

Step 5') first, with a boronyl reagent selected from the group consisting of (pinacolato)diboron and pinacolborane;

Step 5") then mixing the resultant compound of formula (VIa)

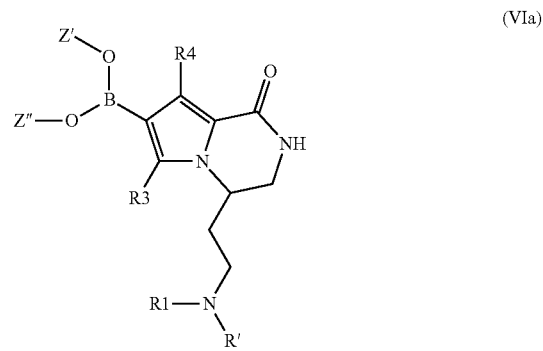

(VIa)

with a compound of formula R2"-Q (XIV) wherein R2" is selected from straight or branched $C_1$-$C_6$ alkyl, $C_3$-$C_7$ cycloalkyl, cycloalkyl-alkyl, aryl, arylalkyl, heterocyclyl and heterocyclylalkyl, and Q is halogen, triflyl, alkylsulfonyloxy, or arylsulfonyloxy group;

or

Step 9) mixing a compound of formula (VII)

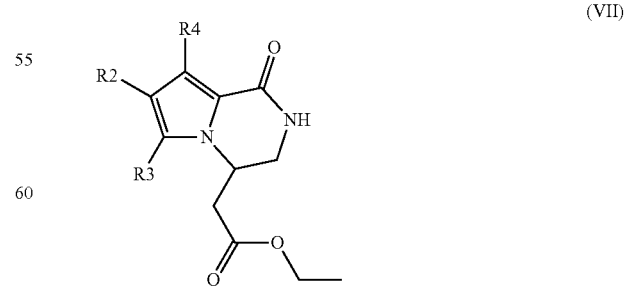

(VII)

wherein R2 is an optionally substituted group selected from straight or branched $C_1$-$C_6$ alkyl, $C_3$-$C_7$ cycloalkyl, cycloalkyl-alkyl, aryl, arylalkyl, heterocyclyl and heterocyclylalkyl, with a reducing agent selected from the group consisting of sodium borohydride and lithium aluminum hydride;

or

Step 12) mixing a compound of formula (X)

(X)

wherein R2 is aryl and R3 is an optionally substituted group selected from straight or branched $C_1$-$C_6$ alkyl, $C_3$-$C_7$ cycloalkyl, cycloalkyl-alkyl, $C_2$-$C_6$ alkenyl, $C_2$-$C_6$ alkynyl, aryl, arylalkyl, heterocyclyl and heterocyclylalkyl, with a reducing agent selected from the group consisting of sodium borohydride and lithium aluminum hydride;

or

Step 14) reacting a compound of formula (XI)

(XI)

wherein R2 is an optionally substituted group selected from straight or branched $C_1$-$C_6$ alkyl, $C_3$-$C_7$ cycloalkyl, cycloalkyl-alkyl, $C_2$-$C_6$ alkenyl, $C_2$-$C_6$ alkynyl, aryl, arylalkyl, heterocyclyl and heterocyclylalkyl; and R3 is hydrogen;

or

Step 23) reacting a compound of formula (XXIII)

(XXIII)

wherein A is an optionally substituted group selected from straight or branched $C_1$-$C_6$ alkyl, heterocyclyl and —$(CH_2)_{1-3}$—X—R1, wherein X is NW, R' is hydrogen or a protecting group selected from the group consisting of tert-butylcarbamate and benzyloxycarbonyl, according to any one of the alternative steps:

Step 23a) with an organoboron of formula (XII)

R2'B(OZ')OZ" (XII)

or

Step 23b) with a terminal alkyne of formula (XIII):

$R^a$C≡CH (XIII)

or

Step 30) reacting a compound of formula (XXIXa)

(XXIXa)

alternatively with:

Step 30a) an organoboron of formula (XII)

R2'B(OZ')OZ" (XII)

or

Step 30b) a terminal alkyne of formula (XIII):

$R^a$C≡CH (XIII)

to give a compound of formula (I)

(I)

and (i) optionally converting a compound of the formula (I) into a different compound of the formula (I), (ii) optionally converting a compound of the formula (I) into a pharmaceutically acceptable salt thereof, or (iii) converting a pharmaceutically acceptable salt of the compound of formula (I) to the compound of the formula (I).

15. A process according to claim 14, characterized in that conversion of a compound of the formula (I) into a different compound of the formula (I) is carried out with one of the following methods:

Conv. b) converting a compound of formula (I) where a group —$CH_2OH$ is present, into the corresponding compound of formula (I) with a group —$CH_2NR'R1$ wherein R' is hydrogen or a protecting group of formula COOR6, by a three-steps sequence encompassing alcohol activation, nucleophilic displacement and manipulation of the post-nucleophile product to an amine;

Conv. e) converting a compound of the formula (I) wherein R3 or R4 is hydrogen into the corresponding compound of the formula (I)

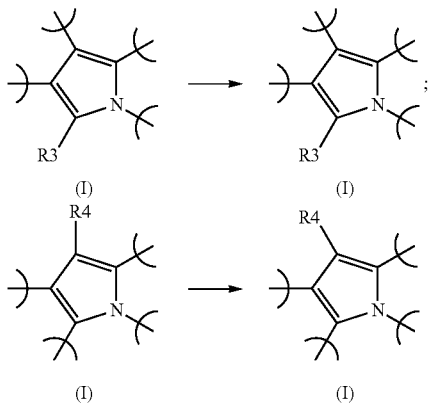

wherein R3 or R4 is a halogen, through reaction with an halogenating agent selected from the group consisting of N-chlorosuccinimide, N-bromo succinimide, N-iodosuccinimide, dichloromethane, dimethylformamide, tetrahydrofuran and methanol;

Conv. g) converting a compound of formula (I) wherein R3 or R4 is halogen into the corresponding compound of formula (I)

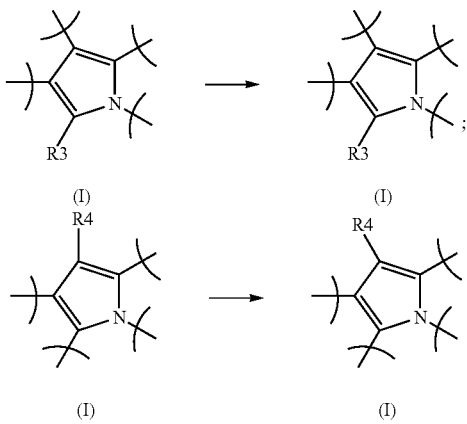

wherein R3 or R4 is an optionally substituted group selected from straight or branched $C_1$-$C_6$ alkyl, $C_3$-$C_7$ cycloalkyl, cycloalkyl-alkyl, aryl, arylalkyl, heterocyclyl and heterocyclylalkyl by reaction with a compound of formula (XXXI) or formula (XXXII) respectively:

R3"-G (XXXI) R4"-G (XXXII)

wherein R3" or R4" is straight or branched $C_1$-$C_6$ alkyl, $C_3$-$C_7$ cycloalkyl, cycloalkyl-alkyl, aryl, arylalkyl, heterocyclyl and heterocyclylalkyl, and G is a suitable group selected from the group consisting of —B(OH)$_2$, —B(OAlk)$_2$, —Sn(Alk)$_4$, ZnCl$_2$ and MgCl$_2$;

Conv. i) converting a compound of the formula (I) where is present a group L-COOPg, wherein L is selected from straight or branched $C_1$-$C_6$ alkyl, $C_3$-$C_7$ cycloalkyl, cycloalkylalkyl, $C_2$-$C_6$ alkenyl, $C_2$-$C_6$ alkynyl, aryl, arylalkyl, heterocyclyl and heterocyclylalkyl, and Pg is a suitable protecting group selected from the group consisting of t-butyl, benzyl, methyl and ethyl, into the corresponding compound of formula (I)

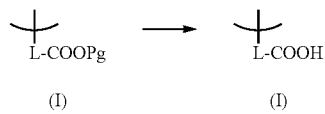

where a group L-COOH is present;

Conv. j) converting a compound of the formula (I) where a group L-COOH is present, into the corresponding compound of formula (I)

where a group L-CONR'R1 is present, by treatment with an amine of formula R1R'—NH (XXX), in the presence of the suitable condensing agents selected from the group consisting of dicyclohexylcarbodiimide, 1-ethyl-3(3'-dimethylaminopropyl)carbodiimide, 3,4-dihydro-3-hydroxy-4-oxo-1,2,3-benzotriazine, O-benzotriazolyltetramethylisouronium tetrafluoroborate, benzotriazol-1-yloxytripyrrolidinophosphonium hexafluorophosphate and 2-(1H-Benzotriazole-1-yl)-1,1,3,3-tetramethyluronium hexafluorophosphate;

Conv. 1) converting a compound of formula (I) where a primary or secondary amine is present, into the corresponding compound of formula (I)

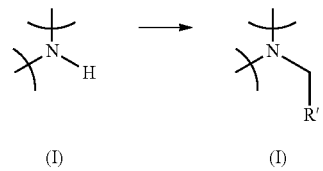

where a secondary or tertiary amine is present, by treatment with a compound of formula R'—CHO (XXXIII) wherein R' is an optionally substituted group selected from straight or branched $C_1$-$C_6$ alkyl, $C_3$-$C_7$ cycloalkyl, cycloalkyl-alkyl, aryl, arylalkyl, heterocyclyl and heterocyclylalkyl; and Conv. r) removing any protecting group or groups.

* * * * *